(12) United States Patent
Barraud et al.

(10) Patent No.: US 11,679,199 B2
(45) Date of Patent: Jun. 20, 2023

(54) SYSTEMS AND METHODS FOR DELIVERING MICRODOSES OF MEDICATION

(71) Applicant: AMF Medical SA, St-Sulpice (CH)

(72) Inventors: Antoine Barraud, Lonay (CH); Benjamin Pruijs, Bienne (CH); Nathanael Sigg, Oulens-sous-Echallens (CH); Christophe Satorre, Lausanne (CH)

(73) Assignee: AMF Medical SA, St-Sulpice (CH)

( * ) Notice: Subject to any disclaimer, the term of this patent is extended or adjusted under 35 U.S.C. 154(b) by 0 days.

(21) Appl. No.: 18/058,041

(22) Filed: Nov. 22, 2022

(65) Prior Publication Data

US 2023/0092485 A1    Mar. 23, 2023

Related U.S. Application Data

(63) Continuation of application No. 17/652,448, filed on Feb. 24, 2022, now Pat. No. 11,529,460.
(Continued)

(51) Int. Cl.
*A61M 5/142* (2006.01)
*A61M 5/158* (2006.01)
(Continued)

(52) U.S. Cl.
CPC ..... *A61M 5/14248* (2013.01); *A61B 5/14865* (2013.01); *A61M 5/1413* (2013.01); *A61M 5/158* (2013.01); *A61M 5/168* (2013.01); *A61M 5/1684* (2013.01); *A61M 5/16827* (2013.01); *A61M 5/172* (2013.01); *A61M 5/1723* (2013.01); *A61M 5/5086* (2013.01); *A61M 2005/14252* (2013.01); *A61M 2005/14256* (2013.01); *A61M 2005/14533* (2013.01);
(Continued)

(58) Field of Classification Search
None
See application file for complete search history.

(56) References Cited

U.S. PATENT DOCUMENTS

| 2,105,200 A | 1/1938 | Phelps |
| 2,412,397 A | 12/1946 | Harper |

(Continued)

FOREIGN PATENT DOCUMENTS

| DE | 102013111800 A1 | 4/2015 |
| EP | 0721358 A1 | 7/1996 |

(Continued)

OTHER PUBLICATIONS

U.S. Appl. No. 15/777,284, filed May 18, 2018.
(Continued)

*Primary Examiner* — Manuel A Mendez
(74) *Attorney, Agent, or Firm* — Eversheds Sutherland (US) LLP; Christopher C. Bolten; Nicola A. Pisano

(57) ABSTRACT

Devices, systems, and methods are provided herein for delivering medication (e.g., insulin) via a wearable pump having a patch-style form factor for adhesion to a user's body. The reusable pump may be coupled to a disposable cap housing a microdosing system for delivering precise, repeatable doses of medication to a cannula configured to deliver medication to a target infusion area beneath the user's outer skin layer. The system further may include an applicator for inserting the cannula into the user's skin and/or applying an adhesive pad to the skin.

30 Claims, 71 Drawing Sheets

Related U.S. Application Data

(60) Provisional application No. 63/195,564, filed on Jun. 1, 2021.

(51) Int. Cl.

| | | |
|---|---|---|
| A61M 5/168 | (2006.01) | |
| A61M 5/172 | (2006.01) | |
| A61B 5/1486 | (2006.01) | |
| A61M 5/14 | (2006.01) | |
| A61M 5/50 | (2006.01) | |
| A61M 5/145 | (2006.01) | |

(52) U.S. Cl.
CPC . *A61M 2005/1586* (2013.01); *A61M 2205/18* (2013.01); *A61M 2205/3317* (2013.01); *A61M 2205/3331* (2013.01); *A61M 2205/582* (2013.01); *A61M 2207/00* (2013.01)

(56) References Cited

U.S. PATENT DOCUMENTS

| | | |
|---|---|---|
| 3,609,069 A | 9/1971 | Martinelli |
| 4,042,153 A | 8/1977 | Callahan et al. |
| 4,199,307 A | 4/1980 | Jassawalla |
| 4,218,416 A | 8/1980 | Gokcen |
| 4,236,880 A | 12/1980 | Archibald |
| 4,273,121 A | 6/1981 | Jassawalla |
| 4,290,346 A | 9/1981 | Bujan |
| 4,322,201 A | 3/1982 | Archibald |
| 4,410,322 A | 10/1983 | Archibald |
| 4,482,347 A | 11/1984 | Borsanyi |
| 4,493,704 A | 1/1985 | Beard et al. |
| 4,596,575 A | 6/1986 | Rosenberg et al. |
| 4,616,802 A | 10/1986 | Tseng et al. |
| 4,617,014 A | 10/1986 | Cannon et al. |
| 4,657,490 A | 4/1987 | Abbott |
| 4,854,836 A | 8/1989 | Borsanyi |
| 4,934,372 A | 6/1990 | Corenman et al. |
| 5,056,992 A | 10/1991 | Simons et al. |
| 5,088,522 A | 2/1992 | Rath et al. |
| 5,137,023 A | 8/1992 | Mendelson et al. |
| 5,217,355 A | 6/1993 | Hyman et al. |
| 5,252,044 A | 10/1993 | Raines et al. |
| 5,318,546 A | 6/1994 | Bierman |
| 5,482,446 A | 1/1996 | Williamson et al. |
| 5,637,095 A | 6/1997 | Nason et al. |
| 5,851,197 A | 12/1998 | Marano et al. |
| 5,964,583 A | 10/1999 | Danby |
| 6,093,172 A | 7/2000 | Funderburk et al. |
| 6,165,151 A | 12/2000 | Weiner |
| 6,293,925 B1 | 9/2001 | Safabash et al. |
| 6,607,509 B2 | 8/2003 | Bobroff et al. |
| 6,723,077 B2 | 4/2004 | Pickup et al. |
| 6,801,420 B2 | 10/2004 | Talbot et al. |
| 6,830,562 B2 | 12/2004 | Mogensen et al. |
| 6,881,043 B2 | 4/2005 | Barak |
| 7,137,964 B2 | 11/2006 | Flaherty |
| 7,204,823 B2 | 4/2007 | Estes et al. |
| 7,315,753 B2 | 1/2008 | Baker, Jr. et al. |
| 7,329,239 B2 | 2/2008 | Safabash et al. |
| 7,356,364 B1 | 4/2008 | Bullock et al. |
| 7,879,023 B2 | 2/2011 | Wood, Jr. |
| 7,879,026 B2 | 2/2011 | Estes et al. |
| 8,152,771 B2 | 4/2012 | Mogensen et al. |
| 8,377,002 B2 | 2/2013 | Hanson et al. |
| 8,657,807 B2 | 2/2014 | Blomquist |
| 9,517,024 B2 | 12/2016 | Kiani et al. |
| 9,610,018 B2 | 4/2017 | Gulati et al. |
| 9,615,779 B2 | 4/2017 | Pryor et al. |
| 9,636,457 B2 | 5/2017 | Newberry et al. |
| 9,735,502 B2 | 8/2017 | Stevens et al. |
| 9,735,893 B1 | 8/2017 | Aleksov et al. |
| 9,820,691 B2 | 11/2017 | Kiani |
| 9,833,152 B2 | 12/2017 | Kiani et al. |
| 9,931,065 B2 | 4/2018 | Pryor et al. |
| 9,967,040 B2 | 5/2018 | Aleksov et al. |
| 9,980,140 B1 | 5/2018 | Spencer et al. |
| 10,137,245 B2 | 11/2018 | Melker et al. |
| 10,278,732 B2 | 5/2019 | Schoonmaker et al. |
| 10,279,106 B1 | 5/2019 | Cook et al. |
| 10,398,320 B2 | 9/2019 | Kiani et al. |
| 11,139,754 B1 | 10/2021 | Shi et al. |
| 11,241,530 B1 | 2/2022 | Fridez et al. |
| 2002/0001530 A1 | 1/2002 | Doi et al. |
| 2002/0071225 A1 | 6/2002 | Sheldon et al. |
| 2002/0091358 A1 | 7/2002 | Klitmose |
| 2002/0169439 A1 | 11/2002 | Flaherty |
| 2004/0064088 A1 | 4/2004 | Gorman et al. |
| 2004/0082920 A1 | 4/2004 | Mori et al. |
| 2004/0158207 A1 | 8/2004 | Hunn et al. |
| 2005/0043687 A1 | 2/2005 | Mogensen et al. |
| 2005/0101912 A1 | 5/2005 | Faust et al. |
| 2005/0124936 A1 | 6/2005 | Mogensen et al. |
| 2005/0277887 A1 | 12/2005 | Douglas et al. |
| 2006/0036214 A1 | 2/2006 | Mogensen et al. |
| 2007/0060874 A1 | 3/2007 | Nesbitt et al. |
| 2007/0191772 A1 | 8/2007 | Wojcik |
| 2007/0191773 A1 | 8/2007 | Wojcik |
| 2007/0219496 A1 | 9/2007 | Kamen et al. |
| 2008/0051727 A1 | 2/2008 | Moberg et al. |
| 2008/0091175 A1 | 4/2008 | Frikart et al. |
| 2008/0097289 A1 | 4/2008 | Steil et al. |
| 2008/0281290 A1 | 11/2008 | Yodfat et al. |
| 2008/0319414 A1 | 12/2008 | Yodfat et al. |
| 2009/0069750 A1 | 3/2009 | Schraga |
| 2009/0118667 A1 | 5/2009 | Haueter et al. |
| 2009/0177146 A1 | 7/2009 | Nesbitt et al. |
| 2010/0004598 A1 | 1/2010 | Eberhart et al. |
| 2010/0017141 A1 | 1/2010 | Campbell et al. |
| 2010/0064236 A1 | 3/2010 | Buck et al. |
| 2010/0064257 A1 | 3/2010 | Buck et al. |
| 2010/0077198 A1 | 3/2010 | Buck et al. |
| 2010/0082167 A1 | 4/2010 | Haueter et al. |
| 2010/0106082 A1 | 4/2010 | Zhou |
| 2010/0174239 A1 | 7/2010 | Yodfat et al. |
| 2010/0211011 A1 | 8/2010 | Haar |
| 2010/0228226 A1 | 9/2010 | Nielsen |
| 2011/0054439 A1 | 3/2011 | Yodfat et al. |
| 2011/0137297 A1 | 6/2011 | Kiani et al. |
| 2011/0152769 A1 | 6/2011 | Ramey et al. |
| 2011/0218495 A1 | 9/2011 | Remde |
| 2011/0247397 A1 | 10/2011 | Friedli et al. |
| 2012/0051946 A1 | 3/2012 | Lee et al. |
| 2012/0059348 A1 | 3/2012 | Haueter et al. |
| 2012/0078181 A1 | 3/2012 | Smith et al. |
| 2012/0093311 A1 | 4/2012 | Nierzwick et al. |
| 2012/0093315 A1 | 4/2012 | Nierzwick et al. |
| 2012/0095393 A1 | 4/2012 | Reinke et al. |
| 2012/0150144 A1 | 6/2012 | Campbell et al. |
| 2012/0157655 A1 | 6/2012 | Yoneda et al. |
| 2012/0209187 A1 | 8/2012 | Kamen et al. |
| 2012/0220939 A1 | 8/2012 | Yodfat et al. |
| 2012/0226124 A1 | 9/2012 | Blomquist |
| 2012/0232485 A1 | 9/2012 | Blomquist |
| 2012/0232486 A1 | 9/2012 | Blomquist |
| 2012/0232521 A1 | 9/2012 | Blomquist |
| 2012/0239362 A1 | 9/2012 | Blomquist |
| 2012/0302991 A1 | 11/2012 | Blomquist et al. |
| 2013/0041342 A1 | 2/2013 | Bernini et al. |
| 2013/0060105 A1 | 3/2013 | Shah et al. |
| 2013/0079709 A1 | 3/2013 | Eberhart et al. |
| 2013/0245555 A1 | 9/2013 | Dirac et al. |
| 2013/0267811 A1 | 10/2013 | Pryor et al. |
| 2013/0338594 A1 | 12/2013 | Da Ros et al. |
| 2014/0128839 A1 | 5/2014 | DiIanni et al. |
| 2014/0148762 A1 | 5/2014 | Haueter et al. |
| 2014/0188516 A1 | 7/2014 | Kamen et al. |
| 2014/0249500 A1 | 9/2014 | Estes |
| 2014/0276419 A1 | 9/2014 | Rosinko et al. |
| 2014/0276420 A1 | 9/2014 | Rosinko |
| 2014/0276574 A1 | 9/2014 | Saint |
| 2014/0288399 A1 | 9/2014 | Regittnig |
| 2014/0378898 A1 | 12/2014 | Rosinko |
| 2015/0073337 A1 | 3/2015 | Saint et al. |

(56) References Cited

U.S. PATENT DOCUMENTS

| | | |
|---|---|---|
| 2015/0182689 A1 | 7/2015 | Dhami |
| 2015/0182695 A1 | 7/2015 | Rosinko |
| 2015/0182697 A1 | 7/2015 | Panzer |
| 2015/0222517 A1 | 8/2015 | McLaughlin et al. |
| 2015/0265768 A1 | 9/2015 | Vazquez et al. |
| 2016/0008539 A1 | 1/2016 | Miyazaki |
| 2016/0030669 A1 | 2/2016 | Harris et al. |
| 2016/0067403 A1 | 3/2016 | Moberg et al. |
| 2016/0106910 A1 | 4/2016 | Yap et al. |
| 2016/0228641 A1 | 8/2016 | Gescheit et al. |
| 2016/0243302 A1 | 8/2016 | Gyrn |
| 2016/0254952 A1 | 9/2016 | Harvey et al. |
| 2016/0296715 A1 | 10/2016 | Clemenz et al. |
| 2016/0303333 A1 | 10/2016 | Momose |
| 2016/0339172 A1 | 11/2016 | Michaud et al. |
| 2017/0014572 A1 | 1/2017 | Newberry et al. |
| 2017/0027523 A1 | 2/2017 | Venkatraman et al. |
| 2017/0056582 A1 | 3/2017 | Niklaus |
| 2017/0072140 A1 | 3/2017 | Bazargan et al. |
| 2017/0112534 A1 | 4/2017 | Schoonmaker et al. |
| 2017/0188911 A1 | 7/2017 | Halac et al. |
| 2017/0238805 A1 | 8/2017 | Addison et al. |
| 2017/0259015 A1 | 9/2017 | Caspers |
| 2017/0274146 A1 | 9/2017 | Newberry et al. |
| 2017/0368258 A1 | 12/2017 | Fleischer |
| 2018/0000999 A1 | 1/2018 | Dolmatch et al. |
| 2018/0025120 A1 | 1/2018 | Cronrath et al. |
| 2018/0060520 A1 | 3/2018 | Degen et al. |
| 2018/0207356 A1 | 7/2018 | Joseph et al. |
| 2018/0256813 A1 | 9/2018 | Chow et al. |
| 2018/0280608 A1 | 10/2018 | Gillett et al. |
| 2018/0318550 A1 | 11/2018 | Chiu et al. |
| 2018/0333532 A1 | 11/2018 | Wei |
| 2018/0339102 A1 | 11/2018 | Barraud et al. |
| 2019/0001055 A1 | 1/2019 | Gyrn |
| 2019/0083712 A1 | 3/2019 | List |
| 2019/0091404 A1 | 3/2019 | Nazzaro et al. |
| 2019/0133505 A1 | 5/2019 | Jager |
| 2019/0151568 A1 | 5/2019 | Cardinali et al. |
| 2019/0160225 A1 | 5/2019 | Verlaak et al. |
| 2019/0175818 A1 | 6/2019 | Meenken |
| 2019/0184072 A1 | 6/2019 | Madden et al. |
| 2019/0255251 A1 | 8/2019 | Diianni et al. |
| 2019/0351134 A1 | 11/2019 | Cook et al. |
| 2020/0016335 A1 | 1/2020 | DiPerna et al. |
| 2020/0023122 A1 | 1/2020 | McCullough |
| 2020/0037891 A1 | 2/2020 | Kiani et al. |
| 2020/0069875 A1 | 3/2020 | Nazzaro et al. |
| 2020/0101219 A1 | 4/2020 | Wang et al. |
| 2020/0329433 A1 | 10/2020 | Kruse et al. |
| 2020/0360235 A1 | 11/2020 | Møller |
| 2020/0373009 A1 | 11/2020 | Shapley et al. |
| 2021/0038813 A1 | 2/2021 | O'Connor et al. |
| 2021/0162119 A1 | 6/2021 | Barraud et al. |
| 2021/0213198 A1 | 7/2021 | Gyory |
| 2021/0272687 A1 | 9/2021 | Klopfenstein et al. |
| 2021/0280309 A1 | 9/2021 | Klopfenstein et al. |
| 2022/0226568 A1 | 7/2022 | Oberg et al. |

FOREIGN PATENT DOCUMENTS

| | | |
|---|---|---|
| EP | 1410814 A2 | 4/2004 |
| EP | 1716879 A1 | 11/2006 |
| EP | 1944150 A1 | 7/2008 |
| EP | 2436414 A2 | 4/2012 |
| EP | 2698178 A2 | 2/2014 |
| EP | 2852122 A1 | 3/2015 |
| GB | 2065789 A | 7/1981 |
| WO | WO-8001934 A1 | 9/1980 |
| WO | WO-0220073 A2 | 3/2002 |
| WO | WO-2005016534 A1 | 2/2005 |
| WO | WO-2008155377 A1 | 12/2008 |
| WO | WO-2016196587 A1 | 12/2016 |
| WO | WO-2017085624 A1 | 5/2017 |
| WO | WO-2017205816 A1 | 11/2017 |
| WO | WO-2019110839 A1 | 6/2019 |
| WO | WO-2022107078 A1 | 5/2022 |

OTHER PUBLICATIONS

U.S. Appl. No. 16/769,566 / U.S. Pat. No. 11,529,458, filed Jun. 3, 2020 / Dec. 20, 2022.
U.S. Appl. No. 17/102,334 / U.S. Pat. No. 11,241,530, filed Nov. 23, 2020 / Feb. 8, 2022.
U.S. Appl. No. 17/257,733, filed Jan. 4, 2021.
U.S. Appl. No. 17/257,775, filed Jan. 4, 2021.
U.S. Appl. No. 17/652,448 / U.S. Pat. No. 11,529,460, filed Feb. 24, 2022 / Dec. 20, 2022.
U.S. Appl. No. 17/652,453 / U.S. Pat. No. 11,529,461, filed Feb. 24, 2022 / Dec. 20, 2022.
U.S. Appl. No. 17/652,456 / U.S. Pat. No. 11,529,464, filed Feb. 24, 2022 / Dec. 20, 2022.
U.S. Appl. No. 17/652,460, filed Feb. 24, 2022.
U.S. Appl. No. 17/652,463, filed Feb. 24, 2022.
U.S. Appl. No. 18/058,003, filed Nov. 22, 2022.
U.S. Appl. No. 18/058,074, filed Nov. 22, 2022.
U.S. Appl. No. 18/058,088, filed Nov. 22, 2022.
Accu-Check Solo, User's Manual, Accu-Check Solo micropump system, Roche Diabetes Care (2019).
Camara et al., "Security Mechanism Based on Hospital Authentication Server for Secure Application of ImplantableMedical Devices", Journal of Biomedical Informatics, vol. 55, Jun. 1, 2015, pp. 272-289.
Ebrahim et al., "New secure healthcare system using cloud of things", Cluster Computing, vol. 20, No. 3, May 5, 2017,pp. 2211-2229.
Fomichev et al., "Survey and Systematization of Secure Device Pairing", ARXIV.org, Cornell University Library, Sep. 8, 2017.
International Search Report & Written Opinion dated Feb. 23, 2022 in Int'l PCT Patent Appl. Serial No. PCT/IB2021/060766.
International Search Report & Written Opinion dated Oct. 4, 2022 in Int'l PCT Patent Appl. Serial No. PCT/IB2022/054863.
International Search Report and Written Opinion of the ISA for PCT/IB2016/056870, dated Feb. 3, 2017, 11 pages.
International Search Report for PCT/EP2018/084069, dated Apr. 8, 2019, 7 pages.
International Search Report for PCT/EP2019/068053, dated Sep. 19, 2019, 4 pages.
International Search Report for PCT/EP2019/068054, dated Sep. 19, 2019, 4 pages.
Lewotsky, Kristin, Tutorial: The Basics of Stepper Motors—Part I, Association for Advancing Automation (Feb. 12, 2014).
Medtronic MiniMed (tm) 770G, System User Guide, https://www.medtronicdiabetes.com/sites/default/files/library/download-library/user-guides/MiniMed_770G_System_User_Guide.pdf (2020).
Omnipod-Insulin Management System, UST400 User Guide, https://www.omnipo.com/sites/default/files/2021-04/Omnipod-System_User-Guide_English (Apr. 2021).
Osram—Light is Wearable, Health Monitoring and Fitness Tracking, Osram Opto Semiconductors, Flyer posted online Jan. 22, 2015, file:///C:/Users/jponton/Desktop/Osram_676865_Flyer_Health_Monitoring_and_Fitness_Tracking_2016_(GB).pdf (Year: 2015).
Park, "Security Mechanism Based on Hospital Authentication Server for Secure Application of Implantable Medical Devices", Biomed Research International, vol. 2014, Jul. 24, 2014, pp. 1-12.
T:slim Insulin Pump, User Guide, Tandem Diabetes Care, https://www.tandemdiabetes.com/docs/default-source/product-documents/tslim-insulin-pump (2017).
Written Opinion of the ISA for PCT/EP2018/084069, dated Apr. 8, 2019, 9 pages.
Written Opinion of the ISA for PCT/EP2019/068053, dated Sep. 19, 2019, 7 pages.
Written Opinion of the ISA for PCT/EP2019/068054, dated Sep. 19, 2019, 9 pages.

(56) References Cited

OTHER PUBLICATIONS

Wu et al., "A Secure Proxy-based Access Control Scheme for Implantable Medical Devices", ARXIV.org, Cornell University Library, Mar. 21, 2018.

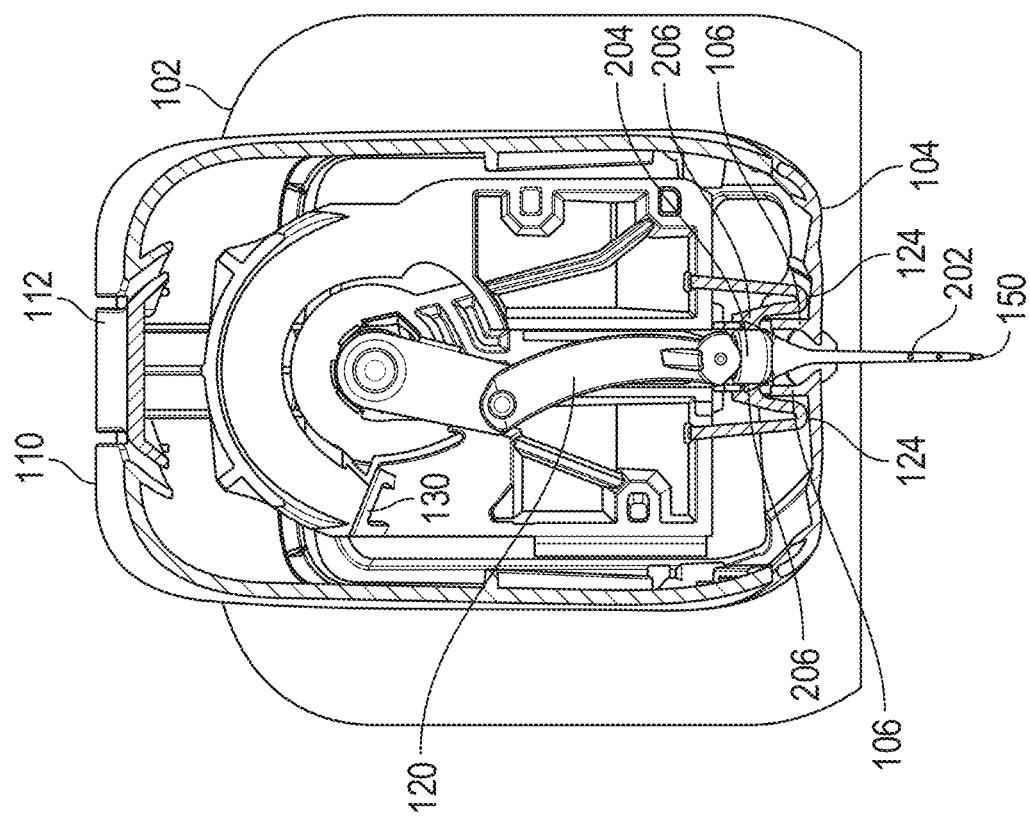
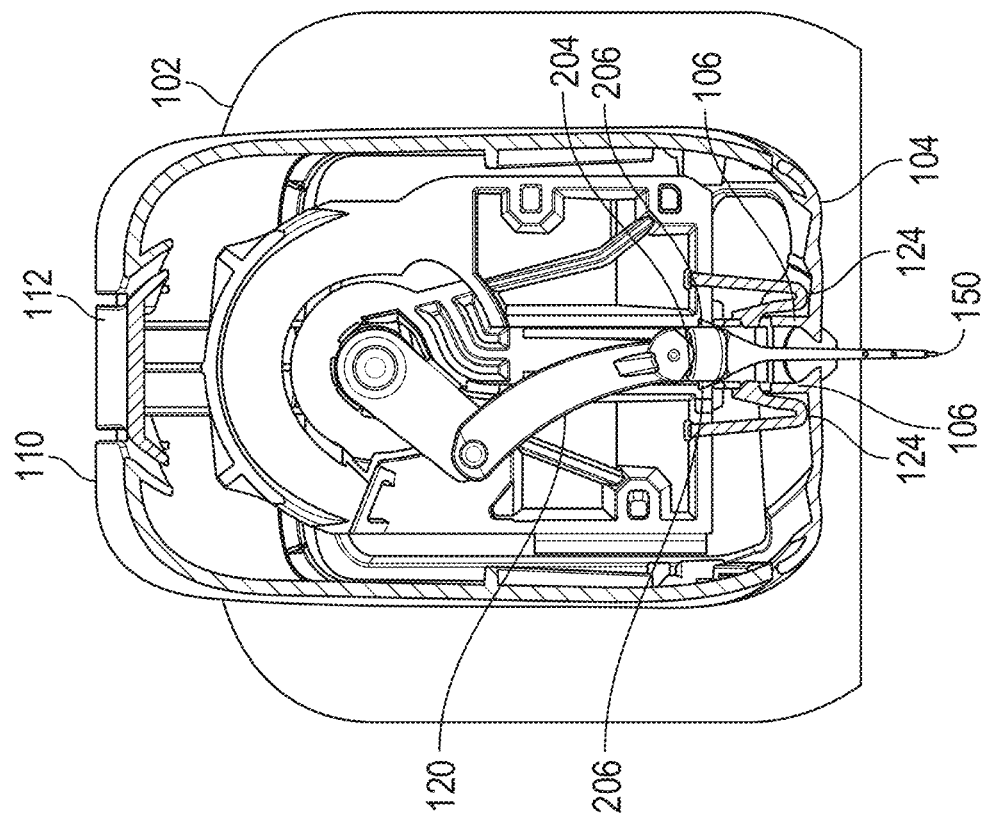

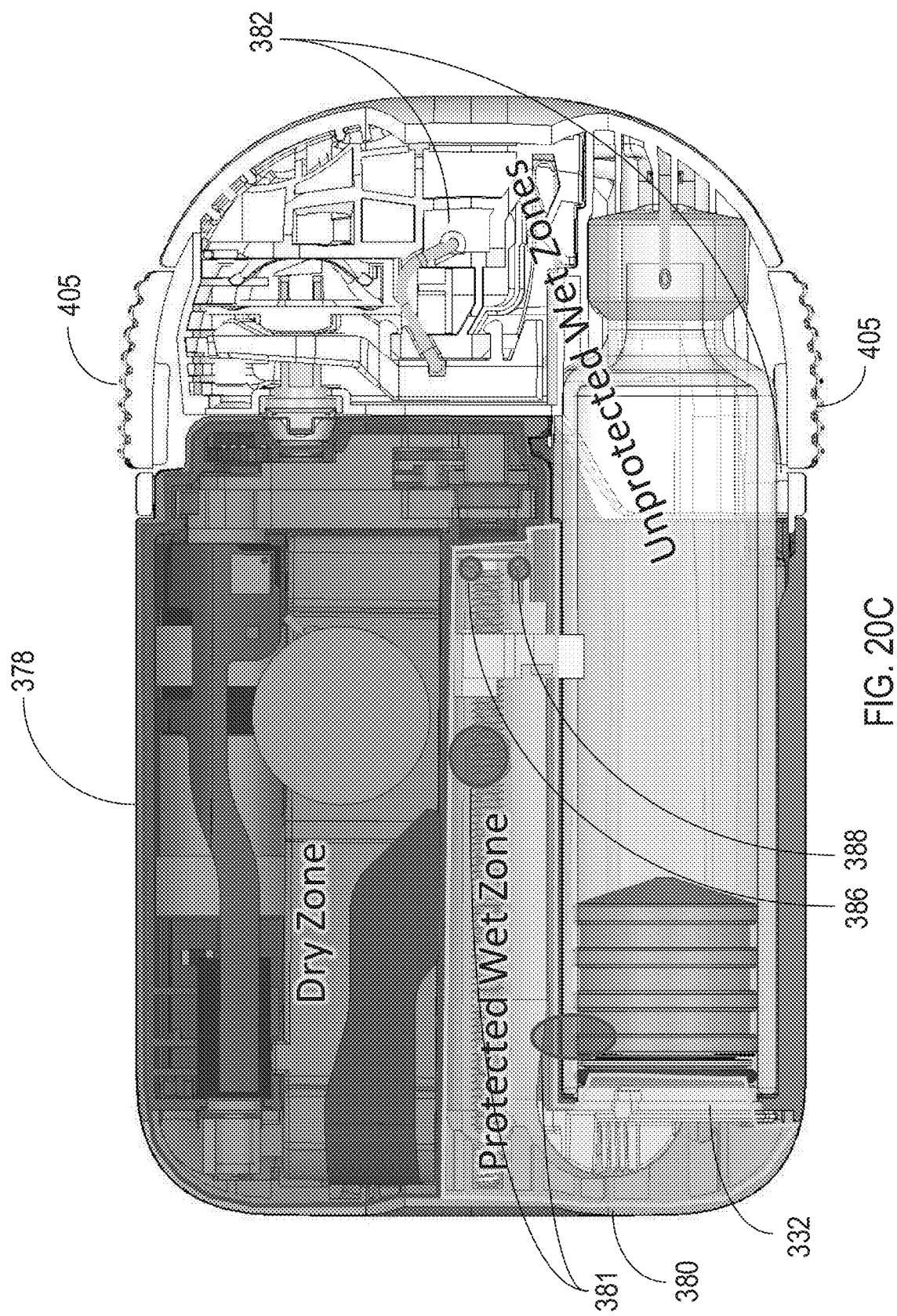

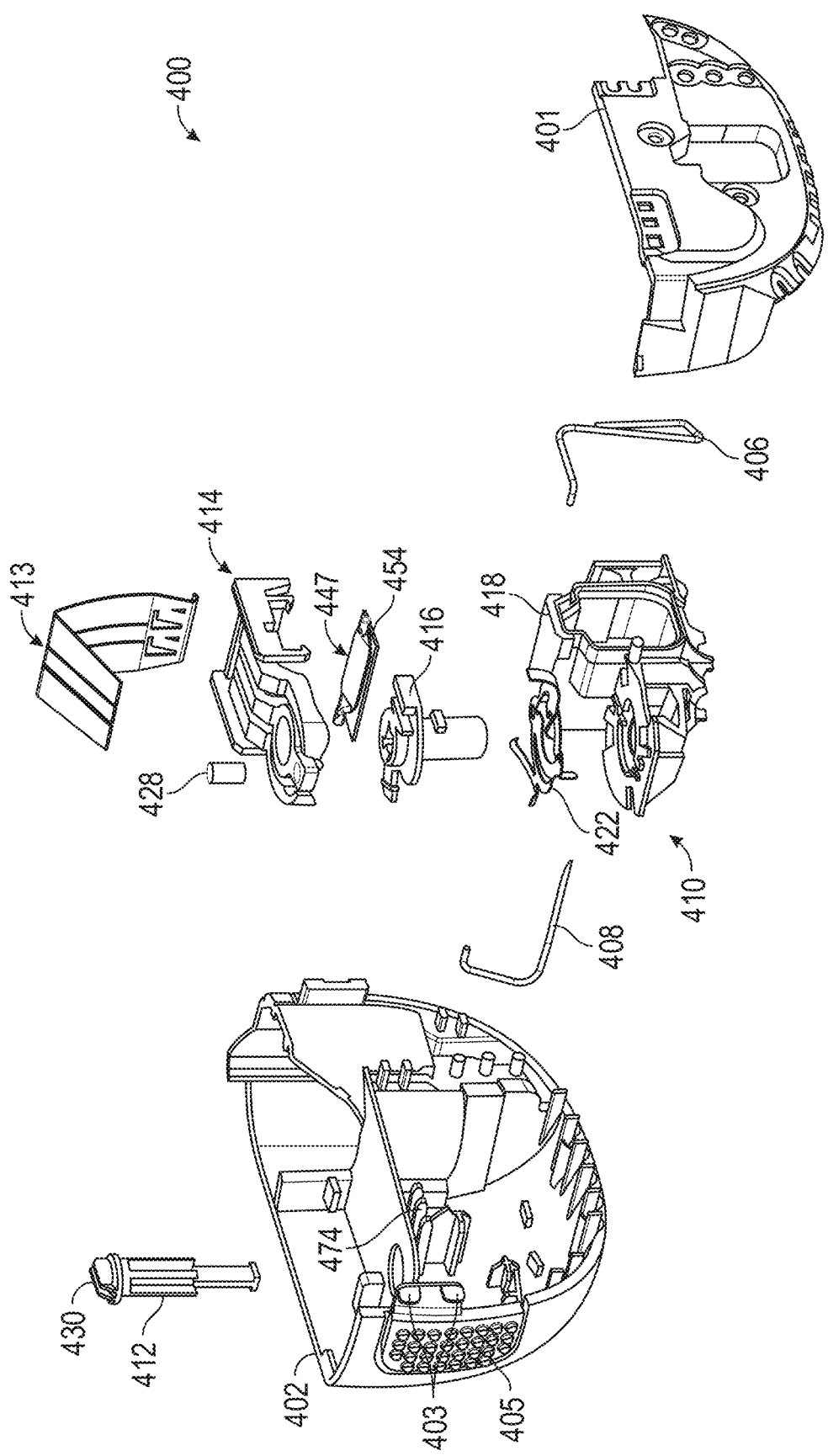

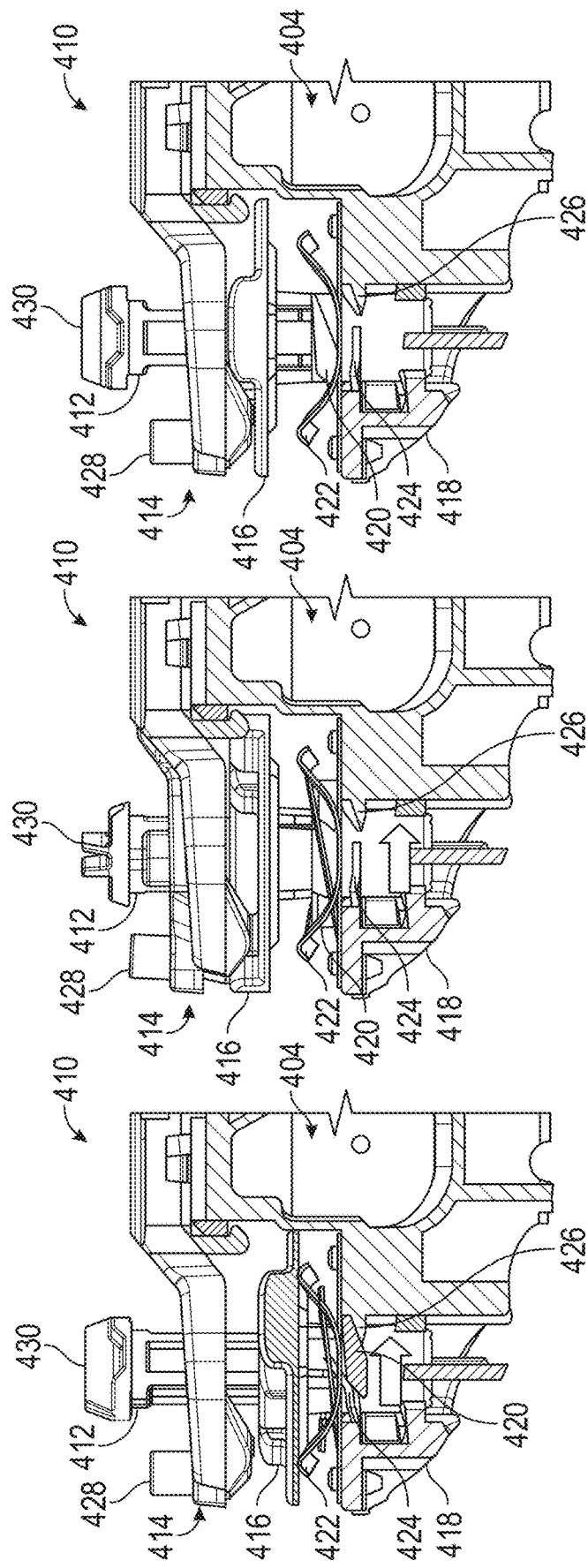

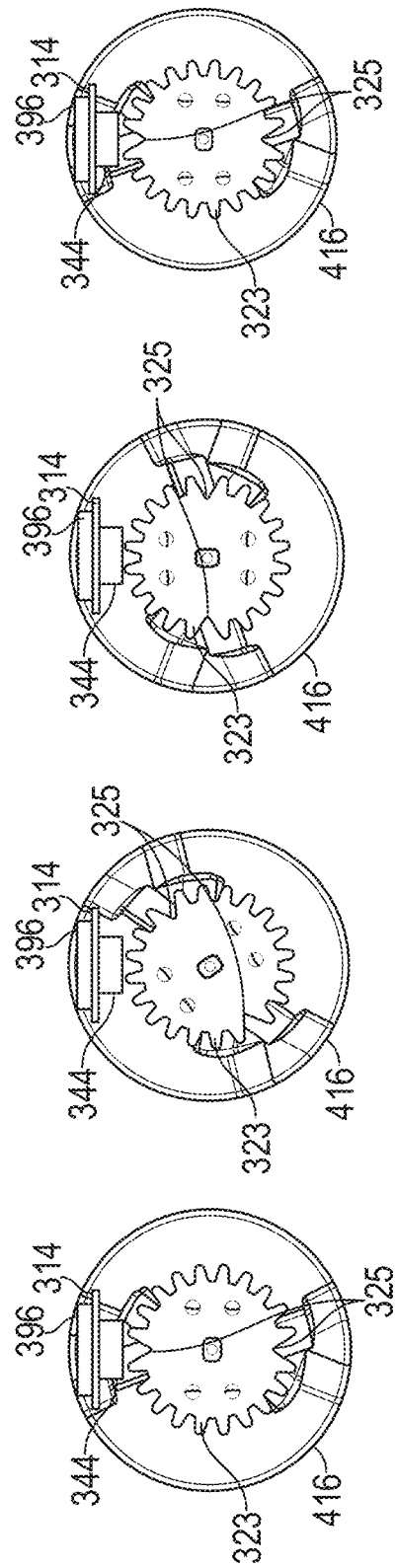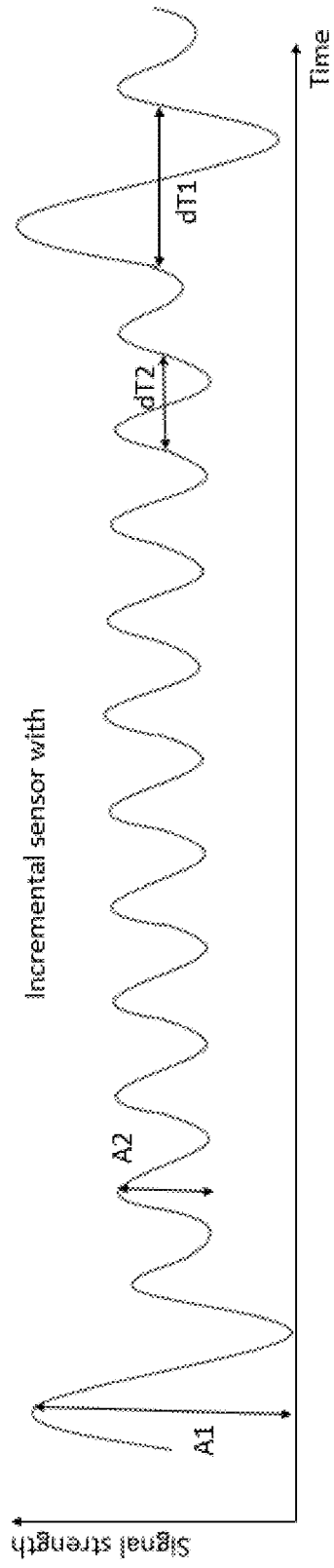

SYSTEMS AND METHODS FOR DELIVERING MICRODOSES OF MEDICATION

CROSS-REFERENCE TO RELATED APPLICATIONS

This application is a continuation of U.S. patent application Ser. No. 17/652,448, filed Feb. 24, 2022, which claims the benefit of priority of U.S. Provisional Patent Application No. 63/195,564, filed Jun. 1, 2021, the entire contents of each of which are incorporated herein by reference.

TECHNICAL FIELD

The technology relates to systems and methods for delivering medication such as insulin to a user, for example, wearable insulin pumps having a patch-style form factor for adhesion to a user's body surface and accessories for applying and managing the same.

BACKGROUND

Wearable insulin pumps are known for providing a Type I Diabetes Mellitus patient with small doses of short acting insulin continuously (basal rate). The device also is used to deliver variable amounts of insulin when a meal is consumed (bolus). The basal insulin rates are usually programmed in a pump by a physician, and one or multiple basal settings may be programmed in the pump based on the patient's needs. The patient may program the amount of insulin for mealtime bolus directly on the pump. Most pumps also include bolus calculators to help the patient determine the amount of insulin the patient may need at mealtime based on the patient's glucose levels and the amount of carbohydrates the patient may consume. The objective is to control the patient's blood glucose level within a desired range. Some such insulin pumps are coupled to an adhesive patch that permits the pump to be directly adhered to a user's body surface, for example the abdomen, and are referred to as "patch pumps." In addition, some previously known systems were configured to interface wirelessly with a continuous glucose monitor, which typically also may be disposed on a patch designed to be adhered to the user's body. Other previously known systems employ still further modules designed to monitor user activity and report that activity to a controller associated with the patch pump to titrate the insulin delivery in accordance with the user's activity level.

WO 02/20073 describes an ambulatory patch pump for delivering insulin to manage diabetes. The pump is part of a system that includes the fluid delivery device, a separate, remote control device, and accessories for transcutaneous delivery of fluid medications.

U.S. Pat. No. 7,879,026 describes an infusion pump that is designed to be wearable, e.g., on a user's belt, and is coupled to an infusion cannula that extends through and is fixed to a user's skin using an adhesive patch. The infusion pump may include an accelerometer or other motion sensor to detect the user's activity level, the output of which may be used to automatically adjust a rate of insulin infusion to the user based at least in part on a detected activity level of the user.

U.S. Pat. No. 9,735,893 describes a patch system for in-situ therapeutic treatment wherein a plurality of biological parameter monitoring devices may be disposed on separate stretchable patches designed to adhere to a user's skin. The monitoring devices communicate with each other, and other therapeutic devices, via short-range wireless, such as Bluetooth. The patent describes that patch-based monitoring devices may be configured to communicate to a belt-worn insulin pump, and that one patch-based monitoring device may include pulse oximetry electronics for measuring blood volume. The patent does not describe a patch-based insulin pump and requires intercommunication between its various components, providing a potential failure mode.

U.S. Patent App. Pub. No. 2018/0339102, the entire contents of which are incorporated herein by reference, assigned to the assignee of the instant application, describes a self-contained patch pump having a motor-actuated syringe together with a microdosing pump chamber.

WO 2019/110839, the entire contents of which are incorporated herein by reference, assigned to the assignee of the instant application, describes a drug delivery device comprising a pumping system and a liquid reservoir fluidly connected to a delivery system outlet. The liquid reservoir has an elastic plunger sealingly slidable within a container wall of the liquid reservoir for expelling liquid out of the reservoir.

There exists a need for systems and methods for delivering medication such as insulin that are user-friendly, environmentally-friendly, lower cost, discreet, less prone to errors, and/or that deliver precise, repeatable doses of medication.

SUMMARY

Provided herein are systems and methods for delivering medication, such as insulin, that are user-friendly, environmentally-friendly, lower cost, discreet, less prone to errors, and/or that deliver precise, repeatable doses of medication, as well as accessories for applying and managing the same. In a preferred embodiment, the system includes a wearable insulin pump having a patch-style form factor for adhesion to a user's body surface.

In accordance with one aspect, a medication infusion system is provided that includes a patch pump configured to be removably adhered to a wearer's skin for delivering doses of medication (e.g., insulin). For example, the doses of medication may be delivered from a cartridge (e.g., a pre-filled cartridge) through a transcutaneous portion. The transcutaneous portion may include a cannula and/or needle configured to be fluidically coupled to the cartridge. The patch pump may include a pump housing configured to house a controller, a rechargeable battery, and/or a pump motor configured to pump the medication towards the transcutaneous portion. Further, a cap may be included that is configured to be removably coupled to the pump housing. The cap and cartridge may be disposable after the doses of medication are delivered from the pre-filled cartridge while the patch pump may be reusable with additional caps and pre-filled cartridges.

The medication infusion system may include a charging station configured to charge the rechargeable battery when the patch pump is coupled to the charging station. The pump housing may include a first inductive coil coupled to the rechargeable battery and the charging station may include a second inductive coil. In some embodiments, the second inductive coil emits power to the first inductive coil. The medication infusion system may include a wireless communication chip within the pump housing configured to wirelessly communicate data to and from the patch pump.

The medication infusion system may include an adhesive pad configured to be removably adhered to the wearer's skin to couple the patch pump to the wearer. The adhesive pad may include one or more pad clips holes and the pump and cap assembly (e.g., at lateral sides of the cap) may include one or more cap clips sized and shaped to fit within the one or more pad clips holes. In this manner, the pump and cap assembly may be locked to the adhesive pad for secure coupling of the patch pump to the wearer's skin. The cap further may include one or more unclipping buttons coupled to the one or more cap clips. When pressed, the unclipping buttons, may deflect the one or more cap clips such that the one or more cap clips uncouple from the one or more pad clips holes. Thus, the pump and cap assembly may be easily unlocked from the adhesive pad by the wearer in a user friendly manner.

The patch pump and the cap may not include a reservoir to hold multiple doses of medication separate from the pre-filled cartridge. Advantageously, in such embodiments, there is no need to inject/introduce medication from an insulin cartridge into a reservoir in the patch pump like some commercially available devices. Instead, the patch pump works seamlessly with a pre-filled cartridge, which is easier on the user. The pump housing and the cap, when coupled together, may completely encase the pre-filled cartridge.

The transcutaneous portion may include a cannula configured to extend into the wearer's skin. The cannula may have one or more apertures beneath the outer skin layer for delivery of the dose of medication. The transcutaneous portion may include a needle configured to be fluidically coupled to the cannula.

In accordance with another aspect, a medication infusion device is provided that includes a patch pump configured to be removably adhered to a wearer's skin for delivering doses of medication (e.g., insulin) from a cartridge (e.g., a pre-filled cartridge) through a transcutaneous portion. The medication infusion system may include a pump motor disposed within a pump housing, the pump motor configured to pump the medication towards the transcutaneous portion. The medication infusion system further may include a sensor configured to sense a parameter, a vibration motor separate from the pump motor, and a controller operatively coupled to the sensor and the vibration motor. The sensor may be disposed in a housing separate from the pump housing.

The controller may be configured to cause the vibration motor to vibrate to alert the wearer based on the parameter sensed by the sensor, for example, when the sensed parameter falls outside a predetermined threshold. The controller further may be configured to determine that an error has occurred associated with operation of the patch pump based on the sensed parameter to cause the vibration motor to vibrate based on the determination of the error.

For example, the sensor may be configured to sense a pressure within the cartridge and the controller may be configured to cause the vibration motor to vibrate when the pressure within the cartridge falls outside a predetermined pressure range. The medication infusion system further may include a dosing tube disposed within the pump housing and the dosing tube may be configured to receive medication from the cartridge. The sensor may be configured to detect an occlusion within the dosing tube or the transcutaneous portion and the controller may be configured to cause the vibration motor to vibrate when the sensor detects information indicative of an occlusion within the dosing tube or the transcutaneous portion. Alternatively, the controller is configured to cause the vibration motor to vibrate only when the sensor detects repeated occlusions.

The sensor may be configured to monitor glucose levels of the wearer and the controller may configured to cause the vibration motor to vibrate when the wearer's glucose level falls outside a predetermined glucose level range. Alternatively, the sensor may be a photoplethysmographic module configured to sense at least one of the wearer's heart rate or physiologic parameters and the controller may be configured to cause the vibration motor to vibrate when the at least one of the wearer's heart rate or physiologic parameters fall outside a predetermined photoplethysmographic threshold. In another embodiment, the sensor may be an accelerometer and the sensed parameter may be associated with the wearer's activity level. The controller may be configured to cause the vibration motor to vibrate when the wearer's activity level is outside a predetermined threshold. In another embodiment, the sensor may be configured to detect a temperature within the patch pump and the controller may be configured to cause the vibration motor to vibrate when the temperature falls outside a predetermined range.

In accordance with another aspect, a medication infusion device is provided that includes a patch pump configured to be removably adhered to a wearer's skin for delivering doses of medication (e.g., insulin) from a cartridge (e.g., a pre-filled cartridge) through a transcutaneous portion. The medication infusion device further may include a pusher and a pump motor disposed within a pump housing and a sensor. The pump motor may be coupled to the pusher and may be configured to move the pusher to move the medication in the cartridge towards the transcutaneous portion.

The sensor may be configured to sense a position of the pusher within the pump housing to indicate a state of the patch pump. The position of pusher may also indicate that the pusher transitioned to a first position such that the cartridge is permitted to be removed and exchanged for a subsequent cartridge. The sensor may be a contact sensor that senses the position of the pusher based on contact with a component of the pusher.

The medication infusion device further may include a controller disposed within the pump housing and operatively coupled to the pump motor and the sensor. The controller may execute instructions, which indicate that a battery within the patch pump is charged to a power level sufficient to empty the medication from the cartridge based on the position of the pusher sensed by the sensor. The controller further may be configured to cause the component to move in an opposite direction after sensing contact with the component, for example, to a home position.

The medication infusion device further may include a cap configured to be locked to the pump housing during delivery of the doses of medication. The position of the pusher may indicate that the cap is permitted to be unlocked from the pump housing for removal of the cartridge. In addition, a level of battery charge further may indicate that the cap is permitted to be unlocked. The medication infusion device may include a second sensor configured to monitor the level of battery charge.

In accordance with another aspect, a component for use in a medication infusion device, is provided. The component may be a cap configured to be removably coupled to a pump housing of the patch pump. The component may be configured to measure and deliver a predetermined dose of medication to the wearer. The component may include a dosing tube configured to receive medication, a plurality of levers configured to contact the dosing tube to move a predetermined dose of medication towards the transcutaneous portion, and a circular cam. The circular cam may include a shaft oriented in a first plane and a circular plate oriented in a second plane, the first and second plane may be orthogonal. The circular plate may be coupled to the shaft and may include surfaces configured to move the plurality of levers in a series of steps upon rotation of the shaft. The rotation of the shaft may deliver the predetermined dose of medication towards the wearer.

The plurality of levers may include a first lever disposed on a first portion of the dosing tube, a second lever disposed on a second portion of the dosing tube, and a middle lever disposed adjacent to a reservoir portion (e.g., a compartment) between the first portion and the second portion. The reservoir portion may be configured to hold the predetermined dose of medication. The first portion, second portion, and reservoir portion of the dosing tube are disposed on a flattened portion of the dosing tube. The reservoir portion of the dosing tube may include one or more welded portions that are configured to increase the accuracy of the volume within the reservoir.

The plurality of levers may be independently movable and configured to sequentially transition from a raised position to a lowered position. The raised position may permit medication to flow from the cartridge towards the transcutaneous portion and the lowered position may position the plurality of levers in contact with the dosing tube such that medication is prevented from flowing from the cartridge towards the transcutaneous portion.

The plurality of levers may move in a predetermined sequence of steps configured to deliver the predetermined dose of medication to the wearer. The first lever may be configured to move to a raised position, the middle lever may be configured to move to a raised position, and, after the middle lever moves to the raised position, the first lever may be configured to move to a lowered position such that the predetermined dose of medication is disposed within the reservoir portion. After the first lever moves to the lowered position, the second lever may be configured to move to a raised position, the middle lever may be configured to move to a lowered position, and the second lever may be configured to move to a lowered position such that the predetermined dose of medication is delivered towards the wearer.

The first lever may include a first extended arm having a first ramped portion, the second lever may include a second extended arm having a second ramped portion, and the middle lever may include a middle extended arm having a middle ramped portion. The first, second, and middle ramped portions may be configured to contact the surfaces of the circular cam, which may include a first surface and a second surface. The first lever may transition from a lowered position to a raised position when the first ramped portion contacts the first surface of the circular cam, the second lever may transition from a lowered position to a raised position when the second ramped portion contacts the first surface of the circular cam, and the middle lever may transition from a lowered position to a raised position when the middle ramped portion contacts the second surface of the circular cam.

The first surface may be sized and shaped such that the first surface is disposable between the first ramped portion and the second ramped portion without contacting the first ramped portion or the second ramped portion. The first second surface of the circular plate and the first, second, and middle ramped portions of the plurality of levers may include rounded edges such that the noise from rotation of the circular cam is minimized.

The first surface of the circular cam may be positioned radially outward of the second surface of the circular cam. The surfaces on the circular plate may include a third surface and a fourth surface that mirror the first surface and the second surface, respectively. During a 360 degree rotation of the circular cam, contact between the first and second surfaces and the plurality of levers may move the predetermined dose of medication to the wearer. Contact between the third and fourth surfaces and the plurality of levers may move a second predetermined dose of medication to the wearer. A 180 degree rotation of the shaft may deliver the predetermined dose of medication and another 180 degree rotation of the shaft may deliver a second predetermined dose of medication having the same volume of medication as the predetermined dose.

The transcutaneous portion may include a cannula configured to extend into the wearer's skin. The cannula may have one or more apertures beneath the outer skin layer for delivery of the dose of medication. The transcutaneous portion may include a needle configured to be fluidically coupled to the cannula. The needle may be configured to extend from the dosing tube to the cannula.

A method for delivering doses of medication is also provided, the method including providing a patch pump having a dosing tube, a plurality of levers, and a circular cam, as described above, and rotating the shaft of the circular cam. Rotating the shaft may cause the circular cam to rotate such that the surfaces contact the plurality of levers during rotation to cause the plurality of levers to move in a predefined pattern to selectively open and close sections of the dosing tube to deliver the predetermined dose of medication transcutaneously to the wearer. Rotating the shaft further may cause at least one lever of the plurality of levers to transition from a lowered position to contact the dosing tube such that medication is prevented from flowing from the cartridge towards the transcutaneous portion to a raised position such that medication flows from the cartridge towards the transcutaneous portion.

The plurality of levers may include a first lever disposed on a first portion of the dosing tube, a second lever disposed on a second portion of the dosing tube, and a middle lever disposed adjacent to a reservoir portion between the first portion and the second portion, the reservoir portion configured to hold the predetermined dose of medication. The first lever may include a first extended arm having a first ramped portion, the second lever may include a second extended arm having a second ramped portion, and the middle lever may include a middle extended arm having a middle ramped portion. The first, second, and middle ramped portions may be configured to contact the surfaces of the circular cam.

Rotating the shaft may cause the first lever to transition to the raised position, the middle lever to transition to the raised position, and, after transitioning the middle lever to the raised position, the first lever to transition to the lowered position such that the predetermined dose of medication is disposed within the reservoir portion. Rotating the shaft further may cause, after transitioning the first lever to the lowered position, the second lever to transition to the raised position, after transitioning the second lever to the raised position, the middle lever to transition to the lowered position, and the second lever to transition to the lowered position such that the predetermined dose of medication is delivered transcutaneously to the wearer.

The surfaces on the circular plate may include a first surface and a second surface such that rotating the shaft further causes the first ramped portion to contact the first surface of the circular cam such that the first lever transitions from a lowered position to a raised position, the second ramped portion to contact the first surface of the circular cam such that the second lever transitions from a lowered position to a raised position, and the middle ramped portion to contact the second surface of the circular cam such that the middle lever transitions from a lowered position to a raised position.

The surfaces on the circular plate may include a third surface and a fourth surface that mirror the first surface and the second surface, respectively, such that rotating the shaft 360 degrees causes the first and second surfaces to contact the plurality of levers such that the predetermined dose of medication is delivered to the wearer and the third and fourth surfaces to contact the plurality of levers such that a second predetermined dose of medication is delivered to the wearer. Further, rotating the shaft 180 degrees may deliver a predetermined dose of medication and rotating the shaft another 180 degrees may deliver a second predetermined dose of medication having the same volume of medication as the predetermined dose.

In accordance with another aspect, a medication infusion device is provided that includes a patch pump configured to be removably adhered to a wearer's skin for delivering doses of medication (e.g., insulin) from a cartridge (e.g., a prefilled cartridge) through a transcutaneous portion. The patch pump may include a pump housing and a cap housing configured to be locked together to hold the cartridge. The medication infusion device further may include a rechargeable battery disposed within the pump housing and a controller configured to monitor battery life of the rechargeable battery. The controller may be configured to unlock the pump housing from the cap housing based on determining that the battery life has been charged to a predetermined state.

The medication infusion device further may include a pusher disposed within the pump housing. The pusher may be configured to push medication out of the cartridge during pumping. The controller, upon determining that the battery life has been charged to a state below full charge, may cause the pusher to move from an empty position to a full position within the pump housing. The state below full charge may be a predetermined time before battery life sufficient to empty the medication from the cartridge.

The pusher may include a component that, in the full position, contacts a contact sensor. The component of the pusher may include a nut configured to move along a thread of a screw. After contacting the contact sensor, the component of the pusher may move to a home position wherein the pusher does not contact the contact sensor. The controller may be configured to only unlock the pump housing from the cap housing if the controller determines that the patch pump is in the home position.

The cap housing may include a tab and the pump housing may include a mechanical coupling sized and shaped to receive the tab. The mechanical coupling and the tab may be configured to rotate upon movement of the pusher and may be oriented in a first direction when the pump housing is locked to the cap housing. The mechanical coupling and the tab may be oriented in a second direction, different from the first direction, when the pump housing is unlocked to the cap housing.

In accordance with another aspect, a medication infusion device is provided that includes a patch pump configured to be removably adhered to a wearer's skin for delivering doses of medication (e.g., insulin) from a cartridge (e.g., a prefilled cartridge) through a transcutaneous portion. The medication infusion device further may include a pump motor disposed within a pump housing, a sensor, and a controller operatively coupled to the pump motor and the sensor. The pump motor may be configured to pump the medication in the cartridge towards the transcutaneous portion. The sensor may be configured to detect the wearer's skin, for example, by measuring capacitance, and to generate information to indicate detection of the wearer's skin. The controller may be configured to cause the pump motor to activate only if the information indicates detection of the wearer's skin.

The sensor may be disposed on a first side of the pump housing and may be configured to detect the wearer's skin on the first side. The medication infusion device further may include a second sensor disposed on a second side of the pump housing, the second side different from the first side. The second sensor may be configured to detect the wearer's skin on the second side. The controller may cause the pump motor to activate only if the second sensor does not detect the wearer's skin. By ensuring that only one sensor detects the wearer's skin, this ensures that the patch pump does not deliver medication while the wearer is holding the patch pump.

The medication infusion device further may include a photoplethysmography module. The controller may be configured to cause the pump motor to activate only if both the sensor and the photoplethysmography module detect the wearer's skin. The sensor may be incorporated in a photoplethysmography module.

In accordance with another aspect, a component for use in a medication infusion device including a patch pump is provided. The component may be configured to complete an initialization process such that delivery of medication to the wearer is prevented until the pressure within the cartridge reaches a predetermined pressure range. The component may include a dosing tube configured to receive medication, a plurality of levers configured to contact the dosing tube to move a predetermined dose of medication towards the transcutaneous portion, and a cam configured to move from an initialization position to a dosing position. In the initialization position, the cam may not be coupled to the plurality of levers such that movement of the cam does not cause movement of the plurality of levers and, in the dosing position, the cam may be coupled to the plurality of levers such that movement of the cam causes movement of the plurality of levers in a predetermined manner to generate the predetermined dose of medication for delivery to the wearer.

The cam may include a shaft oriented in a first plane and a circular plate oriented in a second plane. The cam further may include a spring configured to apply an upward force on the circular plate in the initialization position. The shaft may include an outer shaft and an inner shaft disposed within the outer shaft. The outer shaft may include at least one wing configured to transition to a position above the spring when the cam moves to the dosing position. The component further may include a microdosing structure configured to house at least a portion of the inner shaft and the outer shaft in the initialization position. The microdosing structure may include at least one damper configured to interact with the at least one wing such that noise from movement of the cam is reduced.

The cam may be configured to move from an initialization position to a dosing position when the cam is moved in a first direction. In the dosing position, the cam may be configured to move the plurality of levers when the cam is moved in a second direction, different from the first direction. During initialization, prior to moving from the initialization position to the dosing position, the cam may be configured to move in the second direction. Movement of the cam in the second direction may prevent the cam from transitioning from the initialization position to the dosing position. Movement of the cam in the first direction may transition the cam from the initialization position to the dosing position permanently without the ability to move back to the initialization position.

The patch pump may include a sensor configured to sense a pressure within the cartridge and a controller operatively coupled to the sensor. The controller may be configured to cause the cam to move from the initialization position to the dosing position when the pressure within the cartridge reaches a predetermined value, for example, a value between 600 mbar and 900 mbar.

The transcutaneous portion may include a cannula configured to extend into the wearer's skin. The cannula may have one or more apertures beneath the outer skin layer for delivery of the dose of medication. The transcutaneous portion may include a needle configured to be fluidically coupled to the cannula. The needle may be configured to extend from the dosing tube to the cannula. A distal end of the needle may be configured to pierce a septum at a proximal region of the cannula and reside below the septum such that the septum fluidically seals the proximal region of the cannula around the needle.

A method for initializing a patch pump in preparation for transcutaneously delivering doses of medication from a cartridge via the patch pump is also provided. The method may include adhering the patch pump having a dosing tube and a plurality of levers, as described above, to a wearer's skin to permit transcutaneous delivery of the doses of medication. The method further may include moving a cam within the patch pump in an initialization position wherein the cam is not coupled to the plurality of levers such that movement of the cam does not cause movement of the plurality of levers. The method further may include moving the cam from the initialization position to a dosing position and moving the cam in the dosing position wherein the cam is coupled to the plurality of levers such that movement of the cam causes movement of the plurality of levers in a predetermined manner to generate the predetermined dose of medication for delivery to the wearer.

In accordance with another aspect, a medication infusion device is provided that includes a patch pump configured to be removably adhered to a wearer's skin for delivering doses of medication (e.g., insulin) from a cartridge (e.g., a pre-filled cartridge) through a transcutaneous portion. The patch pump may include a pump housing and cap housing configured to be removably coupled to the pump housing. The medication infusion device further may include a dosing tube disposed within the cap housing and configured to be fluidically coupled to the cartridge to receive the medication and to be fluidically coupled to the transcutaneous portion, a pump motor disposed within a pump housing and configured to pump the medication in the cartridge towards the dosing tube and the transcutaneous portion, a sensor, and a controller operatively coupled to the pump motor and the sensor. The sensor may be configured to generate information indicative of pressure within the cartridge.

The controller may be configured to cause the pump motor, in an initialization position, to activate to increase pressure within the cartridge while the dosing tube is closed such that the medication cannot travel to the transcutaneous portion. The controller further may be configured to determine that the pressure within the cartridge is above a predetermined threshold based on the information from the sensor. For example, the predetermined threshold may be 600-900 mbar. The predetermined threshold may be selected such that the cartridge is pressurized to eliminate bubbles and the formation of bubbles in the medication. After the determination, the controller may be configured to transition the patch pump from the initialization position to a dosing position to permit the dosing tube to open for medication to travel to the transcutaneous portion.

The medication infusion device further may include a plurality of levers and a cam. The plurality of levers may be configured to contact the dosing tube to move a predetermined dose of medication towards the transcutaneous portion. The cam may be configured to move from the initialization position to the dosing position. In the initialization position, the cam may not coupled to the plurality of levers such that movement of the cam does not cause movement of the plurality of levers. In the dosing position, the cam may be coupled to the plurality of levers such that movement of the cam causes movement of the plurality of levers in a predetermined manner to generate the predetermined dose of medication for delivery to the wearer.

The pump motor may be activated to pump in the initialization position an amount of pumping greater than required for 10 doses of medication. The medication infusion device further may include a pusher coupled to the pump motor and the cartridge. Responsive to activation of the pump motor, the pusher may push on the cartridge to increase the pressure within the cartridge to the predetermined threshold in the initialization position. The pusher may push on the cartridge in the dosing position for a predetermined dose of medication to be delivered to the wearer.

A method for initializing a patch pump in preparation for transcutaneously delivering doses of medication from a cartridge via the patch pump is also provided. The method may include adhering the patch pump to permit transcutaneous delivery of the doses of medication. The patch pump may include a dosing tube configured to receive the medication and a pump motor disposed within a pump housing and configured to pump the medication in the cartridge towards the dosing tube. The method further may include activating the pump motor, in an initialization position, to increase pressure within the cartridge while the dosing tube is closed such that the medication cannot travel to the transcutaneous portion. The method further may include sensing information indicative of pressure within the cartridge using a sensor and determining that the pressure within the cartridge is above a predetermined threshold based on the information from the sensor. Only after determining that the pressure within the cartridge is above the predetermined threshold, the patch pump may be transitioned from the initialization position to a dosing position to permit the dosing tube to open for medication to travel to the transcutaneous portion.

The patch pump further may include a cam and a plurality of levers configured to contact the dosing tube to move a predetermined dose of medication towards the transcutaneous portion. The method further may include causing the cam to move from the initialization position to the dosing position, as described above. The pump motor may be activated, in the initialization position, to increase pressure within the cartridge comprises pressurizing the cartridge to reduce bubbles and the formation of bubbles in the medication.

The patch pump further may include a pusher coupled to the pump motor and the cartridge. The method may include causing the pusher to push on the cartridge to increase the pressure within the cartridge to the predetermined threshold in the initialization position. The method further may include causing the pusher to push on the cartridge in the dosing position for a predetermined dose of medication to be delivered to the wearer.

In accordance with another aspect, a method of making a component for use in a medication infusion device is provided. The component may be a flattened dosing tube that may be used to measure a predetermined dose of medication. The method may include selecting a polymer tube sized for receiving a dose of medication, flattening a portion of the polymer tube, selecting a support, and welding the flattened portion of the polymer tube to the support. Welding the flattened portion may include laser welding and may create a reservoir sized for generating the dose of medication with a predetermined volume selected for delivery to the wearer, for example, 0.08-1 uL, 0.2-0.6 uL, or 0.2-0.3 uL.

The polymer tube may be transparent to a laser and the support may not be transparent to the laser. The flattened portion may include a tube wall having a uniform thickness. The flattened portion may be flexible such that when the medication has a predetermined pressure, the reservoir is sized to hold the predetermined volume of medication, when the medication has a pressure greater than the predetermined pressure, the reservoir is sized to hold a greater volume than the predetermined volume of medication, and when the medication has a pressure less than the predetermined pressure, the reservoir is sized to hold a lesser volume than the predetermined volume of medication.

In accordance with another aspect, a medication infusion device is provided that includes a patch pump configured to be removably adhered to a wearer's skin for delivering doses of medication (e.g., insulin) from a cartridge (e.g., a pre-filled cartridge) through a transcutaneous portion. The medication infusion device further may include a pump housing configured to hold a pump and a controller and to receive the cartridge. The medication infusion device further may include a cap housing configured to be locked to the pump housing to lock the cartridge therebetween. The cap housing may include at least three protrusions radially spaced around a portion of the cap housing configured to receive the cartridge. The at least three protrusions may be configured to engage corresponding receptacles in the pump housing to lock the cap housing to the pump housing.

The protrusions and receptacles may engage in a manner to resist a continuous pushing force on the cap housing from the cartridge and to remain locked. The at least three protrusions may prevent a rotation greater than 90 degrees. The at least three protrusions may include a first protrusion that has a first portion having a wide engagement slit and a second portion having a narrower engagement slit.

The pump housing may be reusable and the cap housing may be disposable. The pump housing may include a first material and the cap housing may include a second material. The first material may have a greater creep resistance and/or a greater thickness than the second material. The pump housing may be designed to have a greater creep resistance such that the cap housing fails, or deforms, before the pump housing fails or deforms.

In accordance with another aspect, a medication infusion device is provided that includes a patch pump configured to be removably adhered to a wearer's skin for delivering doses of medication (e.g., insulin) from a cartridge (e.g., a pre-filled cartridge) through a transcutaneous portion. The medication infusion device further may include a dosing tube configured to receive medication, a plurality of levers configured to contact the dosing tube to move a predetermined dose of medication towards the transcutaneous portion, a sensor configured to sense position of one or more of the plurality of levers, and a controller operatively coupled to the sensor. The sensor further may be configured to sense displacement of one or more of the plurality of levers. The controller may be configured to sense an infusion anomaly (e.g., an occlusion) associated with medication delivery from the dosing tube based on the sensed displacement from the sensor. This method of monitoring the dosing tube provides fast occlusion detection within the patch pump. Alternatively, the pump may be configured to house the sensor, a cap may be configured to house the plurality of levers, and the controller may configured to sense whether the pump is coupled to the cap based on the sensed position of the one or more of the plurality of levers.

The dosing tube may include a flattened portion configured to hold the predetermined dose of medication. The plurality of levers may include a first lever disposed on a first side of the flattened portion, a second lever disposed on a second side of the flattened portion, and a middle lever disposed adjacent to the flattened portion. The plurality of levers may be configured to sequentially transition from a raised position such that medication can flow from the cartridge to the transcutaneous portion to a lowered position to contact the dosing tube such that medication is prevented from flowing from the cartridge to the transcutaneous portion.

The sensor may include a hall-effect sensor configured to detect movement of a magnet coupled to one of the plurality of levers. For example, the hall-effect sensor may be configured to detect movement of a magnet coupled to the middle lever. The controller may sense the infusion anomaly if the sensed displacement is outside a threshold range as determined based on proximity of the magnet to the hall-effect sensor over time. The controller further may sense the infusion anomaly using an algorithm based on the displacement of the magnet to the hall-effect sensor during an injection cycle. The controller may be configured to cause the medication infusion device to vibrate to alert the wearer based on the sensed infusion anomaly. Alternatively, the controller may sense that the medication infusion device is not delivering medication if the sensor does not sense a displacement of the one or more of the plurality of levers. The sensor may further be configured to sense information indicative of the presence or absence of the cap and/or to determine a status of the cap. For example, the information from the sensor may be used to determine whether cap has been used or whether the cap is new. The information may be based on the strength of the magnetic field from a magnet within the cap, as the strength of the field will change based on the position of the magnet in the cap. In some embodiments, the magnet changes position in the cap from the initialization position to the dosing position.

A method for monitoring transcutaneous delivery of doses of medication is also provided, the method including delivering doses of medication using a patch pump adhered to a wearer's skin. The patch pump may include a dosing tube configured to receive the medication responsive to pumping and a plurality of levers configured to contact the dosing tube. The patch pump further may include a transcutaneous portion fluidically coupled to the dosing tube. The dosing tube may include a flattened portion configured to hold the predetermined dose of medication and the plurality of levers may include a first lever disposed on a first side of the flattened portion, a second lever disposed on a second side of the flattened portion, and a middle lever disposed adjacent to the flattened portion. Delivering doses of medication may include sequentially transitioning one or more of the plurality of levers from a raised position such that medication can flow from the cartridge to the transcutaneous portion to a lowered position to contact the dosing tube such that medication is prevented from flowing from the cartridge to the transcutaneous portion.

The method further may include sensing displacement of one or more of the plurality of levers during the pumping and determining an infusion anomaly associated with medication delivery from the dosing tube has occurred based on the sensed displacement of the one or more of the plurality of levers. Sensing displacement of one or more of the plurality of levers may include detecting movement of a magnet coupled to one of the plurality of levers. Determining that the infusion anomaly has occurred may include determining that the dosing tube or the transcutaneous portion is occluded.

In some embodiments, a magnet may be coupled to the middle lever. The method may include determining if the sensed displacement is outside a threshold range as determined by the proximity of the magnet to the sensor over time. Sensing the infusion anomaly may include using an algorithm based on displacement of the magnet to the hall-effect sensor during an injection cycle. The method further may include sensing that the patch pump is not delivering medication if the sensor does not sense a predetermined displacement of the one or more of the plurality of levers.

The patch pump further may include a pump configured to house the sensor and a cap configured to house the plurality of levers. The method may include sensing whether the pump is coupled to the cap based on the sensed displacement of the one or more of the plurality of levers and/or detecting the status of the cap, for example, whether the cap is new or used.

In accordance with another aspect, a medication infusion device is provided that includes a patch pump configured to be removably adhered to a wearer's skin for delivering doses of medication (e.g., insulin) from a cartridge (e.g., a prefilled cartridge) through a transcutaneous portion. The medication infusion device further may include a pump housing, a pump motor disposed within the pump housing, at least one sensor disposed within the pump housing, one or more processors, and a wireless communication chip disposed within the pump housing.

A first processor may be disposed within the pump housing and configured to execute first programmed instructions stored in a first memory to cause the pump motor to pump the medication towards the transcutaneous portion and to monitor sensed parameter generated by the at least one sensor. A second processor may be disposed within the pump housing and configured to execute second programmed instructions stored in a second memory to communicate data to and from the patch pump via the wireless communication chip. The first processor may be configured such that it cannot receive data from outside the patch pump, enhancing the security of the medication infusion device. The first programmed instructions may include class C software and the second programmed instructions may include class B software. The first processor may be an autonomous, real time state machine.

At least one sensor may be configured to sense a pressure within the cartridge or to detect an occlusion within the transcutaneous portion. The at least one sensor may include a sensor disposed on a first side of the pump housing and configured to detect the wearer's skin. The first processor further may be configured to execute first programmed instructions stored in the first memory to cause the pump motor to push the medication in the cartridge towards the transcutaneous portion only when the sensor detects the wearer's skin.

The patch pump further may include a pump housing and a cap housing configured to be locked together to hold the cartridge. A rechargeable battery may be disposed within the pump housing. The first processor further may be configured to execute first programmed instructions stored in the first memory to monitor battery life of the rechargeable battery and to cause the pump housing to unlock from the cap housing when the first processor determines that the battery life has been charged to a predetermined state.

In another embodiment, at least one sensor is configured to sense the position of the pusher to indicate that the cartridge is permitted to be removed and exchanged for a subsequent cartridge. The first processor further may be configured to execute first programmed instructions stored in the first memory to cause a position of a pusher coupled to the pump motor to move to a home position and to cause the pump housing to unlock from the cap housing only when the first processor determines that the pusher is in the home position.

In another embodiment, the at least one sensor may be configured to sense a position of a circular cam including a shaft configured to rotate to deliver a predetermined dose of medication. The sensed position may indicate that a dosing cycle is complete. The first processor further may be configured to execute first programmed instructions stored in the first memory to cause the shaft to stop rotating when the sensor indicates that the dosing cycle is complete.

The second processor may be configured to execute second programmed instructions stored in a second memory to communicate data to and from the patch pump via the wireless communication chip. The data may be indicative of battery life of a rechargeable battery disposed within the pump housing. Alternatively, the data may be indicative of at least one of the wearer's heart rate and physiologic parameters. The second processor may configured to execute second programmed instructions stored in the second memory to calculate when to deliver the doses of medication and/or to adjust the calculation based on the data received.

In accordance with another aspect, a medication infusion device is provided that includes a patch pump configured to be removably adhered to a wearer's skin for delivering doses of medication (e.g., insulin) from a cartridge (e.g., a prefilled cartridge) through a transcutaneous portion. The medication infusion device further may include a pusher configured to be coupled to a plunger of the cartridge and a pump motor coupled to the pusher and configured to move the pusher towards the plunger of the cartridge. The pusher may be configured to deform the plunger of the cartridge to move the medication in the cartridge towards the transcutaneous portion to cause a predetermined volume of medication to be moved out of the cartridge.

The pusher may be coupled to a dosing system comprising a dosing tube configured to receive medication. The dosing tube may have a reservoir sized for generating a predetermined dose of medication with the predetermined volume selected for delivery to the wearer. The plunger may be flexible and configured to deform when a force is applied. The plunger may include a first end coupled to the pusher and a second end, opposite the first end and configured to contact the medication within the cartridge. The pusher may be configured to cause the first end of the plunger to move a first distance relative the transcutaneous portion, when a pressure within the cartridge is a first pressure, to deliver a first dose of medication. The pusher further may be configured to cause the first end of the plunger to move a second distance relative the transcutaneous portion, when the pressure within the cartridge is a second pressure, the second pressure greater than the first pressure, to deliver a second dose of medication. The first distance may be the same as the second distance.

The pusher may be configured to cause the second end of the plunger to move a third distance relative the transcutaneous portion, when the pressure within the cartridge is the first pressure, to deliver the first dose of medication. The pusher further may be configured to cause the second end of the plunger to move a fourth distance relative the transcutaneous portion, when the pressure within the cartridge is the second pressure, to deliver the second dose of medication. The third distance may be greater than the fourth distance. Further, the third distance may less than the first distance and the fourth distance may be less than the second distance.

The volume of the first dose of medication and the volume of the second dose of medication may be the same ±5%. The predetermined volume of the predetermined dose of medication may be 0.08-1 uL, 0.2-0.6 uL, 0.2 to 0.3 uL., or 0.25 uL ±5%. The pusher may apply a force on the plunger of the cartridge to maintain pressure within the cartridge between 250 mbar to 2000 mbar, between 400 mbar to 1200 mbar, or between 600 mbar to 900 mbar.

The pusher may include a screw (e.g., a worm screw), a nut configured to move along the screw, a bendable rod coupled to the nut, and a cartridge contactor coupled to the nut and configured to deform the plunger. The dosing system further may include a plurality of levers configured to contact the dosing tube to move a predetermined dose of medication towards the transcutaneous portion and a circular cam including a shaft oriented in a first plane and a circular plate oriented in a second plane. The circular plate may be coupled to the shaft and may include surfaces configured to move the plurality of levers in a series of steps upon rotation of the shaft. The rotation of the shaft may deliver the predetermined dose of medication towards the wearer. The shaft may be configured to rotate upon rotation of the screw. The plurality of levers may be configured such that at least one lever is configured to be in a lowered position to close a portion of the dosing tube during the entire time the pump motor moves the pusher.

In accordance with another aspect, a medication infusion device is provided that includes a patch pump configured to be removably adhered to a wearer's skin for delivering doses of medication (e.g., insulin) from a cartridge (e.g., a prefilled cartridge) through a transcutaneous portion. The medication infusion device may include a first pumping system including a pusher configured to be coupled to a plunger of the container and a pump motor coupled to the pusher and configured to move the pusher towards the plunger of the container such that medication is moved out of the container. The medication infusion device further may include a second pumping system configured to receive the medication pumped out of the container by the first pumping system, the second pumping system disposed between the container and the wearer's skin. The second pumping system may include a plurality of levers configured to contact a dosing tube to move a predetermined dose of the medication towards the transcutaneous portion. The plurality of levers may be configured such that at least one lever is configured to be in a lowered position to close the flow between the container and the wearer's skin at all times. The at least one lever may be configured to be in the lowered position at all times to maintain pressure in the container at all times. The second pumping system may be configured to inject a volume of medication that varies slightly around a predetermined volume (e.g., 0.2-0.3 uL) according to its input pressure.

The plunger may be flexible and configured to deform when a force is applied. The plunger may include a first end coupled to the pusher and a second end, opposite the first end and configured to contact the medication within the cartridge. The pusher may apply a force on the plunger of the container to maintain pressure within the container between 600 mbar and 900 mbar. The pusher may include a screw, a nut configured to move along the screw, a bendable rod coupled to the nut, and a container contactor coupled to the nut and configured to deform the plunger. Alternatively or additionally, the pusher may include a screw, a nut configured to move along the screw, a bendable rod coupled to the nut, and a container contactor coupled to the nut and configured such that the pusher incorporates a certain strain.

The second pumping system further may include a dosing tube configured to receive medication, the dosing tube having a reservoir sized to hold the predetermined dose of medication for delivery to the wearer. The second pumping system further may include a circular cam having a shaft oriented in a first plane and a circular plate oriented in a second plane. The circular plate may be coupled to the shaft and may include surfaces configured to move the plurality of levers in a series of steps upon rotation of the shaft, wherein rotation of the shaft delivers the predetermined dose of medication towards the wearer. The shaft may be configured to rotate upon rotation of the screw.

In accordance with another aspect, an applicator for use with a medication infusion device is provided. The applicator may be configured to be removed from the wearer's skin after application and prior to delivery of the doses of medication. The applicator may include an applicator needle configured to be positioned within a lumen of a cannula in a pre-deployment state, a link coupled to the applicator needle, an actuator. The actuator may be configured to, upon actuation, cause the link to rotate about an axis to advance the applicator needle and the cannula into the wearer's skin. The actuator further may be configured to fully withdraw the applicator needle from the cannula in a deployment state such that at least a portion of the cannula remains in the wearer's skin. The link may rotate in a single direction to advance the applicator needle and the cannula into the wearer's skin and to fully withdraw the applicator needle from the cannula.

The applicator may include a biasing member configured to bias the link to cause the link to rotate about the axis upon actuation. The applicator further may include a stopping zone configured to clamp the link and the applicator needle to reduce the noise of the link and the applicator needle. The link and the applicator needle may stop rotation when the biasing member is fully unloaded. The link and the applicator needle may stop rotation without contacting a hard stopping surface. The link may include a first interface and the cannula may include a second interface configured to contact the first interface and to permit rotational movement during insertion of the cannula into the wearer's skin.

The applicator further may include a channel comprising at least one ledge. The cannula may include at least one clip disposed at a proximal end. Upon actuation, the at least one clip of the cannula may be configured to slide along the at least one ledge of the channel such that the cannula moves along a substantially straight path. The actuator may be configured to, upon actuation, cause the cannula to be inserted below the derma layer of the wearer's skin, for example, at an angle of 40-50 degrees from the surface of the wearer's skin.

In another embodiment, the applicator for inserting a cannula into a wearer's skin may include an applicator needle, a link, and an actuator, as described above, as well as a biasing member coupled to the link. The biasing member may be configured to bias the link to cause the link to rotate about the axis upon actuation. The biasing member further may be configured to transition from a biased position to an unbiased position upon actuation. In the pre-deployment state, the biasing member may be configured to interact with a blocking mechanism such that the biasing member is fixed in a biased state and, upon actuation, the blocking mechanism may be configured to transition to release the biasing member such that the biasing member transitions from the biased state to the unbiased state. The link may configured to rotate in a single direction to advance the applicator needle and the cannula into the wearer's skin and to fully withdraw the applicator needle from the cannula.

The applicator further may include a channel having at least one ledge and/or at least one guiding arm. The cannula may have at least one clip disposed at a proximal end and/or at least one wing disposed at the proximal end. Upon actuation, the at least one clip of the cannula is configured to slide along the at least one ledge of the channel such that the cannula moves along a substantially straight path and the at least one wing of the cannula is configured to slide along the at least one guiding arm in order to minimize rotation of the cannula around the longitudinal axis of the cannula A method for inserting a cannula for delivering doses of medication to a wearer's skin is also provided, the method including selecting an applicator including an applicator needle, a link, and an actuator, as described above, and actuating the actuator to cause the applicator to rotate the link about an axis, advance the applicator needle and the cannula into the wearer's skin, and withdraw the applicator needle from the cannula in a deployment state. Actuating the actuator further may cause the applicator to transition a biasing member, as described above, from a biased state to an unbiased state, which may cause rotation of the link and then withdrawal of the applicator needle from the cannula. The applicator further may include at least one stopping zone configured to slow the rotation of the link about the axis, for example, during withdrawal of the applicator needle from the cannula.

In the pre-deployment state, the biasing member may be configured to interact with a blocking mechanism such that the biasing member is fixed in a biased state. Actuating the actuator further may cause the applicator to transition the blocking mechanism to a position wherein the biasing member does not interact with the blocking mechanism such that the biasing member transitions from the biased state to the unbiased state.

Advancing the applicator needle and the cannula into the wearer's skin may include advancing the applicator needle and the cannula along a channel having at least one ledge. The cannula may have at least one clip disposed at a proximal end and configured to slide along the at least one ledge of the channel such that the cannula moves along a substantially straight path. The channel further may include at least one guiding arm and the cannula may have at least one wing disposed at the proximal end such that advancing the applicator needle and the cannula into the wearer's skin includes sliding the wings along the at least one guiding arm in order to minimize rotation of the cannula around the longitudinal axis of the cannula.

In accordance with another aspect, a system for use with a medication infusion device is provided. The system may include a pad configured to be adhered to the wearer's skin and an applicator configured to be locked to the pad during placement of the pad on the wearer's skin. The applicator may include a housing configured to house a cannula therewithin during a pre-deployment state and an actuator. The actuator may be configured to, upon actuation, cause the cannula to be advanced to lock the cannula to the pad and unlock the applicator from the pad such that at least a portion of the cannula is advanced into the wearer's skin in a deployment state wherein the pad remains adhered to the wearer's skin and the applicator, once unlocked, is removable from the pad.

The applicator further may include at least one attachment pad coupler configured to lock the applicator to the pad in a pre-deployment state. The cannula may include at least one clip disposed at a proximal end and configured to lock the cannula to the pad in a deployment state. The actuator may be configured to, upon actuation, cause the at least one clip of the cannula to be advanced such that the at least one attachment pad coupler of the applicator is moved to unlock the applicator from the pad.

In accordance with another aspect, a cannula for use with a medication infusion device is provided. The cannula may include an elongated shaft, a tip, and a cannula head. The elongated shaft may have a lumen extending therethrough and one or more apertures for medication infusion. The one or more apertures may include a proximal aperture oriented away from a skin surface of the wearer. The elongated shaft may have a conical shape configured to limit kinking during deployment of the cannula. The tip may be disposed at a distal end of the elongated shaft and may be configured to be inserted into the wearer's skin. The tip may be cut with an angle and oriented to avoid unintentional piercing of a wall of an applicator.

The cannula head may be disposed at a proximal end of the elongated shaft and may include one or more clips oriented relative to the one or more apertures to axially orient the one or more apertures relative to a target infusion area within the wearer. The one or more clips may include one or more protrusions configured to protrude outwardly from the cannula head. The cannula head further may include one or more wings that protrude towards the wearer's skin. The wings may be configured to further axially orient the one or more apertures relative to the target infusion area within the wearer. The cannula head further may include one or more interfaces to couple with an applicator during deployment of the cannula. The one or more interfaces may permit rotational movement during deployment of the cannula and may include first and second rounded interfaces. The first rounded interface may be convex and the second rounded interface may be concave.

The elongated shaft, the tip, and the cannula head may be integrally formed from a single piece of material. For example, the cannula may be injection molded from a single piece of material. The cannula further may include self-sealing septum disposed within the cannula head and one or more knife blades at the tip configured to extend outwardly from the elongated shaft.

A method for deploying a transcutaneous device for use with a medication infusion device for delivering doses of medication is also provided, the method including providing a cannula including an elongated shaft, a tip, and a cannula head having clips, as described above, inserting the tip into a wearer's skin, and guiding the one or more clips during cannula insertion such that the one or more apertures are axially oriented relative to a target infusion area within the wearer when the cannula is transcutaneously deployed. The method further may include delivering doses of the medication transcutaneously into the lumen of the cannula and out the one or more apertures to the target infusion area.

After inserting the tip into the wearer's skin, the cannula may be coupled to an adhesive pad. Coupling the cannula to the adhesive pad may include inserting the one or more clips into one or more pad attachments disposed on the adhesive pad. The cannula head further may include one or more wings that protrude towards the wearer's skin. Coupling the cannula to the adhesive pad further may include inserting the one or more wings between two pad attachments of the one or more pad attachments such that rotation of the cannula is reduced. To further reduce rotation of the cannula, the tip of the cannula may include one or more knife blades that extend outwardly from the elongated shaft.

In accordance with another aspect, a system for orienting a cannula is provided. The system may include a cannula for use with a medication infusion device configured to be removably adhered to a wearer's skin for delivering doses of medication transcutaneously and an adhesive pad configured to be removably adhered to the wearer's skin. The cannula may include an elongated shaft, a tip, and a cannula head, as described above. The cannula may be configured to couple to the adhesive pad, which may have one or more pad attachments. One or more clips of the cannula may be sized and shaped to fit within the one or more pad attachments.

The cannula may be configured such that the cannula is oriented a particular way upon insertion, for example, such that a proximal aperture of the one or more apertures of the cannula is oriented away from a skin surface of the wearer. The tip of the cannula may be cut with an angle and oriented to avoid unintentional piercing of a wall of an applicator. Further, the cannula head may include one or more wings that protrude towards the wearer's skin. The wings may be sized and shaped to fit between two pad attachments of the one or more pad attachments and may be configured to further axially orient the one or more apertures relative to the target infusion area within the wearer.

In accordance with another aspect, a cannula for use with a medication infusion device is provided. The cannula may include an elongated shaft having a lumen extending therethrough and one or more apertures for medication infusion and a tip at a distal end of the elongated shaft configured to be inserted into the wearer's skin. The cannula further may include a biodegradable material disposed in or adjacent to at least one of the one or more apertures to block delivery of medication therethrough in an initial state. The biodegradable material may be configured to biodegrade within the wearer over a period of time (e.g., 2-3 days or 4-6 days) to unblock the at least one aperture to permit delivery of medication therethrough. The use of biodegradable materials expands the insulin infusion area and volume over time.

At least one of the one or more apertures may be unblocked in the initial state to permit delivery of medication therethrough. The at least one aperture unblocked in the initial state may be a distal-most aperture. Alternatively, the at least one aperture unblocked in the initial state may be a proximal-most aperture.

The cannula further may include a second biodegradable material disposed at least one of the one or more apertures to block delivery of medication therethrough in a second state, the second biodegradable material configured to biodegrade within the wearer over a second period of time, different from the period of time, to unblock the at least one aperture to permit delivery of medication therethrough. The one or more apertures may include a proximal aperture and a distal aperture. The biodegradable material may be disposed in or adjacent to the proximal aperture and the second biodegradable material may be disposed in or adjacent to the distal aperture such that the proximal aperture and the distal aperture are unblocked at different times. The period of time may be 2-3 days and the second period of time may be 4-6 days.

The cannula further may include a tip aperture disposed at the tip of the cannula. The biodegradable material may be disposed within the lumen such that the tip aperture is blocked. Alternatively, the biodegradable material may be disposed within the one or more apertures such that the tip aperture is unblocked.

BRIEF DESCRIPTION OF THE DRAWINGS

These and other features, aspects, and advantages of the present invention will become apparent from the following description, appended claims, and the accompanying exemplary embodiments shown in the drawings, which are briefly described below.

FIGS. 10A and 10B are plan views of the applicator and pad during insertion of the cannula.

FIG. 20C is a cross-section plan view of the wet and dry zones within the patch pump.

FIG. 25A is an exploded view of an exemplary cap.

FIG. 25C-25F are side views of the microdosing system wherein the circular cam is in a non-gripping position, a gripping position, a sliding position, and a dosing position.

FIGS. 35A-35D are plan views of the circular cam and an exemplary system configured to determine the position of the circular cam.

FIG. 35E is a graph showing signal strength over time as the circular cam rotates.

DETAILED DESCRIPTION

Provided herein are systems and methods for delivering fluid to a patient. For example, medication such as insulin may be delivered transcutaneously using patch pumps that are user-friendly, environmentally-friendly, lower cost, discreet, less prone to errors, and/or that provide precise, repeatable doses of medication. As another example, the patch pump may incorporate components for rapid occlusion detection. Accessories for applying the patch pump to the patient's skin and managing the patch pump also are provided. In a preferred embodiment, the system includes a wearable insulin pump having a patch-style form factor for adhesion to a user's body surface.

The systems and methods described herein may be used to deliver medication including, but are not limited to, insulin, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics. The types of medical conditions that the systems and methods might be used to treat include diabetes, cardiovascular disease, pain, chronic pain, cancer, ADDS, neurological diseases, Alzheimer's Disease, ALS, Hepatitis, Parkinson's Disease or spasticity. Preferably, the systems and methods are optimized for transcutaneous delivery of insulin to users with diabetes including Type I Diabetes Mellitus patients.

Figure 1:
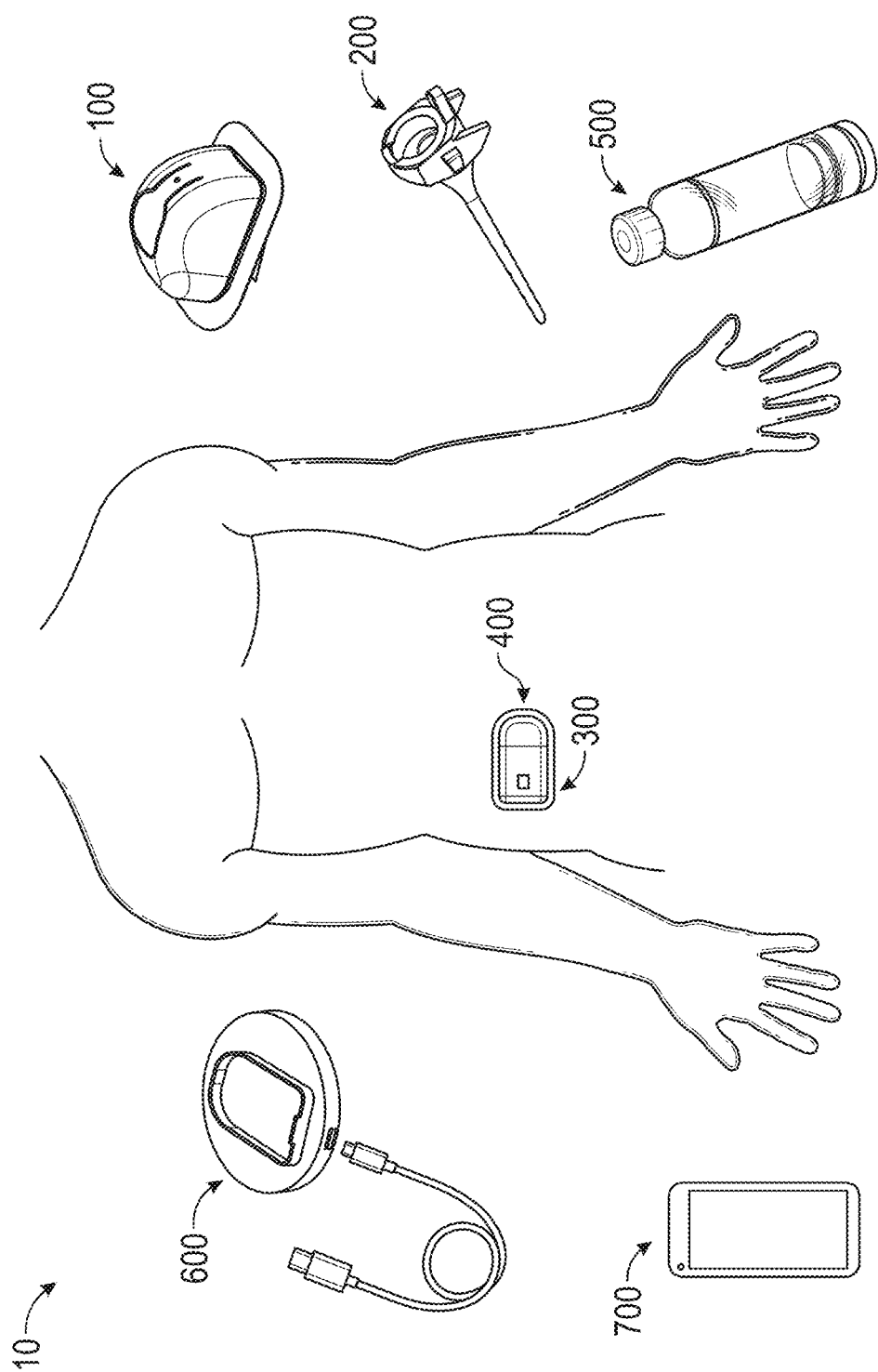
FIG. 1 illustrates an exemplary medication infusion system having a patch pump for delivering medication in accordance with the principles of the present invention.

Referring to FIG. 1, an exemplary medication infusion system including a patch pump for delivering medication is described. In FIG. 1, components of the system are not depicted to scale on either a relative or absolute basis. Medication infusion system 10 may include applicator 100, cannula 200, pump 300, cap 400, cartridge 500, charging system 600, and/or software application 700. Preferably, applicator 100, cannula 200, cap 400, and cartridge 500 are disposable components that may be replaced approximately every 3-10 days and/or once the pre-filled cartridge is empty, while pump 300 is reusable and may last for an extended period of time, e.g., approximately 2-4 years. As such, pump 300 may be used with many different applicators, cannulas, caps, and pre-filled cartridges. Such a configuration is expected to promote sanitary use of the system, as the components exposed to the patient and the insulin are disposable, while reducing costs for components containing more expensive electronics, e.g., pump 300, charging system 600, and/or software application 700, which may be used repeatedly. In a preferred embodiment, system 10 includes a second pump, such that the wearer may charge the second pump while using the first pump and vice versa. In this manner, the wearer will always have a pump that is charged and ready to be used once the cartridge of the pump in use is empty. Further, this system is designed to reduce waste while reducing the number of times the wearer is required to insert a new cannula. Medication infusion system 10 may be used to apply cannula 200 and a pad to a wearer and to deliver medication through cannula 200 via a patch pump coupled to the pad.

Applicator 100 is configured to apply an adhesive pad to the wearer and, upon actuation, to insert cannula 200 into the wearer. The pad is configured to be secured to the wearer for a period of time, e.g., at least 3 days, 7-10 days, and then may be replaced by a similar pad using a similar applicator. The pad may include a pad skeleton having one or more locking mechanisms that are configured to couple the pad to applicator 100 for insertion of cannula 200 or to the assembled pump for delivery of medication. Applicator 100 may include an internal component configured to support an insertion mechanism designed to insert cannula 200 through the skin of the wearer via rotational movement and to guide and orient cannula 200 during insertion.

Preferably, applicator 100 is designed to suppress noise during insertion. The insertion mechanism may include an applicator needle configured to pierce the wearer's skin and a biasing member, which may be coupled to one or more links configured to interact with cannula 200 and the applicator needle. Upon actuation by the wearer, the insertion mechanism preferably rotates and applies a distal force on cannula 200 and the applicator needle within cannula 200, such that cannula 200 is inserted through the wearer's skin. Cannula 200 may include a proximal cannula head configured to couple to one or more locking mechanisms on the pad skeleton and, at the same time, uncouple applicator 100 from the pad skeleton. The insertion mechanism further may be configured to continue rotating to withdraw the applicator needle from cannula 200 and to store the applicator needle within the applicator after cannula 200 is inserted.

Cannula 200 is designed to receive medication doses from a patch pump and to deliver the medication through one or more apertures. The one or more apertures may be disposed at the distal tip and/or along the elongated shaft of cannula 200 such that the medication is delivered along the length of elongated shaft. Preferably, the apertures are arranged and oriented such that the medication is delivered only below the derma layer of skin. Cannula 200 may include a cannula head having a self-sealing septum configured to support and guide the applicator needle during insertion of cannula 200 and the outflow needle of cap 400 during delivery of medication. In some embodiments, cannula 200 may be designed to change the location at which medication is delivered to the patient via the aperture(s) over time without repositioning cannula 200 in the patient's skin. Such a design is expected to extend the life of cannula 200 within the patient, allowing transcutaneous implantation for around 10 days or more. Further, such design may reduce the risk of cannula occlusion. In some embodiments, cannula 200 may include one or more biodegradable materials disposed within the lumen and/or the apertures of cannula 200 that are configured to dissolve over a period of several days, thereby opening new apertures over time through which medication is delivered via the cannula.

Pump 300 is designed to pump medication from cartridge 500 through the microdosing system, through a transcutaneous portion, and into the wearer. The transcutaneous portion preferably includes a cannula inserted into the wearer's skin, the cannula configured to be fluidically coupled to a needle and having one or more apertures beneath the outer skin layer for delivery of the dose of medication. Pump 300 is designed to be removably coupled to cap 400 and the pad to form a patch pump, which is configured to deliver doses of medication through cannula 200 transcutaneously to the patient. The pump-cap assembly advantageously provides precise, repeatable microdoses of medication to the wearer. Pump 300 preferably is designed to be used for an extended period of time, e.g., over 1 year and more preferably up to 2-4 years, and may be manufactured to include a minimal number of parts. For example, in order to lower the cost of the patch pump, pump 300 may include less than 15 parts. After a cartridge of medication is used, a battery within pump 300 is charged and, after charging, the cartridge and cap may be removed and discarded, leaving pump 300 ready to be used again with a new cartridge and a new cap. Pump 300 may include a motor disposed within the pump housing and may be configured to move a pusher towards a plunger of cartridge 500 such that insulin is advanced through an inflow needle of cap 400 and to a microdosing system designed to measure and deliver predetermined doses of medication.

Pump 300 preferably includes a controller disposed within the pump housing for controlling operation of pump 300. For example, the controller may store instructions that, when executed, cause pump 300 to perform the operations described herein. In some embodiments, the controller of pump 300 may include a two processor architecture to, for example, to enhance the security of the pump. The first processor may control pumping while the second processor communicates data to and from the pump via a wireless chip. Advantageously, the first and second processors may be operatively de-coupled such that communication of data from outside the pump, handled by the second processor, does not interfere with the pump-related workings executed by the first processor. By isolating the pump processing from the external communication processing, security of the pump is enhanced.

Pump 300 further may include one or more sensors designed to sense information associated with operation of pump 300 and/or physiological information associated with the wearer. The controller receives information from the sensor(s) and may adjust the algorithms associated with the pump based on such information. Additionally or alternatively, the controller may cause an alert based on the information from the sensor(s) to be issued. In some embodiments, pump 300 includes one or more skin sensors that detect skin of the wearer. The controller may cause the pump motor to activate only if a skin sensor on the skin-facing side of the pump housing detects skin. Pump 300 further may include a locking mechanism to lock pump 300 to cap 400 and the controller further may only unlock the pump after pump 300 reaches a predetermined state (e.g., the battery is charged and/or the pusher is reset to a home position). The controller further may monitor one or more sensors disposed within, on, or separate from the pump housing and alert the wearer via a vibration motor, an LED(s) of a user interface of the pump housing, a sound generator, or a mobile application based on the information sensed by the sensors.

The sensors may include a contact sensor configured to detect a position of pumping components within the pump housing, a sensor configured to monitor the function of cap 400, (e.g., to detect an occlusion in the dosing pathway, such as within the microdosing system of cap 400 or within the cannula), a position sensor configured to detect a position of a cam plate within the microdosing system of cap 400, a pressure sensor configured to detect the pressure within cartridge 500, a photoplethysmography sensor configured to detect a wearer's heart rate or other physiologic parameters, an accelerometer, a temperature sensor, a pressure sensor, a humidity sensor, an optical sensor to detect the insulin concentration in the cartridge via a specific marking on the cartridge that indicates the insulin concentration, and/or a continuous glucose monitoring sensor.

Cap 400 preferably receives medication from cartridge 500 moved into tubing of cap 400 as a result of pumping by pump 300. Further, cap 400 may deliver predetermined doses of the medication through an outflow needle, into cannula 200, and to the wearer. Cap 400 preferably is designed to be replaced after the cartridge is empty or when the temperature sensor detects a temperature exceeding a predetermined temperature threshold, the temperature indicating that the insulin was damaged due to long exposure at a high temperature. Preferably, cap 400 is also manufactured to include a minimal number of parts, such as 15 parts, in order to lower the cost of cap 400. Cap 400 may include a microdosing system configured to measure and deliver the predetermined doses of medication. The microdosing system may be configured to only deliver the predetermined dose of medication upon initialization of the microdosing system, for example, once the controller determines, based on information from the sensor, that the pressure within cartridge 500 is within a predetermined range. The microdosing system may include a dosing tube having a flattened portion configured to hold the predetermined dose, a cam plate coupled to a cam shaft, the cam plate having one or more raised surfaces, and/or a lever system configured to transition between a raised position and a lowered position upon contact with the raised surfaces of the cam plate when the cam shaft is rotated. Cap 400 further may include locking mechanisms configured to lock cap 400 to pump 300 and/or to the pad skeleton.

Cartridge 500 is an enclosed container designed to hold the medication for infusion into the patient. Cartridge 500 may be a commercially available insulin container such as the NovoRapid PumpCart available from Novo Nordisk A/S of Bagsverd, Denmark. Cartridge 500 preferably is pre-filled with a plurality of doses of medication such as insulin. The patch pump is designed such that when cartridge 500 is inserted into the pump patch, the cartridge 500 is completely encased by pump 300 and cap 400. Cartridge 500 may include a cartridge cap through which is disposed an inflow needle of cap 400. Cartridge 500 further may include a flexible plunger configured to be advanced towards the cartridge cap, responsive to pumping by pump 300. As the plunger is displaced, insulin is delivered to a microdosing system of cap 400, which in turn delivers predetermined doses of medication to the wearer one at a time. Once cartridge 500 is empty, it may be replaced by a similar pre-filled cartridge.

Charging system 600 is configured to charge one or more batteries within pump 300, e.g., via respective inductive coils disposed within the housing of a charger and pump 300. The charger is delivered with a USB-C to USB-A cable. The cable may be plugged into a standard USB-A socket (e.g. on an adapter put into a conventional wall electrical socket, on a computer, or in public transport), for charging components within the charger to permit charging pump 300.

Software application 700 is designed to cause a computer (e.g., smartphone, laptop, desktop, tablet, smartwatch, etc.) to communicate data with pump 300 and display information on the pump to a wearer in a user-friendly manner. Software application 700 may cause the computer to securely exchange data between two or more pumps that are used by a single wearer. Software application 700 preferably receives data from the second processor of pump 300 and may cause the computer to transmit such data to a second pump while pump 300 is charging. Software application 700 further may cause the computer to transmit to the patch pumps data indicative of the wearer's activity level and this data may be used to modify how the wearer is alerted and/or when the doses of medication are delivered.

Figure 2:
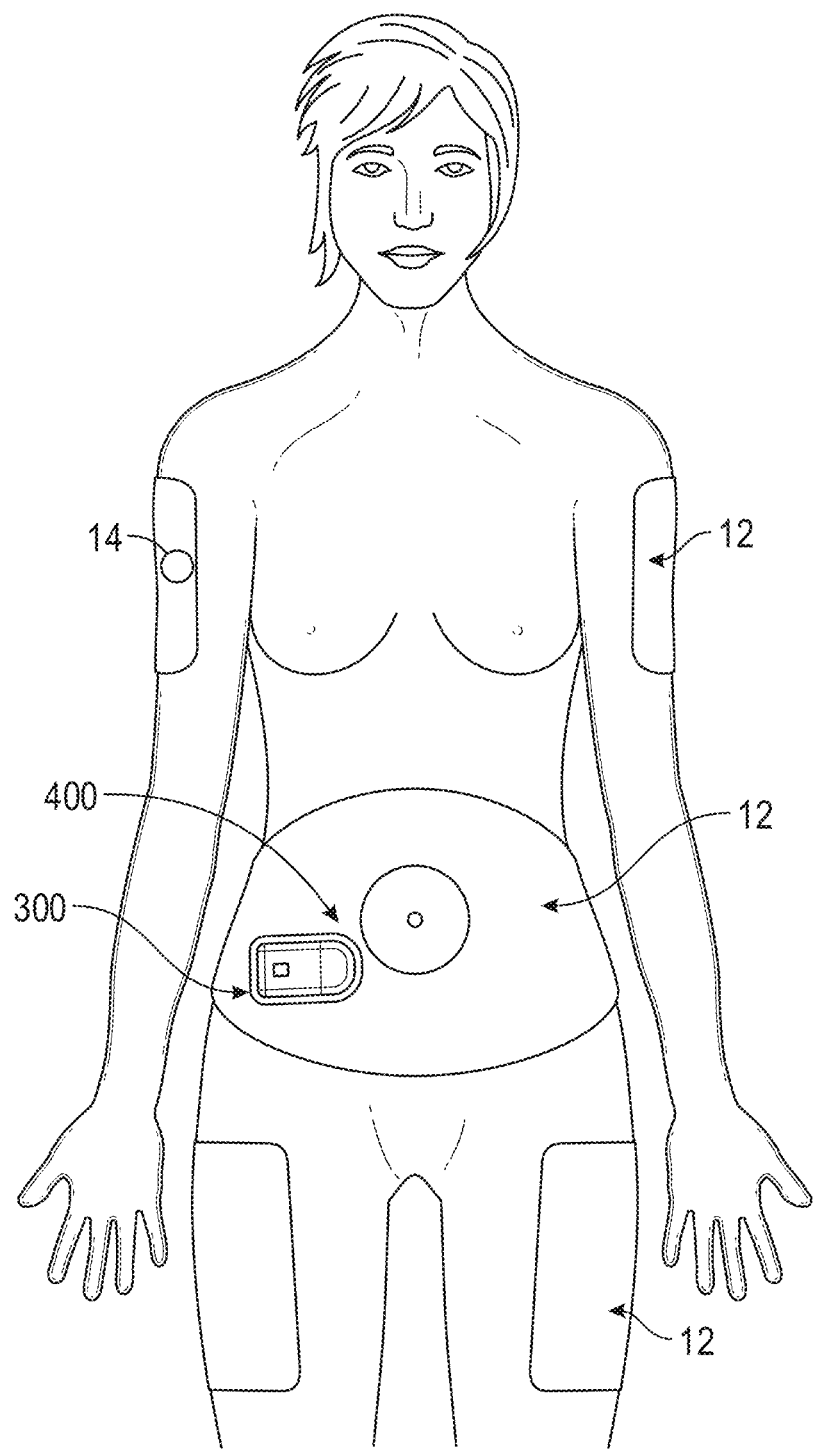
FIG. 2 is a diagram showing exemplary attachment zones for the patch pump and an external sensor such as a continuous glucose monitoring sensor.

Referring now to FIG. 2, exemplary attachment zones for the patch pump and an optional external sensor, such as a continuous glucose monitoring sensor are illustrated. Attachment zones 12 illustrate several locations on the wearer's body where the applicator may attach the adhesive pad and insert the cannula and to which the patch pump is secured. For example, the patch pump may be secured to the upper arms, abdomen, or thighs of the wearer. As will also be understood by one of ordinary skill in the art, the patch pump may be secured to other locations on the wearer.

The patch pump also may be operatively coupled to an optional continuous glucose monitoring sensor, which may transmit data to a controller of the patch pump, which data may be used to adjust the time of insulin delivery or the amount of each dose. Preferably, the patch pump receives data from continuous glucose monitoring sensor 14, which is configured to be attached within attachment zones 12. Exemplary continuous glucose monitors include sensors commercially available from DexCom, Abbott, Eversense, Indigo, or Biolinq.

The sensed glucose levels may be used to adjust the dosing cycles. For example, the patch pump may include an algorithm configured to determine when to deliver insulin to the wearer. The algorithm may recalculate the time of delivery depending upon the sensed glucose level such that the wearer's glucose level remains within a safe range. For example, if the wearer's glucose levels fall below a predetermined threshold, the controller may cause the patch pump to stop delivering insulin for a period of time. Or, if the wearer's glucose levels rise above a certain level, the controller may cause the patch pump to deliver a microdose of insulin. In addition, responsive to the sensed glucose levels, the algorithm may adjust the amount of insulin in the dose. For example, a standard dose of insulin may include the amount of insulin delivered over eight dosing cycles. If the wearer's glucose levels fall below a predetermined threshold, the controller may cause the patch pump to deliver a smaller dose of insulin than the standard dose, for example by permitting only 4 dosing cycles or 0 dosing cycles (stopping the pump).

Further, as described above, software application 700 may receive information from the continuous glucose monitoring sensor or other monitoring systems, for example, sensed glucose levels, information about patient food intake, and/or information about patient's activity levels (e.g., due to exercising, playing sports). This information may be transferred to the patch pump via the communication circuitry and the processor of the pump and the patch pump may respond to the transferred information, causing the patch pump to adjust the timing and/or amount of each dose. In this manner, the pump is modular and interchangeable with many continuous glucose monitoring sensors or other monitoring systems, making the pump "universal." Advantageously, the patch pump described herein may be used with a minimal amount of external monitoring while still being effective at delivering accurate microdoses of medication at levels to treat the wearer. The inclusion of sensors within the patch pump, such as the PPG sensor and a sensor for determining activity level, may result in less external monitoring systems, which can be beneficial for the wearer. For example, in one embodiment, the patch pump may only be used with a commercially available CGM sensor.

Applicator, Pad, and Method for Inserting Cannula

Figure 3A:
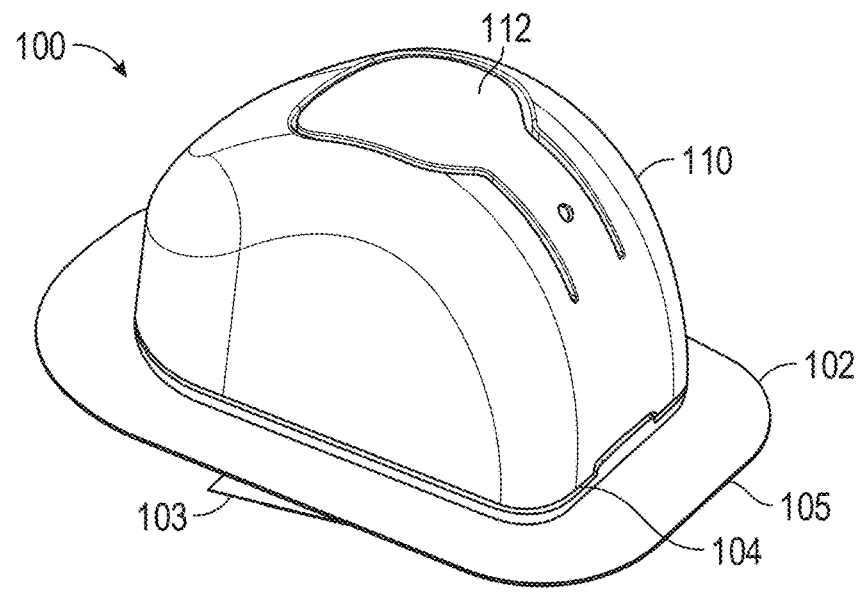
FIGS. 3A and 3B are, respectively, perspective and exploded views of an exemplary pad and applicator for attaching a pad and inserting a cannula.
Figure 3B:
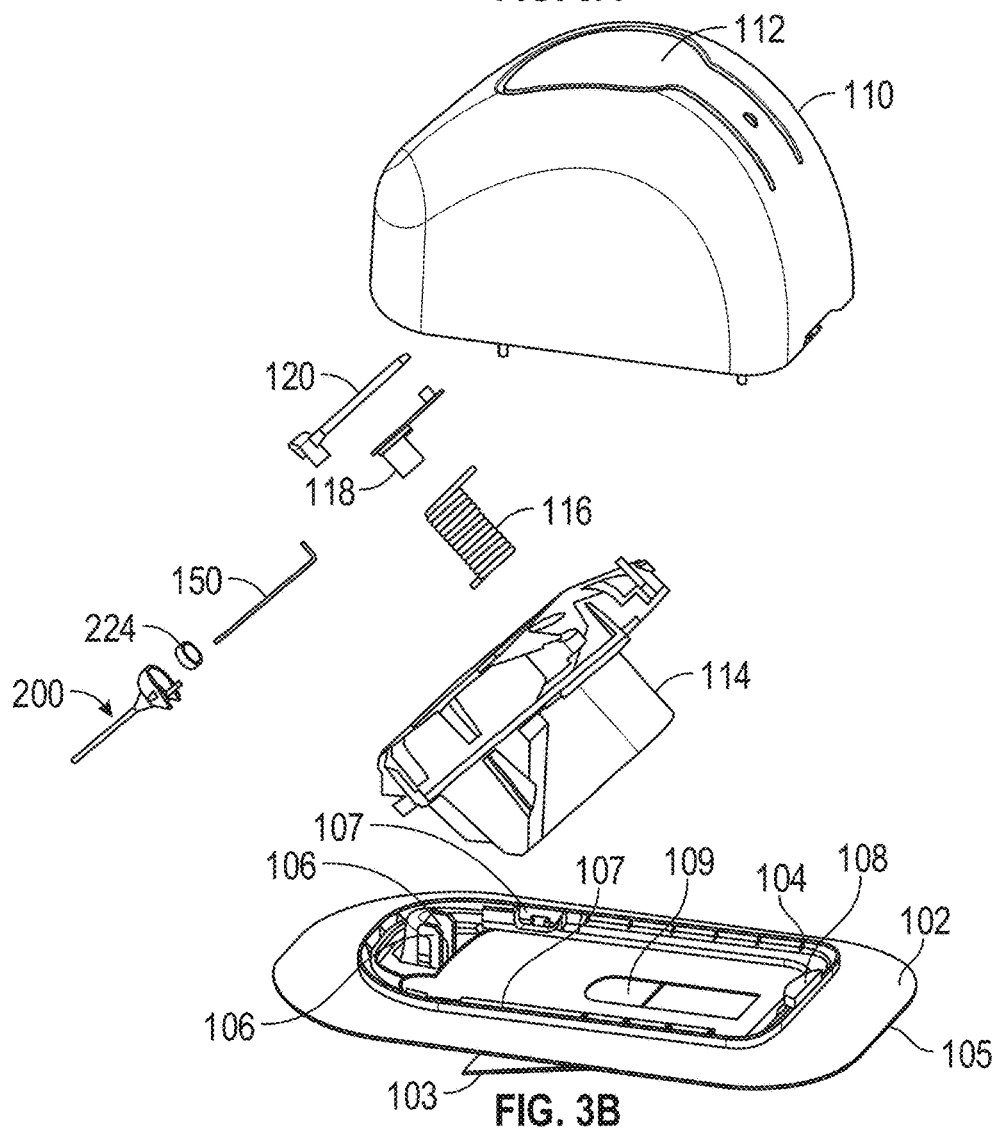

Referring now to FIGS. 3A and 3B, perspective and exploded views of an exemplary pad and applicator are described. Applicator 100 may transcutaneously apply a cannula, upon actuation by a user, which is designed to deliver doses of medication (e.g., insulin) from a patch pump configured to be removably coupled to the cannula. Advantageously, applicator 100 further may apply a pad that is adhered to the wearer's skin and then coupled to the patch pump. For example, actuation of applicator 100 may both insert the cannula and cause the cannula to be locked to the adhesive pad in a single actuation. Further, applicator 100 may include internal components designed to minimize noise during the actuation process. For example, applicator 100 may avoid clicks and/or hard stops that make audible noises during insertion of the cannula.

In a pre-actuation state, applicator 100 may be coupled to pad 102 as shown in FIG. 3A. For example, applicator 100 may be coupled to pad 102 via pad skeleton 104 of pad, which is disposed on a first surface of pad 102. Skin-safe pad adhesive 105 may be disposed on a second, skin-facing surface of pad 102 such that the pump-pad assembly may be attached to a wearer for a period of time, for example, 3-5 days, 3-10 days, or 10 days or more. One or more release liners 103 may be attached to pad adhesive 105 until pad 102 is ready to be secured to the wearer. Pad skeleton 104 may be a frame with a shape designed to surround the pump-cap assembly so as to securely couple the adhesive pad to the pump-cap for wearing by the patient. Pad skeleton 104 may be designed to removably couple portions of pad 102 to applicator 100 in the pre-actuation state. For example, pad skeleton 104 may have one or more attachment mechanisms to lock pad 102 to applicator 100 and unlock upon actuation of applicator 100. Advantageously, the attachment mechanisms also may lock the cannula to pad 102 after actuation. As depicted in FIG. 3A, pad skeleton 104 may have pad attachments 106 at a first end of pad 102 and pad back clip 108 at a second end of pad 102. Pad attachments 106 and pad back clip 108 may interact with applicator 100 or a patch pump to lock the pad to applicator 100 or the patch pump. Pad attachments 106 may include at least two arms that protrude upwards from the pad and away from the skin surface of the wearer. Each arm may have an opening (e.g., slot) to receive extensions from the applicator during pre-actuation and extensions from the cannula post-actuation. Thus, the arms, which may have a U-shape, and openings may be used to lock to both the applicator and the cannula. Pad skeleton 104 may also include pad clips holes 107 disposed on the sides of pad skeleton 104. Pad clips holes 107 may be a hole or receptacle sized and shaped to interact with a corresponding feature of the pump-cap assembly such that the pump-cap assembly may be locked to the pad. Further, pad 102 may include pad opening 109 to allow direct sensing of the wearer's skin by one or more sensors of the pump. For example, the skin sensor(s) and/or the PPG sensor(s) may be positioned at pad opening 109 when the pump is coupled to the pad.

Applicator 100 may include applicator housing 110 and actuator 112. Applicator housing 110 is configured to house the mechanisms for inserting the cannula. After insertion of the cannula, internal component 114 is designed to withdraw and safely store the needle used to pierce the wearer's skin. Actuator 112, upon actuation, causes the cannula to be transcutaneously inserted into the wearer's skin. Actuation of actuator 112 also may unlock applicator 100 from pad 102. Actuation of actuator 112 also may lock the transcutaneously inserted cannula into pad 102. For example, actuation of applicator 100 may insert the cannula transcutaneously, unlock the applicator from the pad, and lock the cannula to the pad in a single actuation. Actuator 112 may release the internal mechanism disposed within applicator housing 110 when actuated by the wearer, thus causing the cannula to advance through the wearer's skin. Actuator 112 may be a button configured to be pressed by the wearer as illustrated, or may be a lever, snap, knob, or the like. The mechanism for inserting the cannula may include internal component 114, biasing member 116, and links 118 and 120, which are disposed within applicator housing 110, and are configured to advance cannula 200 through pad 102 and into the wearer's skin. The mechanism may further include applicator needle 150, which is configured to be disposed within cannula 200 during insertion and withdrawn from cannula 200 after insertion. Self-sealing septum 224 may be disposed within the cannula head of cannula 200 in order to support and guide applicator needle 150 and minimize backflow out of cannula 200.

Figure 4A:
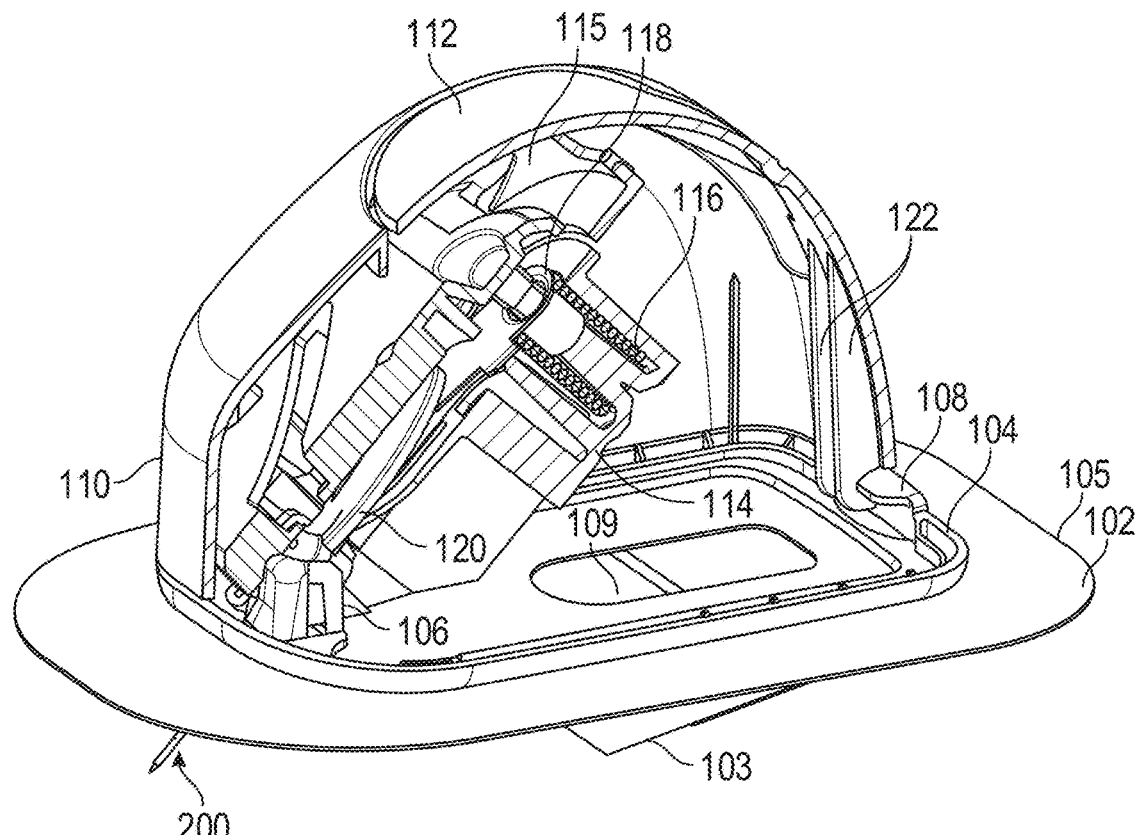
FIGS. 4A and 4B are cross-sectional perspective and side views of the applicator and pad.
Figure 4B:
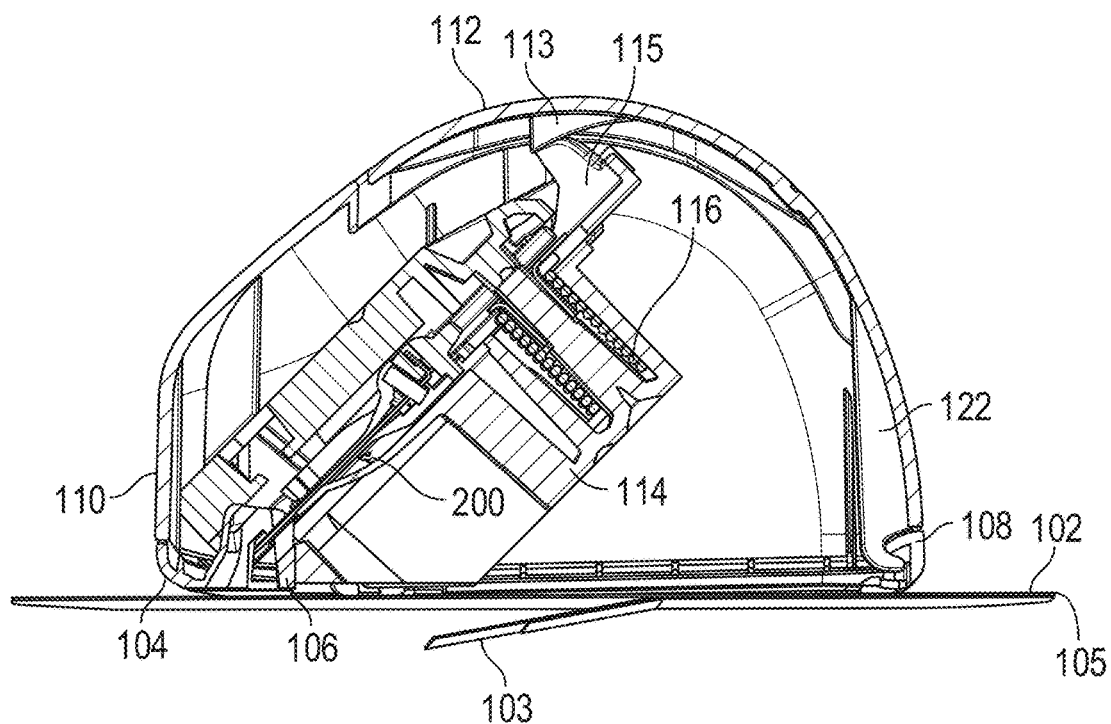

Referring now to FIGS. 4A and 4B, cross-sectional perspective and side views of the applicator and pad are described. Applicator 100 may include one or more attachment mechanisms that are configured to interact with corresponding features of pad skeleton 104 to lock applicator 100 to pad 102. These locking mechanisms may help retain applicator 100 locked to pad 102 when cannula 200 is inserted into the skin of the wearer. For example, applicator 100 may include one or more back pad couplers 122, which may be coupled to pad back clip 108 at the second end of pad 102. Back pad couplers 122 may be extensions that extend out from the applicator housing to couple with the pad skeleton. As described further below, applicator 100 also may be coupled to pad 102 via pad attachments 106 and may be uncoupled from pad 102 at the same time that cannula 200 is fully inserted into the wearer and locked to pad 102.

Internal component 114 supports the insertion mechanisms for inserting the cannula and, after insertion, withdrawing the needle disposed within the cannula. Internal component 114 may be coupled to applicator housing 110 at an angle. Preferably, internal component 114 is disposed at the angle (e.g., 30-60° angle, 40-50° angle, 45° angle) such that cannula 200 is inserted into the skin of the wearer at the same angle. Internal component 114 may be configured to position the tip of cannula 200 near pad 102, between pad attachments 106, in a pre-deployed state, as shown in FIG. 4B. The insertion mechanisms supported by internal component may include biasing member 116 and links 118 and 120. Biasing member 116 may be disposed at the proximal end of internal component 114 and preferably is a spring that may be coupled to one or more links that interact with cannula 200. For example, as described further with respect to FIGS. 7A-7D, biasing member 116 may be coupled to link 118, link 118 may be coupled to link 120, and link 120 may be coupled to cannula 200.

Actuator 112 may be disposed above internal component 114, such that, when actuator 112 is pressed towards the skin by the wearer, a force also is applied to internal component 114. Actuator 112 may include one or more activation ribs 113, which are configured to engage with corresponding protrusions 115 disposed on the top of a lower portion of internal component 114. Activation ribs 113 preferably are curved such that when a force is applied to actuator 112 by the wearer, the force applied to internal component 114 is perpendicular to the angle at which internal component 114 is disposed within applicator housing 110. Activation ribs 113 reorient the force to be perpendicular to the internal component, such that friction is reduced, providing smoother insertion of the cannula without a stick-slip effect. Activation ribs 113 also allow a longer stroke upon activation, which results in more reliable insertion of the cannula.

Figure 5A:
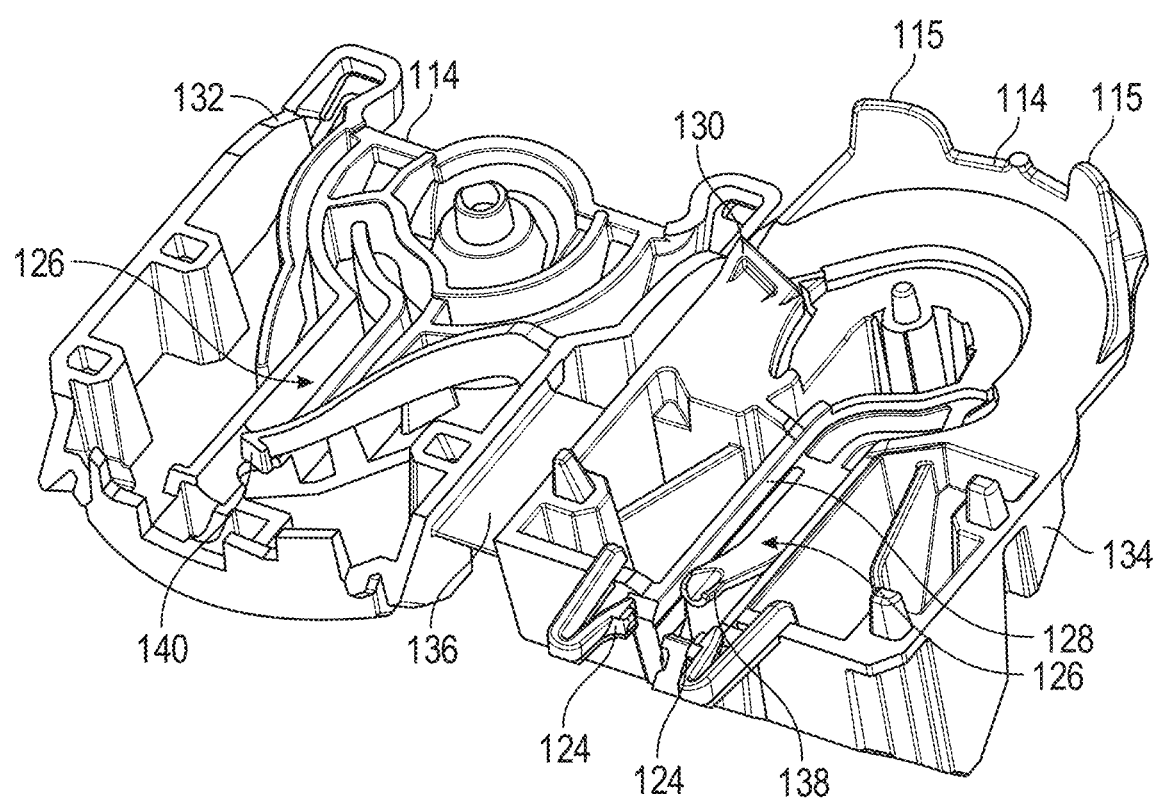
FIG. 5A is a perspective view of exemplary internal components of the applicator of FIG. 4 in a pre-assembled state and FIG. 5B is a perspective view of the internal components of the applicator in an assembled state.
Figure 5B:
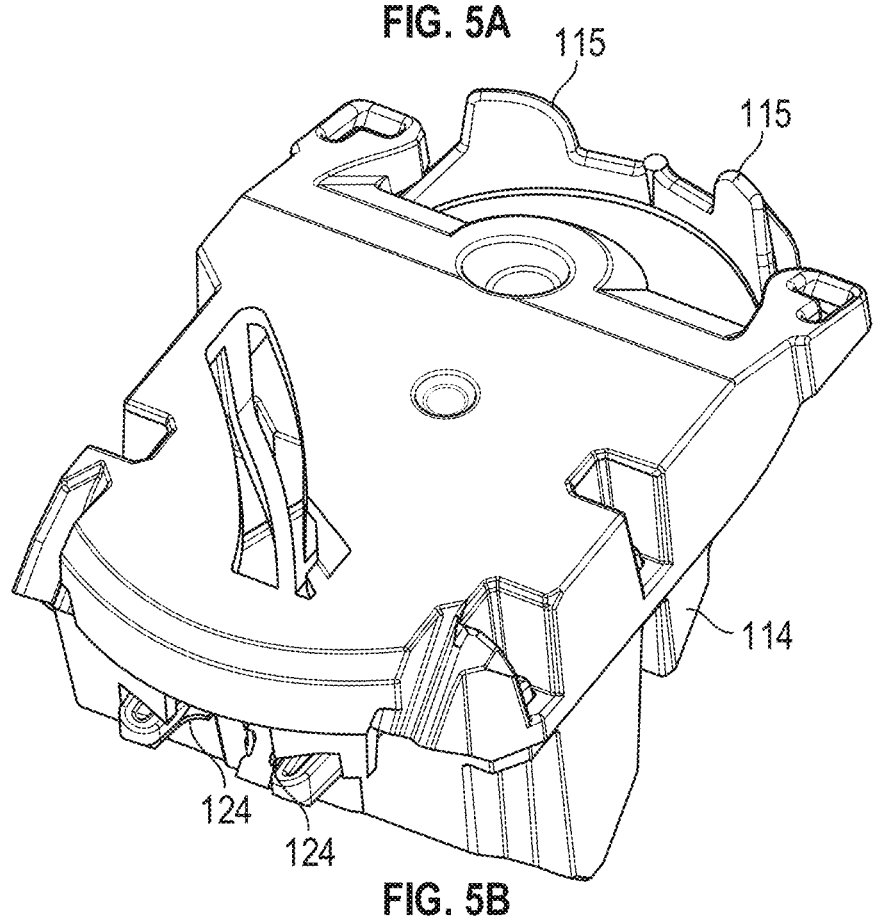

Referring now to FIGS. 5A and 5B, the internal components of the applicator are described. Internal component 114 may be injection molded to form a single piece of material and may be configured to fold in half, as depicted in FIG. 5B, such that the internal component is sized and shaped to fit within the applicator housing. Internal component 114 may include upper portion 132 and lower portion 134 connected via hinge 136. This configuration reduces the number of parts of the applicator, which contributes to a reduction in costs.

Internal component 114 preferably includes a channel and one or more guiding mechanisms that are configured to help guide the cannula during insertion. An accurate location of insertion helps ensure that insulin is only delivered below the dermal layer of the wearer's skin. Upper portion 132 may include an upper portion of channel 126 and lower portion 134 may include a corresponding lower portion of channel 126 such that, when upper portion 132 is folded on top of lower portion 134, the upper and lower portions of channel 126 form a complete channel. Channel 126 preferably is sized and shaped such that the cannula can move through the channel toward the wearer's skin. To ensure accurate control of the cannula as it moves through channel 126, additional guiding mechanisms may guide the cannula on its insertion path. For example, the lower portion of channel 126 further may include one or more ledges 128 configured to interact with corresponding features of the cannula when the cannula is advanced in a distal direction. Advantageously, such ledges 128 ensure that cannula is inserted into the wearer's skin at a particular orientation, which may be helpful for aligning radially spaced apertures in the cannula within the wearer's skin. Further, the guiding mechanisms may extend into channel 126 to contact and guide cannula on the insertion path during insertion. For example, the cannula further may be guided by guiding arm 140 disposed on upper portion 132 and guiding arm 138 disposed on lower portion 134. As described in further detail below, the cannula may have clips and wings sized and shaped to interact with ledges 128 and guiding arms 138 and 140 such that the cannula is advanced into the skin of the wearer in a substantially linear direction and with minimal rotation.

Internal component 114 (e.g., at lower portion 134) further may include blocking mechanism 130, which is configured to interact with the biasing member and links such that, in an initial state, blocking mechanism 130 prevents rotation of the links. Attachment pad couplers 124 may interact with corresponding locking mechanisms of the pad skeleton to lock the applicator to the pad. For example, attachment pad couplers 124 may be coupled to the pad attachments at the first end of the pad. Attachment pad couplers 124 may be extensions (e.g., arms) that extend toward the pad. Further, attachment pad couplers 124 preferably are flexible such that contact from the cannula moves attachment pad couplers 124 away from the position that locks the applicator to the pad during cannula delivery.

Figure 6:
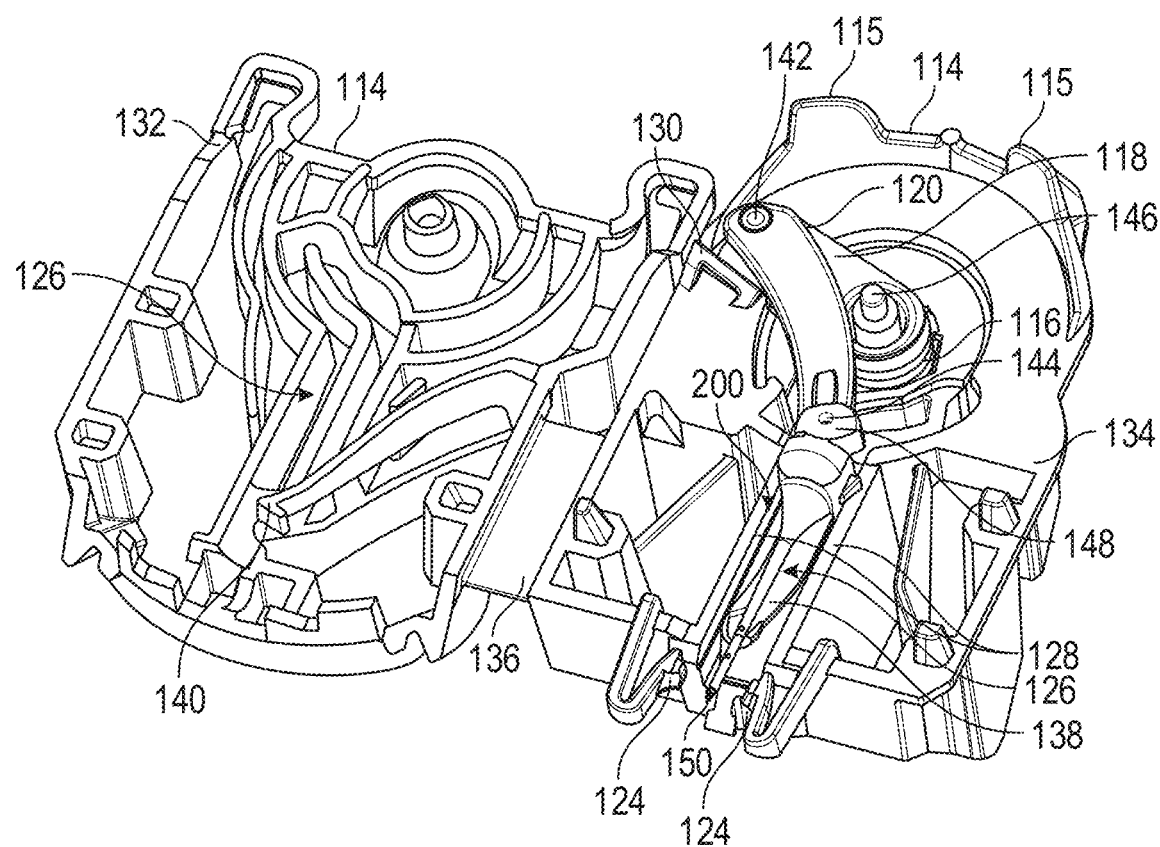
FIG. 6 is a perspective view of the internal components and mechanism for inserting the cannula.

Referring now to FIG. 6, operation of the internal component and mechanism for inserting the cannula is described. In FIG. 6, internal component 114 is shown in a pre-assembled state. Lower portion 134 may include axis 146 around which link 118 is designed to rotate. Biasing member 116 extends around and along axis 146. Biasing member 116 biases link 118 to rotate about axis 118. Prior to actuation, blocking mechanism 130 contacts and holds link 118 in place. Upon actuation by the wearer, blocking mechanism 130 moves relative to link 118 such that blocking mechanism 130 no longer contacts link 118, thereby allowing force applied by biasing member 116 to cause one or more links to rotate and advance the cannula and needle distally, through the skin of the wearer. Link 118 may be coupled to biasing member 116 such that link 118 cannot move relative to biasing member 116. In a pre-deployed state, biasing member 116 may be biased in a direction (e.g., clockwise) such that link 118 applies a force to blocking mechanism 130 in a different direction (e.g., opposite, counterclockwise). Link 120 may be coupled to link 118 via joint 142 and applicator needle 150 may be coupled to link 120 via joint 144. In a pre-deployed state, joint 144 may be disposed adjacent to cannula interface 148 and applicator needle 150 may be positioned within a lumen of cannula 200. Applicator needle 150 may be sized and shaped such that the distal end of applicator needle 150 extends past the distal end of cannula 200. Applicator needle 150 may have an angled tip that is configured to minimize the risk of hitting pad skeleton 104 or applicator housing 110 during insertion of cannula 200. Cannula 200 may be disposed within channel 126 and may be configured to slide in a distal direction along ledges 128, through channel 126, and through the skin of the wearer.

Figure 7B:
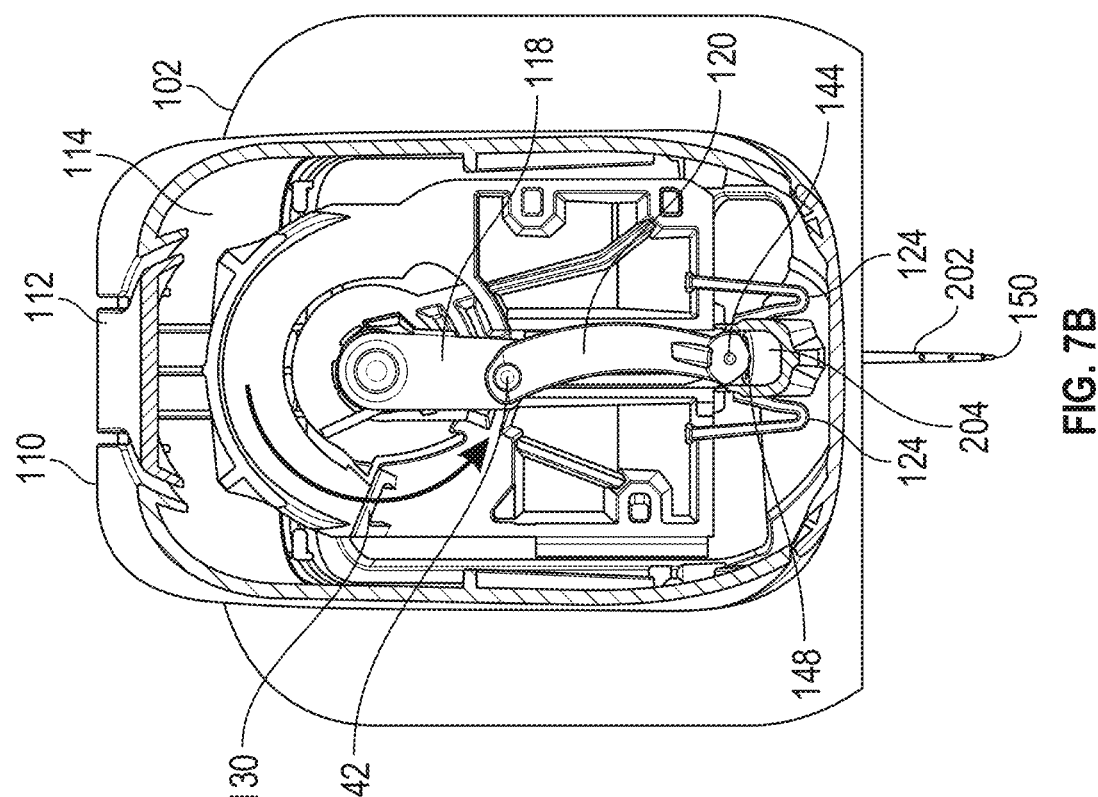
FIGS. 7A-7D are plan views of the mechanism and steps for inserting the cannula.
Figure 7A:
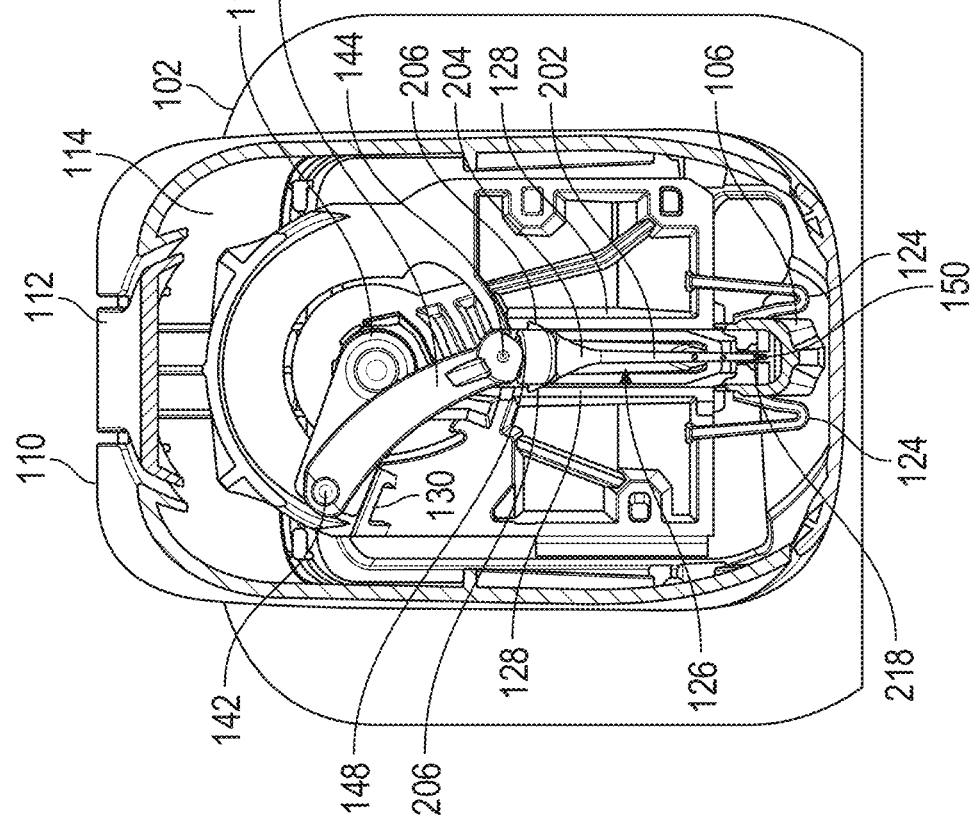

Referring now to FIGS. 7A-7D, operation of the mechanism and steps for inserting the cannula are described. The applicator is configured to insert cannula 200 via rotational movement of the insertion mechanism of the applicator. This rotational movement provides several benefits over the mechanisms employed in previously known devices, including, for example, minimizing hard stops, thus reducing the noise of the applicator. FIG. 7A depicts the applicator in a pre-deployed state. Pad 102 is partially cut near the location of insertion of cannula 200 in FIGS. 7A-7D to better show how cannula 200 and applicator needle 150 are deployed. Biasing member 116 is biased in a clockwise direction and blocking mechanism 130 is disposed in a position that prevents link 118, which is coupled to biasing member 116, from moving in a counterclockwise direction. As will also be understood by one of ordinary skill in the art, biasing member 116 may instead be biased in a counterclockwise direction such that, upon actuation, link 118 rotates in a clockwise direction.

The applicator may include a needle configured to pierce the skin of the wearer, and to provide a path for cannula 200 to advance through the skin. Alternatively, as described further below, a portion of cannula 200 may instead be used to pierce the wearer's skin. Applicator needle 150 may be disposed within the lumen of cannula 200 and may extend from cannula head 204, through elongated shaft 202, and past cannula tip 218. In the pre-deployed state, cannula head 204 preferably is disposed at the proximal end of channel 126 such that cannula 200 is disposed entirely within applicator housing 110. Cannula 200 may include one or more clips 206 disposed on cannula head 204, which are configured to guide cannula 200 in a substantially linear direction. Clips 206 may extend outward from cannula and may be two wings disposed on either side of cannula head 204 and sized and shaped to slide along ledges 128. Preferably, in the pre-deployed state, cannula tip 218 is disposed near pad 102, between pad attachments 106, such that clips 206 may be coupled to pad attachments 106 advancement of cannula 200.

FIG. 7B depicts the applicator in a partially-deployed state, wherein cannula 200 is inserted into the skin of the wearer, but applicator needle 150 is not yet withdrawn. Upon actuation of actuator 112, a downward force is applied to internal component 114, which causes lower portion 134 to deflect. The downward force on blocking mechanism 130 transitions blocking mechanism 130 to a position beneath link 118 such that link 118 is able to freely rotate. Because biasing member 116 is biased in a clockwise direction and is coupled to link 118, link 118 then rotates about axis 146 in a counter-clockwise direction. The rotation of link 118 causes link 120, which is coupled to link 118 via joint 142, to move distally and apply a distal force to applicator needle 150 and cannula 200. Applicator needle 150 and cannula 200 are configured to move in a distal direction through channel 126 such that the distal end of applicator needle 150 pierces the skin of the wearer and at least a portion of cannula 200 is inserted. Preferably, clips 206 are disposed on cannula head 204 such that clips 206 slide along ledges 128, guiding cannula 200 and applicator needle 150 in a substantially linear direction.

As described further below, when cannula 200 is inserted, the proximal end of cannula 200 preferably is coupled to one or more pad attachments disposed on the pad skeleton in order to lock cannula 200 to the pad. At the same time that cannula 200 is coupled to the pad skeleton, the applicator may be uncoupled from pad skeleton in a single actuation.

Figure 7D:
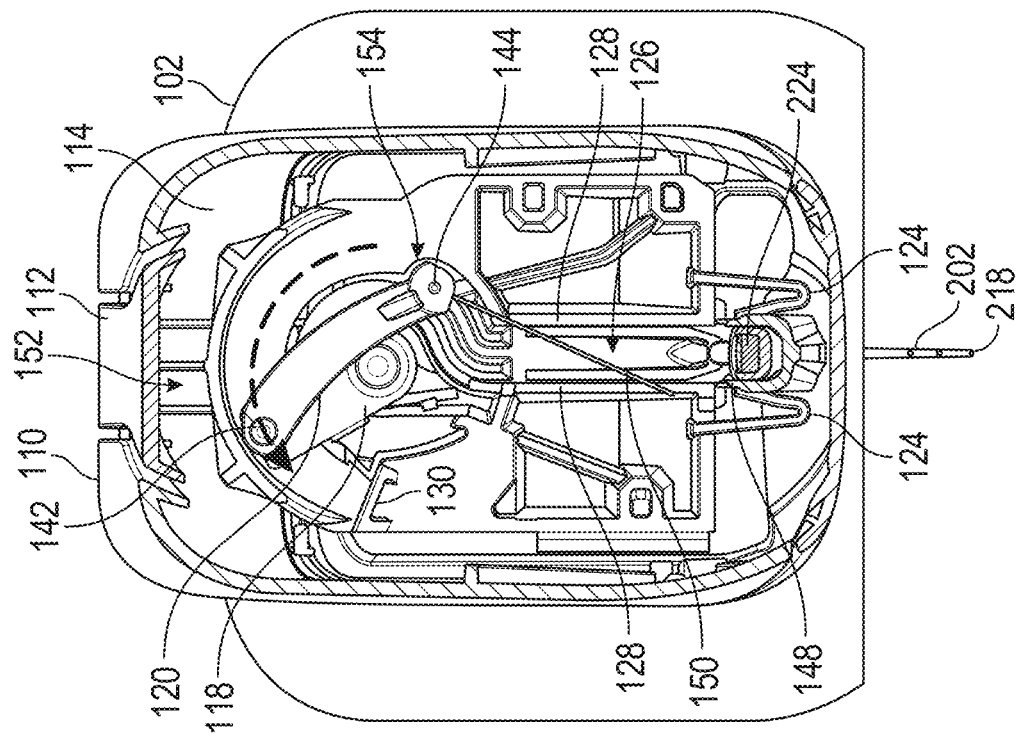
Figure 7C:
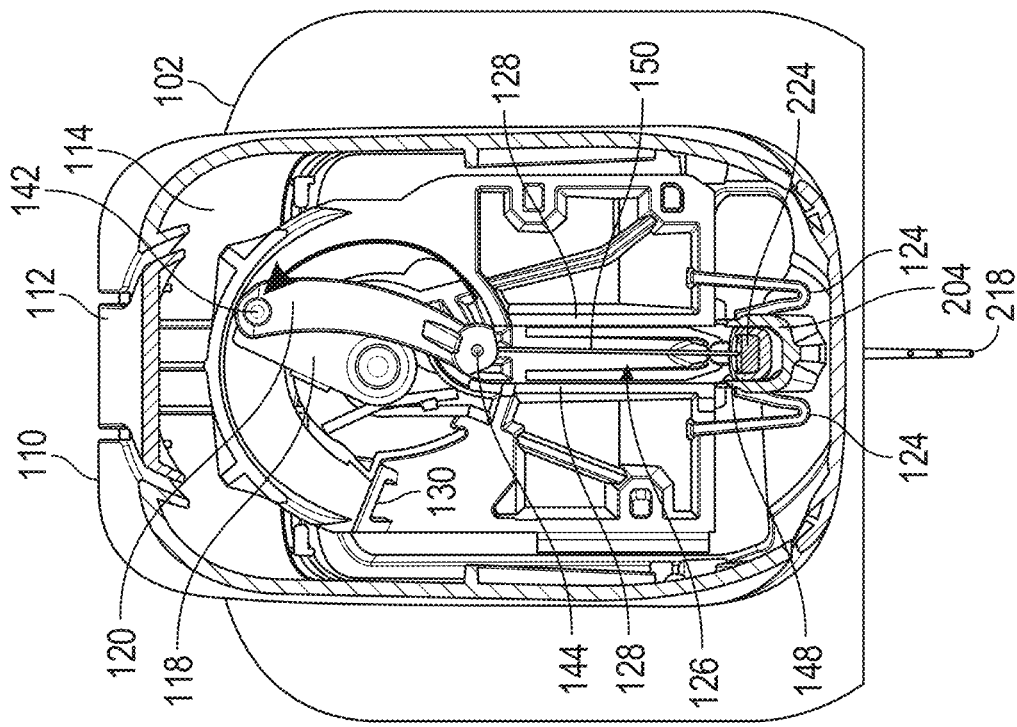

In FIG. 7C, the applicator is depicted in a fully-deployed state, wherein cannula 200 is inserted into the skin of the wearer and applicator needle 150 is withdrawn. After cannula 200 is inserted, biasing member 116 may continue to apply a force to link 118 such that link 118 continues to rotate in a counter-clockwise direction, forcing link 120 to move in a proximal direction. Preferably, cannula 200 remains coupled to the pad skeleton and applicator needle 150 remains coupled to link 120 via joint 144 such that cannula 200 and applicator needle 150 are separated. As link 120 moves in a proximal direction, applicator needle 150 is withdrawn from cannula 200 and into the applicator, at least a portion of cannula 200 remaining in the wearer's skin. The withdrawal of applicator needle 150 into the applicator ensures the needle is stored in a safe, remote place.

Referring to FIG. 7D, the applicator is depicted in a fully-deployed state, wherein applicator needle 150 is stored within applicator housing 110, biasing member 116 is completely unloaded, and the rotation of link 118 is stopped. Links 118 and 120 and applicator needle 150 may stop rotating without contacting any surfaces. Internal component 114 may include one or more stopping zones that are configured to allow slowing of the rotation of links 118 and 120. For example, internal component 114 may include upper stopping zone 152 and lower stopping zone 154. Upper stopping zone 152 may be positioned at the proximal end of internal component 114, where joint 142 is configured to stop rotating when biasing member 116 is completely unloaded. Lower stopping zone 154 may be distal to upper stopping zone 152, where joint 144 is configured to stop rotating when biasing member 116 is completely unloaded.

Figure 8:
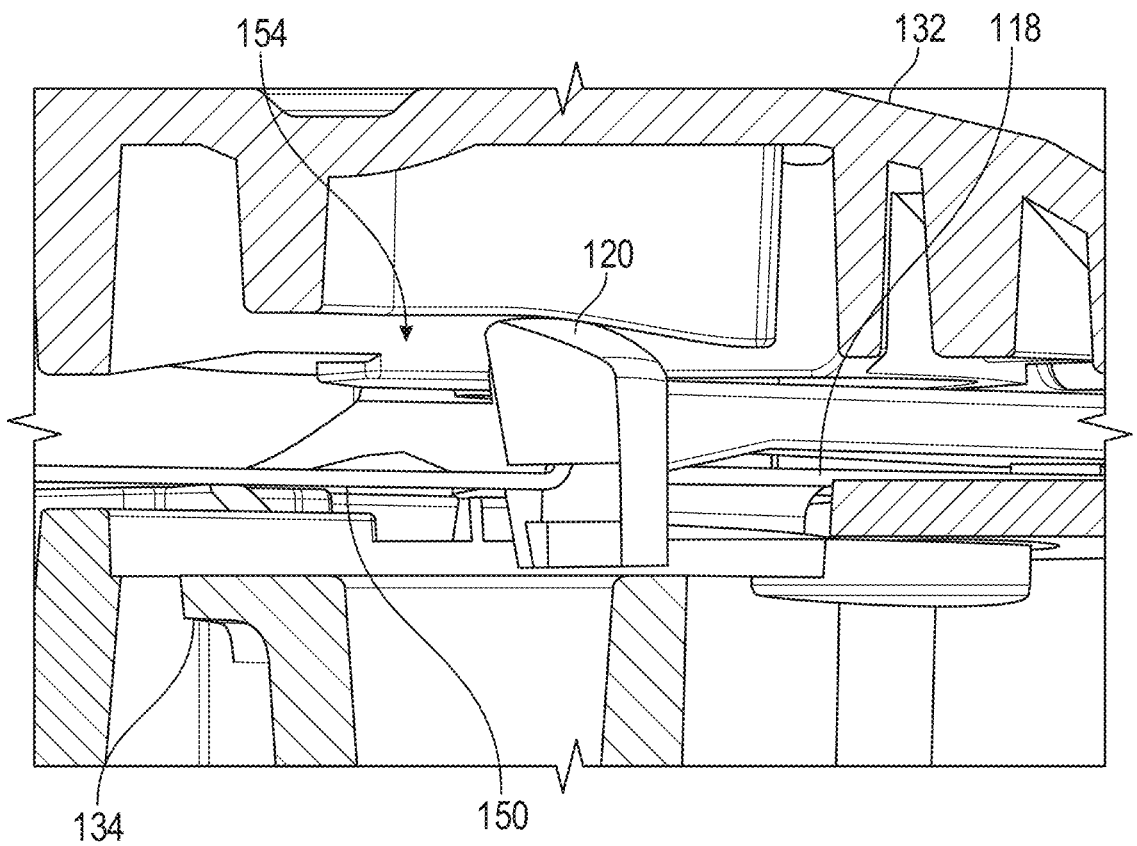
FIG. 8 is a cross-sectional side view of a lower stopping portion of the applicator showing needle retraction.

Referring now to FIG. 8, operation of the lower stopping portion when the applicator withdraws the needle is described. To further reduce the noise from inserting the cannula, lower stopping portion 154 may clamp joint 144 between two surfaces to help slow the rotation of link 120 and applicator needle 150. As shown in FIG. 6, the biasing member, links 118 and 120, and applicator needle 150 are disposed between upper portion 132 and lower portion 134. Upper portion 132 and lower portion 134 may each have a sloped section that narrows the space between the upper and lower portion. When joint 144 reaches lower stopping portion 154, joint 144 becomes clamped between upper portion 132 and lower portion 134, such that link 120 and applicator needle 150 are prevented from continuing to rotate.

Figure 9A:
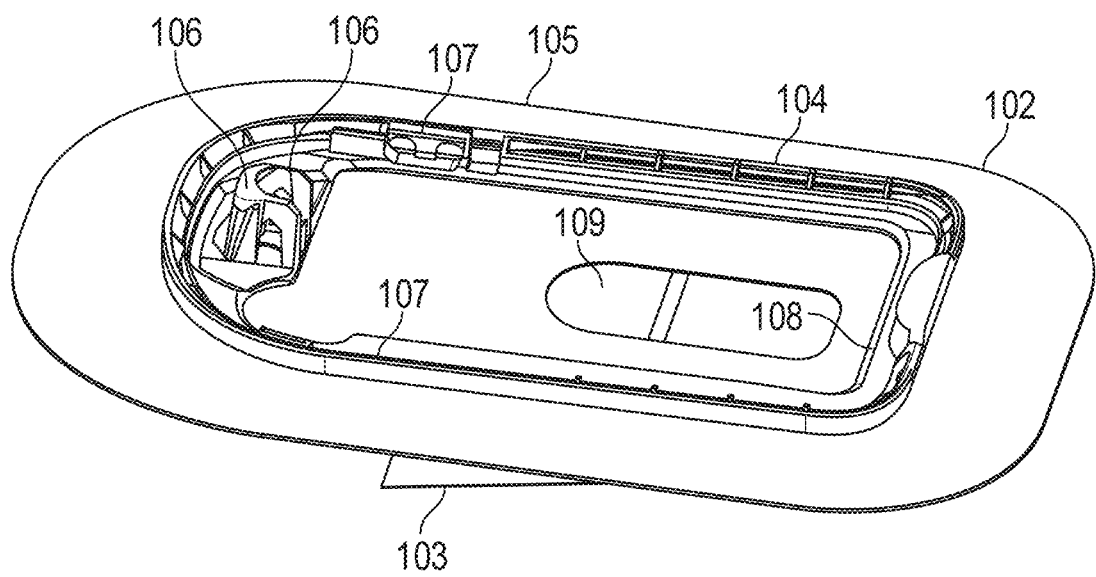
FIGS. 9A and 9B are perspective views of an exemplary pad for attaching the pump to a wearer.
Figure 9B:
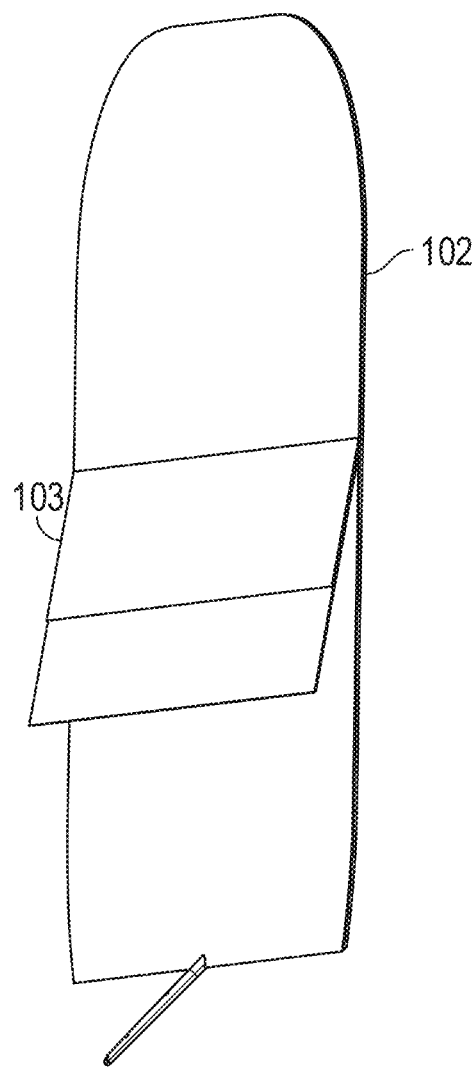

With respect to FIGS. 9A and 9B, an exemplary pad for attaching the pump to a wearer is described. Pad 102 is attached to the wearer and is configured to support the applicator, the patch pump, and the cannula. Pad 102 comprises a first surface, on which pad skeleton 104 is attached, and a second, skin-facing surface that includes pad adhesive 105 that is safe to apply to skin. Pad adhesive 105 is configured to secure the pad to the wearer for a period of at least 3-10 days and preferably is strong enough to hold the patch pump on the wearer during the wearer's normal, daily motions including showering, swimming, and other outdoor activities. One or more release liners 103 may be attached to pad adhesive 105 until pad 102 is ready to be secured to the wearer. FIG. 9B shows release liners 103, which have been partially cut at the location of cannula insertion. Pad skeleton 104 is configured to couple pad 102 to the applicator for insertion of the cannula and to the patch pump for delivery of the medication. Pad skeleton 104 may include one or more locking mechanisms configured to lock the applicator, the pump-cap assembly, and/or the cannula to pad skeleton 104. For example, pad skeleton 104 may include pad attachments 106 at a first end of pad 102, pad back clip 108 at a second end of pad 102, and one or more pad clips holes 107 at one or more sides of pad 102.

Figure 10C:
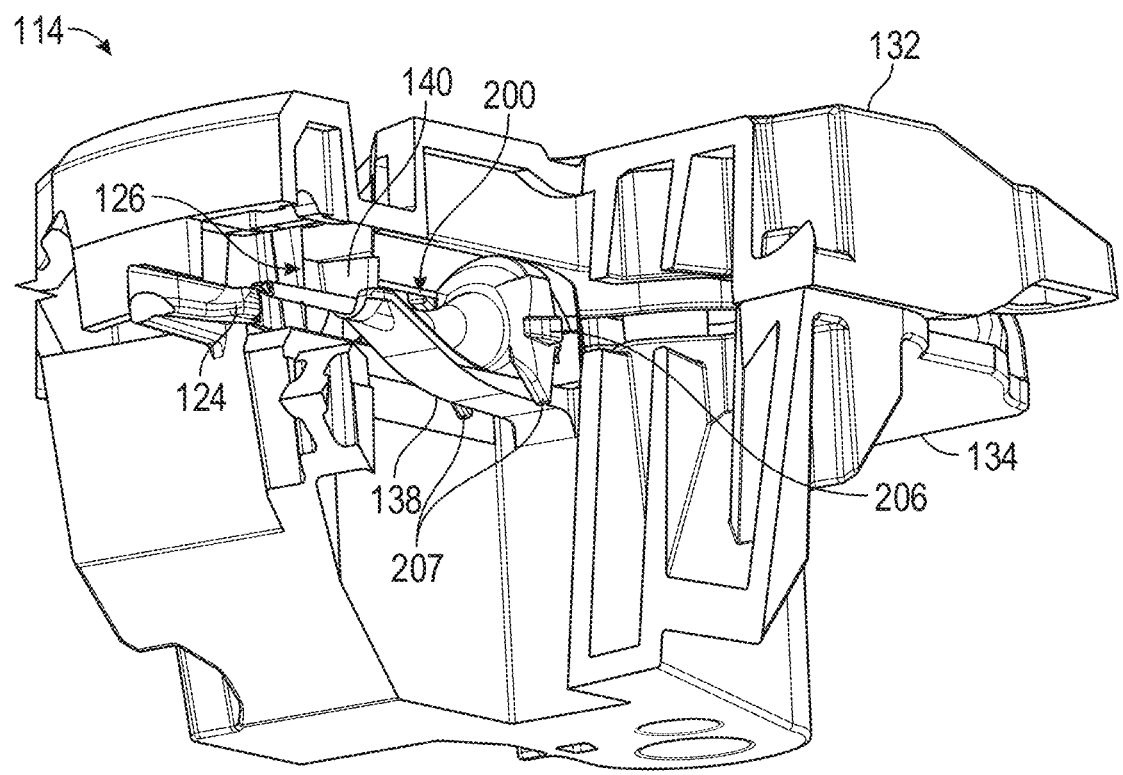
FIG. 10C is a cross-sectional perspective view of the cannula and applicator during insertion of the cannula

Referring now to FIGS. 10A-10F, further details of the applicator, pad, and cannula are described. The applicator and pad may be configured to both insert the cannula and cause the cannula to be locked to the pad in a single actuation. Preferably, pad 102, which is shown as partially cut in FIGS. 10A, 10B, and 10D to better show how cannula 200 and applicator needle 150 are deployed, includes one or more locking mechanisms that may be configured to lock to either the applicator, cannula, and/or the pump-cap assembly. For example, pad 102 may include pad attachments 106, as described above, and the applicator may include flexible attachment pad couplers 124, which are configured to fit within one or more slots of pad attachments 106. In the pre-deployed state, attachment pad couplers 124 are disposed within the slots of pad attachments 106 such that the applicator is coupled to pad 102 via pad skeleton 104, as shown in FIG. 10A.

Upon actuation by the wearer, the cannula is configured to advance distally, through the skin of the wearer. As shown in FIG. 10C, cannula 200 may include one or more clips 206 disposed on cannula head 204 and configured to interact with channel 126 of the applicator and guide cannula 200 in a substantially linear direction during insertion. Cannula head 204 may further include one more wings 207 configured to protrude towards the wearer's skin and to interact with guiding arm 138 to order to prevent cannula 200 from rotating around the longitudinal axis of cannula 200 during and after insertion. As described below with respect to FIGS. 12A and 12B, control of the orientation of the cannula in the wearer's skin is important to ensure precise delivery of medication through the aperture(s).

Figure 10D:
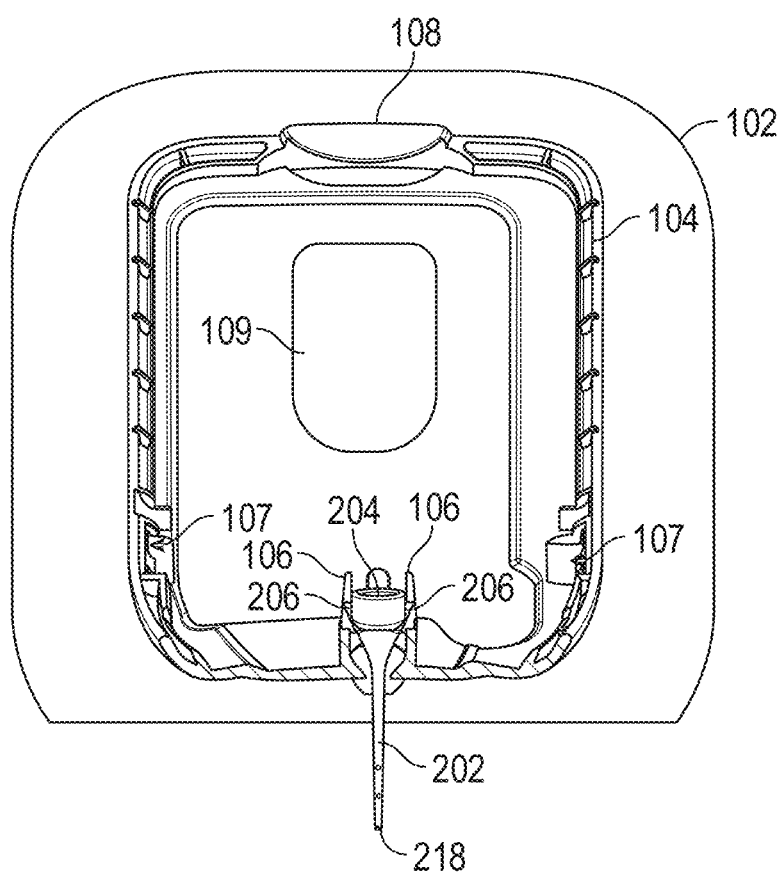
FIGS. 10D-10F are plan, perspective, and side views of the cannula coupled to the pad after the applicator is removed.

Clips 206 preferably are also configured to function as a locking mechanism. For example, clips 206 may be one or more protrusions disposed on a first and second side of cannula head 204. In the deployed state, clips 206 may be disposed within the slots of pad attachments 106 such that the cannula is coupled to pad 102 via pad skeleton 104, as shown in FIG. 10B. This single actuation both locks the cannula to pad 102 and pushes attachment pad couplers 124 away from the slots of pad attachments 106, unlocking the applicator to pad 102. Once the attachment pad couplers 124 are uncoupled to pad attachments 106, the applicator may be removed from the wearer's skin, leaving pad 102 and the cannula in place, as shown in FIGS. 10D-10F.

Figure 10E:
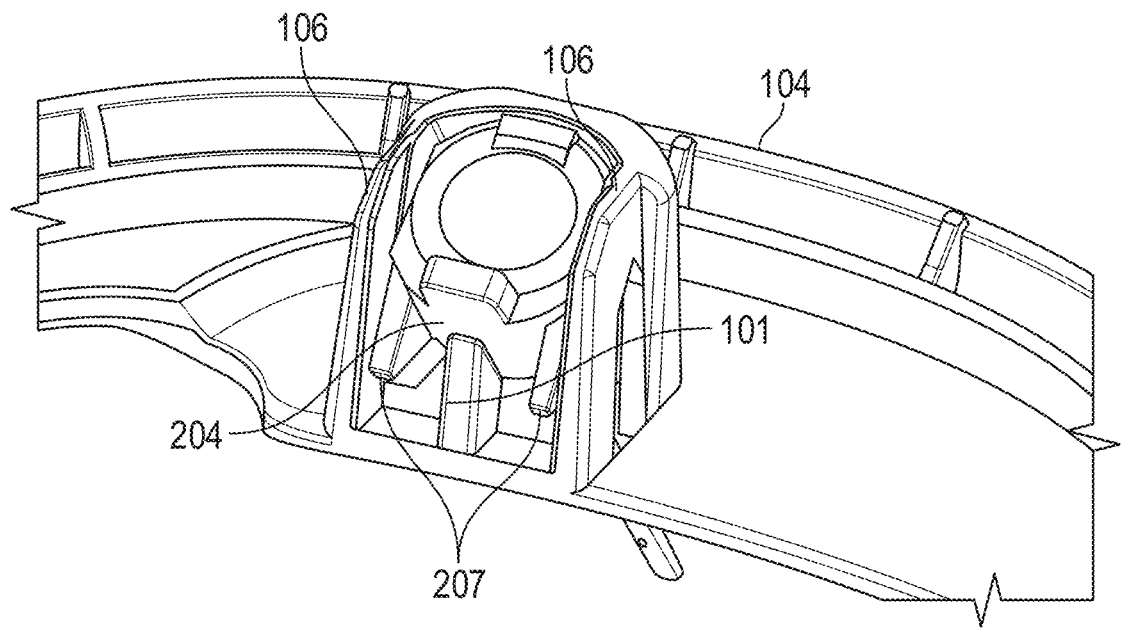
Figure 10F:
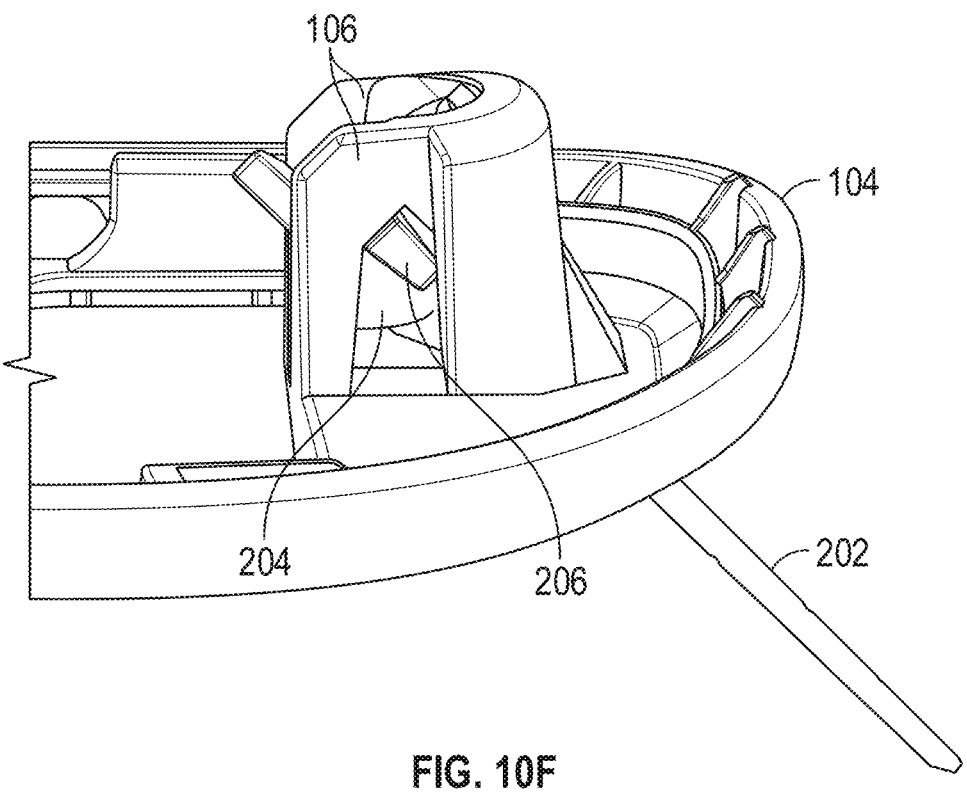

In order to maintain the proper orientation of the cannula, wings 207 are preferably sized and shaped to fit between two pad attachments 106, as shown in FIG. 10E, and clips 206 are preferably sized and shaped to fit within the slots of pad attachments 106, as shown in FIG. 10F. Pad skeleton 104 may further include angled interface 101, which may be disposed between pad attachments 106 and shaped to have an interface at the angle the cannula is inserted such that angled interface 101 engages with cannula head 204 in the deployed state. Ensuring a proper fit of cannula 200 to pad skeleton 104 prevents rotation or other movement of the cannula after insertion, resulting in accurate delivery of medication. After the applicator is removed, the pump-cap assembly may be coupled to the pad-cannula assembly via pad clips holes 107.

Figure 11A:
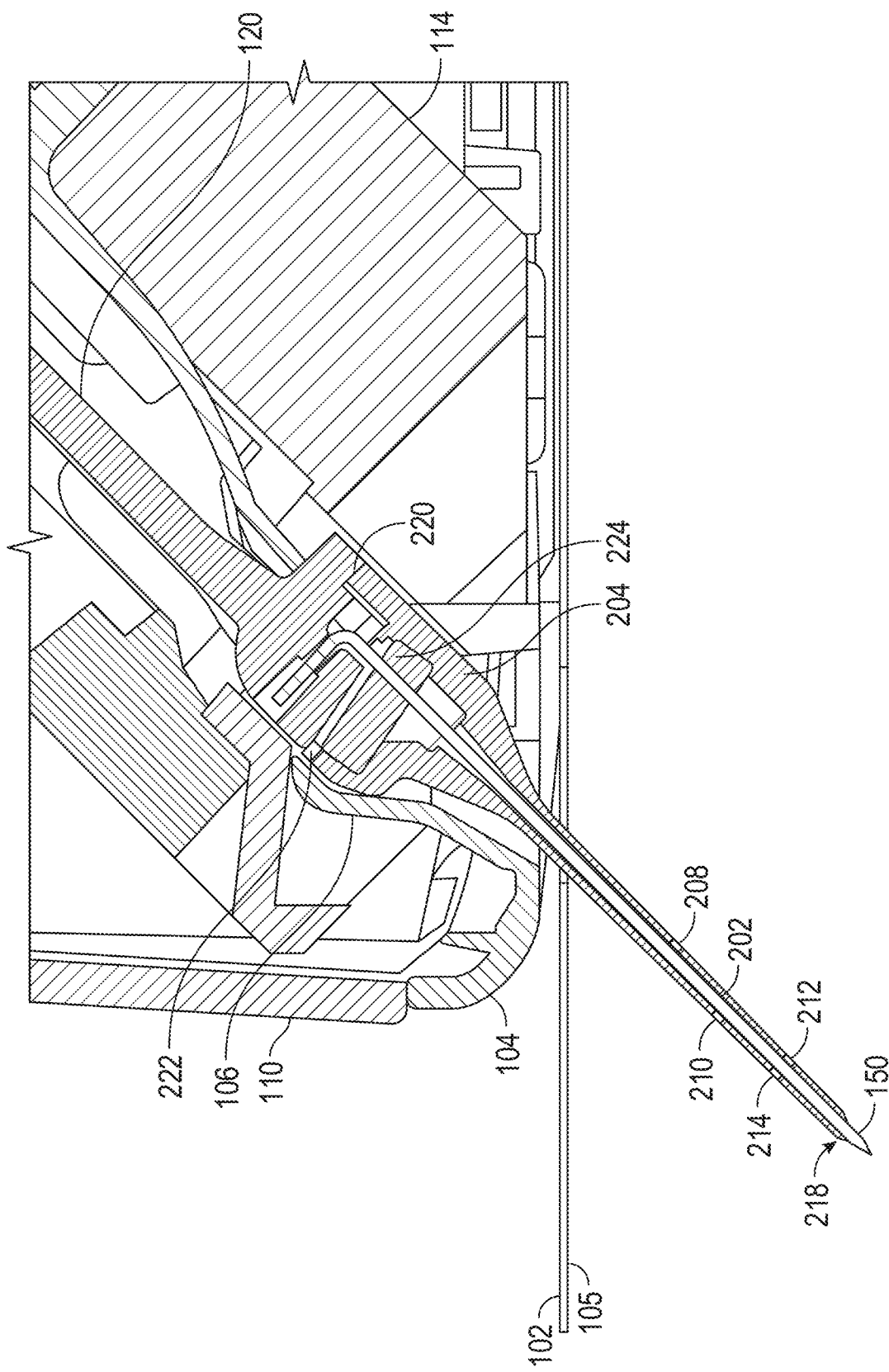
FIG. 11A is a cross-sectional side view of the applicator, pad, and cannula showing the cannula inserted into the wearer.

Referring now to FIG. 11A, further aspects of the applicator, pad, and cannula are described. In FIG. 11A, the applicator is depicted in a partially-deployed state, wherein the cannula is inserted into the skin of the wearer, but applicator needle 150 is not yet withdrawn. The distal end of applicator needle 150 may be disposed distal to cannula tip 218 and the proximal end of applicator needle 150 may be coupled to link 120. Applicator needle 150 preferably is inserted through the septum of the cannula and extends past the distal end of the cannula. Septum 224 is a self-sealing material designed to seal the proximal region of the cannula, such as silicone, and minimizes backflow out of the cannula. Septum 224 may be disposed within cannula head 204 and supports and guides applicator needle 150 such that the needle is withdrawn in a substantially linear direction. Applicator needle 150 may be coupled to link 120, which interacts with applicator interfaces 220 and 222 disposed on cannula head 204 and configured to provide smooth and continuous contact with link 120 during insertion of the cannula. After the cannula is inserted, cannula head 204 of the cannula may be locked to pad attachments 106, as shown in FIG. 10B. Elongated shaft 202 of the cannula extends from pad attachments 106, past pad skeleton 104, through pad 102, and into the skin of the wearer. Depending on the type of medication inserted (e.g., insulin), the cannula may be inserted such that apertures 208, 210, 212, and 214 and cannula tip 218 are disposed below the dermal layer of skin.

Figure 11B:
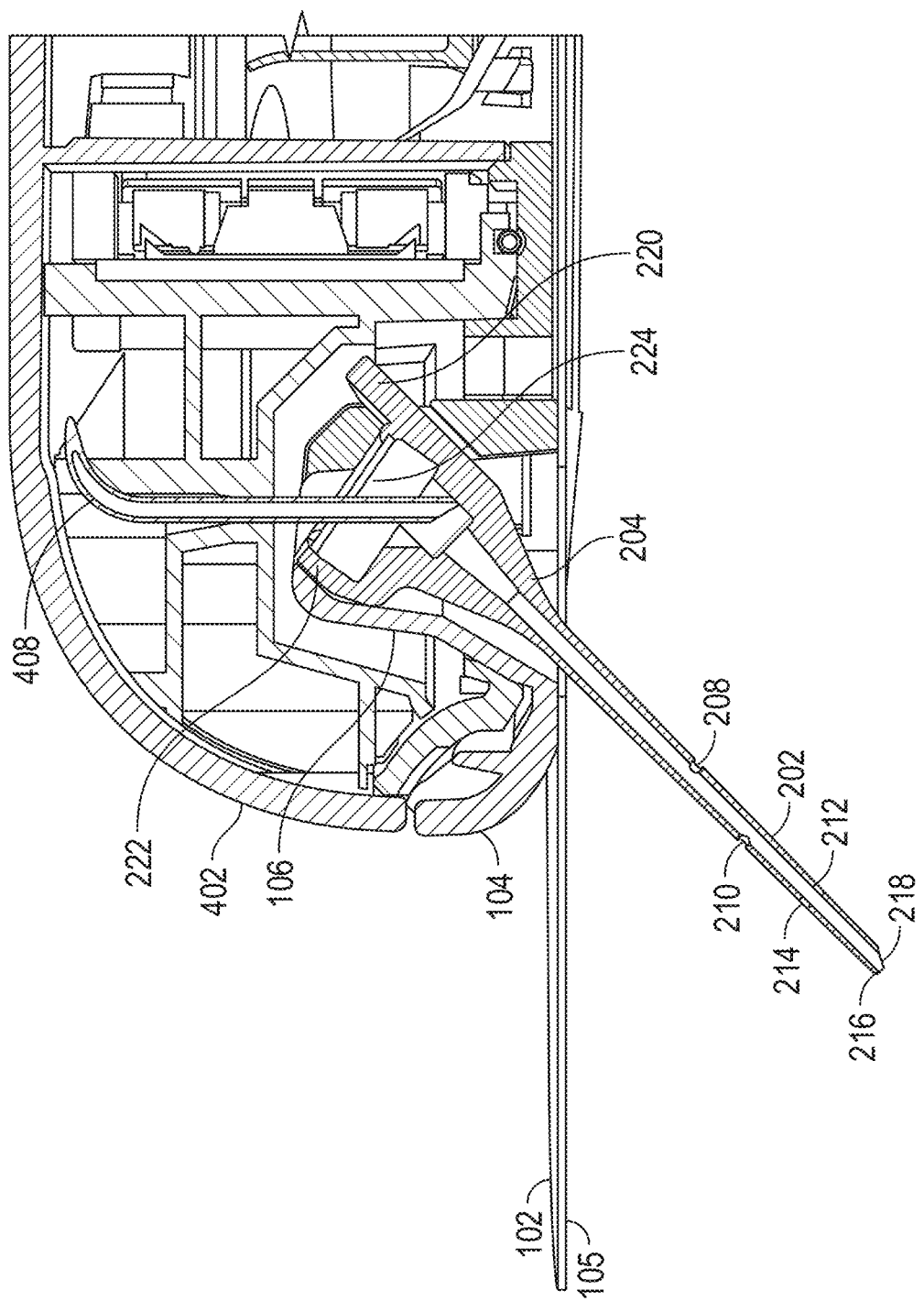
FIG. 11B is a cross-sectional side view of the pad, cannula, and assembled pump showing how the microdosing tubing couples to the cannula to deliver microdoses of medication transcutaneously.

With respect to FIG. 11B, interengagement of the pad and an exemplary patch pump is described. After the cannula is deployed and is coupled to pad 102 via pad attachments 106, as shown in FIG. 10B, the applicator is removed from pad 102. A patch pump constructed in accordance with the principles of the present invention, which preferably includes a disposable cap and a reusable pump, is coupled to pad 102 to deliver medication via the cannula. For example, the patch pump may include a housing that is configured to lock to pad skeleton 104 such that the patch pump is secured to the wearer during the wearer's normal, daily motions. The patch pump may include outflow needle 408, which is in fluid communication with the cannula and to deliver a predetermined dose of medication from a cartridge to the cannula responsive to pumping at the patch pump. Outflow needle 408 preferably is configured to pierce septum 224 of cannula head 204 such that the distal end of outflow needle 408 is disposed below septum 224 and medication flows into elongated shaft 202, rather than back into the patch pump, for transcutaneous delivery to the wearer via one or more apertures of the cannula. Further, as illustrated, the entirety of cannula head 204 may be designed to stay above the skin line and remain external to the patient while elongated shaft 202 is transcutaneous.

Cannula for Delivering Medication

Figure 12A:
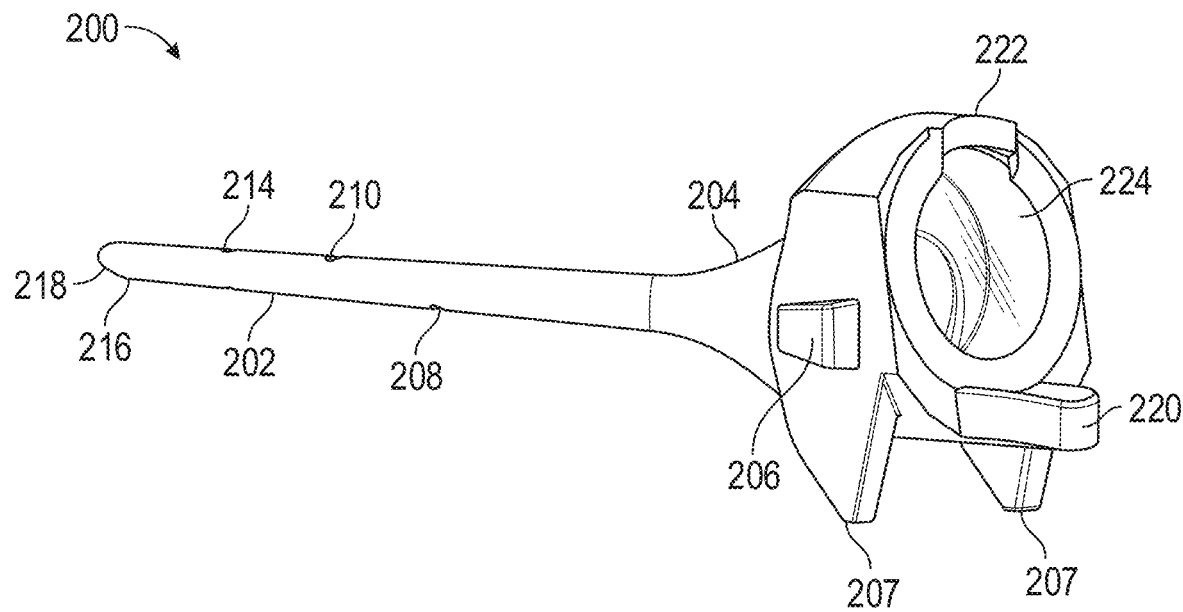
FIGS. 12A and 12B are perspective views of an exemplary cannula for delivering medication.
Figure 12B:
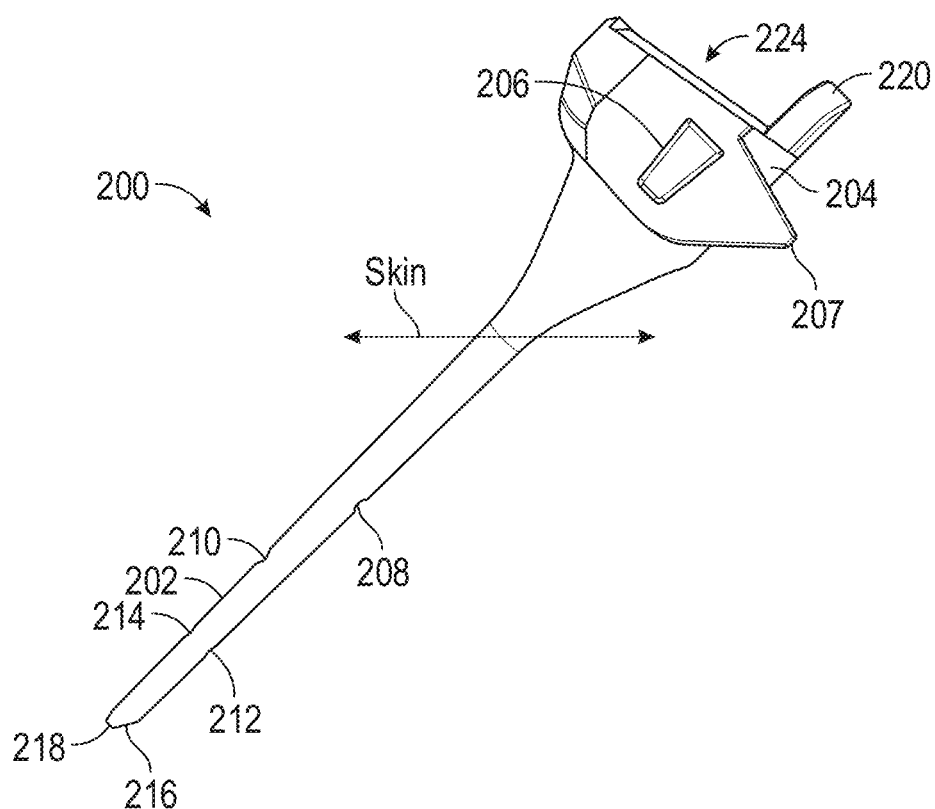

Referring now to FIGS. 12A and 12B, an exemplary cannula for delivering medication is described. Cannula 200 may be injection molded from a single piece of material, which is preferable to extrusion in order to reduce the risk of kinking of cannula 200. Cannula 200 preferably is made from a material that is insulin compatible and flexible and includes cannula head 204, cannula tip 218, and elongated shaft 202. Cannula head 204 is disposed at the proximal end of cannula 200 and configured to interact with the applicator needle and the needle through which the medication is delivered. Cannula tip 218 is disposed at the distal end of cannula 200 and may include distal aperture 216 for delivering medication. Elongated shaft 202 may extend between cannula head 204 and cannula tip 218 and may include one or more apertures for delivery of medication. Elongated shaft 202 may increase in diameter towards cannula head 204 and the wearer's skin surface, to mitigate the risk that the delivered medication travels proximally along the outside surface of the cannula to the dermal layer or the surface of the skin. This conical shape may also reduce the risk of kinking of cannula 200.

Elongated shaft 202 also may have one or more apertures disposed along the elongated shaft in any configuration. Preferably the apertures are disposed such that medication is delivered only below the dermal layer of the skin. As depicted in FIG. 12A, cannula 200 may include aperture 210 and aperture 214, disposed distal to aperture 210, which are oriented towards the skin surface of the wearer. As shown in FIG. 12B, cannula 200 also may include aperture 208 and aperture 212, which are oriented away from the skin surface of the wearer. As will also be understood by one of ordinary skill in the art, the cannula may be configured such that the apertures are axially oriented relative to a different target infusion area within the wearer.

Cannula head 204 may include one or more applicator interfaces that are configured to interact with link 120 to permit rotational movement of the cannula during insertion of the cannula into the skin of the wearer. For example, applicator interface 220 may be disposed on the side of cannula head 204 that is farthest away from the skin surface of the wearer. Applicator interface 220 may be a rounded, convex protrusion, which interacts with a corresponding rounded, concave receptacle of link 120. Cannula head 204 also may include applicator interface 222, which may be disposed on the opposite side of the cannula head, the side closest to the skin surface of the wearer. Applicator interface 222 may be a rounded, concave receptacle, which interacts with a corresponding rounded, convex protrusion of link 120. The rounded shapes of applicator interfaces 220 and 222 and the corresponding features of link 120 are designed such that link 120 maintains smooth and continuous contact with cannula head 204 during insertion of cannula 200 into the wearer's skin.

Cannula head 204 also may include one or more clips 206 configured to guide cannula 200 in a substantially linear direction. Clips 206 may be any component of cannula head 204 that is configured to interact with the channel of the internal component of the applicator during insertion of cannula 200 into the wearer's skin. For example, clips 206 may be one or more wings disposed on a first and second side of cannula head 204 and sized and shaped to slide along the ledges of the channel. Clips 206 alternatively may be receptacles disposed on cannula head 204 and configured to slide along corresponding protrusions of the channel. Cannula head 204 may further include wings 207, which may be configured to interact with the guiding arm to order to prevent cannula 200 from rotating around the longitudinal axis of cannula 200 during and after insertion. Preferably, wings 207 are configured to protrude towards the wearer's skin and the guiding arm and are sized and shaped such that the guiding arm fits between the two wings. Clips 206 and wings 207 are designed to control orientation of the cannula during delivery and insertion. Because the apertures along the shaft of the cannula may be radially and longitudinally offset from one another, control of the orientation of the cannula in the wearer's skin is important to ensure precise delivery of medication through the aperture(s). Thus, clips 206 and wings 207 ensure axial orientation in a target direction of the apertures.

Figure 13A:
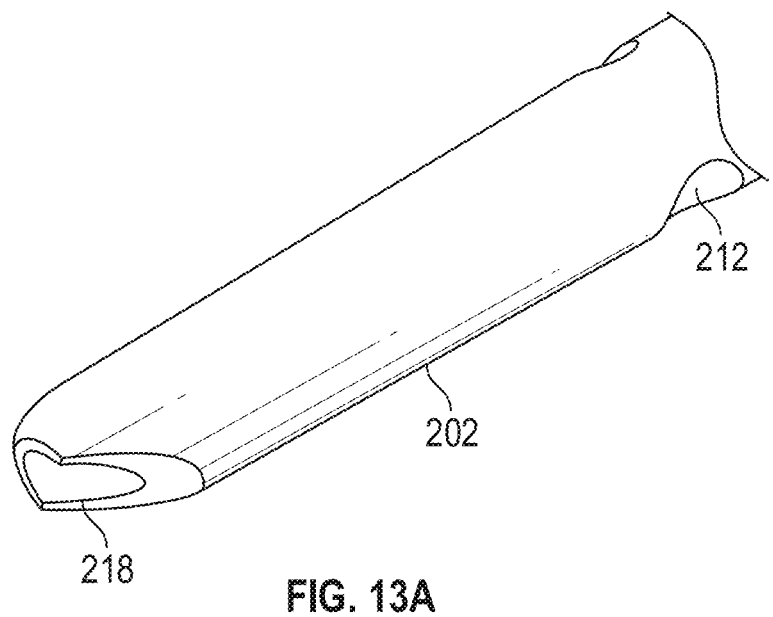
FIGS. 13A and 13B are perspective views of alternative embodiments of the distal end of the cannula.
Figure 13B:
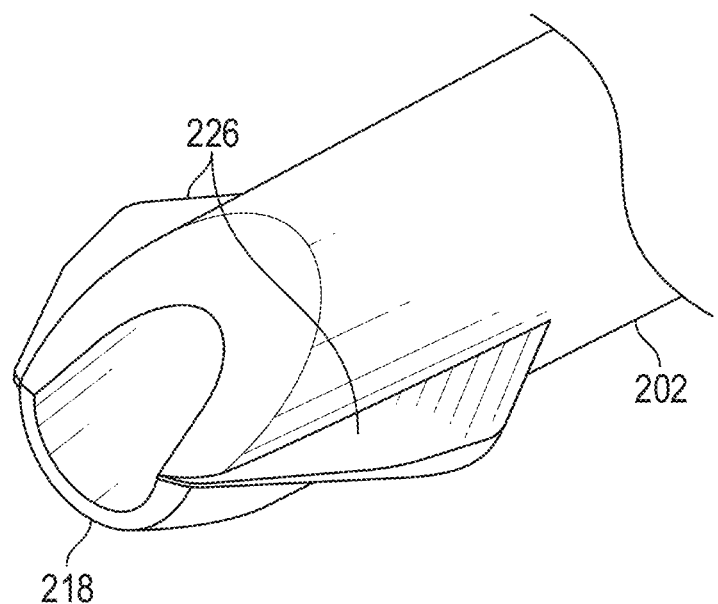

Referring to FIGS. 13A and 13B, alternative embodiments of the distal end of the cannula are described. In FIG. 13A, cannula tip 218 has an angled tip for inducing curvature in the cannula during insertion. Preferably, the cannula is curved towards the surface of the skin, which permits the cannula to have a greater length without being inserted too deep within the wearer's skin. The greater the length of the cannula, the more apertures that may be positioned along elongated shaft 202, which may extend the life of the cannula. Further, the angled tip may be oriented such that the distal portion of the angled tip is configured to be oriented nearer the skin surface than the proximal portion of the angled tip.

FIG. 13B depicts an alternative embodiment of the distal end of the cannula, which includes one or more knife blades 226, which are configured to reduce the pain from insertion of the cannula and maintain the preferred axial orientation of the cannula during and after insertion. Knife blades 226 may extend proximally from cannula tip 218 along a portion of elongated shaft 202. Knife blades 226 have sharpened edges to facilitate piercing the skin and insertion of the distal end of the cannula. Preferably, two knife blades disposed on opposing sides of the cannula shaft, adjacent to the distal end, may be employed.

Figure 14A:
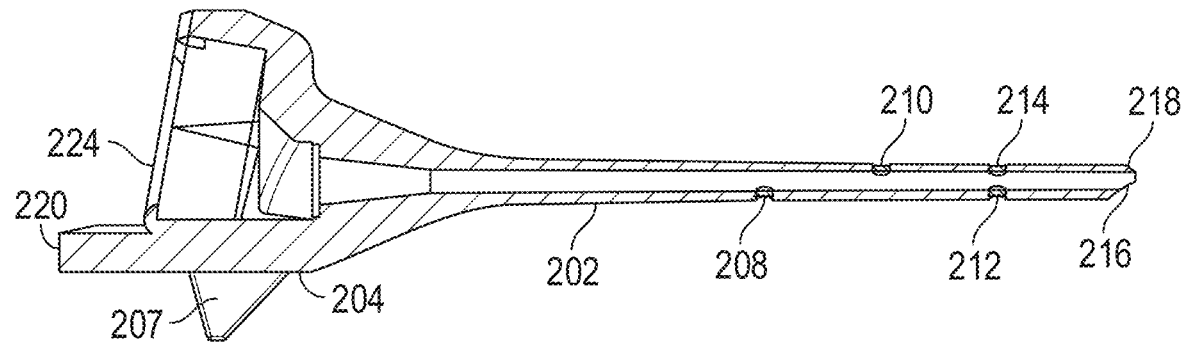
FIG. 14A is a cross-sectional side view of the cannula and multiple exemplary apertures.

Turning to FIG. 14A, an embodiment of a cannula having multiple apertures is described. The apertures are preferably arranged in a configuration that ensures the medication is delivered to the appropriate location within the wearer's skin. The multiple apertures also may be arranged such that medication is delivered along the length of elongated shaft 202. The cannula may include cannula head 204, cannula tip 218, and elongated shaft 202. Cannula head 204 may include septum 224, which is configured to both support the applicator needle during insertion of the cannula into the wearer's skin and to support the needle of the patch pump during delivery of the medication. The applicator needle is disposed through septum 224 during the insertion of the cannula into the wearer's skin.

The cannula may have several apertures for delivery medication, such that medication is delivered only below the dermal layer of skin. Distal aperture 216 may be disposed at cannula tip 218 and four apertures may be disposed along elongated shaft 202. Apertures 208 and 212 are disposed on the side of elongated shaft 202 oriented away from the skin surface of the wearer and apertures 210 and 214 are disposed on the side of elongated shaft 202 oriented towards to the skin surface of the wearer. Aperture 208 may be the proximal most aperture such that medication delivered through aperture 208 is delivered in the direction away from the skin surface of the wearer. This configuration of apertures mitigates the risk of delivering medication into the derma layer of the wearer's skin. Delivery below the dermal layer of skin is particularly important for insulin delivery in order to ensure stable absorption. As described above, clips 206 and wings 207 may be used to ensure a desired orientation of cannula shaft during and after insertion to align the apertures in the desired manner.

With respect to FIGS. 14B-14E, alternative embodiments of cannula comprising biodegradable materials are described. The use of biodegradable materials within the cannula expands the insulin infusion area and volume over time. One of the main issues with previously known cannula is the risk of occlusion, which occurs when insulin reacts with fat. The typical life of a cannula with a single aperture at the distal end (e.g., distal aperture 216) is about 3-4 days. The addition of biodegradable materials that dissolve to open additional apertures over time may extend the life of the cannula to at least 7-10 days. The greater the life of the cannula, the fewer times the wearer is required to insert a new cannula into their skin at a different location and the less waste created from used cannulas.

The biodegradable materials may either be disposed within the lumen of the cannula ("lumen plug") or within the apertures of the cannula ("aperture plug") such that medication may still travel through the lumen and distal aperture 216. The biodegradable materials preferably have fast degradation rates, e.g., several days. Exemplary biodegradable materials include: polysaccharide-based materials; salt; silk; hyaluronic acid (HA); polyethylene glycol (PEG); saturated aliphatic polyesters:poly(lactic acid) (PLA), polyglycolide (PGA), combination thereof (poly(lactide-co-glycolide), PLGA); polyanhydrides.

Figure 14B:
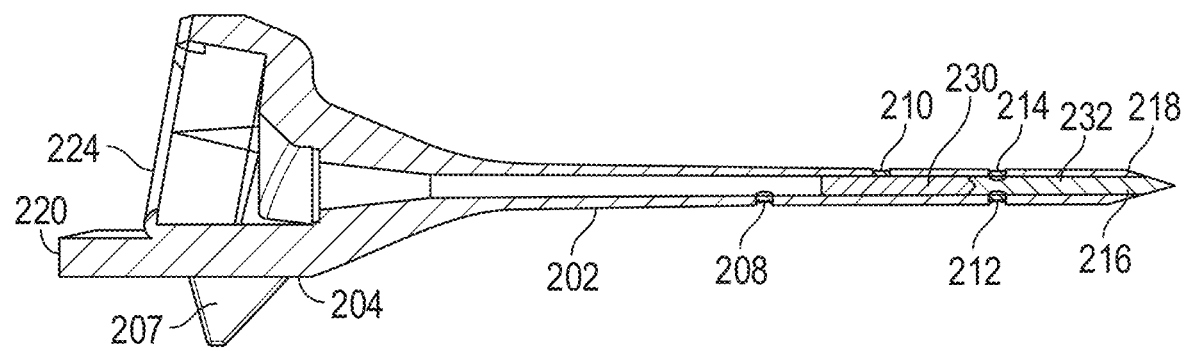
FIGS. 14B-14E are cross-sectional side views of alternative embodiments of the cannula comprising biodegradable materials.

The cannula of FIG. 14B includes two types of lumen plugs in an initial state. First biodegradable material 230 and second biodegradable material 232 may be disposed within elongated shaft 202 and block one or more apertures. First biodegradable material 230 may have a shorter dissolution time than second biodegradable material 232. For example, first biodegradable material 230 may have a dissolution period of 2-3 days and second biodegradable material 232 may have a dissolution period of 4-6 days. First biodegradable material 230 preferably is disposed distal to the proximal-most aperture (e.g., aperture 208) such that, in the initial state, medication may be delivered through the proximal-most aperture. First biodegradable material 230 may block one or more apertures along elongated shaft. For example, first biodegradable material 230 preferably blocks aperture 210 but does not block apertures 212 or 214 or distal aperture 216.

Figure 14C:
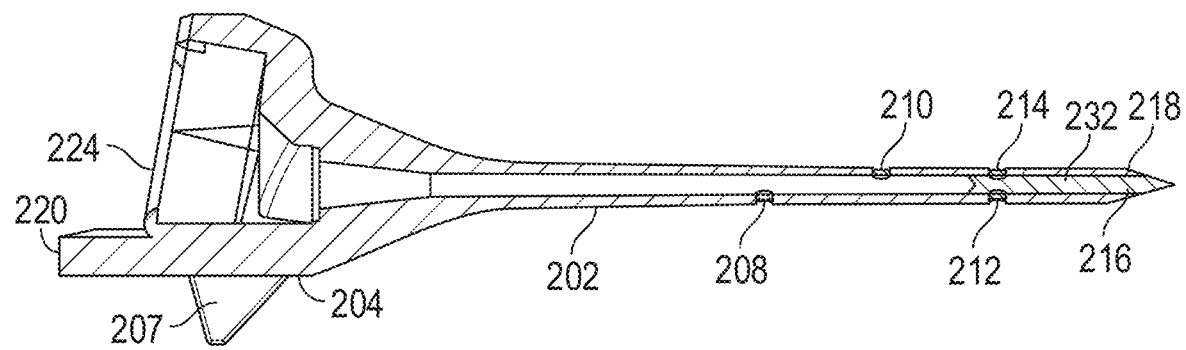

As shown in FIG. 14C, after first biodegradable material 230 dissolves, aperture 210 is opened and second biodegradable material 232 remains disposed within the lumen of the cannula. Second biodegradable material 232 may be disposed distal to first biodegradable material 230 and preferably blocks apertures 212 and 214 and distal aperture 216. After second biodegradable material 232 dissolves, all of the apertures of the cannula may be opened. Over time, the apertures through which medication is initially delivered may become occluded due to the reaction between the delivered insulin and the fat. However, the dissolution of the biodegradable materials at varying times mitigates this issue by periodically opening new apertures.

In the cannula plug embodiment of FIGS. 14B and 14C, a modified applicator needle and method for inserting the cannula may be necessary. For example, the applicator needle may be shortened such that it does not extend through any biodegradable material. If the applicator needle does not extend past the distal tip 218, the distal-most cannula plug, second biodegradable material 232, preferably is configured to have a sharp distal end that is configured to pierce the wearer's skin.

Figure 14D:
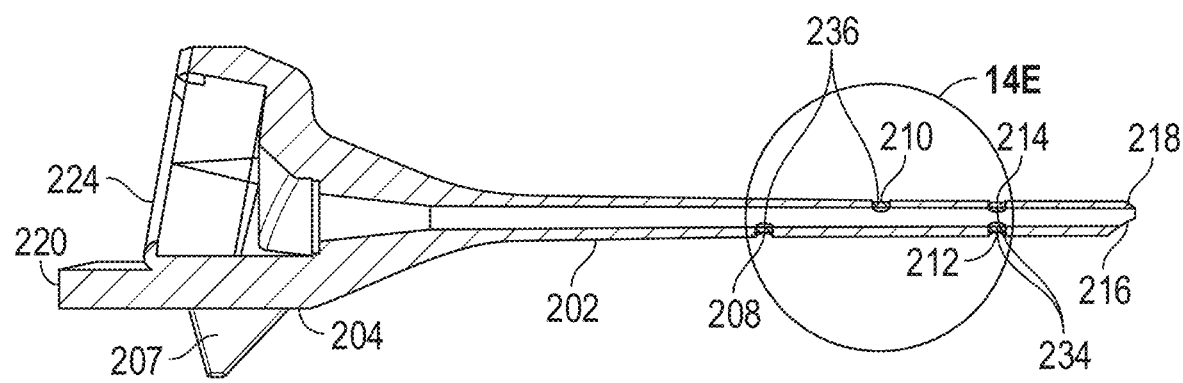
Figure 14E:
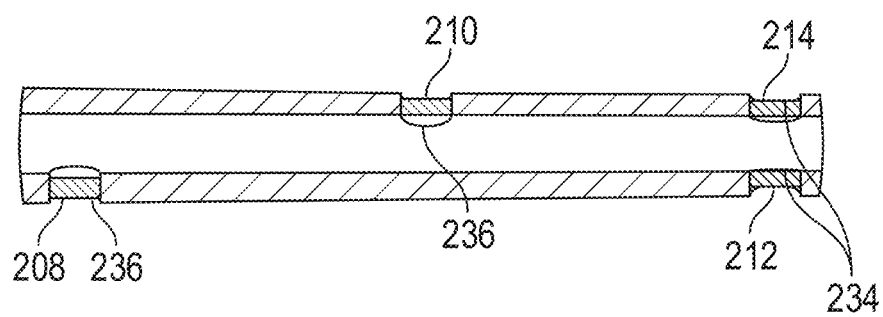

With respect to FIGS. 14D and 14E, a cannula having two types of aperture plugs in an initial state is described. Third biodegradable material 234 and fourth biodegradable material 236 may be disposed within the apertures on elongated shaft 202 such that medication may still travel through the lumen and distal aperture 216, which remains unblocked. Third biodegradable material 234 may have a shorter dissolution time than fourth biodegradable material 236. For example, third biodegradable material 234 may be similar to first biodegradable material 230 and may have a dissolution period of 2-3 days. Fourth biodegradable material 236 may be similar to second biodegradable material 232 and may have a dissolution period of 4-6 days. Third biodegradable material 234 preferably is disposed within apertures 212 and 214 and fourth biodegradable material 236 preferably is disposed within apertures 208 and 210. As the delivered insulin reacts with fat, potentially occluding distal aperture 216 and apertures 212 and 214, fourth biodegradable material 236 will dissolve, opening apertures 208 and 210.

As will also be understood by one of ordinary skill in the art, the cannula may include only one biodegradable material or may include more than two biodegradable materials. In the lumen plug embodiment, the biodegradable materials may be configured to block one or more apertures. In the aperture plug embodiment, the biodegradable materials may be configured to block different apertures than illustrated. As will also be understood, biodegradable materials may have a dissolution period of 0-10 days, and the choice of biodegradable material may depend upon the configuration of the biodegradable materials and the number of different types of biodegradable materials incorporated into the cannula.

Reusable Patch Pump and Disposable Cap for Delivering Medication

Figure 15A:
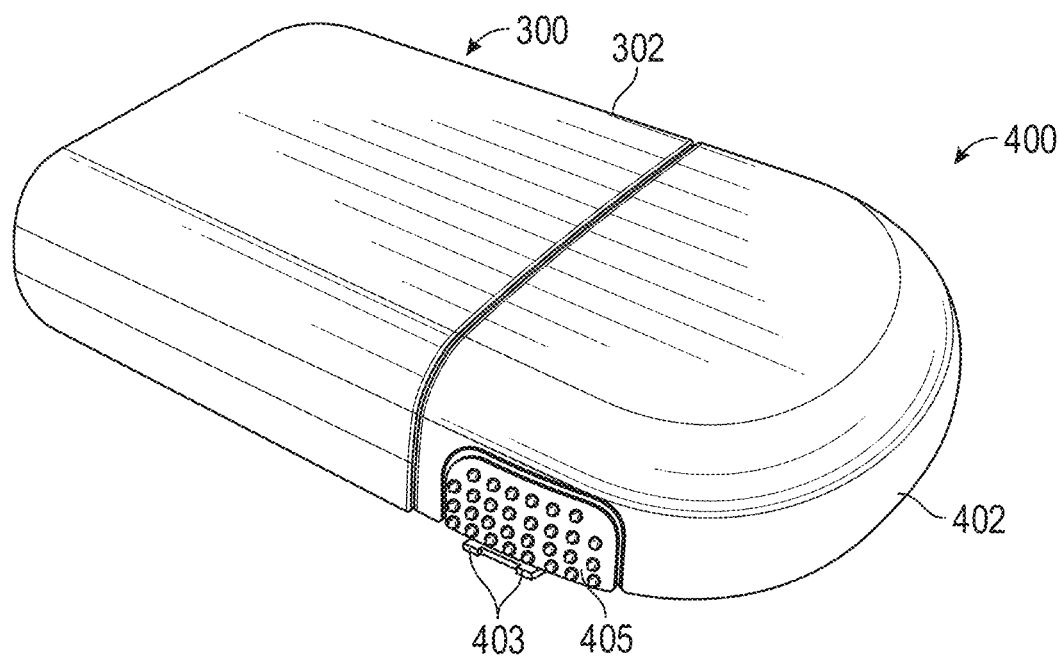
FIGS. 15A and 15B are perspective views of an exemplary patch pump with a pump-cap assembly.
Figure 15B:
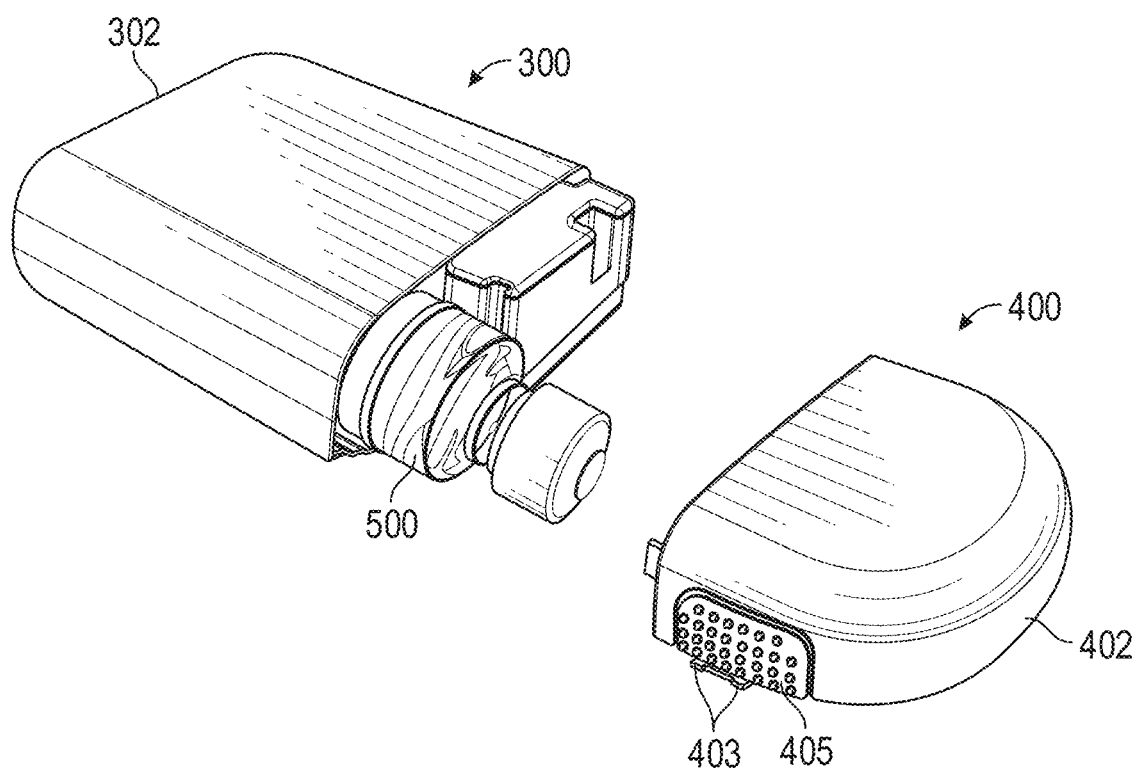

Referring now to FIGS. 15A and 15B, perspective views of an exemplary patch pump and pump-cap assembly constructed in accordance with the principles of the present invention are described. The patch pump is configured to attach to the adhesive pad secured to the wearer and to deliver doses of medication through the inserted cannula. The patch pump preferably includes a reusable pump, a disposable cap, a disposable pre-filled cartridge of medication, and a pad. The pump is configured to be used for several years, thus reducing waste as well as the cost of the system. The user preferably may own two reusable pumps, which allows the user to recharge the first pump while wearing and receiving medication from the second pump. As described above, the first pump may communicate data to or from the second pump, so as to provide continuity of insulin infusion when one pump is changed out for the other pump. The wearer may alternative using two pumps such that one pump is the center of the configuration data system controlling, among other things, the insulin delivery process, the heart rate measurement process, the glucose measurement process, the authentication of the pumps to each other, and the authentication of the user's smartphone, the authentication of the user, and the authentication of the physician. At any given time no or only one pump is active. The pumps share their configuration data when possible, either directly with the other pump or via a file temporarily stored in the patient's smartphone. The data may be secured by encryption and authenticated by a signature, both operations using the best standards in the field. The data may be transferred from the active pump to the non-active pump. Preferably, only the active pump can change the configuration via instructions given by the wearer or the physician.

The patch pump may include pump 300 preferably designed to be used for an extended period of time (e.g., 2-4 years), and cap 400 preferably designed to be replaced after a much shorter period of time (e.g., 3-5 days). The patch pump also may include a pre-filled cartridge of medication, such as cartridge 500, which may be filled during manufacturing or by the wearer prior to inserting cartridge 500 into the pump. For example, the wearer may pre-fill several cartridges configured to last one month and store the pre-filled cartridges in the fridge until the cartridge are to be used. The patch pump may be configured such that the pre-filled cartridges may be inserted into the patch pump as soon as the cartridges are removed from the fridge. For example, the patch pump may complete an initialization process, described further below, which reduces the formation of bubbles within the cartridge. Preferably, the wearer need not wait a certain period of time (e.g., 20 minutes) before inserting the cartridge into the patch pump. Cartridge 500 may include a cartridge cap through which an inflow needle of cap 400 is disposed and a plunger, disposed at the opposite end and configured to be advanced toward the cartridge cap to deliver insulin. Cartridge 500 is configured to be inserted into the patch pump such that cartridge 500 is completely enclosed within the patch pump. For example, cartridge 500 may be inserted first into pump 300 such that a portion of cartridge 500 remains outside of pump housing 302. Cap 400 then may be coupled to cartridge 500 such that an inflow needle disposed within cap 400 pierces the cartridge cap of cartridge 500. While still maintaining inflow needle within cartridge 500, cap 400 then may be rotated relative to pump 300 to lock cap 400 to pump 300, thereby coupling the cap-pump assembly to the pad and the pump.

Pump 300 may include a motor disposed within pump housing 302, the motor configured to move a pusher coupled to the plunger of cartridge 500 such that insulin is advanced through an inflow needle of cap 400 and to a microdosing system designed to measure and deliver predetermined doses of medication. The same motor may simultaneously activate the plunger of the cartridge and the microdosing system, for example, via a gearbox. Doses of medication may be delivered to the user responsive to operation of a processor, in accordance with programming stored in memory associated with the processor or specifically when requested by the user, e.g., using a suitable wireless application on the user's smartphone. The processor may be configured to monitor one or more sensors and modify operation of pump 300 or alert the wearer based on information sensed by one or more sensors.

Cap 400 is configured to receive medication from cartridge 500 and deliver predetermined doses of the medication through an outflow needle, into cannula 200, and to the wearer. Cap 400 preferably includes a microdosing system configured to measure and deliver the predetermined doses of medication. Cap 400 further may include locking mechanisms configured to lock cap 400 to pump 300 such that cartridge 500 is completely enclosed within pump housing 302 and cap housing 402 in a closed and locked position. Cap 400 may include additional locking mechanisms configured to lock the pump-cap assembly to the pad. For example, cap 400 may include one or more cap clips 403, which may be sized and shaped to fit within one or more pad clips holes disposed on the pad skeleton. The pump-cap assembly may be unlocked from the pad by pressing unclipping buttons 405, which preferably are configured to deflect cap clips 403 such that cap clips 403 may be removed from the pad clips holes. This method of locking and unlocking the pump-cap assembly to the pad ensures that the patch pump will remain in place during the wearer's daily motions and is convenient for the wearer to secure and remove the pump-cap assembly. For example, the wearer preferably can clip/unclip the pump-cap assembly from the pad using one hand, even if the patch pump is secured to a difficult to reach area of the body, such as the back of the arm.

Figure 16:
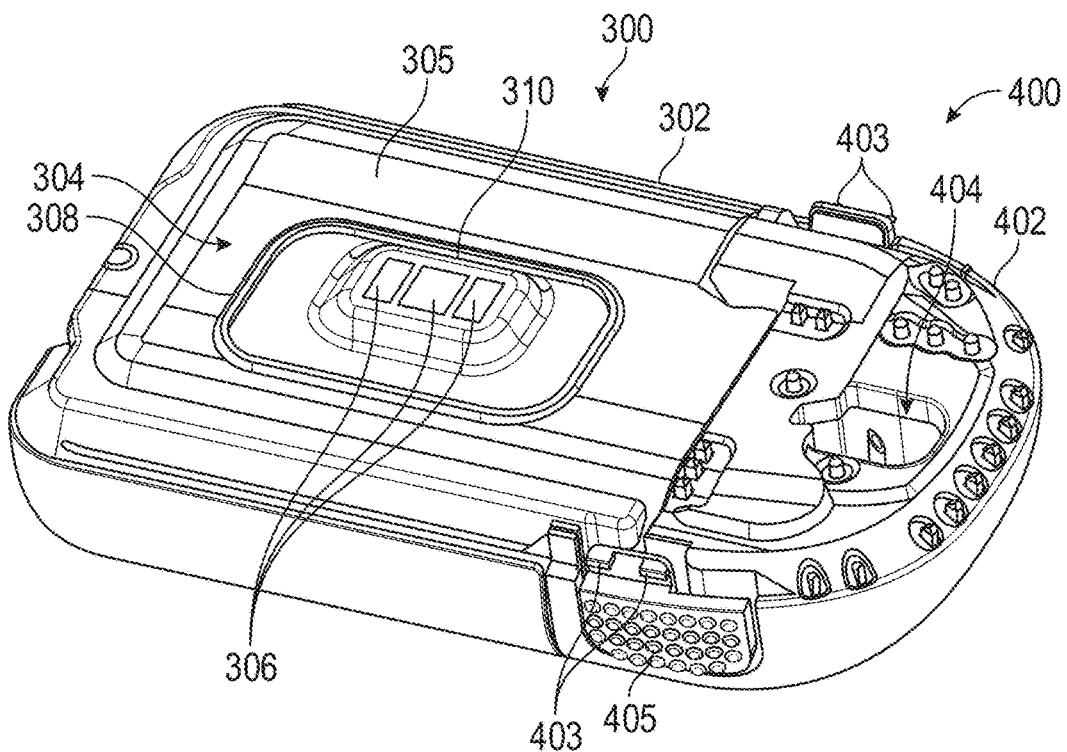
FIG. 16 is a perspective view of the skin-facing side of the pump-cap assembly.

Referring to FIG. 16, the lower side of the assembled patch pump is described. The patch pump includes pump housing bottom 305, which is the lower side, or skin-facing side, of the pump that is oriented toward the wearer's skin. Pump housing bottom 305 may be coupled to pump housing 302, which is an upper side of the pump that is oriented away from the wearer's skin. Pump housing bottom 305 may have a slight concavity such that the patch pump maintains contact with the wearer's skin. The patch pump preferably includes reusable pump 300 having pump housing 302 and disposable cap 400 having cap housing 402, which are coupled together with the pad to form the patch pump. Cap 400 further may include connection cavity 404, sized and shaped to receive the pad attachments and cannula head, which protrude from the pad and lock the cannula to the pad, when the patch pump is locked to the pad. Connection cavity 404 may house an outflow needle that is configured to interact with the cannula. Cap 400 may include one or more cap clips 403, which may be coupled to one or more unclipping buttons 405 that may be pressed to unlock the pump-cap assembly from the pad. Preferably, the cap includes two unclipping buttons 405 disposed on each side of the cap, each unclipping button 405 having two cap clips 403 that are sized and shaped to fit within the pad clips holes disposed on the pad skeleton, thereby allowing lateral clipping.

Pump 300 may include a photoplethysmography sensor configured to determine the wearer's heart rate or other physiologic parameters, which may be used to adjust the delivery of medication from pump 300 to the wearer, as described in U.S. Pat. No. 11,241,530 to Fridez et al. and PCT International Application No. PCT/IB2021/060766, the entire contents of each of which are incorporated herein by reference. For example, using physical activity level, or a determination that the wearer is sleeping or awake, a small change may be made in an algorithm that controls an amount or rate of insulin injection, which could significantly influence blood glucose level. The patch pump controller also could use heart rate, as determined by the photoplethysmography sensor, to implement a sport mode, for example, that permits a slightly higher glucose target to decrease the risk of hypoglycemia after physical exertion.

The photoplethysmography sensor may be electrically coupled to a circuit board disposed within pump 300 and may be disposed within photoplethysmography sensor frame 304, which is disposed on the skin-facing side of pump housing 302. Photoplethysmography sensor frame 304 may extend through a pad opening in the pad attached to the wearer. The skin-facing side of pump housing 302 preferably is configured to include one or more protrusions such that the photoplethysmography sensor maintains contact with the wearer's body surface during motion, while also reducing cross talk between emitters and detectors and from ambient light impinging upon the photoplethysmography sensor. For example, the skin-facing side of pump housing 302 may include optional rib 308, configured to protrude from pump housing 302 to block light. Rib 308 may surround bump 310, which houses the photoplethysmography sensor. Bump 310 preferably protrudes farther from pump housing 302 than rib 308, such that bump 310 maintains contact with the wearer's skin while ensuring that the contact force of bump 310 does not apply excessive pressure to the wearer's skin or cause tissue necrosis.

The photoplethysmography sensor is designed to generate a strong photoplethysmography signal suitable for heart rate monitoring and pulse oximetry and may include one or more LEDs and one or more detectors. The photoplethysmography sensor may include an exemplary multi-chip photoplethysmography package suitable for use in the patch pump, for example, the SFH 7072 BIOFY® Sensor device commercially available from OSRAM Opto Semiconductors GmbH, Regensburg, Germany. The multi-chip photoplethysmography package may include red, infrared, and green LEDs, an infrared cut detector to detect reflected light from green LEDs, and a broadband detector to detect reflected light from red and infrared LEDs. Preferably, the red LED has a centroid wavelength of 655 nm, the infrared LED has a centroid wavelength of 940 nm and the green LEDs have a centroid wavelength of 530 nm. The LEDs and detectors are set in a ceramic package that includes one or more light barriers configured to reduce optical crosstalk between the LEDs and detectors.

As is well known in the photoplethysmography art, green LEDs are commonly used in monitoring heart rate in wearables in view of their good signal-to-noise ratio and resistance to motion artifact, while the combination of red and infrared LEDs provides accurate monitoring of blood oxygen saturation. Suitable algorithms are known in the art for processing photoplethysmographic signals generated with red and infrared LEDs and green LEDs to reduce the effects of motion noise, including frequency domain analysis and Kalman filter analysis techniques. Alternatively, infrared-red LEDs may be used, instead of the green LEDs, to compute heart rates for wearers having darker skin complexions. As will also be understood by one of ordinary skill in the art, more or fewer LEDs advantageously could be employed in the photoplethysmography sensor.

Photoplethysmography sensor frame 304 preferably includes one or more transparent windows 306 and a layer, forming bump 310. Photoplethysmography sensor frame 304 may comprise a sturdy biocompatible plastic or rubber material that may have one or more openings. Windows 306 may consist of a clear plastic material having low absorptivity for light at the wavelengths of the LEDs and may be configured to mate with the openings of photoplethysmography sensor frame 304 to provide a smooth exterior surface for bump 310. The layer preferably is a closed cell foam or similar compressible material against which the photoplethysmography sensor is urged against the layer into contact with windows 306. Photoplethysmography sensor frame 304 and the layer preferably are matte black or gray to reduce light scattering of light reflected from tissue through windows 306. Window 306 may be a single thin window <0.5 mm thick or, alternatively may include more than one window.

Heart rate signals generated by the photoplethysmography sensor may be used by the controller to modulate infusion of insulin from the patch pump. Preferably, the photoplethysmography sensor periodically measures the wearer's heart rate, e.g., once every minute, 2-½ minutes or five minutes, and computes a heart rate and a quality measure for the computed heart rate. The quality measure may be used to determine whether to adjust insulin delivery to better maintain the stability of the wearer's blood glucose level.

In addition, the heart rate data may be used to compute an activity intensity level, similar to that employed in physical activity monitors, such as resting, passive behavior, and low, medium and high levels. Such an activity level could be used to adjust parameters of the insulin delivery algorithm to permit a "sport mode" that adjusts insulin delivery to reduce the risk of hypoglycemia during, and especially after, engaging in vigorous or sports activities. The heart rate also could be evaluated to determine whether the wearer is asleep or awake. For example, when a wearer is asleep, the parameters of the infusion algorithm used in the controller could be switched to a sleep mode. This sleep mode may allow fine-tuning of the wearer's glucose level to allow provide better sleep well and improve time in a targeted glucose range. Such adjustments are expected to be possible because while sleeping, the wearer does not eat, is not physically active, and is not physically or emotionally stressed.

Determination that a wearer is asleep or awake additionally could be based on, or confirmed by, data from an accelerometer. Accelerometer outputs also could be analyzed to assess where the patch pump is being worn by the user, and to determine body orientation. The sleep/wake information also may be analyzed to provide a quality measure of the measurement, and thus allow the infusion algorithm employed by the controller to have a good degree of confidence regarding its insulin delivery adjustments. The output of the photoplethysmography sensor also may be used to validate that the patch pump is adequately adhered to the wearer's skin to allow insulin injection, as described further below. If, for example, patch pump includes a capacitive circuit for continuously detecting that the pump is adhered to a wearer's skin, the photoplethysmography sensor could provide confirmation that the pump is located on the wearer's skin.

Figure 17:
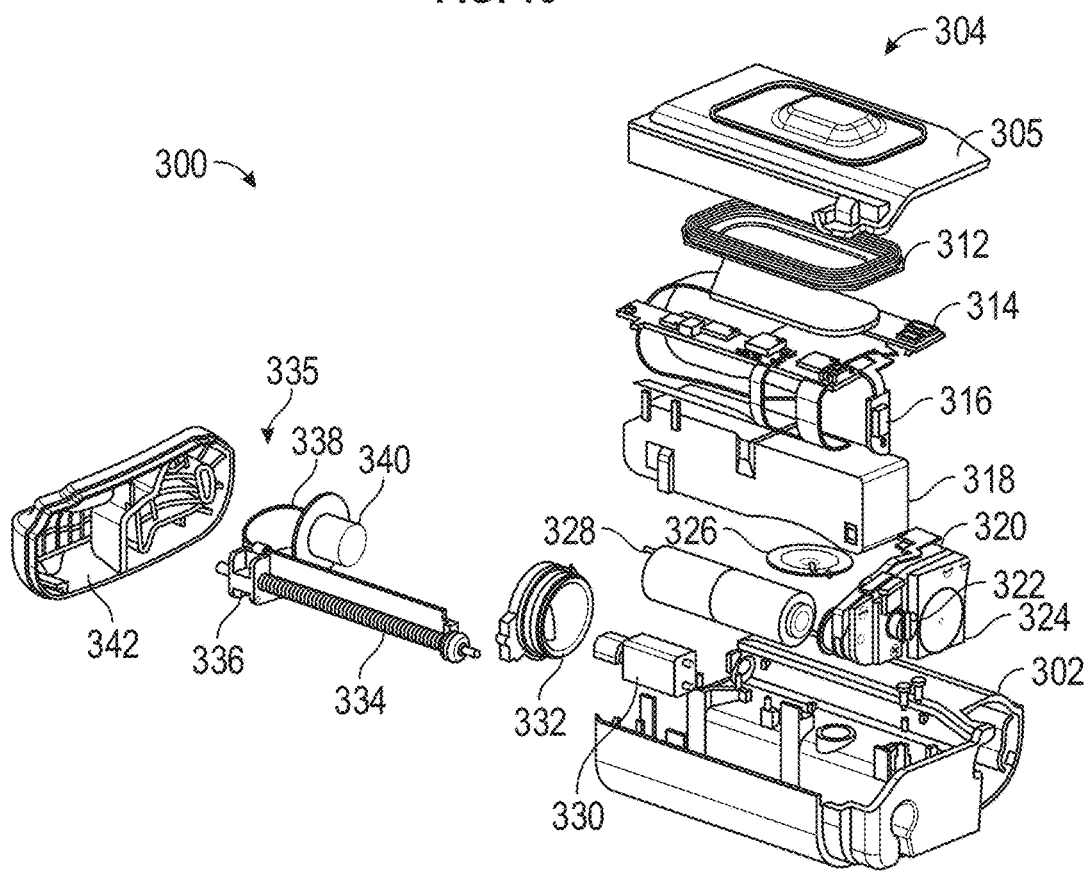
FIG. 17 is an exploded view of the pump.

Referring now to FIG. 17, internal components of an exemplary pump are described. For example, pump 300 may include within pump housing 302 and pump housing bottom 305 the following components: coil 312, circuit board 314, sensor 316, battery 318, sensor 320, mechanical coupling 322, gearbox 324, sound generator 326, pump motor 328, vibration motor 330, cartridge holder 332, and/or pusher 335 (which may include screw 334, nut 336, bendable rod 338, and/or cartridge contactor 340).

Pump 300 may include housing having one or more separate pieces that are configured to couple together to enclose the internal components of the pump. Preferably, pump 300 includes a minimal number of parts such that the cost of the pump is reduced. For example, pump 300 may include pump housing 302 coupled to pump housing bottom 305, which may include photoplethysmography sensor frame 304. Pump housing 302 preferably has a cavity to receive a portion of a pre-filled cartridge. When coupled to the cap housing, the combined housings preferably fully enclose the cartridge. Pump housing 302 may include plethysmography sensor frame 304 and pump housing back 342, which may be disposed on the end of pump housing 302 that does not lock with the cap. Pump housing 302 also may include a dry zone seal and/or one or more dry zone vents, which are configured to separate wet and dry zones of the pump such that the electrical components in the dry zone are isolated from the wet zone and do not contact any fluid and/or to permit humidity and gas to escape the housing such that pressure may equilibrate. In addition, cartridge holder 332 may separate the protected wet zone from the dry zone and may include one or more O-rings to seal off the zones when a cartridge is disposed within the pump-cap assembly.

Coil 312 is electrically coupled to battery 318. Coil 312 may include a magnetic shielding and preferably receives energy from outside pump housing 302 to charge battery 318 of pump 300. For example, a corresponding coil in charging system 600 may transfer energy to coil 312 to charge battery 318. The coils may be inductive coils.

Circuit board 314 permits electrical connection between electrical components within pump housing 302. Circuit board has a controller with one or more processors to execute programmed instructions stored in memory to cause motor 328 to deliver the medication to the wearer and to monitor one or more sensed parameters generated by sensors (e.g., sensors 316 or 320) disposed within or external to pump housing 302.

Sensor 316 is designed to sense information associated with operation of microdosing system 410 and to send the information to the controller for processing. Sensor 316 may, for example, monitor the microdosing function and sense information indicative of the presence of a cap, the status of a cap, and/or an occlusion in the dosing pathway, as described in detail below.

Battery 318 is a rechargeable battery to power the pump. Battery 318 has a capacity sufficient to permit pump 300 to pump all the medication from the cartridge to the wearer with a single charge. Battery 318 may be disposed within the housing and may be charged by a charger via a coil with the charger and coil 312 within pump 300.

Sensor 320 is designed to sense information associated with operation of pump 300 and to send the information to the controller for processing. Sensor 320 may, for example, sense information indicative of the pressure within the cartridge of medication, as described below.

Mechanical coupling 322 is designed to couple with a corresponding portion in the cap of the patch pump to translate motion from pump motor 328 into components of the cap, for example, for microdosing. Mechanical coupling 322 further may be used for locking pump housing 302 to the cap housing. Mechanical coupling 322 is coupled to the output from gearbox 324 such that mechanical coupling 322 may rotate at a reduced ratio as compared to rotation directly output by pump motor 328.

Gearbox 324 may be coupled to motor 328, pusher 335, and/or mechanical coupling 322 such that rotation of the gears with gearbox 324 causes delivery of a predetermined dose of medication to the wearer. As motor 328 turns when activated, gearbox 324 causes a corresponding movement at mechanical coupling 322 and at pusher 335. Gearbox 324 incorporates gears to change the ratio of movement pump shaft rotations of pump motor 328 to generated sufficient torque to drive mechanical coupling 322 and pusher 335. For example, gearbox 324 may utilize gearing that reduces movement generated by pump motor 328 to movement generated by mechanical coupling at a reduction ratio. The reduction ratio may be greater than 10:1, such as 68.42:1. Advantageously, a single pump motor may be used to both push medication out of the cartridge and move the microdosing system to generate the microdose of medication. For example, the single pump motor may simultaneously (1) advance the piston with micro-steps and (2) activate the microdosing system at every pump cycle.

Sound generator 326, responsive to instructions from the controller, generates an audible sound via a buzzer to the wearer. For example, sound generator 326 may generate the audible sound if there is an error with the pump or a sensed physiological parameter is beyond a predetermined threshold.

Motor 328 may be coupled to vibration motor 330, which may be operatively coupled to the controller. The controller may cause the vibration motor to vibrate to alert the wearer based on a sensed parameter by a sensor, which may be operatively coupled to the controller. Preferably the controller is configured to cause vibration motor 330 to vibrate when the sensed parameter falls outside a predetermined threshold stored in memory. In addition, the controller may cause vibration motor 330 to vibrate based on the controller's determination that an error has occurred associated with operation of the patch pump based on the sensed parameter. Alternatively, the controller may be configured to cause vibration motor 330 to vibrate based on the time. For example, the vibration motor may vibrate once every three days to provide regular alerts to the user.

The sensors operatively coupled to the controller may include a sensor configured to sense a pressure within a cartridge, a sensor configured to detect an occlusion in a dosing pathway, a sensor configured to sense the temperature or humidity within the patch pump, a sensor configured to monitor glucose levels of the wearer, a photoplethysmography sensor configured to sense the wearer's heart rate or physiologic parameters, or a sensor configured to sense the wearer's activity level. These sensed parameters may indicate whether the patch pump is running properly, whether the medication is stored at a safe temperature, and whether the wearer's physiologic parameters are at a safe level. Preferably, the controller is configured to cause vibration motor 330 to vibrate when the pressure within the cartridge falls outside a predetermined pressure range, when the wearer's glucose level falls outside a predetermined glucose level range, when the wearer's heart rate or physiologic parameters fall outside a predetermined photoplethysmographic threshold, and/or when the wearer's activity level is outside a predetermined threshold. The controller also may be configured to cause vibration motor 330 to vibrate when the sensor detects information indicative of an occlusion or only when the sensor twice detects information indicative of an occlusion. Additionally or alternatively, the wearer may be alerted via sound generator 326, a user interface having LEDs, which also may be disposed within pump 300, or a mobile application.

Pusher 335 is designed to push, responsive to movement from pump motor 328, on an end of the cartridge. Preferably, pusher 335 pushes on a flexible plunger within the cartridge to move medication out of the cartridge during dosing. Pusher 335 also may push the plunger of the cartridge to increase pressure in the cartridge without moving medication to the wearer, for example, during pump initialization. Pusher 335 may include screw 334, nut 336, bendable rod 338, and/or cartridge contactor 340. Screw 334 is coupled to pump motor 328, e.g., via gearbox 324. Screw 334 may be a worm screw. Responsive to rotational movement at pump motor 328, screw 334 rotates in a corresponding manner (e.g., at a geared ratio). Movement of screw 334 causes nut 336 to move along screw 334. Screw 334 may include a threaded screw and nut 336 may include a threaded nut that moves along the screw responsive to rotation of the screw. Bendable rod 338 is coupled to nut 336 and moves as nut 336 moves. Bendable rod 338 may curve in an approximately 180 degree angle to cause equal and opposite movements between nut 336 and cartridge contactor 340. Cartridge contactor 340 is designed to contact the cartridge and move the plunger of the cartridge responsive to movement of pump motor 328. Cartridge contactor 340 may have a flange that contacts an outer surface of the plunger at a non-insulin-contacting end. Cartridge contactor 340 also may have an extension with a smaller diameter than the flange that extends into the inner part of the plunger. In this manner, cartridge contactor may have a top hat shape.

Figure 18:
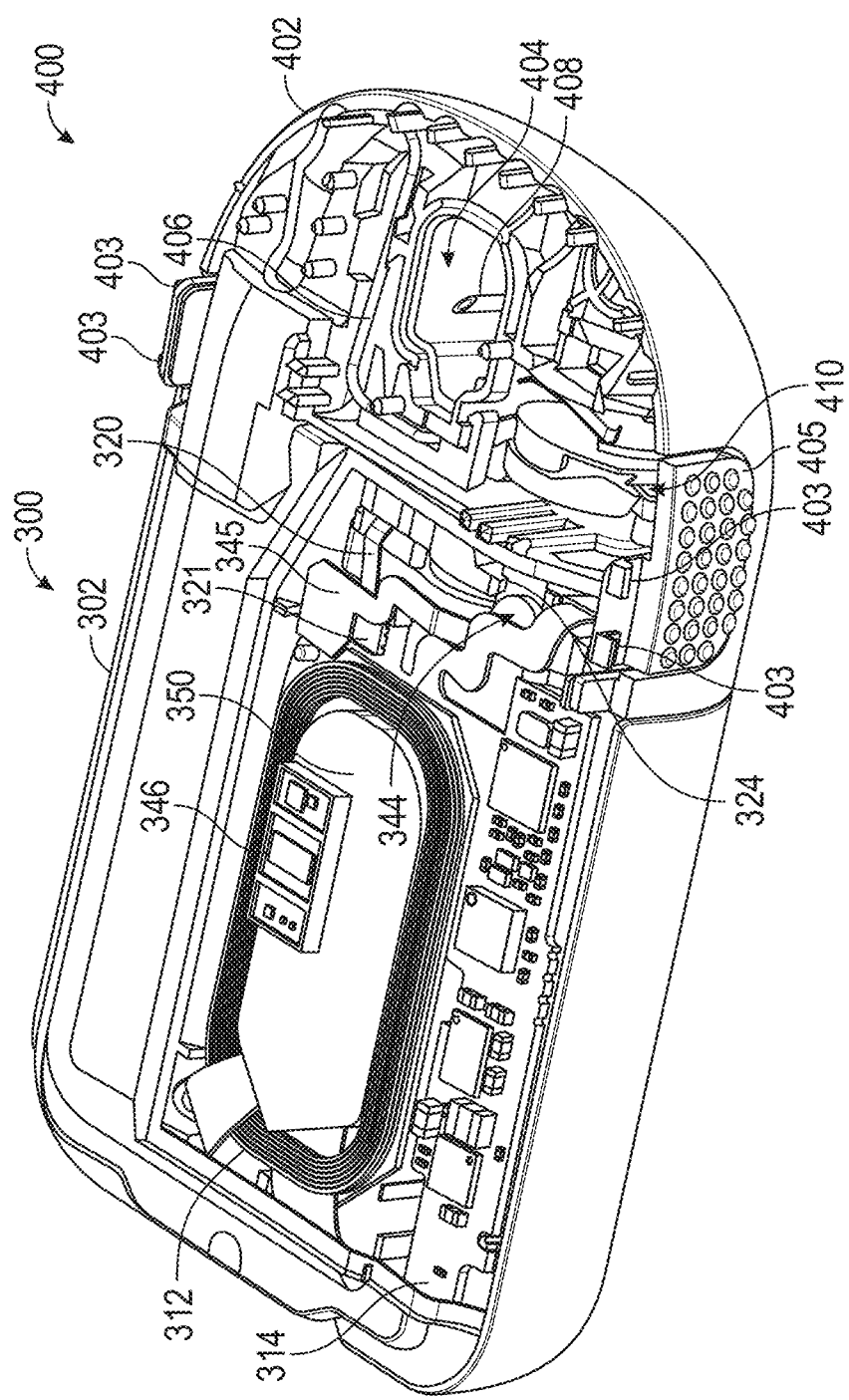
FIG. 18 is a perspective view of the skin-facing side of the patch pump, with a portion of the pump housing and the cap housing removed.

Referring now to FIG. 18, further aspects of the patch pump, are described. The skin-facing side of the patch pump is configured to interact with the pad and the cannula such that the patch pump is secured to the wearer and predetermined doses of medication are delivered to the wearer. Circuit board 314, having photoplethysmography sensor 346, may be disposed within pump 300 and may be configured to cause the motor to pump the medication from the cartridge to the outflow needle 408, which is configured to pierce the cannula. Outflow needle 408 may be disposed within connection cavity 404. Connection cavity 404 preferably is disposed on the skin-facing side of cap 400 and may be sized and shaped to receive the proximal region of the cannula (e.g., cannula head) such that outflow needle 408 can be coupled in fluid communication with the cannula to deliver the microdoses of medication. Connection cavity 404 may be sized and shaped to receive pad attachments, which protrude from the pad and lock the cannula to the pad, when the patch pump is locked to the pad. The patch pump further may include a portion configured to hold a pre-filled cartridge of medication and preferably does not include a reservoir to hold multiple doses of medication separate from the pre-filled cartridge.

Figure 19A:
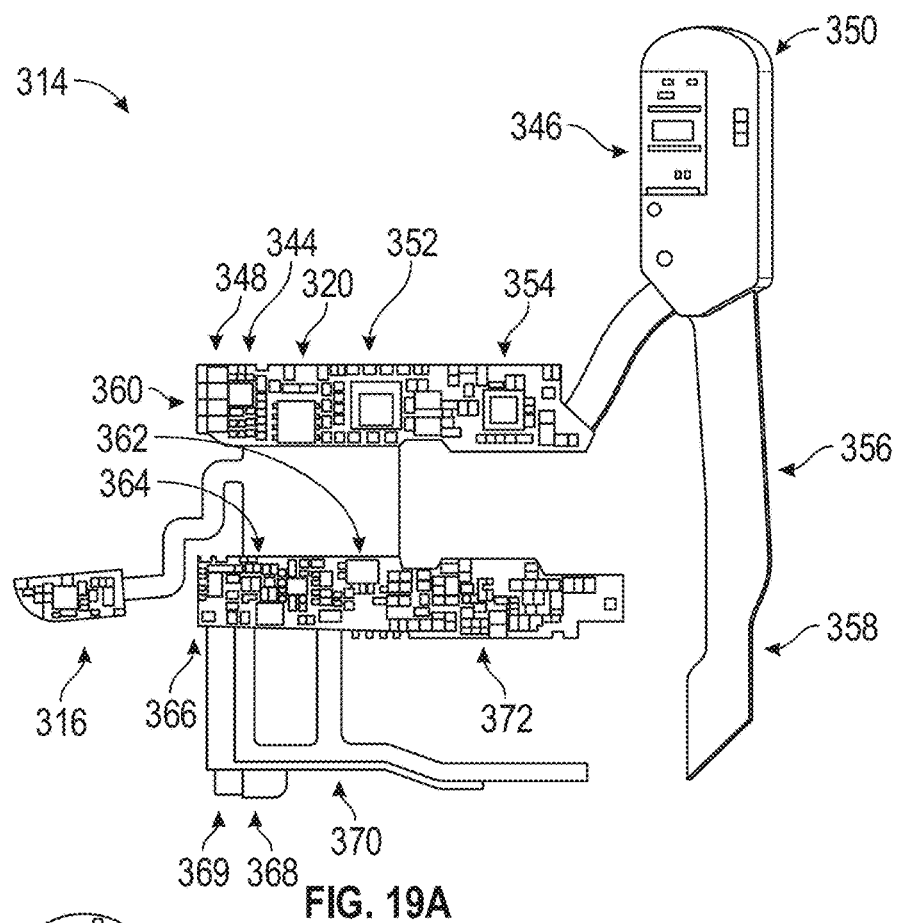
FIGS. 19A and 19B are plan views of the upper and lower sides of an exemplary circuit board disposed within the pump.
Figure 19B:
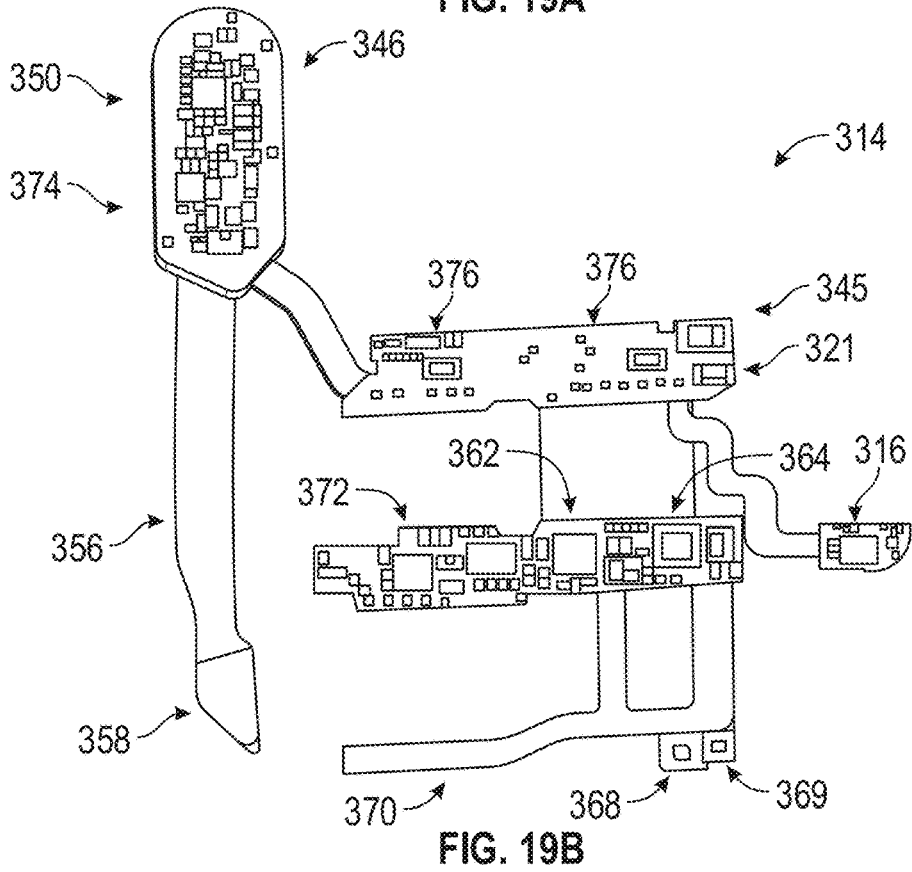

Turning to FIGS. 19A and 19B, an illustrative embodiment of a circuit board is described. Circuit board 314 preferably is disposed on flexible substrate 356 that can bend and fold to fit within the pump housing. Circuit board 314 includes electrical components and permits electrical coupling between the controller and the various electrical components. One or more electrical components and/or circuits may perform some of or all the roles of the various components described herein. Although described separately, as will be understood by one of ordinary skill in the art, the electrical components need not be separate structural elements. For example, a processor and wireless communication chip may be embodied in a single chip. In addition, while the one or more processor is described as having memory, a memory chip may be separately provided.

Circuit board 314 may include sensor 316, sensor 320, sensor connector 321, sensor 344, sensor connector 345, photoplethysmography sensor 346, sensor 348, skin detector 350, processor 352, sensor 354, flexible substrate 356, skin detector 358, controller 360, motors driver 362, processor 364, wireless communication chip 366, user interface 368, sensor 369, wireless antenna 370, battery and wireless charging management 372, accelerometer 374, and/or programming connectors 376.

Controller 360 is disposed within the pump housing for controlling operation of pump 300. For example, the controller may store instructions that, when executed, cause pump 300 to perform the operations described herein. Controller 360 preferably includes electrical components coupled on circuit board 314. Controller 360 may include one or more general purpose processors, digital signal processors (DSP), application specific integrated circuits (ASIC), field programmable gate arrays (FPGA) or other programmable logic devices, discrete gate or transistor logic, discrete hardware components, or any suitable combination thereof designed to perform the functions described herein. A processor also may be implemented as a combination of computing devices, e.g., a combination of a DSP and a microprocessor, a plurality of microprocessors, one or more microprocessors in conjunction with a DSP core, or any other such configuration.

The controller may contain memory and/or be coupled, via one or more buses, to read information from, or write information to, memory. The memory may include processor cache, including a multi-level hierarchical cache in which different levels have different capacities and access speeds. The memory also may include random access memory (RAM), other volatile storage devices, or nonvolatile storage devices. The storage devices can include, for example, hard drives, optical discs, flash memory, and Zip drives.

The processor, in conjunction with firmware/software stored in the memory may execute an operating system, such as, for example, Windows, Mac OS, Unix or Solaris 5.10. The processor also executes software applications stored in the memory. In one non-limiting embodiment, the software comprises, for example, Unix Korn shell scripts. In other embodiments, the software may be programs in any suitable programming language known to those skilled in the art, including, for example, C++, PHP, or Java.

In some embodiments, controller 360 may include two dedicated processors to increase the security of the patch pump. Processor 352 may manage delivery of the medication and may monitor of one or more sensors that may detect sensed parameters that effect the algorithm for delivery. Processor 364 may manage the communications to and from the patch pump.

Processor 352 may be an autonomous, real time state machine that executes class C software. Processor 364 may execute class B software. Preferably, processor 352 is configured such that it cannot receive data from outside the patch pump. For example, any communication from the wearer's mobile device or from an external continuous glucose monitoring sensor must be received by processor 364. This configuration protects processor 352, and thus the delivery of medication, from any disruption by an external device.

Processor 352 may be configured to execute first programmed instructions stored in a first memory to cause the pump motor to pump the medication towards the transcutaneous portion, to monitor sensed parameters generated by at least one sensor, and to monitor the battery life of the battery. For example, processor 352 may monitor sensed parameters generated by a sensor configured to sense a pressure within the cartridge, a sensor configured to detect an occlusion in the dosing pathway, a sensor configured to detect the wearer's skin, a sensor configured to detect the position of the pusher to indicate that the cartridge may be replaced, or a sensor configured to detect the position of the cam to indicate the status of a dosing cycle.

The first programmed instructions may cause one or more components of the pump to move based on the sensed parameters. For example, the first programmed instructions may cause the motor to push the medication in the cartridge towards the transcutaneous portion only when a sensor detects the wearer's skin on the skin-facing side of the pump. The first programming instructions also may cause the cam shaft of the microdosing system to stop rotating when a sensor indicates that a dosing cycle is complete. Further, the first programming instructions may lock or unlock the pump, for example, when a first processor determines that the pusher is in the home position or when the first processor determines that the battery has been sufficiently charged to a predetermined state.

Processor 364 may be configured to execute second programmed instructions stored in a second memory to communicate data to and from the patch pump via the wireless communication chip. The communicated data may include data indicative of a battery life of the rechargeable battery or data indicative of the wearer's hear rate and physiologic parameters, which may be detected by a photoplethysmography sensor. Preferably, the second programmed instructions also use an algorithm to calculate when to deliver the doses of medication and may adjust the calculation based on the data received.

Wireless communication chip 366 is configured to transmit information, such as signals indicative of the sensed parameters, locally and/or to a remote location such as a server. Wireless communication chip 366 is configured for wireless communication over a network such as the Internet, a telephone network, a Bluetooth network, and/or a WiFi network using techniques known in the art. Wireless communication chip 366 may be a communication chip known in the art such as a Bluetooth chip and/or a WiFi chip. Wireless communication chip 366 may include a receiver and a transmitter, or a transceiver, for wirelessly receiving data from, and transmitting data to a remote computing device. In some embodiments, the remote computing device may be a mobile computing device that provides the system with a user interface; additionally or alternatively, the remote computing device is a server. In embodiments configured for wireless communication with other devices, wireless communication chip 366 may prepare data generated by processor 364 for transmission over a communication network according to one or more network standards and/or demodulates data received over a communication network according to one or more network standards.

Wireless communication chip 366 may be coupled to wireless antenna 370 for sending and receiving information. Wireless antenna 370 may include Bluetooth antenna configured to transmit or receive signals in accordance with established standards and protocols, such as Bluetooth and/or BLE. In some embodiments, wireless antenna 370 may be the only means for the patch pump to transfer data. In some embodiments, pump 300 may communicate externally as described in WO 2020/008016 or WO 2020/008017, the entire contents of each of which are incorporated herein by reference.

User interface 368 may be used to receive inputs from, and provide outputs to, the wearer. Illustratively, user interface 368 may alert the wearer when the pressure within the cartridge is outside of a predetermined range or when an occlusion is detected or when the wearer's glucose level, heart rate, or physiologic parameters are outside a predetermined range. User interface 368 may be coupled to processor 364.

User interface 368 may include a touchscreen, LED matrix, other LED indicators, or other input/output devices for receiving inputs from, and providing outputs to, the wearer. Alternatively, user interface 368 is not provided on the patch pump, but is instead provided on a remote computing device communicatively connected to the patch pump via wireless communication chip 366. User interface 368 also may be a combination of elements on the patch pump and a remote computing device.

User interface 368 may be configured to adjust the strength of the LEDs based on sensed parameters from sensor 369. Sensor 369 may be a light sensor configured to detect whether the patch pump is disposed in a bright or dark environment. For example, processor 352 may be configured to adjust user interface 368 such that the strength of the LED is decreased when it is dark and is increased when it is light.

Battery and wireless charging management 372 is configured to recharge the battery within the pump and to ensure the safety of the battery. Battery and wireless charging management 372 may communicate with the charging system to charge the battery and may protect against high voltage or high current which may damage the battery. Further, battery and wireless charging management 372 may be configured to efficiently charge the battery and generate adequate electrical tension for circuit board 314.

Programming connectors 376 may be provided for installing firmware in the on-board memory of the controller attached to circuit board 314. For example, programming connectors 376 may be used to flash the firmware of the pump and may be used during development to output the signals of the sensors to determine whether circuit board 314 is working properly. Programming connectors 376 may be removed after programming, during the manufacturing of the pump.

Motors driver 362 may be used to supply current to both the vibration motor and the pump motor. Controlling the power supply to the motors can have a significant effect on the noise, power consumption, and torque of the motors.

Circuit board 314 also may include one or more sensors configured to sense conditions within the patch pump or external to the patch pump, for example, the wearer's physiologic parameters. For example, circuit board 314 may include sensors 316, 320, 344, 346, 348, 350, 354, 358, 369, and/or 374. The sensor(s) preferably are electrically coupled to controller 360 (e.g., at processor 352) for monitoring and processing the information from the sensor(s).

Sensor 316 is configured to sense information indicative of an occlusion in the dosing pathway, such as within the microdosing system or within the cannula. Sensor 316 preferably is electrically coupled to controller 360 such that sensed signals are sent to controller 360 for processing and detecting an occlusion. Sensor 316 may be located adjacent to the microdosing system but within the pump. In some embodiments, sensor 316 is a hall-effect sensor configured detect movement of a magnet disposed on a lever of the microdosing system.

Sensor 320 may sense information indicative of the pressure within the cartridge. Sensor 320 preferably is electrically coupled to controller 360 such that the sensed signals are sent to controller 360 for processing and detecting the pressure within the cartridge. Sensor 320 may be located adjacent to the pusher and may be coupled to circuit board 314 via sensor connector 321. Sensor connector 321 permits electrical coupling between sensor 320 and components on circuit board 314, such as the controller. In some embodiments, sensor 320 is configured to detect the force applied to the pusher and includes a strain gauge configured to measure deformation, for example, by measuring a change in electrical resistance. Controller 360 processes this information to determine pressure within the cartridge.

Sensor 344 may sense information indicative of the status of a dosing cycle. Sensor 344 preferably is electrically coupled to controller 360 such that sensed signals are sent to controller 360 for processing and detecting whether a dosing cycle is completed. Sensor 344 may be located adjacent to the microdosing system but within the pump and may be coupled to circuit board 314 via sensor connector 345. Sensor connector 345 permits electrical coupling between sensor 344 and components on circuit board 314, such as the controller. In some embodiments, sensor 344 detects oscillations of signals that are generated by a ferromagnetic blade that may be coupled to the cam plate. In some embodiments, a dosing cycle corresponds to a ½ turn of the cam so sensor 344 senses whether the ½ turn has occurred.

Photoplethysmography sensor 346 is configured to sense the wearer's heart rate or other physiologic parameters.

Photoplethysmography sensor 346 preferably is electrically coupled to controller 360 (e.g., to processor 352 of controller 360) such that the sensed parameters are sent to controller 360 for processing and detecting whether the wearer's heart rate or other physiologic parameters are outside a predetermined range. Photoplethysmography sensor 346 may be located on circuit board 314 such that is disposed on the skin-facing side of the patch pump, preferably within a window of the patch pump.

Sensor 348 may sense information indicative of the position of the pusher, which may be indicative of the battery life of the rechargeable battery, whether a new cartridge may be inserted, and/or whether the patch pump may be unlocked. Sensor 348 preferably is electrically coupled to controller 360 such that the sensed position is sent to controller 360 for processing and detecting the position of the pusher. For example, sensor 348 may indicate that a component of the pusher is at the end-of-stroke. Sensor 348 may be located adjacent to the pusher. In a preferred embodiment, sensor 348 is an electrical contact sensor that senses the position of the pusher based on whether a component (e.g., nut 336) of the pusher has contacted the sensor. Sensor 348 may include one or more contacting pins that are configured to contact one or more contacting blades responsive to force applied on the contacting blades by the pusher. For example, the nut of the pusher may contact the blades at the end-of-stroke, causing the blades to move to contact the contacting pins. The contacting pins may be coupled to the circuit board via a conductor (e.g., illustratively a spring) such that when the one or more contacting pins contact the one or more contacting blades, a circuit is completed, which sends an electrical signal to controller 360.

Skin detector 350 senses information indicative of whether the patch pump is touching skin. Controller 360 may cause the motor to run only if skin detector 350 detects skin. Skin detector 350 preferably is electrically coupled to controller 360 such that sensed signals are sent to controller 360 for processing and detecting whether the patch pump is secured to a pad, held by the wearer, or not touching skin. Skin detector 350 may be located on the skin-facing side of the patch pump such that it detects whether the skin-facing side of the patch pump is touching skin. In some embodiments, skin detector 350 measures capacitance.

Sensor 354 is configured to sense information indicative of the temperature and humidity in the patch pump. Sensor 354 preferably is electrically coupled to controller 360 such that sensed signals are sent to controller 360 for processing and detecting whether the temperature and humidity are within respective predetermined ranges. If outside the predetermined range(s), an alert may be generated using the vibration motor, the sound generator, and/or a communication sent to the software application.

In some embodiments, the pump may include a second skin detection sensor. Similar to skin detector 350, skin detector 358 senses information indicative of whether the patch pump is touching skin. Skin detector 358 preferably is electrically coupled to controller 360 such that sensed signals are sent to controller 360 for processing and detecting whether the patch pump is secured to a pad, held by the wearer, or not touching skin. Skin detector 358 may be located on the opposite side of the patch pump such that is detects whether the opposite side of the patch pump is touching skin. In some embodiments, skin detector 358 measures capacitance. Controller 360 may cause the motor to run only if skin detector 350 detects skin and skin detector 358 does not detect skin. If both skin detector 350 and skin detector 358 detect skin, it may indicate that the wearer is holding the patch pump. In such a case, the patch pump should not deliver medication.

Sensor 374 is configured to sense information indicative of the wearer's activity level. Sensor 374 also may be configured to sense information indicative of the location of the patch pump on the wearer's body. Sensor 374 preferably is electrically coupled to controller 360 such that sensed signals are sent to controller 360 for processing and detecting the wearer's activity level. Sensor 374 may be an accelerometer that measures the movement of the wearer.

Figure 20A:
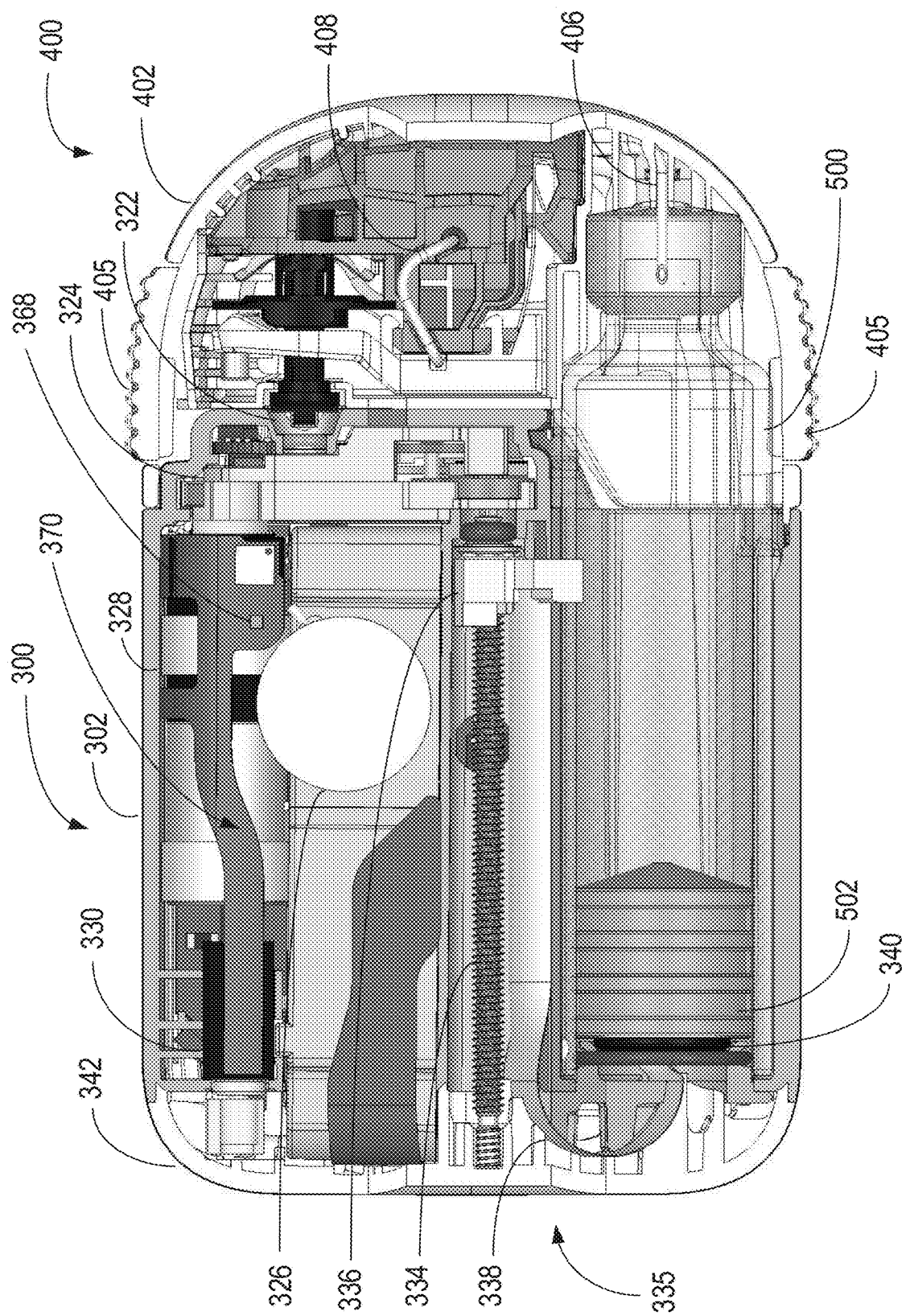
FIG. 20A is a cross-sectional plan view of the patch pump when the cartridge is full.
Figure 20B:
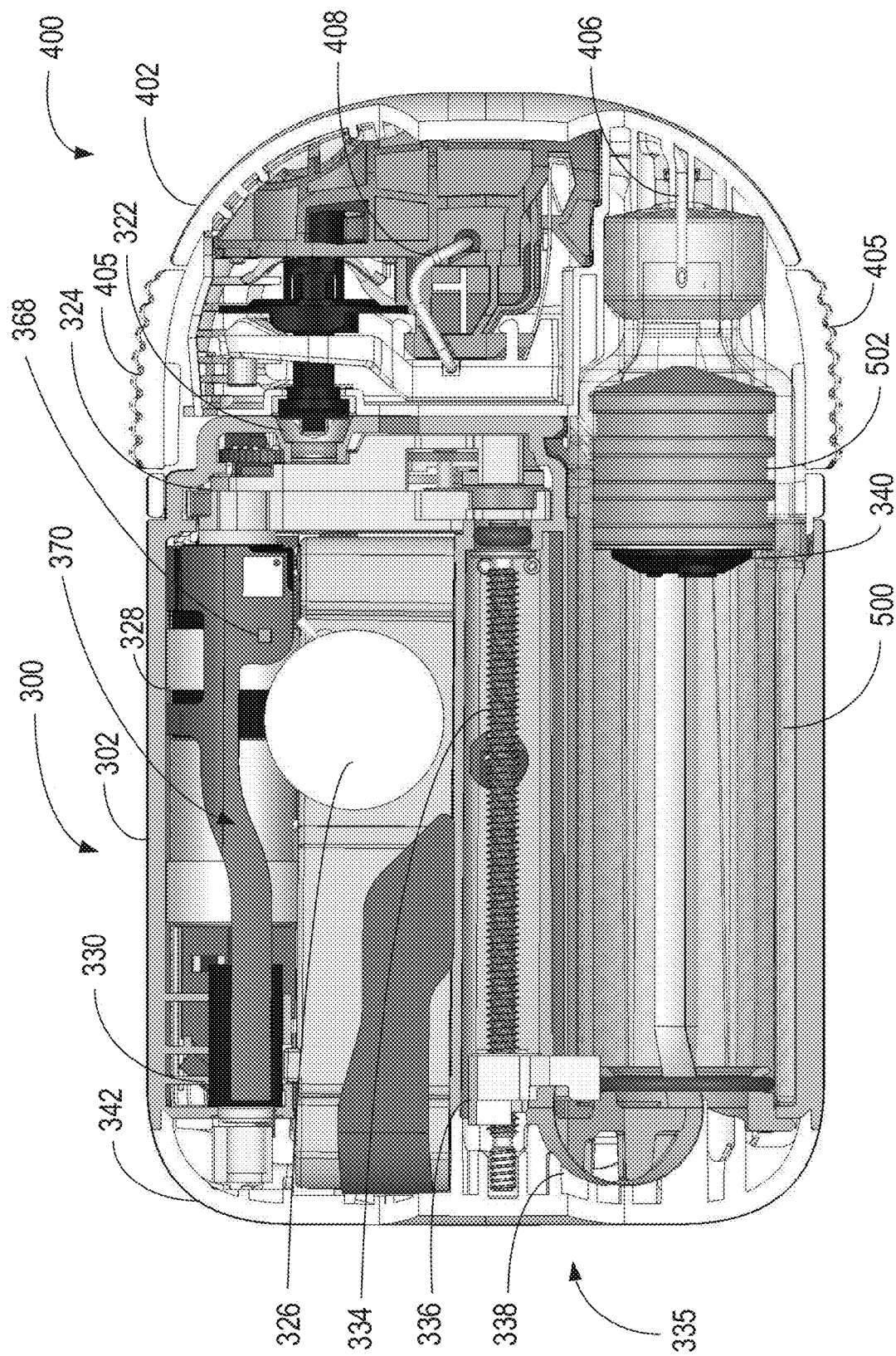
FIG. 20B is a cross-sectional plan view of the patch pump when the cartridge is empty.

Referring now to FIGS. 20A-20B, operation of the exemplary patch pump is described, in which FIG. 20A corresponds to positions of the pump components when the cartridge is full of medication and FIG. 20B corresponds to positions of the pump components when the cartridge is empty. The pump motor may be disposed within the pump housing and may be configured to be coupled to a pusher and a cam (e.g., a circular cam) via a gearbox. Preferably, the pump motor is configured to move the pusher towards the cartridge to move the medication within the cartridge into an inflow needle within the cap. At the same time that the pusher is advancing, the cam disposed within the cap is configured to rotate to deliver a predetermined dose of medication to the cannula inserted into the wearer's skin.

Pusher 335 may include screw 334, which may be coupled to gearbox 324 and configured to rotate upon rotation of one or more gears with gearbox 324. Nut 336 may be coupled to screw 334 such that rotation of screw 334 causes nut 336 to move along screw 334. Nut 336 may be coupled to a first end of bendable rod 338 and a second end of bendable rod 338 may be coupled to cartridge contactor 340, which is configured to contact plunger 502 of cartridge 500. Upon rotation of screw 334 in a first direction, nut 336 is configured to move away from gearbox 324 such that bendable rod 338 applies a force to cartridge contactor 340, causing at least a portion of plunger 502 to move within cartridge 500. Upon rotation of screw 334 in a second direction, opposite the first direction, nut 336 is configured to move towards gearbox 324, such that bendable rod 338 and cartridge contactor 340 move away from the cap of cartridge 500. Bendable rod 338 may also be referred to as a curved piston.

In FIG. 20A, pusher 335 is depicted in a home position, when cartridge 500 is full of medication. In the home position, nut 336 may be disposed adjacent to the location where screw 334 is coupled to the gearbox 324. In FIG. 20B, pusher 335 is depicted in a delivery position, after cartridge 500 has delivered medication. Preferably, after all or substantially all of the medication within cartridge 500 has been delivered, the battery of pump 300 should be recharged. Upon reaching a predetermined state in the charging cycle, pusher 335 is configured to return to the home position. For example, the controller, upon sensing that the battery has reached the predetermined state (e.g., a predetermined time before full charge, such as 20 minutes), will cause pump motor 328 to rewind thereby transitioning the pump back from the empty position of FIG. 20B to the full position of FIG. 20A. In some embodiments, the pump and the cap will not unlock until the battery is sufficiently charged and the pump is in the home position. Gearbox 324 preferably rotates screw 334 in the second direction such that cartridge contactor moves away from plunger 502. Nut 336 may continue moving along screw 334 towards gearbox 324 until it reaches a contact sensor, as described below. Upon sensing contact with nut 336, screw 334 is configured to reverse directions to rotate in the first direction such that nut 336 is advanced a short distance away from gearbox 324 and a small space is created between nut 336 and the contact sensor. Resetting pusher 335 to the home position permits a new, pre-filled cartridge 500 to be inserted into the patch pump.

Plunger 502 is a movable end of cartridge 500 and is configured to seal cartridge 500 such that medication does not leak from the cartridge. Plunger 502 preferably includes a flexible, elastomeric material that is able to deform when a substantial force is applied. Plunger 502 may be configured to flex based on the pressure within cartridge 500 such that the pressure is maintained within a predetermined range. Ensuring the pressure remains within the predetermined range helps ensure the accuracy of each dose of medication, as described below. For example, plunger 502 may be configured to compress or deform when the pressure within cartridge 500 is over 800 or 1000 mbar. For example, plunger 502 may be configured to advance into the cartridge a predetermined distance such as 3-4 um, preferably 3.7 um, after each push from pusher 335. Further, plunger 502 may include a first end that is configured to contact pusher 335 and a second end that is configured to contact the medication within cartridge 500.

A risk with using an elastomeric plunger is the "stick-slip effect," whereby the plunger does not move due to sticking until a force applied to the first end exceeds a displacement needed for a dose of medication. Once the force overcomes the stick, the plunger may travel too far, resulting in an inaccurate dose. By pressurizing the cartridge prior to delivering microdoses, as described herein, the pump reduces the stick-slip effect by providing a counterforce via the pressurized medication on the pushing force caused by the pusher on the cartridge. As a result, the portion of the plunger of the cartridge contacting the medication does not move further than the distance needed to expel the desired volume of medication of the microdose, thereby ensuring enhanced accuracy of microdose volumes of medication. The counterforce from the pressurized medication also may cause the flexible plunger to compress while pumping a microdose. By advancing the piston a micro-step at each delivery of a dose via the microdosing system, pressure in the cartridge is maintained. This pressure within the cartridge varies only minimally due to stick-slip. Preferably, because the system is pressurized, stick-slip has minimal adverse effects on the volume of the microdoses. Advantageously, the patch pump may use this pressure to refill the microdosing system with equivalent amounts of insulin for every delivery cycle.

For example, when the pressure within cartridge 500 is at a first pressure, pusher 335 may be configured to cause the first end of plunger 502 to move a first distance towards the cartridge cap and to deliver a first dose of medication. Pusher 335 also may be configured to cause the second end of plunger 502 to move a third distance towards the cartridge cap. When the pressure within cartridge 500 increases to a second pressure, pusher 335 may be configured to cause the first end of plunger 502 to move a second distance towards the cartridge cap to deliver a second dose of medication. Pusher 335 also may be configured to cause the second end of plunger 502 to move a fourth distance towards the cartridge cap.

Preferably, pusher 335 is configured to advance the same distance every time screw 334 rotates. Plunger 502 may be configured so that each push from pusher 335 causes the first end of plunger 502 to move the same distance. Therefore, the first distance may be the same as the second distance. Plunger 502 further may be configured so that each push from pusher 335 causes the second end of plunger 502 to move a distance that depends upon the pressure within cartridge 500. For example, when the pressure within cartridge 500 increases, the distance that second end of plunger 502 moves may decrease. Therefore, the third distance may be greater than the fourth distance. This adjustment by plunger 502 reduces the risk that the pressure within cartridge 500 will move outside the predetermined range of 600 mbar to 1000 mbar. Further, maintaining a consistent pressure within the cartridge 500 reduces the risk that volume of each dose of medication falls outside the predetermined volume of 0.08-1 uL, 0.2-0.6 uL, or 0.2 to 0.3 uL, preferably 0.25 uL ±5%. Preferably, the volume of each dose of medication is within 5% of the volume of the other doses delivered to the wearer.

The cap of patch pump preferably includes a microdosing system configured to measure and deliver the predetermined doses of medication. Preferably, pusher 335, plunger 502, and the microdosing system work together to ensure the accuracy of the doses of medication. At the same time that pusher 335 applies a force to plunger 502, the microdosing system is configured to rotate to deliver medication to the wearer. The microdosing system may include a lever system comprising one or more levers configured to sequentially transition between a lowered position, wherein one or more levers contact a dosing tube such that medication cannot flow through the dosing, and a raised position, wherein one or more levers sequentially do not contact the dosing tube, such that medication is expelled from the dosing tube and to the wearer. The one or more levers may act as valves that either permit or prevent medication from flowing through the dosing tube. Preferably, the lever system is configured such that at least one lever is configured to be in a lowered position to close a portion of the dosing tube during the entire time the pump motor moves pusher 335.

With respect to FIG. 20C, an arrangement of wet and dry zones within the patch pump is described. The patch pump may include isolated wet and dry zones to protect the electrical components from contacting any leaked medication or other fluids. The patch pump may include dry zone 378 that is configured to house the circuit board, motor, vibration motor, sound generator, battery, coil, gearbox, and one or more sensors. Dry zone 378 may be encapsulated to exclude moisture from reaching the components within the zone. Dry zone 378 may be encased in plastic and/or sealed via welding. One or more dry zone vents 381 may be disposed on the plastic housing of dry zone 378 such that humidity and gas may escape the housing and pressure may equilibrate. For example, dry zone vents 381 may be made of Gore-Tex®. Dry zone 378 may be separated from protected wet zone 380 and unprotected wet zone 382 via one or more sealing members, for example, dry zone seals 379. Protected wet zone 380 may be configured to house the pusher and unprotected wet zone 382 may be configured to house the cartridge and the components of the cap including the needles and microdosing system. In addition, cartridge holder 332 may separate the protected wet zone from the dry zone and may include one or more O-rings to seal off the zones when a cartridge is disposed within the pump-cap assembly.

Figure 21A:
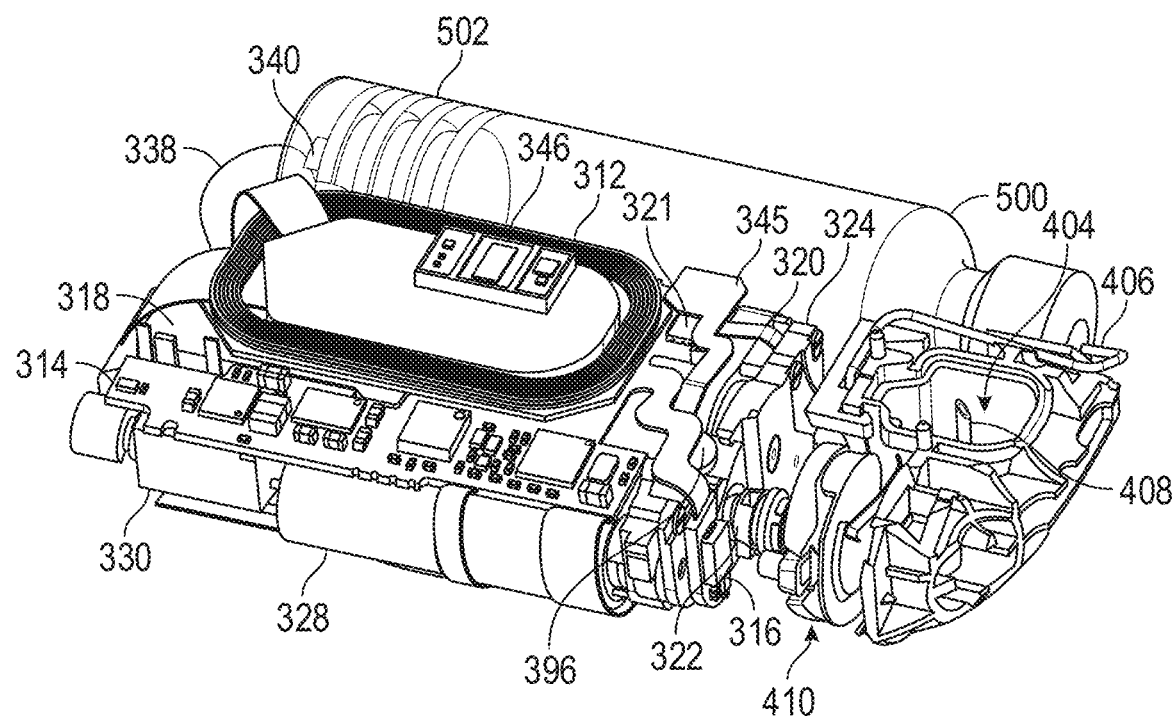
FIG. 21A is a perspective view of exemplary internal components of the patch pump.

Referring now to FIG. 21A, further details of exemplary internal components of the patch pump are described. Circuit board 314 preferably is configured to have a flexible substrate that can bend and fold to fit to surround battery 318, gearbox 324, motor 328, and vibration motor 330 within the pump housing. The components of circuit board 314 may be strategically positioned in particular locations relative to the corresponding components of the pump or cap. For example, photoplethysmography sensor 346 may be positioned on the skin-facing side of the pump patch so that photoplethysmography sensor 346 may detect the wearer's heart rate or other physiologic parameters. Sensor 320, which is configured to detect a parameter indicative of the pressure within cartridge 500, may be coupled to gearbox 324 and/or the pusher such that sensor 320 may detect the force applied to the pusher. Sensor 320 preferably is coupled to circuit board 314 via sensor connector 321. Sensor 316, which is configured to detect an occlusion in the dosing pathway, may be a hall-effect sensor. Preferably, sensor 316 is disposed adjacent to microdosing system 410 such that sensor 316 can detect the position of a magnet of microdosing system 410 based on proximity of the magnet to the hall-effect sensor. Sensor 344, which is configured to determine the position of a cam plate of microdosing system 410, may be coupled to gearbox 324 and disposed adjacent to microdosing system 410 and magnet 396. Sensor 344 preferably is coupled to circuit board 314 via sensor connector 345.

Cartridge 500 is inserted into the patch pump such that the cartridge cap is disposed within the cap when the patch pump is locked. The longer the distance the medication must travel through before delivering the medication to the wearer, the higher the risk that an occlusion will form within the needles. Preferably, cartridge 500 is positioned as close as possible to microdosing system 410 and connection cavity 404 such that the lengths of inflow needle 406 and outflow needle 408 are as short as possible.

Figure 21B:
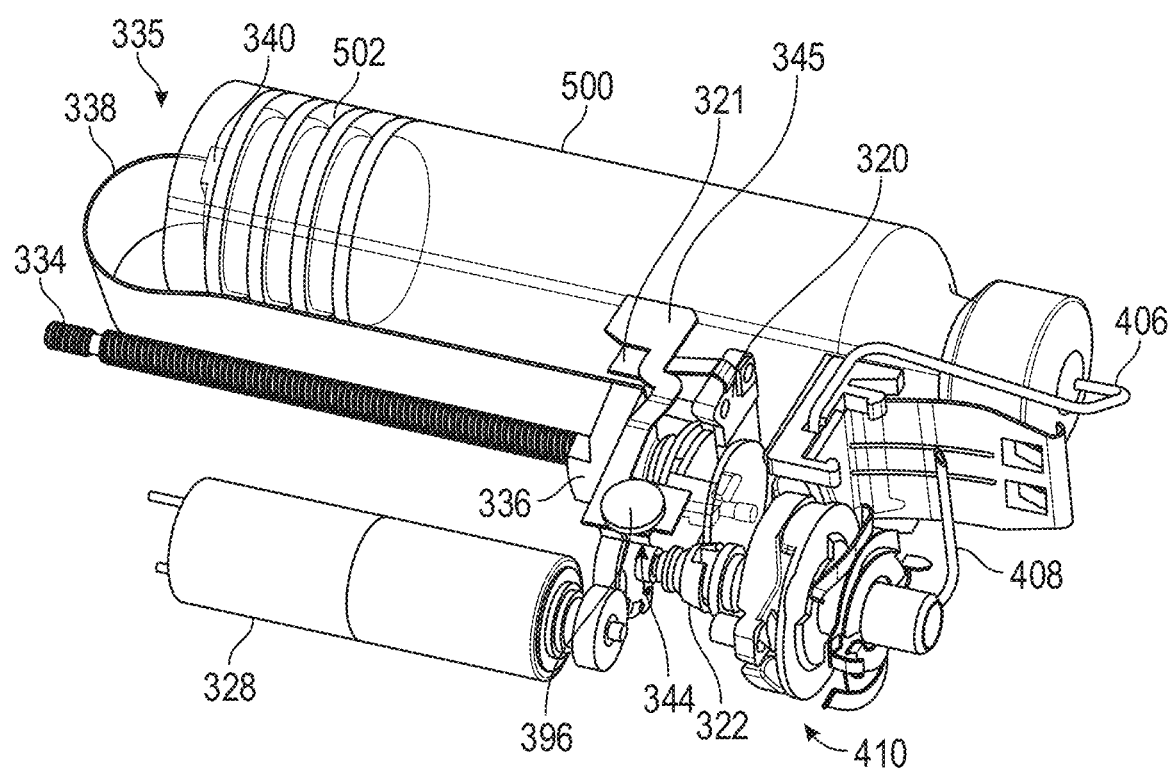
FIGS. 21B and 21C are, respectively, perspective and plan views of the internal components of the patch pump, with certain electrical components removed.
Figure 21C:
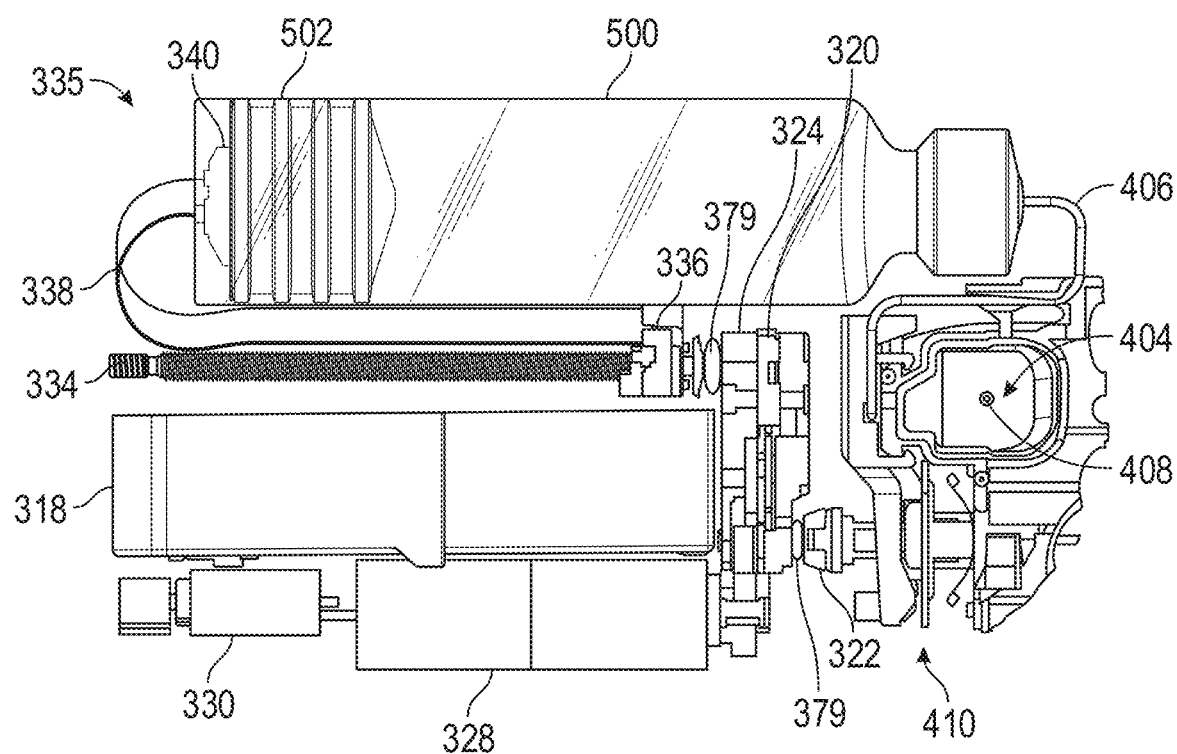

With respect to FIGS. 21B and 21C internal components of the pump-cap assembly are shown with certain electrical components removed. FIG. 21B depicts the components within the gearbox. Motor 328, mechanical coupling 322, and screw 334 are coupled to the gearbox. One or more dry zone seals 379 may be disposed between the gearbox and mechanical coupling 322 and/or screw 334. Upon rotation of motor 328, the gears within the gearbox rotate, causing mechanical coupling 322 to rotate. Mechanical coupling 322 is coupled to a cam shaft of microdosing system 410 such that rotation of mechanical coupling 322 causes the cam shaft to rotate, which in turn causes the lever system to deliver a predetermined dose of medication to the wearer. At the same time, the gears within the gearbox also cause screw 334 to rotate. Rotation of screw 334 causes nut 336 to move along screw 334, preferably in the direction towards plunger 502 of cartridge 500.

FIG. 21C depicts another view of the system. Inflow needle 406 and outflow needle 408 may be configured to have a short length in order to reduce the risk of occlusion. Inflow needle 406 preferably extends from the cartridge cap of cartridge 500, around connection cavity 404 and to microdosing system 410. Outflow needle 408 preferably extends from microdosing system 410 through connection cavity 404, and into the cannula inserted into the wearer's skin. Coupled between the inflow and outflow needle is a dosing tube configured to hold the predetermined dose of medication.

Figure 22A:
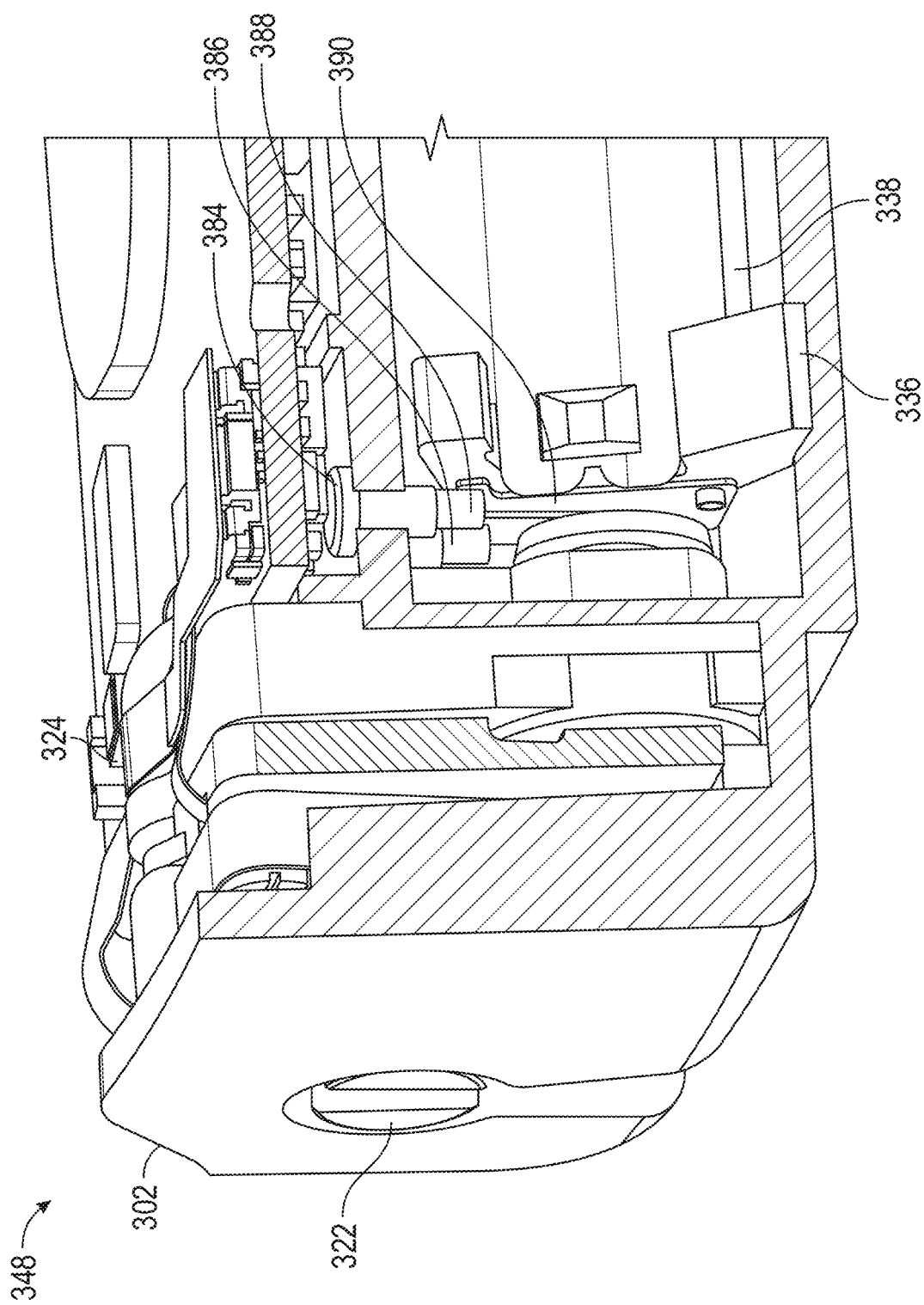
FIG. 22A is a cross-sectional perspective view of an exemplary contact sensor disposed within the pump.
Figure 22B:
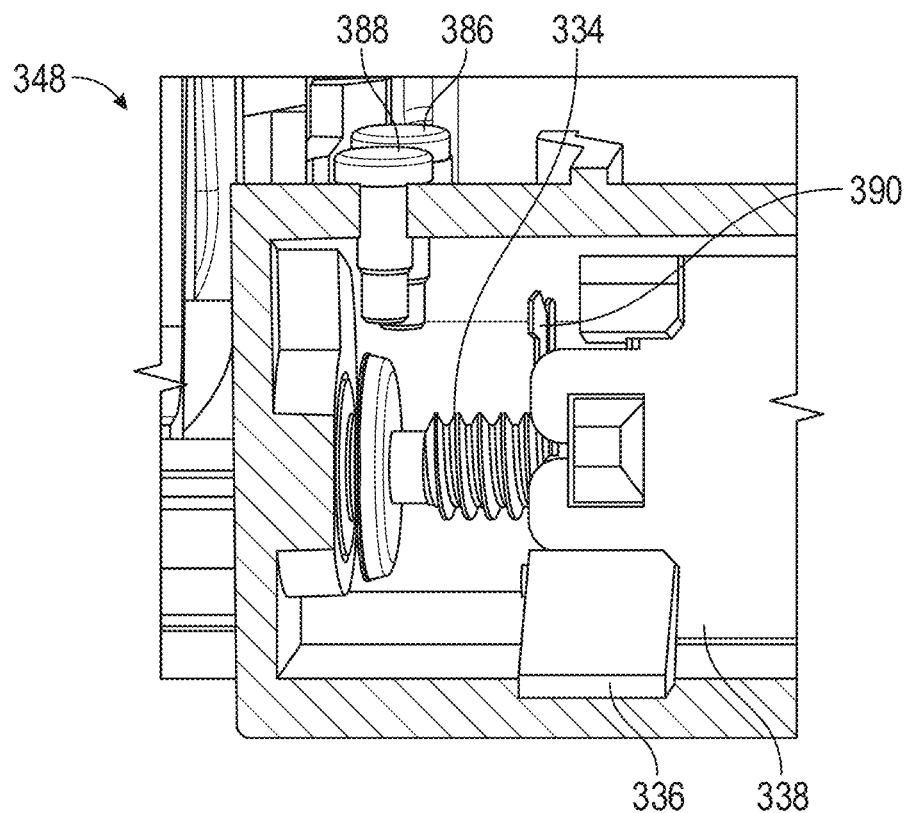
FIGS. 22B and 22C are, respectively, cross-sectional side views of the contact sensor in a contacting and non-contacting position.
Figure 22C:
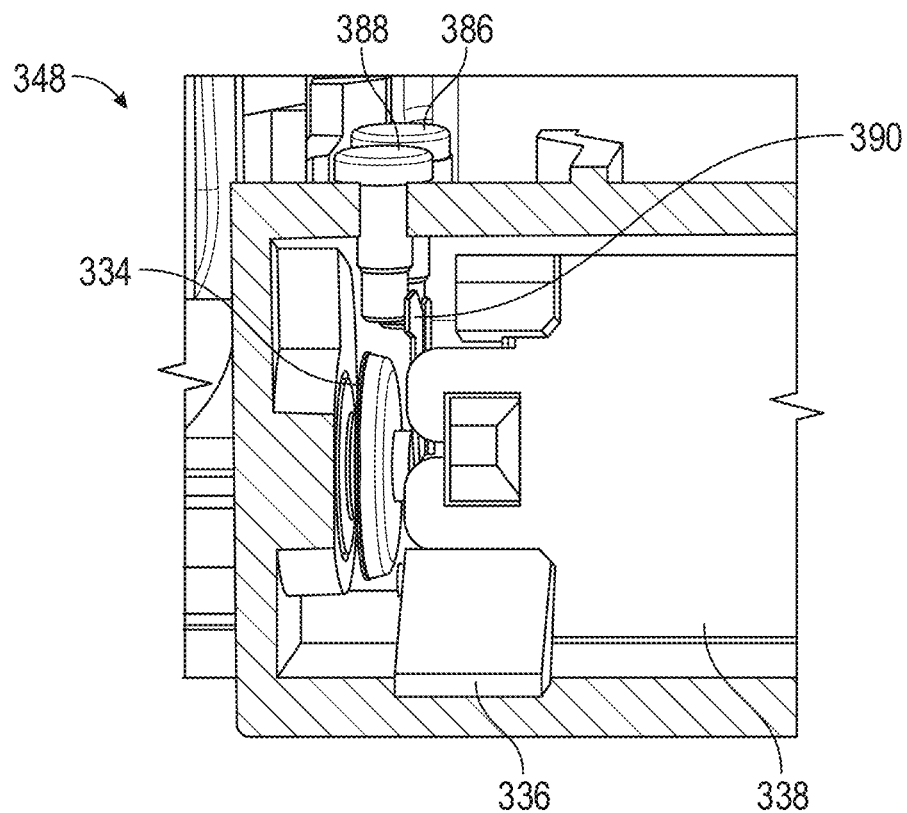

Turning now to FIGS. 22A-22C, an exemplary contact sensor is described. The pump may include a sensor configured to detect the position of the pusher within the pump, which may indicate a state of the patch pump. The sensed position may be used to determine whether the pusher is positioned within the pump such that a new, pre-filled cartridge may be inserted into the patch pump. The sensed position further may be used to make sure that, when the pusher moves in the opposite direction to return to a home position, it does not stops moving before it reaches the pump housing. The sensed position also may be used to determine the battery level of the patch pump. As described below, until a sufficient battery level is reached, the pump may remain locked to the cap, preventing replacement of the emptied cartridge.

In FIG. 22A, exemplary contact sensor 348, which may be an electrical contact sensor, is disposed within the pump and configured to detect the position of the pusher. For example, sensor 348 may include one or more contacting pins that are configured to contact one or more contacting blades coupled to the pusher. The contacting pins may be coupled to the circuit board via a conductor such that when the one or more contacting pins contact the one or more contacting blades, a circuit is completed, which indicates that the pusher is disposed in a starting position.

The pusher may include screw 334, nut 336 configured to move along screw 334 such that bendable rod 338, which is coupled to nut 336, pushes a cartridge contactor (not shown) to contact a plunger disposed within the cartridge. Upon movement of the pusher, the plunger is configured to advance into the cartridge such that medication is moved towards the inflow needle of the cap. After the cartridge is empty, the pusher moves in an opposite direction, away from the cartridge and back to the starting position. The position of the pusher may indicate that the pusher transitioned to a first position such that the cartridge is permitted to be removed and exchanged for a subsequent cartridge.

One or more contacting blades 390 may be coupled to nut 336. Sensor 348 preferably is disposed within pump housing 302 and adjacent to contacting blades 390 of the pusher. For example, sensor 348 may include one or more contacting pins 386 and 388 that are configured to contact contacting blade 390 when the pusher is positioned near the pump housing back such that a new, pre-filled cartridge may be inserted into the patch pump. Contacting pins 386 and 388 may be coupled to conductor 384, which is configured to electrically connect contacting pins 386 and 388 to the circuit board. In FIG. 22B, the contact sensor in a non-contacting position, wherein contacting blades 390 are not connected to contacting pins 386 and 388. In FIG. 22C, the contact sensor in a contacting position, wherein contacting blades 390 are connected to contacting pins 386 and 388.

Sensor 348 may be electrically coupled to a controller such that sensed signals are sent to the controller for processing and determining a state of the patch pump. For example, if sensor 348 detects that the pusher is in contact with contacting pins 386 and 388, the controller may be configured to cause the pusher to move in an opposite direction to a home position, The controller further may be configured to monitor the battery level of the patch pump and unlock the pump and cap if both the battery level is at a sufficient level and sensor 348 senses contact with the pusher.

Figure 23A:
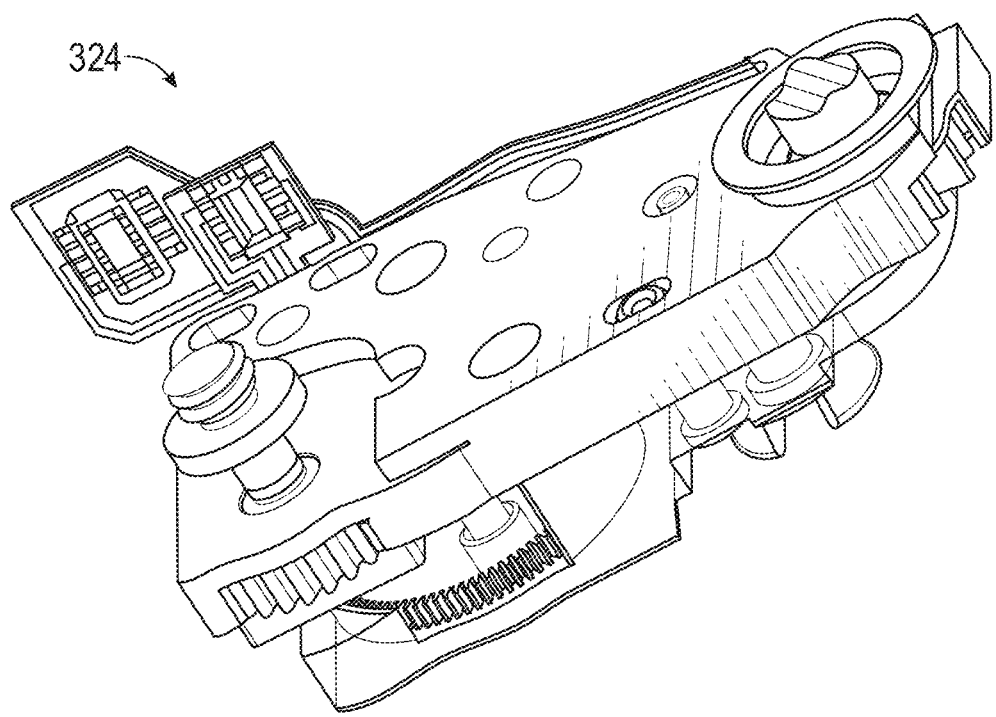
FIG. 23A is a perspective view of an exemplary gearbox within the pump.

Referring now to FIG. 23A, aspects of the gearbox of the pump are described. Gearbox 324 is configured to cause simultaneous movement of the pusher and rotation of the microdosing system. One or more sensors may be disposed within gearbox 324 to determine the position of a cam plate within the microdosing system or the pressure within the cartridge. For example, as described below, the position of the cam plate may be used to validate that a dose of medication was properly delivered to the wearer or may be used to ensure that pump and cap remain locked together. Gearbox 324 may include a ferromagnetic blade that may be coupled to the cam plate and, upon rotation, may generate an oscillation of a signal that can be used to count the teeth on the ferromagnetic blade and accordingly whether the dosing cycle is complete. Gearbox 324 further may include a sensor that is configured to measure a force that is indicative of the pressure within the cartridge.

Figure 23B:
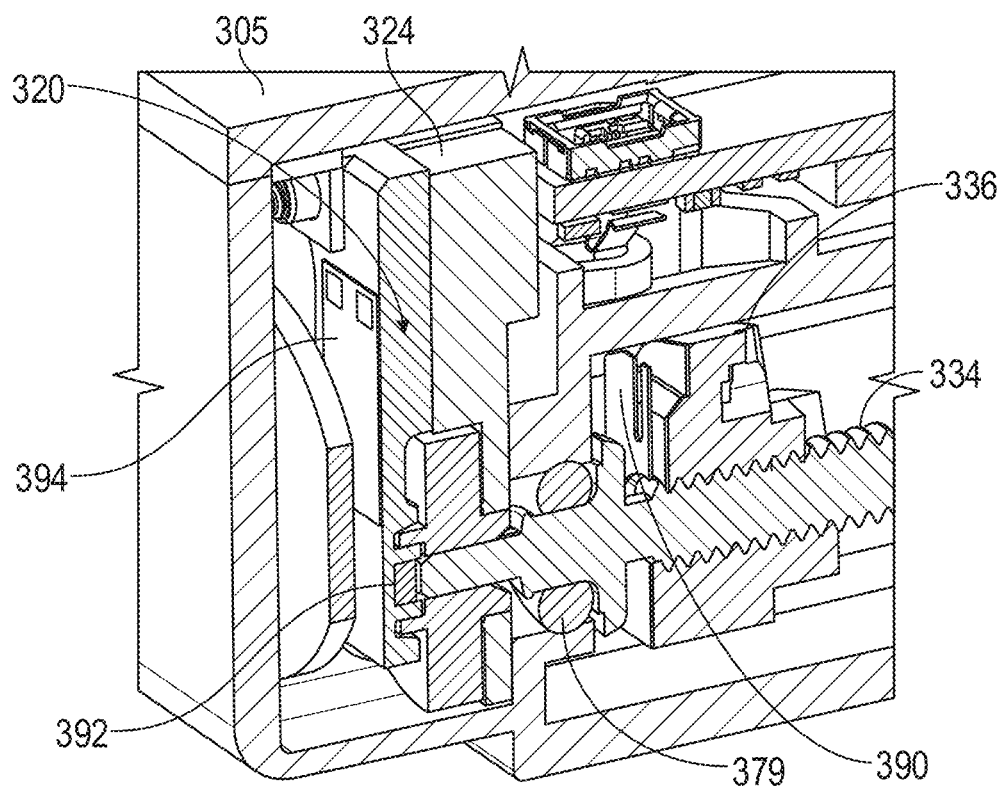
FIG. 23B is a cross-sectional side view of an exemplary pressure sensor disposed within the pump.

Referring now to FIG. 23B, an exemplary pressure sensor disposed within the pump is described. To ensure accurate doses of medication, the patch pump may be configured such that the pressure within the cartridge is maintained within a predetermined range. For example, the predetermined range may be between 600 mbar and 1000 mbar. A sensor may be coupled to a pusher and configured to measure the force on the pusher, which may be indicative of the pressure within the cartridge.

For example, sensor 320 may include strain gauge 394 configured to measure deformation, for example, by measuring a change in electrical resistance. The pusher may include screw 334 having a first end, coupled to gearbox 324 and disposed adjacent to strain gauge 394, and a second end, coupled to the cartridge. As the pressure within the cartridge increases, a greater force is applied to the pusher, and the pusher applies the same force to gearbox 324 at force application point 392. The greater the force applied to the pusher, the greater the deformation of strain gauge 394. Sensor 320 preferably is operatively coupled to a controller that may monitor the sensed pressure. The pressure within the cartridge must be increased until it falls within the predetermined range in order to ensure that the proper dose of medication is delivered to the wearer. Further the controller may be configured to alert the wearer when the pressure falls outside the predetermined range. For example, a pressure under 600 mbar may indicate that a cartridge is not disposed within the patch pump or that a cartridge was inserted incorrectly. A pressure over 1000 mbar may indicate that there is an occlusion within the cartridge cap, the inflow needle, and/or the cannula.

In a preferred embodiment, the patch pump is configured to be "initialized" prior to pumping medication from the cartridge past the microdosing system and into the user. In this manner, the controller of the pump causes the pump to increase pressure within the cartridge into a predetermined range prior to delivering the first dose of medication from the cartridge to the wearer. By pressurizing the cartridge, the patch pump ensures that precise volumes of microdoses of medication and are consistently and predictably provided to the user, including the first dose of medication from the cartridge. Further, the initialization ensures that bubbles within the cartridge and the tubing connected thereto are reduced and that the formation of bubbles is reduced. Advantageously, the patch pumps described herein may be generally "bubble free."

Figure 24A:
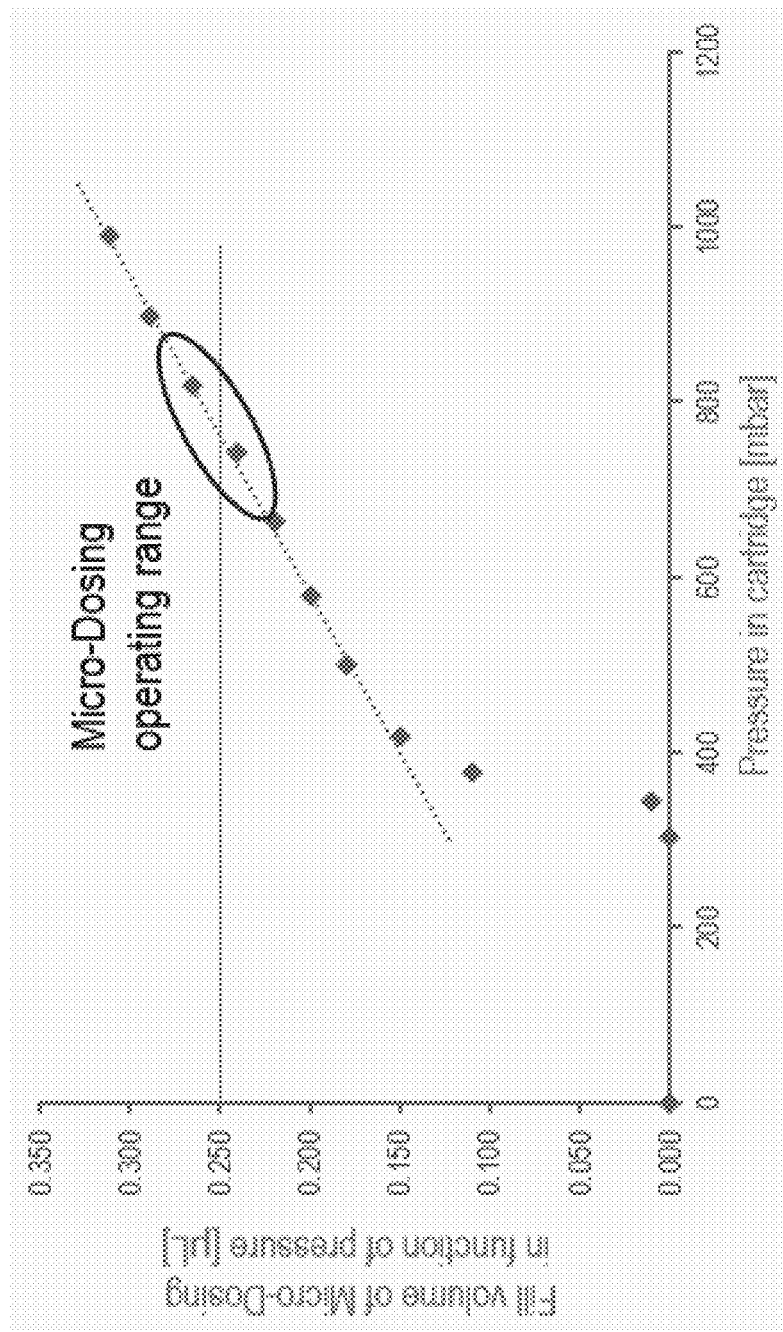
FIG. 24A is a graph showing the relationship between pressure and volume of medication within the cartridge and microdosing unit.
Figure 24B:
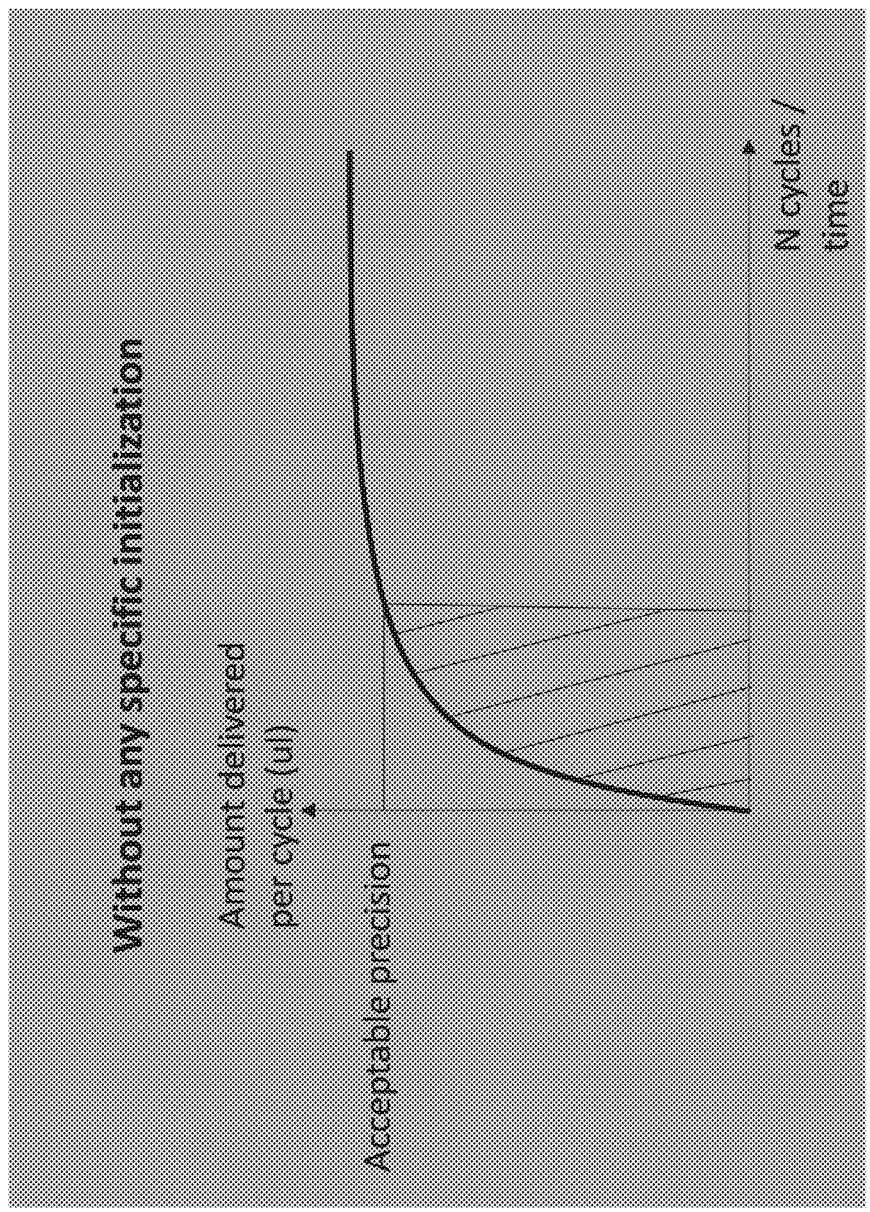
FIGS. 24B and 24C, are, respectively, graphs showing the relationship between the number of dosing cycles and the amount of medication delivered per cycle, without and with initialization.
Figure 24C:
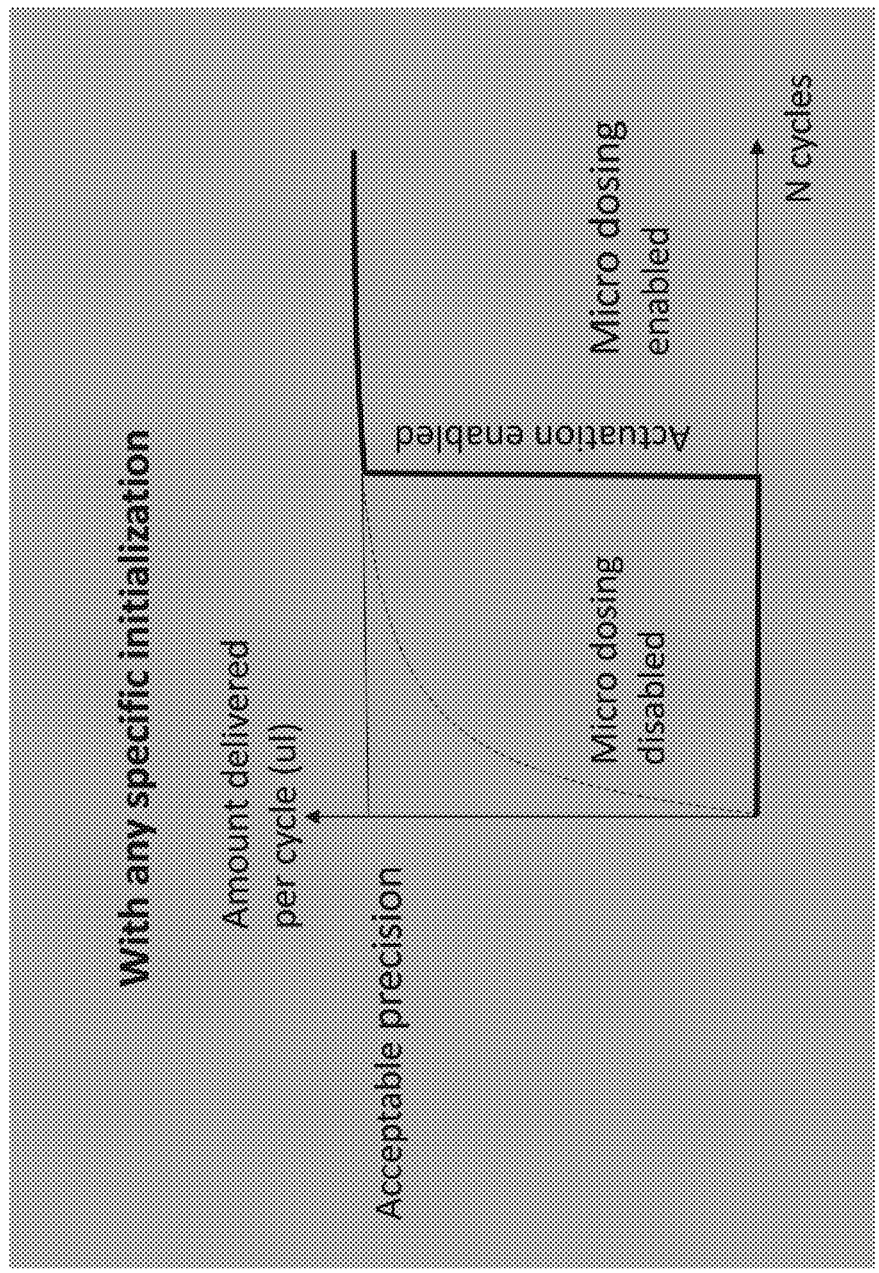
Figure 24D:
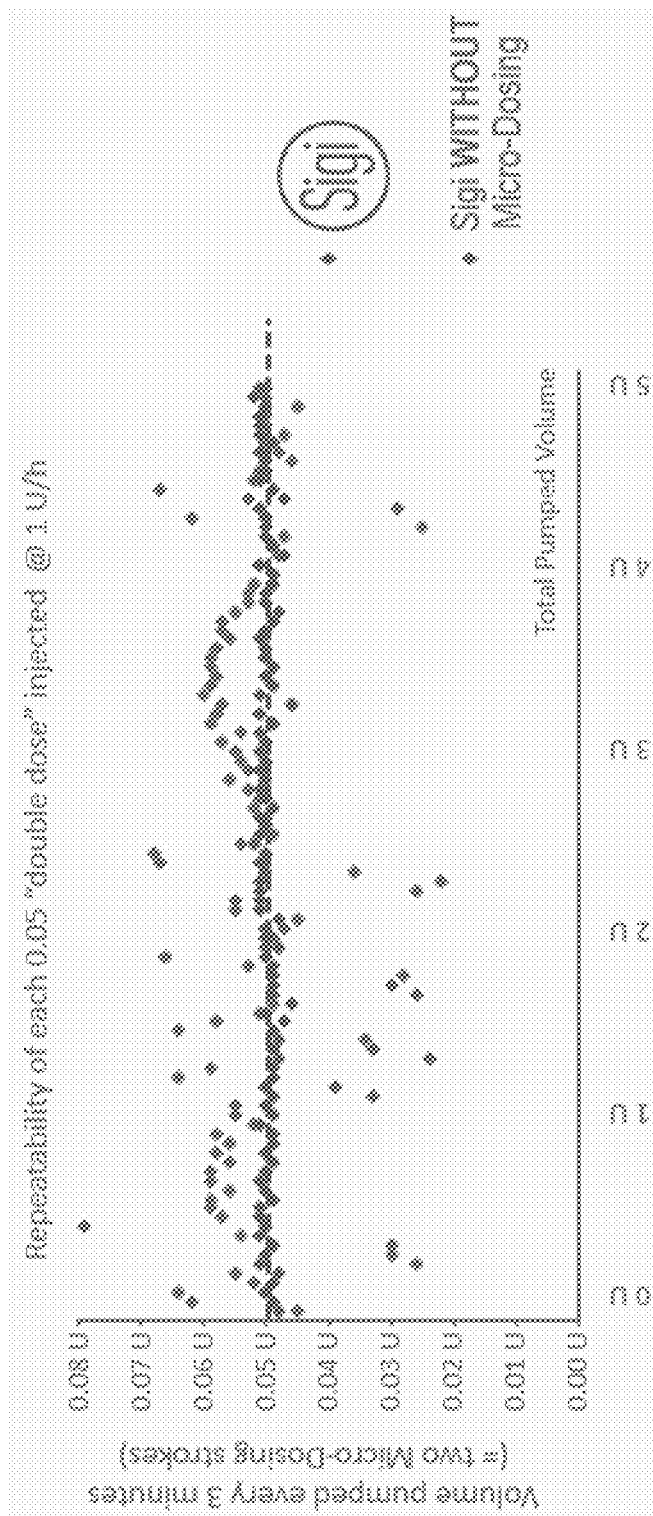
FIG. 24D is a graph showing the accuracy of the pump with and without the microdosing system.
Figure 24E:
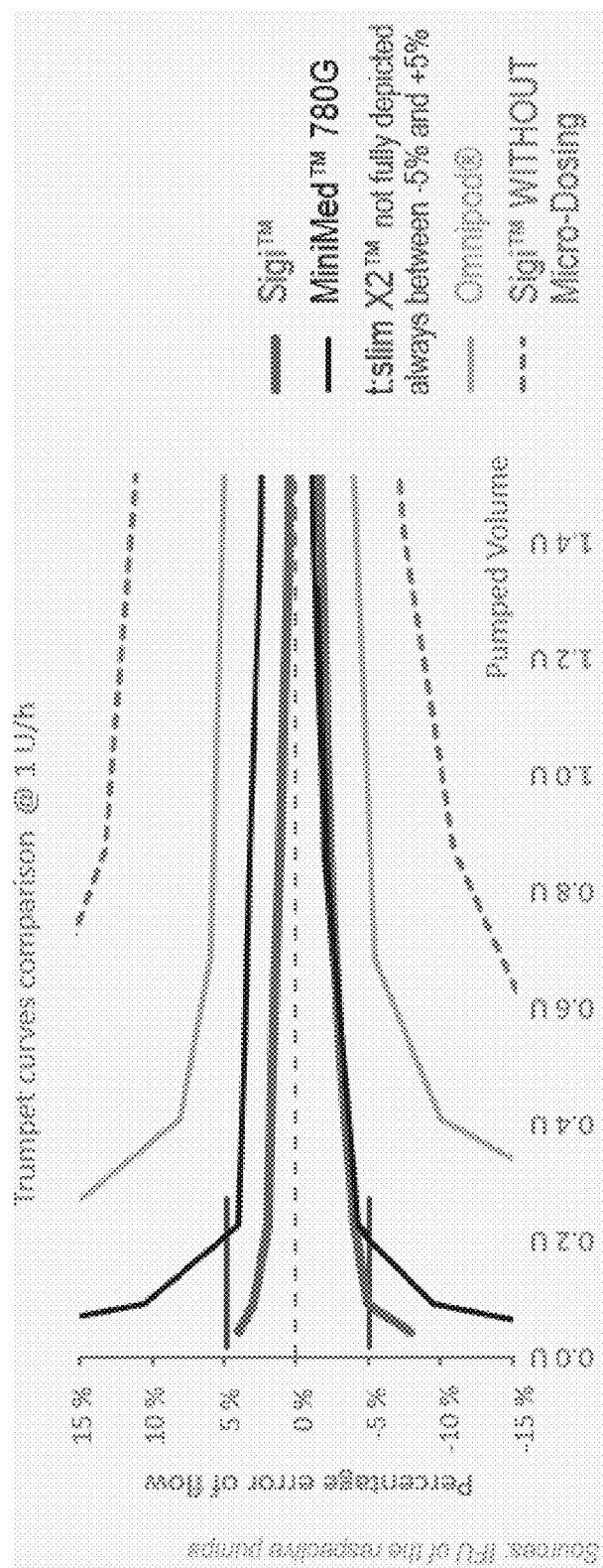
FIG. 24E is a graph showing a comparison of the percentage error of flow for the patch pump and other commercially available pumps.

With respect to FIG. 24A, a graph showing the relationship between pressure and volume is described, while FIGS. 24B and 24C show the relationship between the number of dosing cycles and the amount of medication delivered per cycle, without and with initialization. FIG. 24D shows the accuracy of the patch pump with and without the microdosing system and FIG. 24E shows a comparison of the percentage error of flow for the patch pump described herein and other commercially available pumps. Accurate dosing requires that the pressure within the cartridge remains within a predetermined range. As further explained below, the patch pump may include a microdosing system that is configured to measure and deliver a predetermined dose of medication. The microdosing system preferably includes a dosing tube with a flattened reservoir portion or compartment configured to hold a predetermined dose of medication. Because the reservoir portion is flexible, as the pressure of the medication increases, the reservoir portion expands more, allowing it to hold a greater volume of medication. Accordingly, pressure variations may result in delivery of inconsistent and inaccurate doses of the medication. This relationship is depicted in FIG. 24A. Preferably, the pressure within the cartridge is between 600 mbar and 1000 mbar, and the ideal pressure is 800 mbar. When the pressure is at 800 mbar, the volume of medication is 0.25 ul, which is the preferred predetermined dose of medication.

As the pusher advances towards the plunger of the cartridge, moving the plunger into the cartridge, the pressure within the cartridge builds. As the pressure builds to 800 mbar, the expected volume of the medication that would be held within the dosing tube—if the levers allowed medication to flow into the dosing tube—increases until it reaches the preferred dose of 0.25 ul. Preferably, the microdosing system is configured to complete an initialization process such that delivery of medication to the wearer is prevented until the pressure within the cartridge reaches the predetermined range (e.g., 250 mbar to 2000 mbar, 400 mbar to 1200 mbar, or 600 mbar to 900 mbar). If the microdosing system is configured to complete an initialization process such that delivery of medication to the wearer is prevented until the pressure within the cartridge reaches the predetermined range, the pressure increases at a faster rate than if the there is no initialization of the microdosing system.

FIG. 24B depicts what may occur if the microdosing system is configured to deliver medication prior to initialization. The first dosing cycle would deliver a first dose of medication having a much smaller volume than the preferred volume of 0.25 ul. The second dosing cycle would deliver a second dose of medication having a larger volume than the first dose of medication, but the volume would still be less than the preferred volume of 0.25 ul. As the dosing cycles continue, the pressure would slowly increase to the predetermined range and the volume of medication delivered would slowly reach the predetermined volume. However, the first doses that the wearer would receive would be less than the predetermined dose of medication. Preferably, as in FIG. 24C, microdosing is disabled until the pressure is within 600 mbar and 1000 mbar, such that the volume of each dose of medication is within 5% of 0.25 ul. As the dosing cycles continue, the volume of each dose of medication should remain within 5% of the volume of the previous dose of medication.

Referring now to FIG. 24D, a graph showing the volume pumped per two microdoses over the total volume pump is described. Each data point represents two microdoses, each microdose preferably 0.25 uL. The measurements for the patch pump without the microdosing system shows that the system delivers accurate microdoses but with limited precision. In contrast, the measurements for the patch pump including the microdosing system is both accurate and precise.

Referring now to FIG. 24E, a graph showing the percentage error of flow measurements for the patch pump with and without microdosing and the percentage error of flow measurements for other commercially available pumps is described. The percentage error of flow corresponds to the precision of the pumps, a higher percentage error of flow indicating that the volume of each microdose has a greater variance and thus the pump is less precise. For each pump, the percentage error of flow decreases with each delivery of a microdose. As shown in FIG. 24E, the patch pump described herein ("Sigi") is as precise or more precise than other commercially available pumps.

Figure 24F:
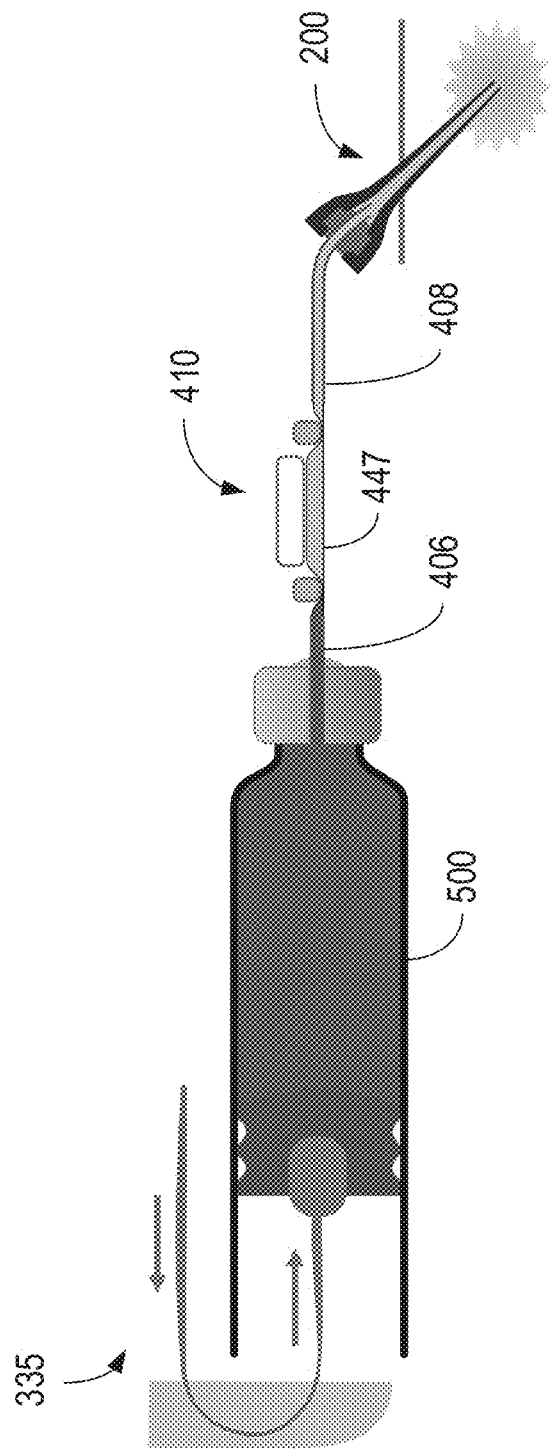
FIG. 24F is a schematic depiction of an exemplary pusher and microdosing system.

Referring now to FIG. 24F, a schematic depiction of an exemplary pusher and microdosing system is described.

Medication may be delivered from cartridge 500, through inflow needle 406, and into flattened dosing tube 447. Upon rotation of the microdosing system, the medication may then be forced out of flattened dosing tube 447, delivered through outflow needle 408 to cannula 200, and inserted into the wearer. Preferably, microdosing system 410 and pusher 335 work together to maintain the pressure within cartridge 500 within a predetermined pressure range. For example, the strain of the plunger and the bendable rod of pusher 335 within cartridge 500 at one end and the levers of microdosing system 410 at the other end create a closed system in which the medication is disposed, the closed system helping maintain the pressure within the predetermined pressure range. The motor within the pump simultaneously advances the plunger and activates microdosing system 410 at each dosing cycle. Preferably, the plunger advances in microsteps (e.g., 3-4 um, preferably 3.7 um) at each dosing cycle such that the pressure within cartridge 500 varies only minimally due to the "stick-slip" effect that occurs at the elastomeric portion of the plunger. The patch pump uses the constant pressure to refill the reservoir of flattened dosing tube 447 with equivalent volumes of medication at every dosing cycle. Inflow needle 406, outflow needle 408, and dosing tube 447 are preferably made from materials compatible with insulin. For example, the inflow and outflow needles may be made of stainless steel and dosing tube 447 may be made of fluoropolymer tubing. Because the flow path for insulin may be directly from cartridge 500 into inflow needle 406, then into dosing tube 447, then into outflow needle, then into cannula 200 (which is also made from insulin compatible material), all materials in contact with the insulin are insulin compatible.

With respect to FIG. 25A, an exploded view an exemplary cap is described. For example, cap 400 may include within cap housing 402 and internal cap housing 401 the following components: cap clips 403, unclipping buttons 405, inflow needle 406, outflow needle 408, microdosing system 410, cam shaft 412, lever spring system 413, lever system 414, cam plate 416, microdosing structure 418, spring 422, magnet 428, tabs 430, flattened dosing tube 447, dosing tube support 454, and/or prongs 474. These components are described further herein.

Figure 25B:
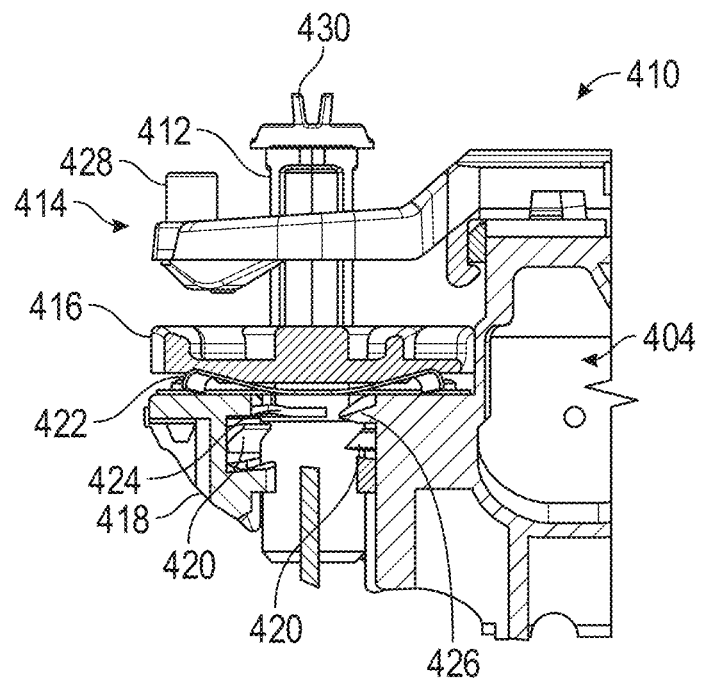
FIG. 25B is a side view of an exemplary microdosing system disposed within the cap, wherein an exemplary circular cam is in an initialization position.

Referring now to FIG. 25B, an exemplary microdosing system disposed within the cap, wherein an exemplary cam is in an initialization position, is described. The cap is configured to deliver medication from the cartridge to the wearer and preferably includes microdosing system 410 configured to measure and deliver the predetermined doses of medication. Preferably, microdosing system 410 is configured such that the insulin travels through a simple pathway designed for low shear stress, which avoids compromising the insulin. Microdosing system 410 may be configured to only deliver the predetermined dose of medication upon initialization of the microdosing system, when the pressure sensor, as described above, senses that the pressure within the cartridge is within the predetermined range. The initialization process helps ensure that the microdosing system accurately measures the predetermined doses of medication. The predetermined pressure range may depend upon the cartridge or medication used, but preferably is between 600 mbar and 1000 mbar. When the pressure sensor senses that the pressure is within the predetermined range, the processor, may be configured to execute programmed instructions stored in the memory to cause the microdosing system to move from an initialization position to a dosing position, such that medication may be delivered to the wearer.

Microdosing system 410 is configured to provide for more accurate dosing and to reduce the noise from the delivery of the medication. Microdosing system 410 preferably is coupled to an inflow needle, which may extend from the cartridge to microdosing system 410, and an outflow needle, which may extend from microdosing system 410 to the cannula. Coupled between the inflow and outflow needle is a dosing tube configured to receive the medication, the dosing tube having a flattened portion including a reservoir portion configured to hold the predetermined dose of medication. The reservoir portion may comprises one or more welded portions that help ensure that a predetermined volume of medication is delivered to the wearer.

Microdosing system 410 further may include a cam, which is configured to rotate, and lever system 414, which is configured to contact the dosing tube and release the predetermined dose of medication into the outflow needle upon interaction with the cam. The cam may be circular in shape to reduce the overall size of the cam and/or to permit two microdoses with a full 360 degree turn of the cam, although other shapes may be suitable. Lever system 414 may include one or more levers, each lever configured to be independently movable such that the movement of a first lever does not affect the position of a second lever. The cam may include cam shaft 412, which is oriented in a first plane, and cam plate 416, which is coupled to cam shaft 412 and oriented in a second plane, the second plane preferably orthogonal to the first plane. The cam plate may be circular in shape to reduce the overall size of the cam plate and/or to permit two microdoses with a full 360 degree turn of the cam plate, although other shapes may be suitable. Cam plate 416 may include a top surface having one or more raised surfaces that are configured to interact with one or more levers of lever system 414 upon rotation of cam shaft 412 such that the predetermined dose of medication is delivered to the wearer. The raised surface(s) may extend away from the circular portion of cam plate 416, such as in a direction generally parallel to the longitudinal axis of the cam. Lever system 414 further may include magnet 428, which is configured to be used to detect an occlusion in the dosing pathway.

Microdosing system 410 further may include tabs 430, which are configured to rotate upon actuation by the motor. Tabs 430 preferably are disposed at the end of cam shaft 412 such that tabs 430 may extend towards and interact with the pump. Additionally, tabs 430 may be configured to function as a locking mechanism. For example, tabs 430 may interact with the mechanical coupling of the pump such that the cap remains locked to the pump. The patch pump may be configured to remain locked until the pusher of the pump is reset in a home position and until the battery is sufficiently charged.

Until a predetermined pressure range is detected within the cartridge, microdosing system 410 preferably remains in an initialization position, wherein cam plate 416 is disposed in a lowered position, as shown in FIG. 25B. In the initialization position, cam plate 416 is separate from and not coupled to lever system 414 such that movement of cam plate 416 does not cause movement of lever system 414. After the cap and the pump are locked together, cam shaft 412 is configured to rotate in a first direction while the pusher is advanced into the cartridge, causing the pressure within the cartridge to increase.

Cam plate 416 may be configured to remain in the initialization position until the pressure within the cartridge is within a predetermined pressure range. To transition cam plate 416 to the dosing position, the direction of rotation may be reversed to a second direction, opposite of the first direction. Cam plate 416 may have a lower portion disposed below the top surface of cam plate 416, the lower portion comprising an outer shaft that surrounds a lower shaft (e.g., cam shaft 412). One or more wings may be disposed on the outer shaft such that wings 420 extend outwards at a slight angle, similar to a thread. In the initialization position, wings 420 interact with components of microdosing structure 418 such that cam plate 416 is prevented from transitioning from the lowered, initialization position to a raised, dosing position to contact lever system 414. The components of microdosing structure 418 may include spring 422, dampers 424, and mating surfaces 426. Spring 422 may be disposed on the top surface of microdosing structure 418 and may apply an upward force on cam plate 416. Dampers 424 may include a plastic material that is configured to minimize the noise from the rotation of the circular cam. Dampers 424 also may act as a gripping mechanism on wings 420 when cam plate 416 transitions from the initialization position to the dosing position. Mating surfaces 426 may be configured to be positioned on microdosing structure 418 at a slight angle, similar to a thread, such that wings 420 may only transition to the dosing position when cam plate 416 rotates in a particular direction.

Figure 25C:
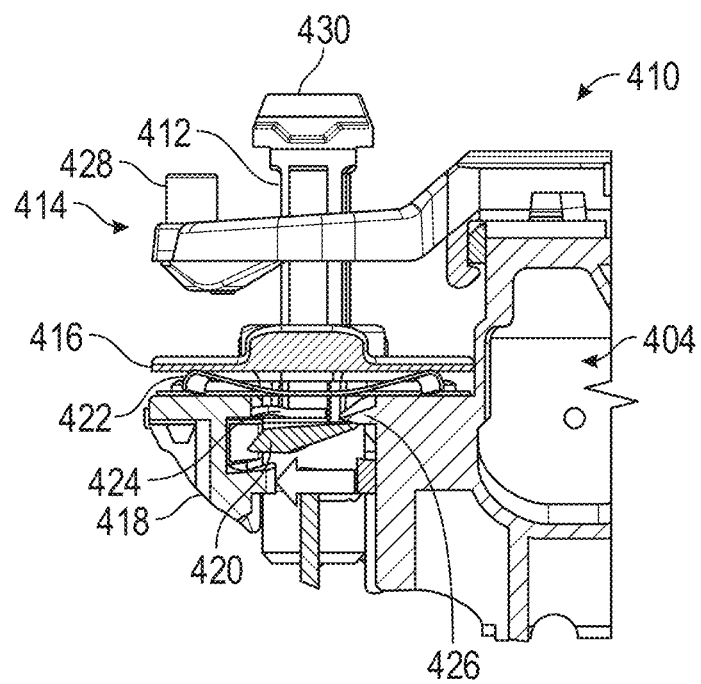

Referring now to FIGS. 25C-25F, further details of operation of the circular cam is described. As the pressure within the cartridge is increased to an optimal pressure, cam shaft 416 is rotated in a first direction, as depicted in FIG. 25C. Spring 422 applies an upwards force on cam plate 416 such that wings 420 contact dampers 424 and mating surfaces 426 but the circular cam remains in a non-gripping position. After the pressure is determined to be within the predetermined pressure range, the direction of rotation of the circular cam is reversed to a second direction, as depicted in FIG. 25D. The circular cam is transitioned to a gripping position wherein wings 420 are gripped between dampers 424 and mating surfaces 426. As cam plate 416 continues to rotate and spring 422 continues to apply an upward force, wings 420 slide upwards through mating surfaces 426, transitioning the circular cam to a sliding position, as depicted in FIG. 25E. Wings 420 continue to slide between dampers 424 and mating surfaces 426 until wings 420 are disposed on top of microdosing structure 418. In the last step of the initialization process, cam plate 416 shifts to the dosing position such that cam plate 416 contacts lever system 414, as depicted in FIG. 25F. The circular cam may be configured such that the transition from the initialization position to the dosing position is permanent and, once in the dosing position, the circular cam cannot return to the initialization position.

Figure 26A:
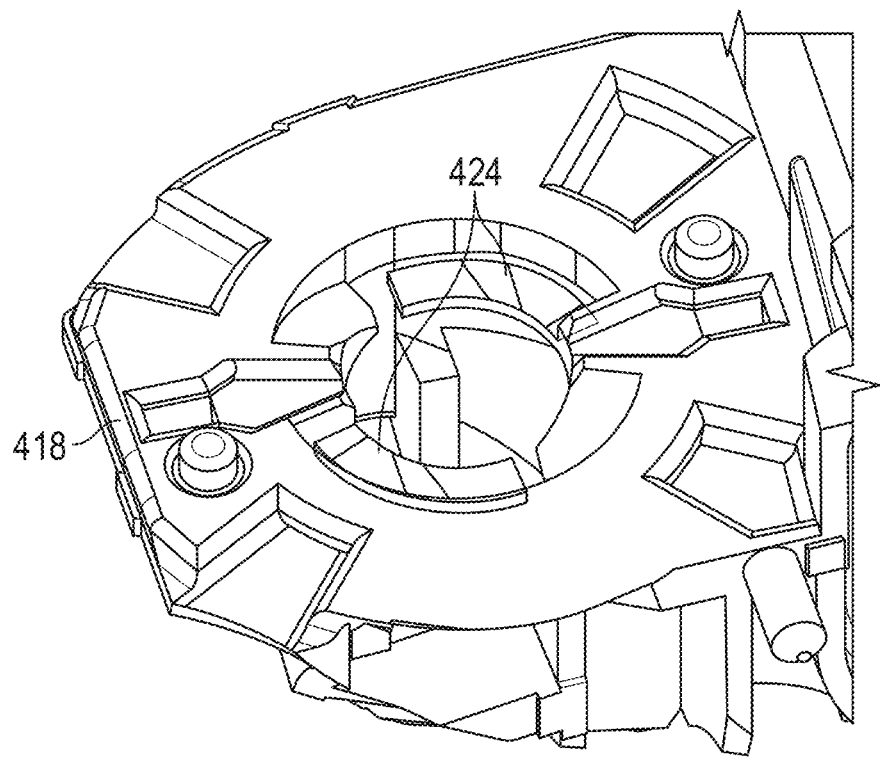
FIGS. 26A and 26B are, respectively, perspective views of exemplary dampers and mating surfaces.
Figure 26B:
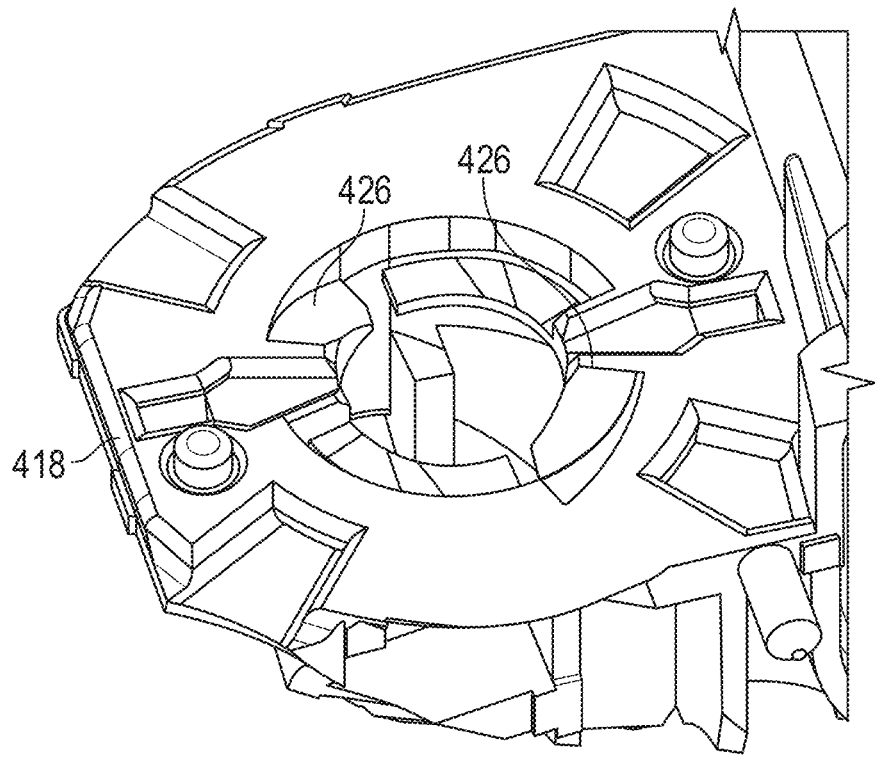

In FIGS. 26A and 26B, the locations and functions of exemplary dampers and mating surfaces are described. Microdosing structure 418 may be configured to hold the circular cam in an initialization position until the pressure within the cartridge is within a predetermined range. Microdosing structure 418 may include dampers 424 and mating surfaces 426, which are configured to interact with and grip the wings of the cam plate when the circular cam transitions from the initialization position to the dosing position. Mating surfaces 426 preferably are configured to have an angled interface that functions as a thread when the wings rotate upwards towards the lever system. Microdosing structure 418 also may be configured to minimize the noise from the rotation of the circular cam. For example, dampers 424 may be made from a flexible plastic material that is designed to minimize the sound from the contact between microdosing structure 418 and the top surface of cam plate 416.

Figure 27A:
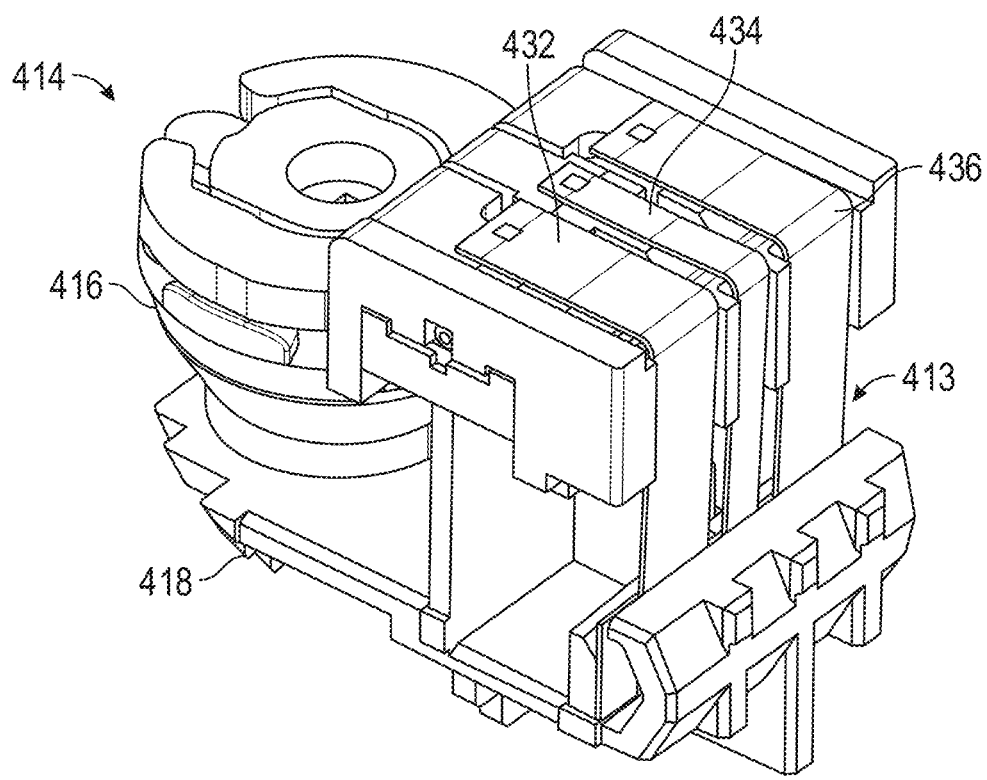
FIGS. 27A and 27B are perspective views of an exemplary microdosing system that may be incorporated in the cap.
Figure 27B:
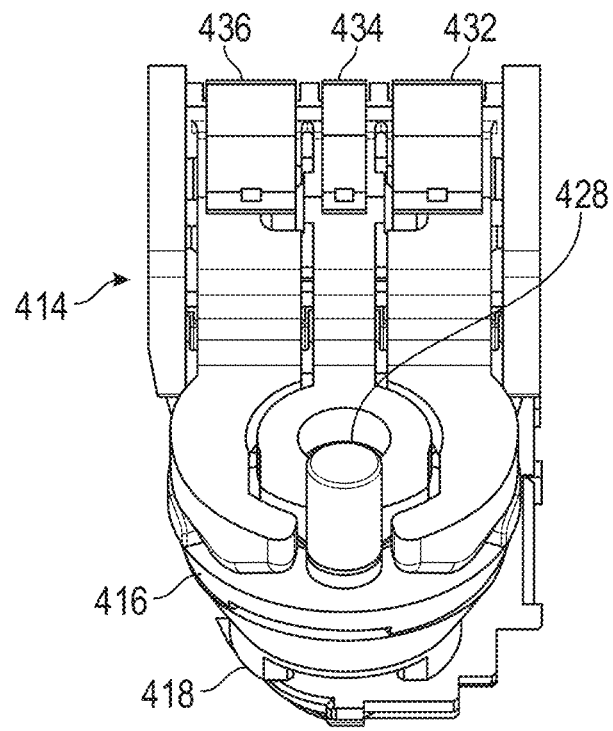

Referring now to FIGS. 27A and 27B, details of a preferred microdosing system are described. Microdosing system 410 is configured to move a predetermined dose of medication towards an outflow needle and into the wearer's skin and may include a dosing tube, lever system 414 configured to contact the dosing tube, and a circular cam configured to rotate. The circular cam preferably includes a cam shaft and cam plate 416, which, upon rotation of the cam shaft, is configured to interact with lever system 414 and deliver the predetermined dose of medication towards the wearer. Lever system 414 may be coupled to lever spring system 413 having one or more springs that are configured to keep the levers of lever system 414 in a lowered position. For example, microdosing system 410 may include first lever spring 432 coupled to a first lever, middle lever spring 434 coupled to a middle lever, and second lever spring 436 coupled to a second lever. Lever spring system 413 may be a single structure comprising one or more levers or may include separate structures, each structure comprising a lever.

Figure 27C:
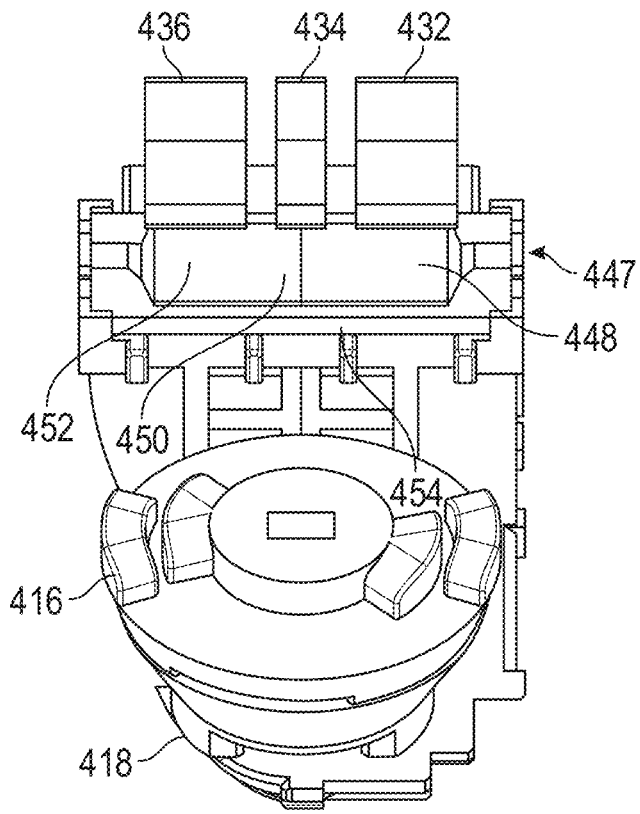
FIG. 27C is a perspective view of the microdosing system, wherein an exemplary lever system is spaced apart from the tube of the microdosing system.

FIG. 27C depicts the microdosing system with the lever system spaced apart to reveal the dosing tube. The lever springs are configured to provide a force on the lever system such that the levers of the lever system maintain contact with the dosing tube and the pressure from the levers prevents the medication from flowing through the dosing tube until intended. The lever springs preferably are disposed above corresponding sections of flattened dosing tube 447, which is coupled to dosing tube support 454. Flattened dosing tube 447 may include a flattened portion having three sections, dosing tube first portion 448, dosing tube reservoir portion 450, and dosing tube second portion 452. Preferably, dosing tube reservoir portion 450 is a compartment between dosing tube first portion 448 and dosing tube second portion 452, the compartment designed to hold a predetermined dose of medication. For example, first lever spring 432 may be disposed above dosing tube first portion 448, middle lever spring 434 may be disposed above dosing tube reservoir portion 450, and second lever spring 436 may be disposed above a dosing tube second portion 452.

Figure 27D:
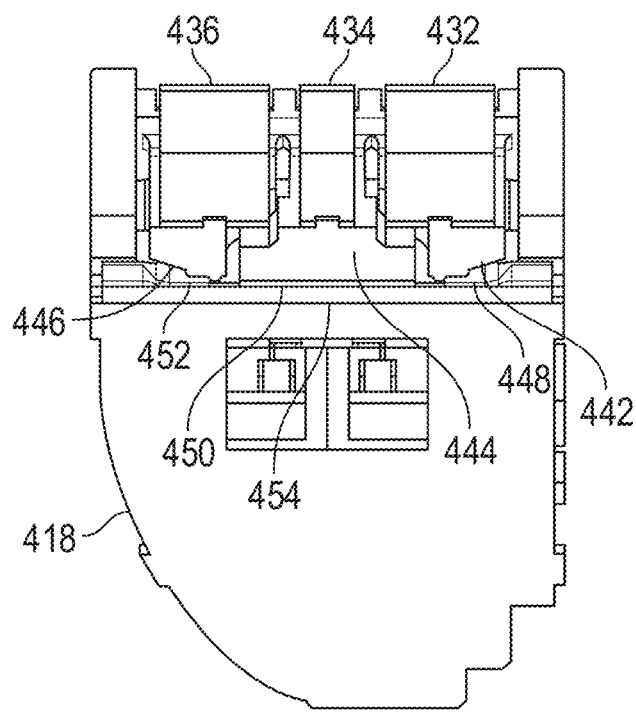
FIG. 27D is a cross-sectional side view of the microdosing system with the lever system in an assembled position.

With respect to FIG. 27D, further details of the microdosing system are described. The lever system preferably includes first lever 442, middle lever 444, and second lever 446, which are configured to contact the dosing tube and act as valves to either permit or prevent medication from flowing through the respective portion of the dosing tube. First lever 442 may be configured to be coupled to first lever spring 432 and to contact dosing tube first portion 448. Middle lever 444 may be configured to be coupled to middle lever spring 434 and to contact dosing tube reservoir portion 450. Second lever 446 may be configured to be coupled to second lever spring 436 and to contact dosing tube second portion 452.

Figure 28A:
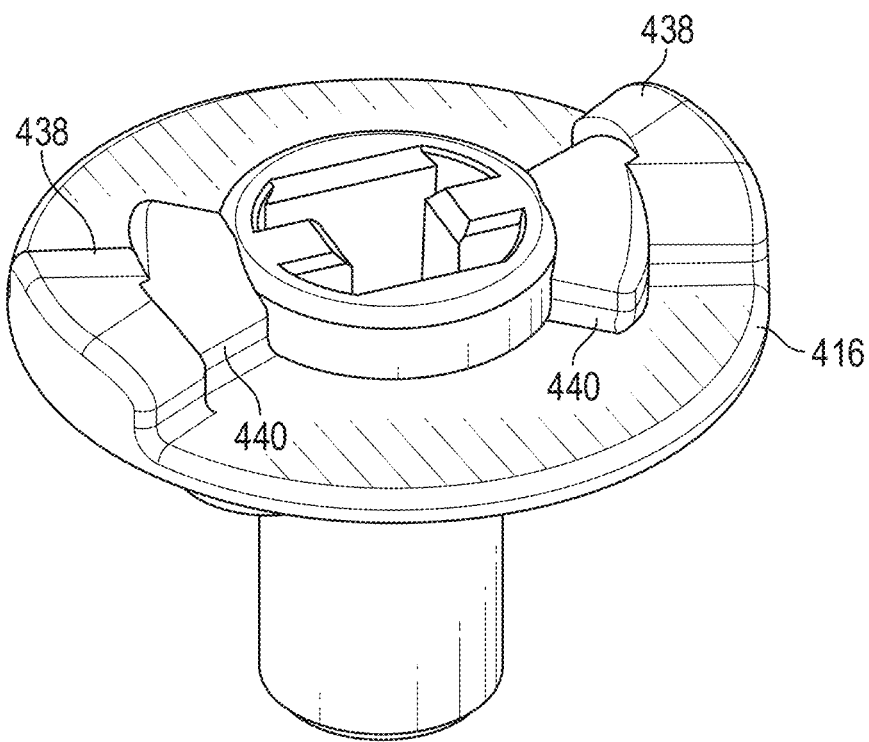
FIGS. 28A and 28B are, respectively, perspective views of an exemplary circular cam and lever system that may be used in the microdosing system.
Figure 28B:
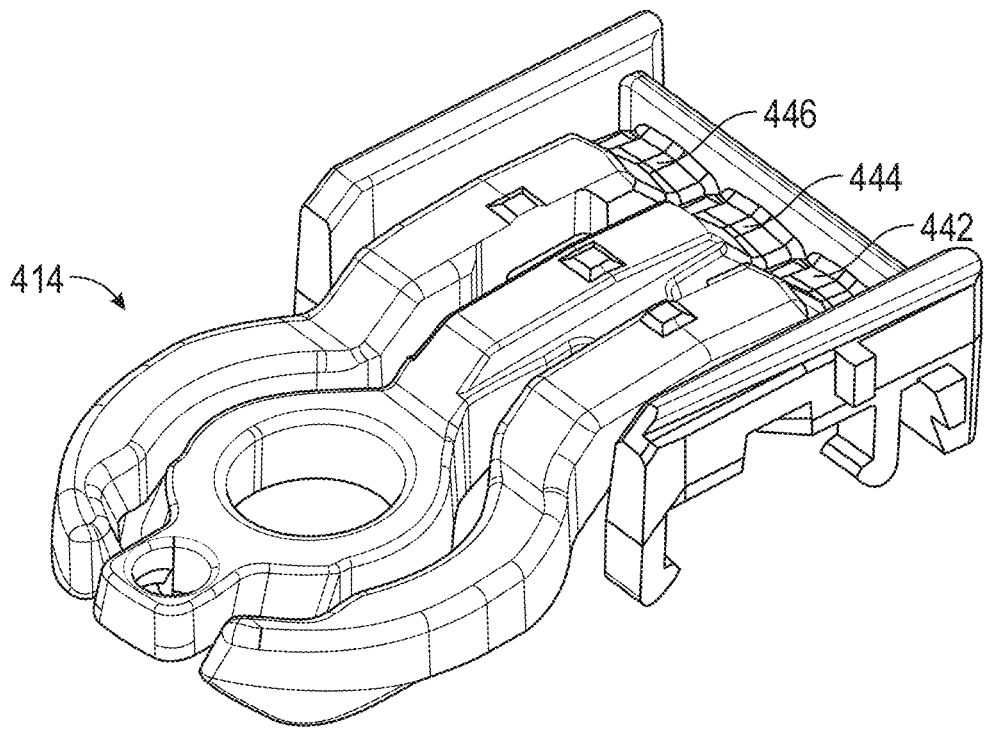

Referring now to FIGS. 28A and 28B, details of the circular cam and lever system are described. Cam plate 416 is configured to interact with lever system 414 such that, upon rotation of cam plate 416, the levers of lever system 414 move in a series of steps and deliver a predetermined dose of medication to the wearer. Cam plate 416 may include one or more rounded, raised surfaces that interact with corresponding rounded lever ramps on the levers of lever system 414. The rounded surfaces ensure smooth movement between of the levers and may help mitigate the sound of the microdosing system. Each time a lever contacts the raised surfaces of cam plate 416, the lever transitions from a lowered position to a raised position, allowing medication to flow through the corresponding section of the dosing tube.

Cam plate 416 may include outer raised surfaces 438 and inner raised surfaces 440, positioned radially outward of outer raised surfaces 438. Outer raised surfaces 438 may be configured to contact the first lever ramp of first lever 442 and the second lever ramp of second lever 446. Preferably, outer raised surfaces 438 are sized and shaped such that the outer raised surface may be disposed between the first lever ramp and the second lever ramp without contacting either the first lever ramp or the second lever ramp. Inner raised surfaces 440 may be configured to contact only the middle lever ramp of middle lever 444. The raised surfaces on cam plate 416 may be configured such that a complete 360 degree rotation of cam plate 416 delivers two predetermined doses of medication towards the wearer. For example, in FIG. 28A, cam plate 416 includes two outer raised surfaces 438 and two inner raised surfaces 440, the second outer and inner raised surfaces mirror images of the first outer and inner raised surfaces. As will be understood by one of ordinary skill in the art, cam plate 416 may include more than two raised surfaces and may be configured such that a 360 degree rotation or a rotation of less than 180 degrees is required for delivery of a predetermined dose of medication.

Figure 29A:
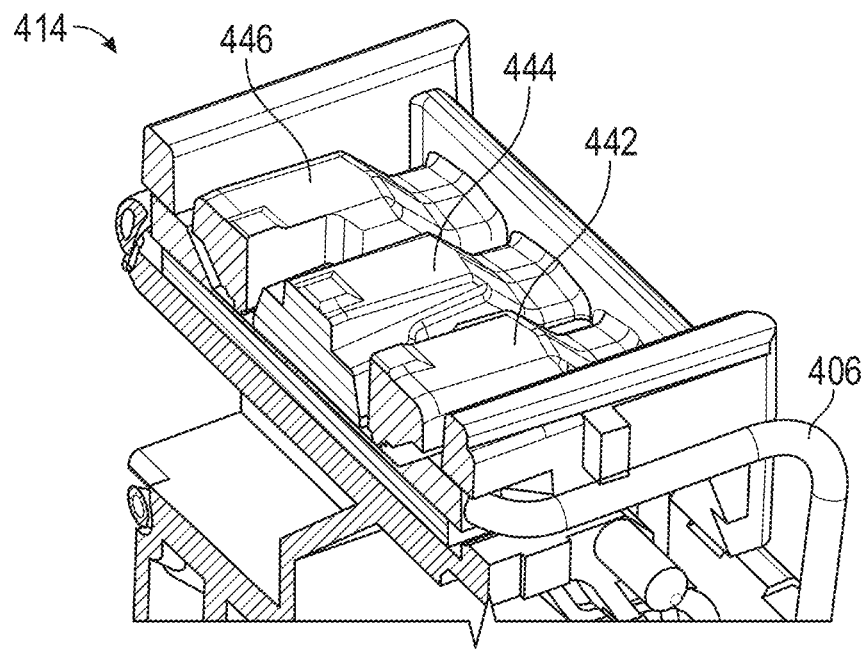
FIGS. 29A-29C are, respectively, cross-sectional perspective and cross-sectional side views of the lever system and exemplary dosing tube.
Figure 29B:
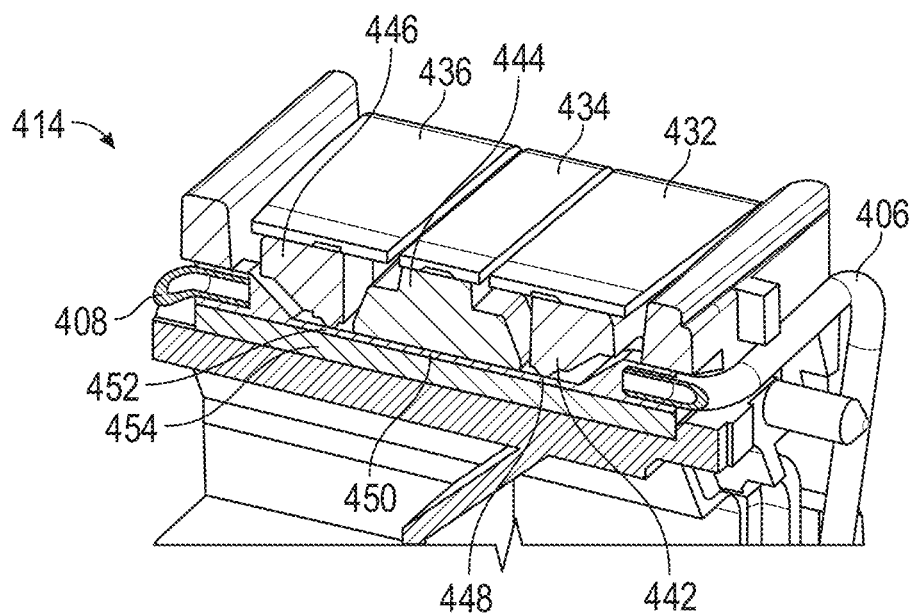
Figure 29C:
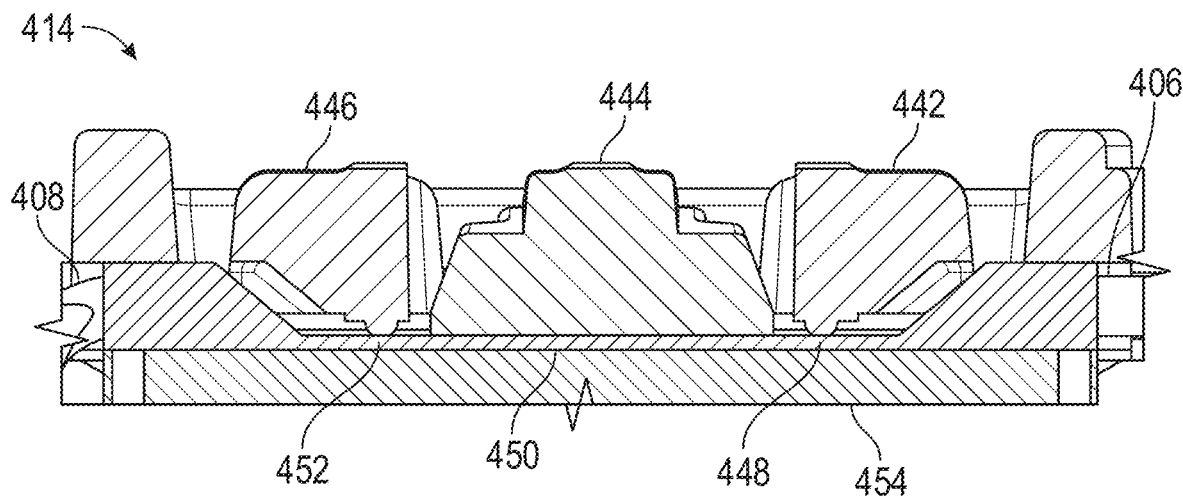

Turning to FIGS. 29A-29C, operation of the lever system and exemplary dosing tube is described. The levers of lever system 414 are configured to transition between a lowered position, such that the levers sequentially contact the dosing tube to prevent medication from flowing through the dosing tube, and a sequentially raised position, to expel medication from the dosing tube to the wearer. Medication is delivered first through inflow needle 406, which is configured to extend from the cartridge to a first end of the dosing tube, next though the dosing tube, and then through outflow needle 408, which is configured to extend from a second end of the dosing tube to the cannula inserted into the wearer. The first end of the dosing tube is adjacent to first lever 442 and dosing tube first portion 448. The second end of the dosing tube is adjacent to second lever 446 and dosing tube second portion 452. Inflow needle 406 and outflow needle 408 preferably are coupled to the dosing tube such that the needles are disposed within the dosing tube, as shown in FIG. 29B. For example, the outer diameter of inflow needle 406 and outflow needle 408 may be the same as or substantially similar to the inner diameter of the first and second ends of the dosing tube.

FIG. 29C depicts a close up of the levers and dosing tube. The dosing tube preferably is disposed on dosing tube support 454, which is configured to provide a support for the dosing tube, which includes a flattened portion having three sections. Dosing tube first portion 448 is a first end of the flattened portion and may be disposed adjacent to first lever 442 such that, when first lever 442 is in a lowered position, medication is prevented from flowing from inflow needle 406 through dosing tube first portion 448. Dosing tube second portion 452 is a second end of the flattened portion and may be disposed adjacent to second lever 446 such that, when second lever 446 is in a lowered position, medication is prevented from flowing through dosing tube second portion 452 and into outflow needle 408. Dosing tube reservoir portion 450 is the middle portion that is substantially surrounded by one or more welded portions. Dosing tube reservoir portion 450 may be disposed adjacent to middle lever 444 such that, when middle lever 444 is lowered and second lever 446 is raised, medication is expelled from dosing tube reservoir portion 450 through dosing tube second portion 452.

Preferably, the levers are sized and shaped to correspond with the size and shape of the dosing tube portions. For example, first lever 442 and second lever 446 may contact only a small section of the flattened portion of the dosing tube. Middle lever 444 may contact a large section of the flattened portion of the dosing tube and may be sized and shaped such that, when middle lever 444 transitions from a raised position to a lowered position, substantially all the medication held within dosing tube reservoir portion 450 is expelled towards the wearer.

Figure 29D:
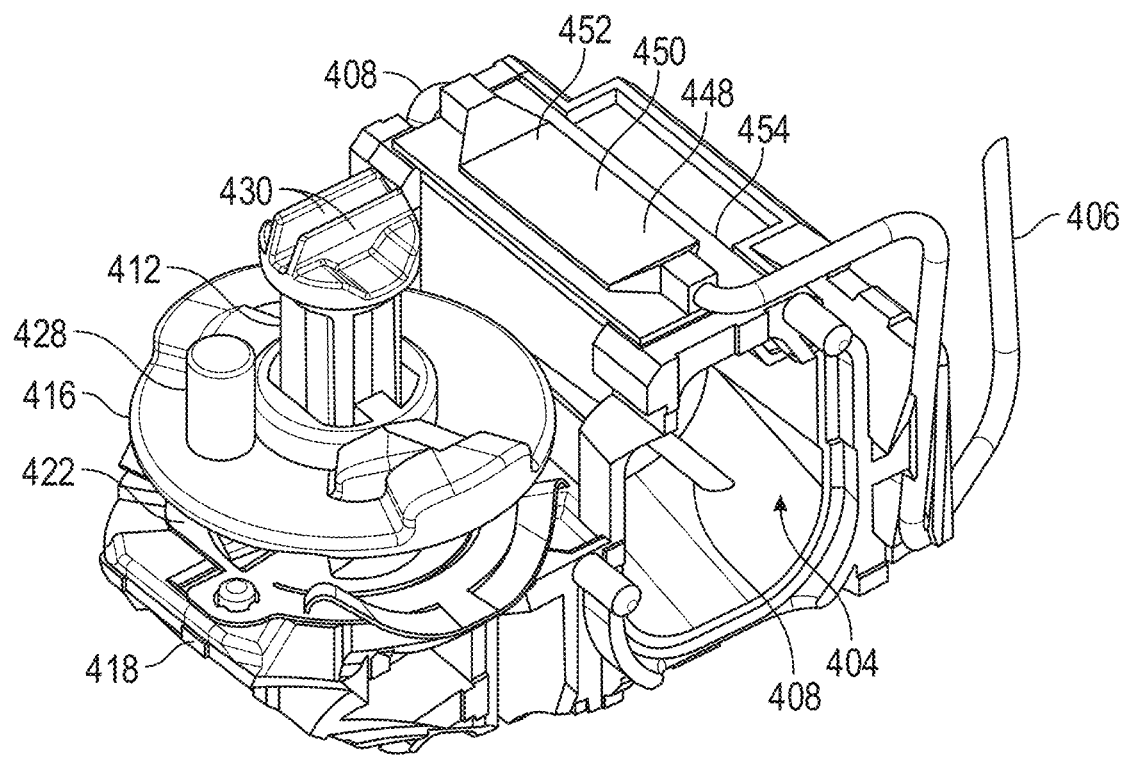
FIG. 29D is a perspective view of the microdosing system, wherein the exemplary lever system and lever springs are removed.

Referring now to FIG. 29D, further details of the microdosing system, are described. In FIG. 29D, the lever system and lever springs are removed to reveal how the inflow and outflow needles are disposed within the pump housing. Inflow needle 406 preferably extends from the cartridge to the first end of the dosing tube. Inflow needle 406 may be configured to contact microdosing structure 418 and extend around connection cavity 404 of the cap housing. Outflow needle 408 preferably extends from the second end of the dosing tube, through connection cavity 404, and into the cannula inserted into the wearer's skin.

Turning to FIGS. 30A-K, operation of microdosing system is described in an exemplary series of steps to deliver a predetermined dose of medication to the wearer. A predetermined dose of medication may be delivered upon rotation of the circular cam, which is configured to interact with the lever system. First lever 442 may include a first extended arm having first lever ramp 456 that is configured to contact the outer raised surfaces of cam plate 416, middle lever 444 may include a middle extended arm having middle lever ramp 458 that is configured to contact the inner raised surfaces of cam plate 416, and second lever 446 may include a second extended arm having second lever ramp 460 that is configured to contact the outer raised surfaces of cam plate 416. Each extended arm may extend from the lever ramps to the dosing tube. Preferably, the lever ramps are configured to maintain smooth and continuous contact with the raised surfaces of cam plate 416 such that the noise from rotation of the circular cam is minimized. For example, the lever ramps may have a rounded shape and the raised surfaces may have a corresponding rounded shape.

Figure 30C:
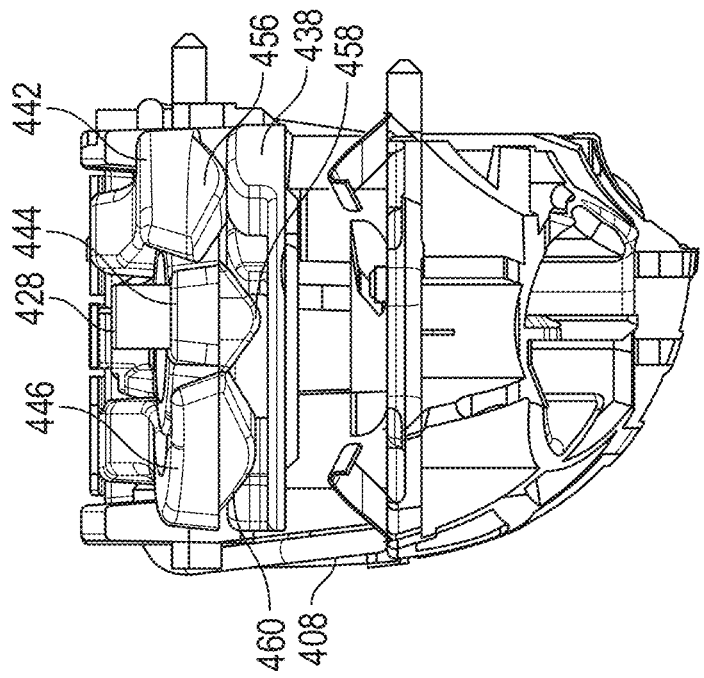
FIGS. 30A, 30C, 30E, 30G, 30I, and 30K are side views of the microdosing system over an exemplary series of steps configured to deliver a predetermined dose of medication to the wearer.
Figure 30D:
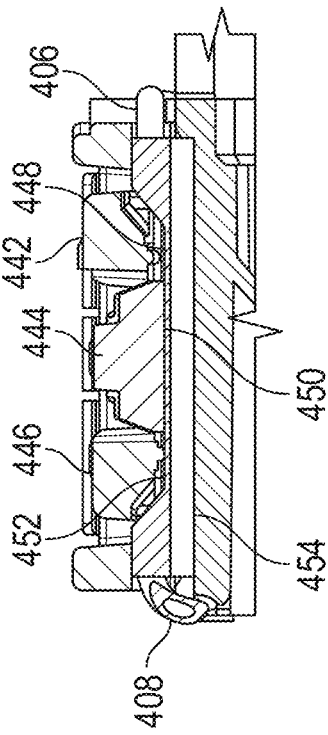
FIGS. 30B, 30D, 30F, 30H, 30J, and 30L are cross-sectional side views of the microdosing system over the series of steps configured to deliver the predetermined dose of medication to the wearer.
Figure 30A:
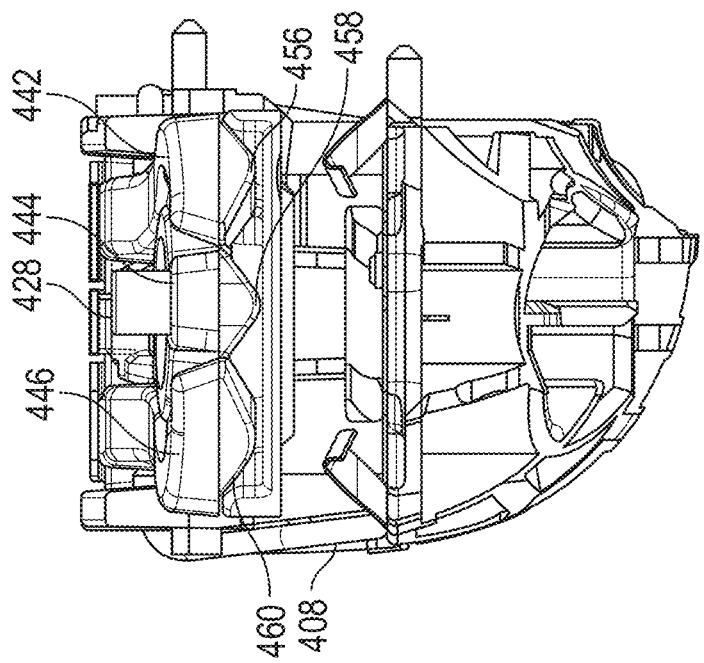
Figure 30B:
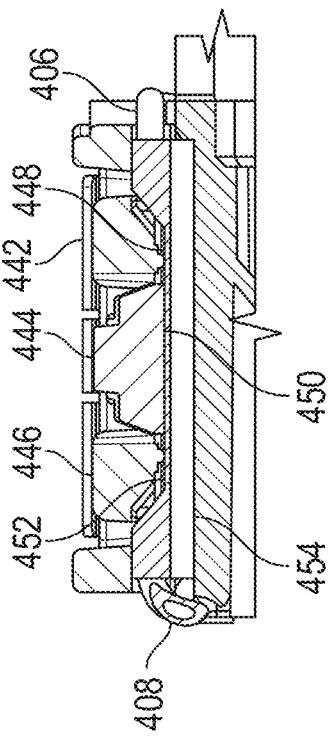

FIGS. 30A and 30B show the microdosing system in a first position, wherein first lever 442, middle lever 444, and second lever 446 are in a lowered position such that the levers are pressing down on the corresponding portions of the dosing tube and medication cannot flow past any of the levers. In the first position, none of the lever ramps contact the raised surfaces of the cam plate.

FIGS. 30C and 30D show the microdosing system in a second position. Upon rotation of the cam plate, outer raised surface 438 contacts first lever ramp 456, moving first lever 442 from a lowered position to a raised position. Middle lever 444 and second lever 446 remain in a lowered position such that medication can flow through dosing tube first portion 448 but cannot flow past dosing tube reservoir portion 450.

Figure 30E:
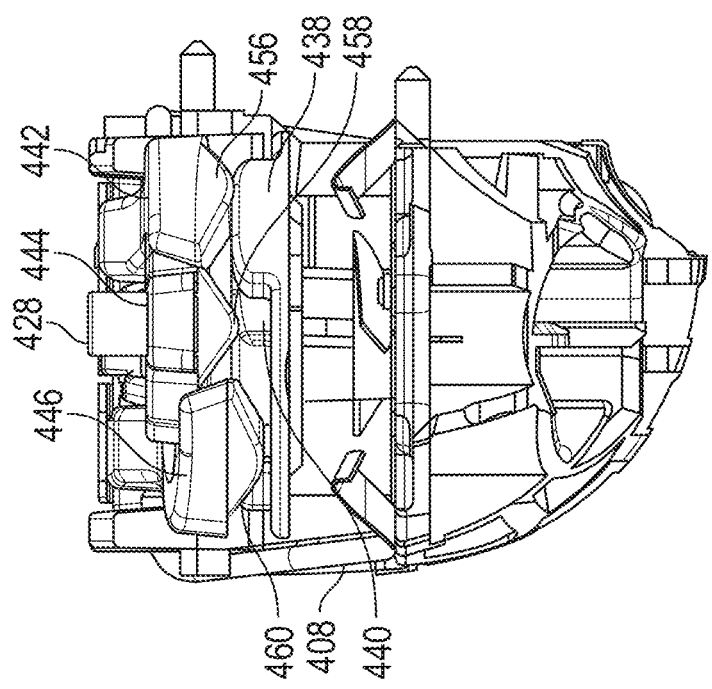
Figure 30F:
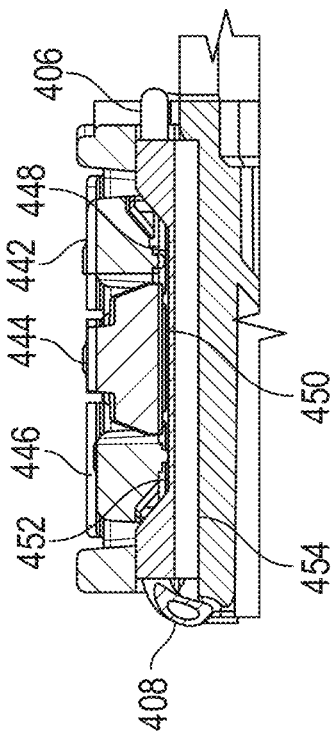

FIGS. 30E and 30F show the microdosing system in a third position. Upon further rotation of the cam plate, outer raised surface 438 remains in contact with first lever ramp 456 such that first lever 442 remains in a raised position and inner raised surface 440 contacts middle lever ramp 458, moving middle lever 444 from a lowered position to a raised position. Second lever 446 remains in a lowered position such that medication can flow through dosing tube first portion 448 and into dosing tube reservoir portion 450 but cannot flow past dosing tube second portion 452. In the third position, dosing tube reservoir portion 450 is configured to fill and expand with the predetermined dose of medication.

Figure 30G:
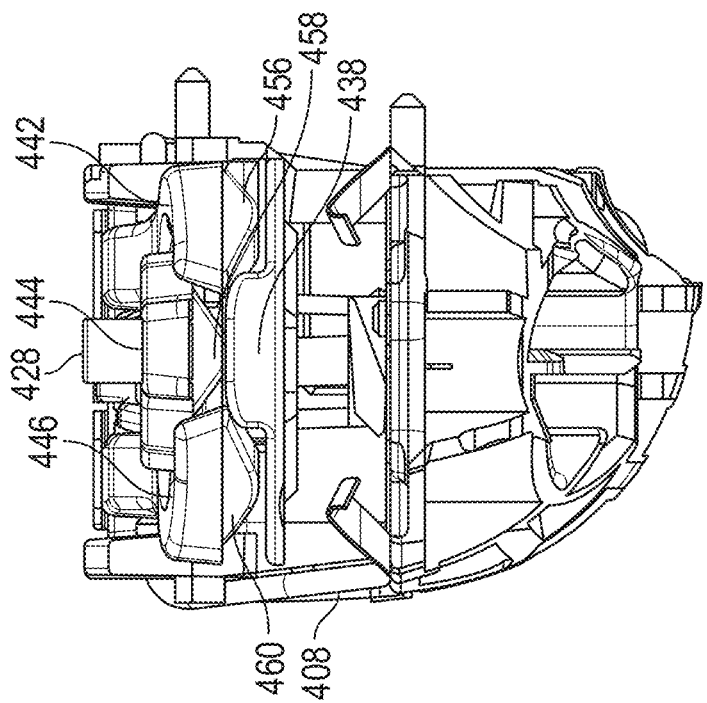
Figure 30H:
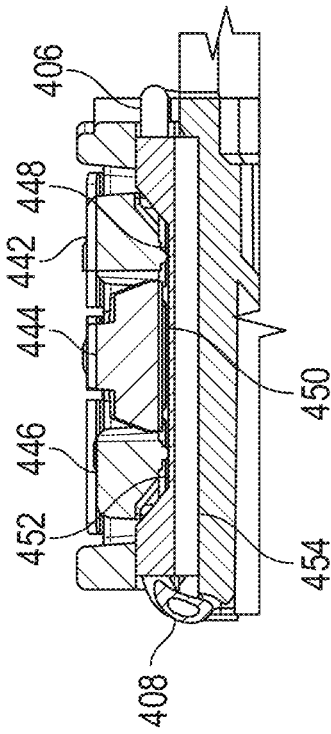

FIGS. 30G and 30H show the microdosing system in a fourth position. Upon further rotation of the cam plate, outer raised surface 438 moves to a position between first lever ramp 456 and second lever ramp 460 such that outer raised surface 438 is not in contact with either first lever ramp 456 or second lever ramp 460. Inner raised surface 440 remains in contact with middle lever ramp 458 such that middle lever 444 remains in a raised position. First lever 442 moves from a raised position to a lowered position and second lever 446 remains in a lowered position such that the predetermined dose of medication is held within dosing tube reservoir portion 450 and is unable to flow past dosing tube second portion 452.

Figure 30I:
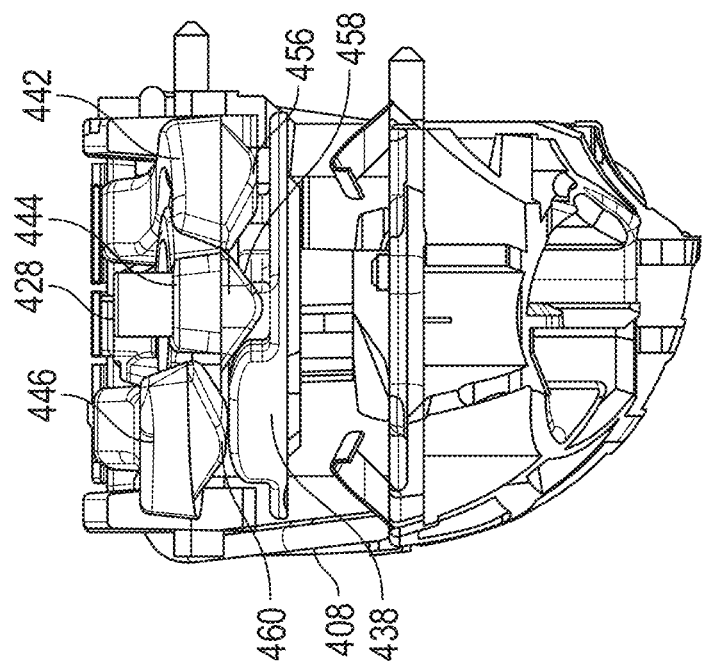
Figure 30J:
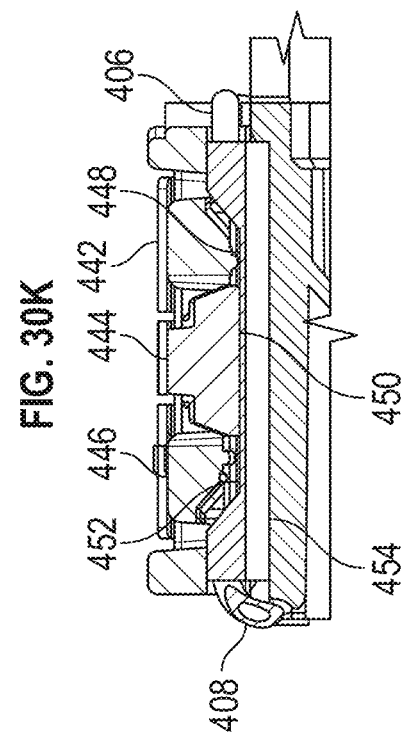

FIGS. 30I and 30J show the microdosing system in a fifth position. Upon further rotation of the cam plate, outer raised surface 438 contacts second lever ramp 460, moving second lever 446 from a lowered position to a raised position, and inner raised surface 440 remains in contact with middle lever ramp 458 such that middle lever 444 remains in a raised position. First lever 446 remains in a lowered position such that medication can flow through dosing tube second portion 452 to outflow needle 408, but cannot flow back through dosing tube first portion 448.

Figure 30K:
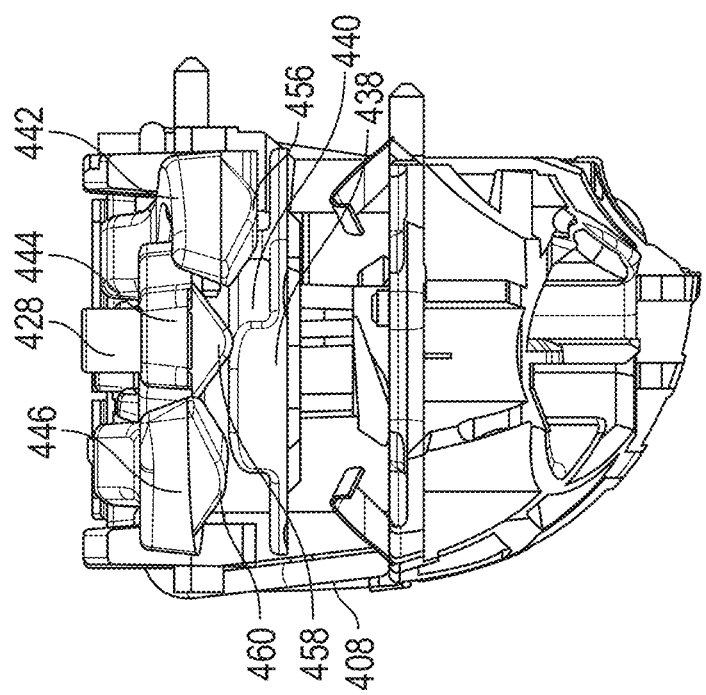
Figure 30L:
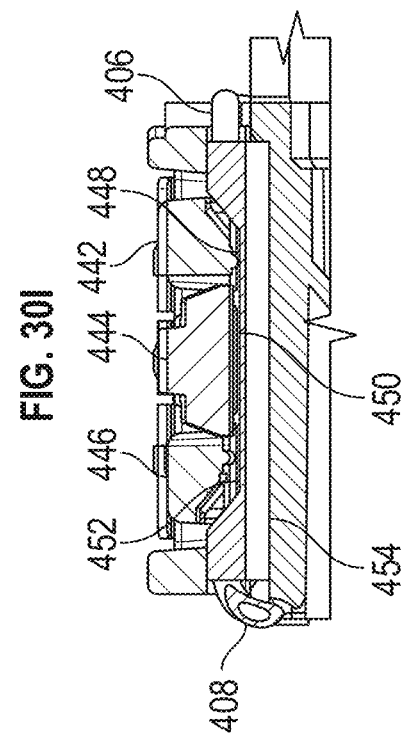

FIGS. 30K and 30L show the microdosing system in a sixth position. Upon further rotation of the cam plate, outer raised surface 438 remains in contact with second lever ramp 460 such that second lever 446 remains in a raised position and inner raised surface 440 moves to a position past middle lever ramp 456 such that middle lever 444 moves from a raised position to a lowered position such that middle lever 444 applies pressure to dosing tube reservoir portion 450, forcing the predetermined dose of medication past dosing tube second portion 452 and into outflow needle 408. This step ensures the accuracy of the medication delivery and that all of the predetermined dose of medication is delivered to the wearer such that no medication remains in dosing tube reservoir portion 450.

Figure 31:
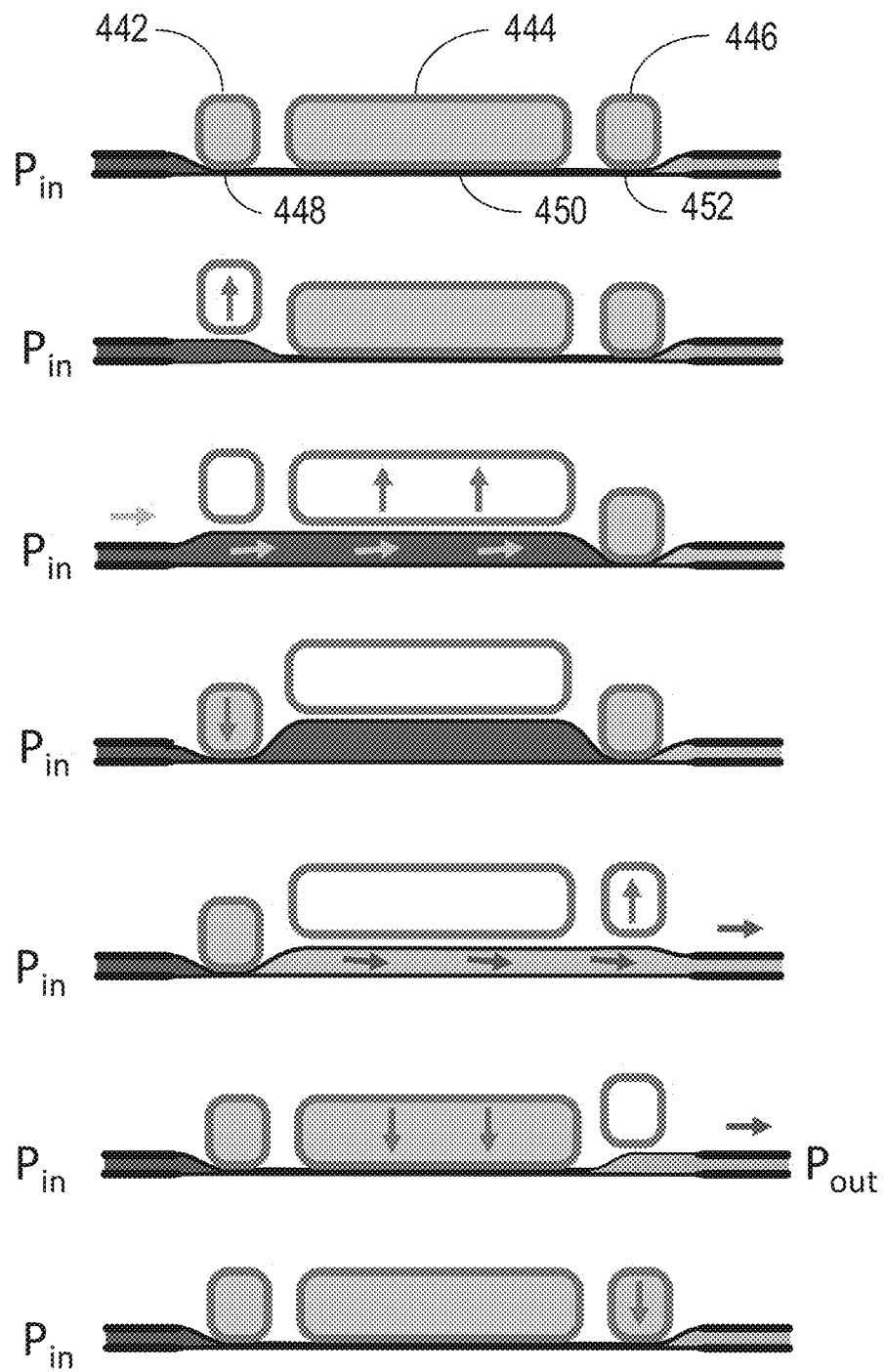
FIG. 31 is a schematic depiction of the series of steps configured to deliver the predetermined dose of medication to the wearer.

FIG. 31 provides a schematic depiction of the series of steps configured to deliver the predetermined dose of medication to the wearer. As described with respect to FIGS. 30A-L above, the lever system includes lever ramps, which are configured to move the levers between a lowered position and a raised position upon contact with raised surfaces on the cam plate. Each lever is configured to contact a different portion of the dosing tube. Preferably, first lever 442 contacts dosing tube first portion 448, middle lever 444 contacts dosing tube reservoir portion 450, and second lever 446 contacts dosing tube second portion 452.

The steps depicted in FIG. 31 correspond with the steps shown in FIGS. 30A-L. In the first position, first lever 442, middle lever 444, and second lever 446 are in a lowered position and contact the corresponding portions of the dosing tube such that the medication cannot flow through the dosing tube or past any of the levers. In the second position, first lever 442 moves to a raised position and middle lever 444 and second lever 446 remain in a lowered position such that medication may only flow through dosing tube first portion 448. In the third position, first lever 442 remains in a raised position, middle lever 444 moves to a raised position, and second lever 446 remains in a lowered position such that medication may flow into dosing tube reservoir portion 450, but not past second lever 446. In the fourth position, first lever 442 moves to a lowered position, middle lever 444 remains in a raised position, and second lever 446 remains in a lowered position such that the predetermined dose of medication is measured within dosing tube reservoir portion 450 and cannot flow past either first lever 442 or second lever 446. In the fifth position, first lever 442 remains in a lowered position, middle lever 444 remains in a raised position, and second lever 446 moves to a raised position such that predetermined dose of medication may flow from dosing tube reservoir portion 450 and through dosing tube second portion 452. In the sixth position, first lever 442 remains in a lowered position, middle lever 444 moves to a lowered position, and second lever 446 remains in a raised position such that the all of the predetermined dose of medication is forced out of dosing tube reservoir portion 450 and through dosing tube second portion 452 towards the wearer. Following this step, the microdosing system returns to the first position wherein all of the levers are in a lowered position.

Figure 32A:
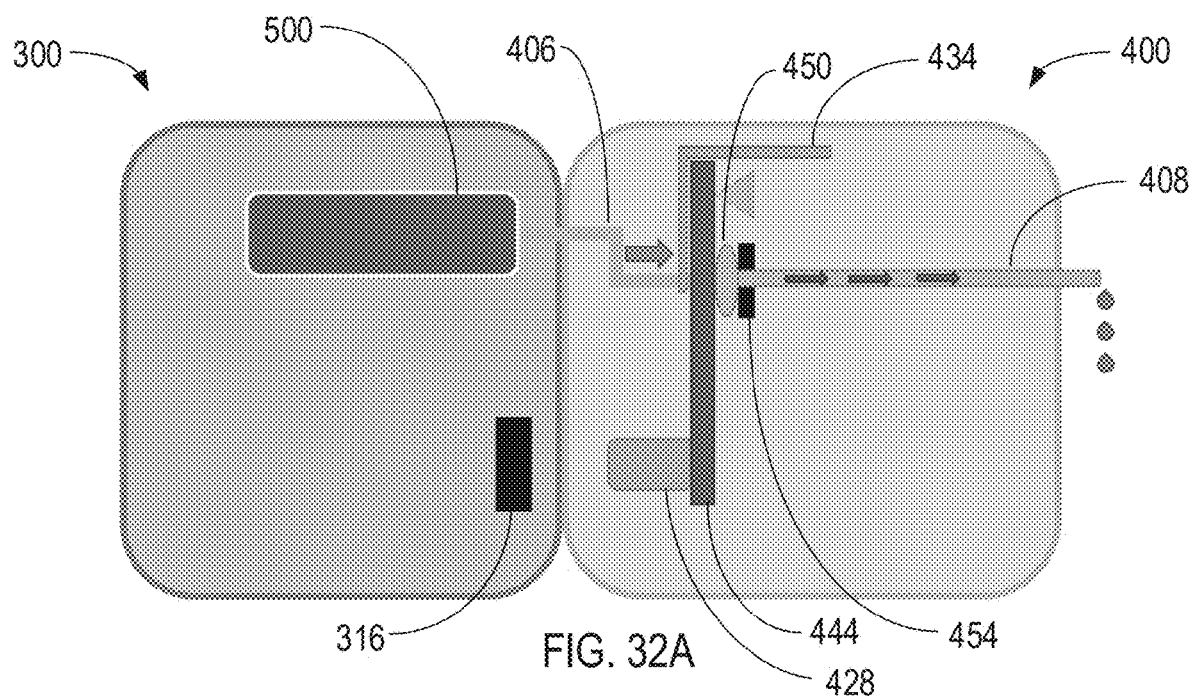
FIGS. 32A and 32B are, respectively, schematic depictions of an exemplary system configured to detect an occlusion in the dosing pathway.
Figure 32B:
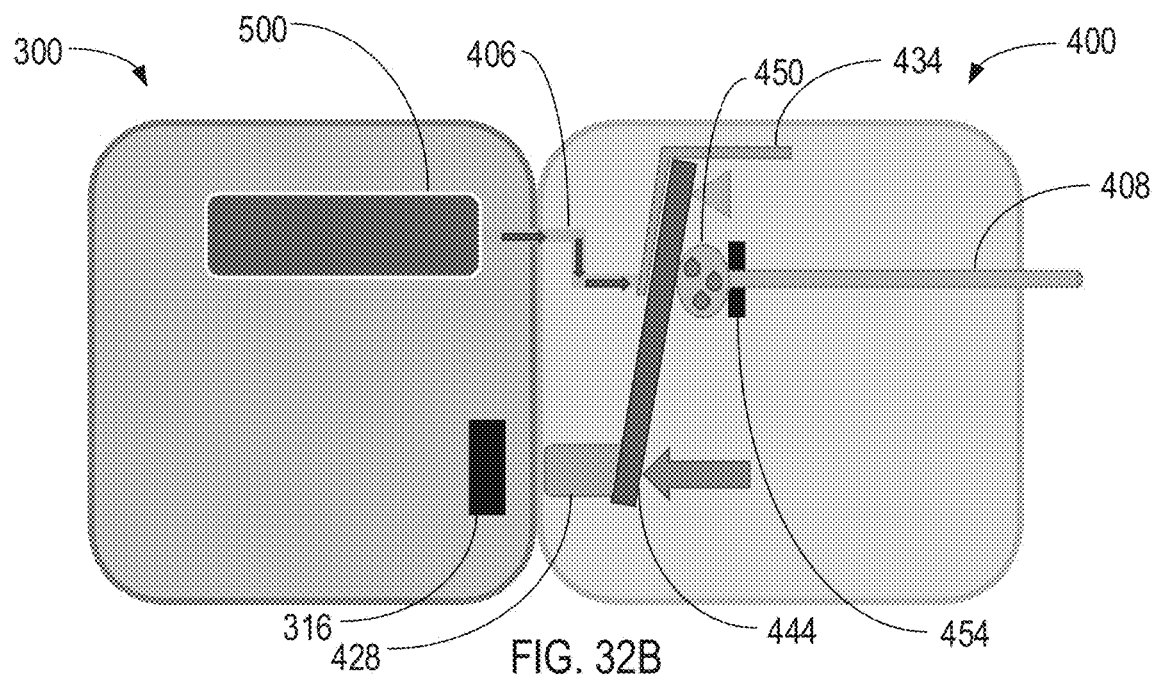

Referring now to FIGS. 32A and 32B, an exemplary system for detecting an occlusion in the dosing pathway, from cartridge 500 to the location medication is delivered within the skin of the wearer, is described. An occlusion in the dosing pathway may occur within the dosing tube, within outflow needle 408, or within the cannula. Fast detection of an infusion anomaly (e.g., an occlusion) in the dosing pathway allows the microdosing system to monitor the accuracy of the microdosing system and mitigates the risk that the wearer fails to receive a proper dose of medication. Pump 300 may include sensor 316, which may be configured to confirm the accuracy of the microdosing system and that the predetermined dose of medication was delivered to the wearer. Sensor 316 preferably is configured to sense displacement of one or more levers, which may be indicative of whether there is an occlusion disposed within the dosing tube, within outflow needle 408, or within the cannula. Sensor 316 may be electrically coupled to a controller such that sensed signals are sent to the controller for processing and detecting an occlusion. The controller may sense an occlusion if the sensed displacement is outside a threshold range, the determination based on the proximity of the magnet to the hall-effect sensor over time. For example, the controller may be configured to monitor whether the measured Hall-effect sensor values are within predetermined Hall-effect sensor value ranges that are expected for each step of the dosing cycle or if the measured Hall-effect sensor values change at a time it should remain the same. The controller may determine there is an occlusion based on one or more sensed signals. For example, detection of an occlusion may be based on sensed signals over more than one dosing cycles.

Sensor 316 may also be used to determine whether the microdosing system is in the initialization position. For example, the controller may sense that the microdosing system is in the initialization position if the sensor does not sense any displacement of the one or more levers over a predetermined period of time. Further, sensor 316 may be used to determine whether the cap is coupled to the pump. The controller may confirm that the cap and pump are properly coupled together if sensor 316 senses that the one or more levers is disposed in a predetermined position. Alternatively or additionally, information sensed by sensor 316 may be used to determine a status of the cap, for example, whether the cap is "new" or "used." For example, the when the cam plate moves from the initialization position to the dosing position, the magnet coupled to the lever system may move slightly towards the pump. Information from sensor 316 may be used to determine that the microdosing system has completed the initialization process and therefore the cap is "used." Information sensed by sensor 316 may be used to determine if the cap is coupled to the pump. For example, if a magnetic field is not sensed by sensor 316, the controller indicates that the cap is not coupled to the pump because the magnet in the cap is not being sensed. As such, the controller will not activate pumping until the cap is coupled to the pump. Further, the position of the magnet within the cap, as sensed by sensor 316 based on the strength of the magnetic field, may indicate the status of the cap. For example, if the magnetic field is within a predetermined range, the controller will indicate that the cap is in the initialization position. If the magnetic field is within a second predetermined range, the controller will indicate that the cap is in the dosing position. In some embodiments, the strength of the magnetic field is weaker when the cap is in the initialization position because the magnet is further from the pump. As the cap moves from the initialization position to the dosing position, the magnet is moved closer to the cap, thereby increasing the strength of the sensed magnetic field. As such, the second predetermined range may be higher than the first predetermined range to indicate that the pump is in the dosing position, as determined by the controller.

FIGS. 32A and 32B show a simplified view of the microdosing system in two positions. Disposed within pump 300 is sensor 316 and cartridge 500, which may be coupled to inflow needle 406. Inflow needle 406 may be coupled to the dosing tube and the dosing tube may be coupled to outflow needle 408. The lever system may include middle lever spring 434, which may apply a force on middle lever 444 such that middle lever 444 remains in a lowered position adjacent to dosing reservoir portion 450. At the opposite end of middle lever 444, magnet 428 may be disposed. Magnet 428 may be positioned such that when middle lever 444 moves from a lowered position to a raised position, in FIG. 32B, magnet 428 moves closer to sensor 316. Sensor 316 preferably is a Hall-effect sensor that is configured to detect a magnetic field of a magnet disposed on the lever system.

In FIG. 32A, the dosing tube reservoir portion 450 is in a compressed state, such that no medication is disposed within dosing tube reservoir portion 450. In the compressed state, middle lever 444 is positioned in a lowered position such that magnet 428 is disposed farther away from sensor 316. The farther magnet 428 is away from sensor 316, the smaller the Hall-effect value will be. In FIG. 32B, when dosing tube reservoir portion 450 is in an expanded state, medication is disposed within dosing tube reservoir portion 450. In the expanded state, middle lever 44 is positioned in a raised position such that magnet 428 is disposed closer to sensor 316 such that the Hall-effect value is greater than the Hall-effect value when dosing tube reservoir portion 450 is in the compressed state.

Figure 32C:
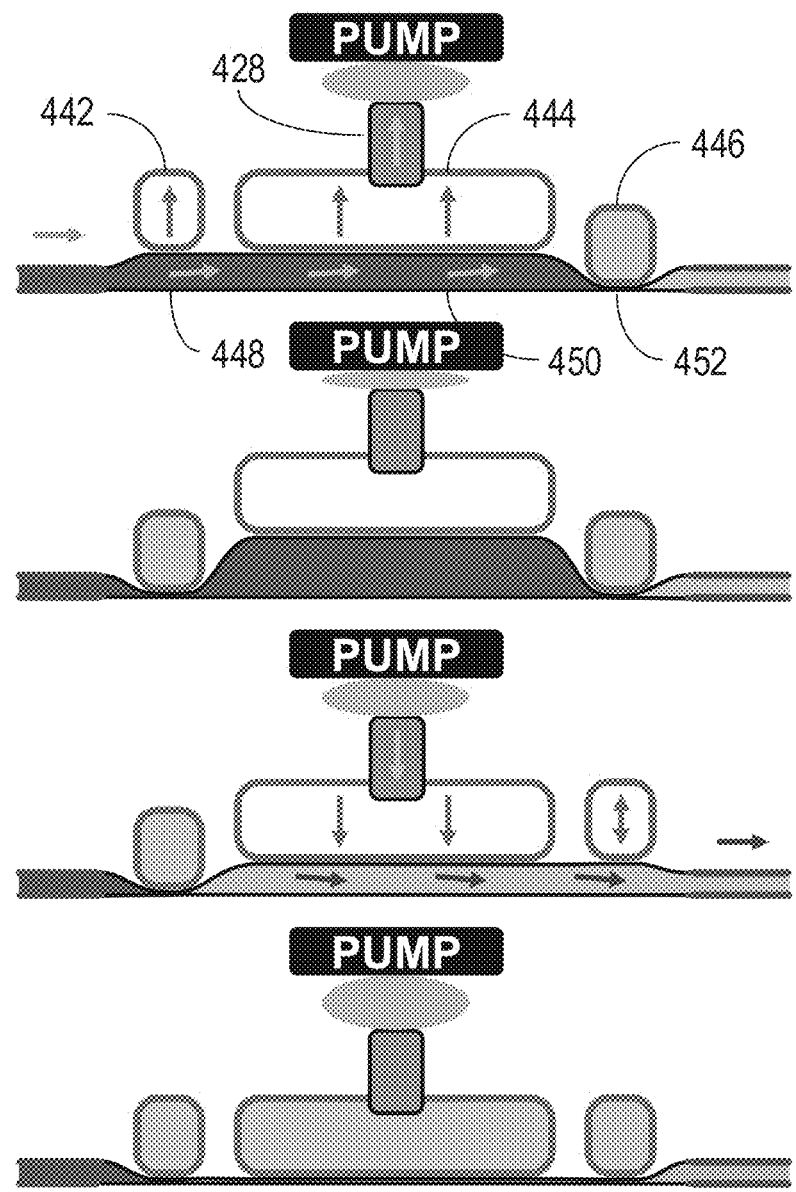
FIG. 32C is a schematic depiction of the position of a lever of the microdosing system during a dosing cycle, wherein the dosing pathway is not occluded.

Referring now to FIG. 32C, the changing position of the magnet disposed on the middle lever of the microdosing system during a dosing cycle is described. In the first step, first lever 442 and middle lever 444 are in a raised position such that medication may flow into dosing tube reservoir portion 450. After first lever 442 moves to a lowered position, second lever 446 moves to a raised position. A portion of the medication within dosing tube reservoir portion may flow into the outflow needle and thus middle lever 444 and magnet 428 may move a slightly farther away from the pump and sensor. In the third step, middle lever 444 moves to a lowered position such that a force is applied to dosing tube reservoir portion 450. If there are no occlusions within the dosing tube or within the outflow needle or cannula, the remaining medication disposed within dosing tube reservoir portion 450 is forced into the outflow needle and middle lever 444 and magnet 428 move to a lowered position. In the last step, middle lever 444 and magnet 428 move to the farthest position away from the pump and sensor.

Figure 33A:
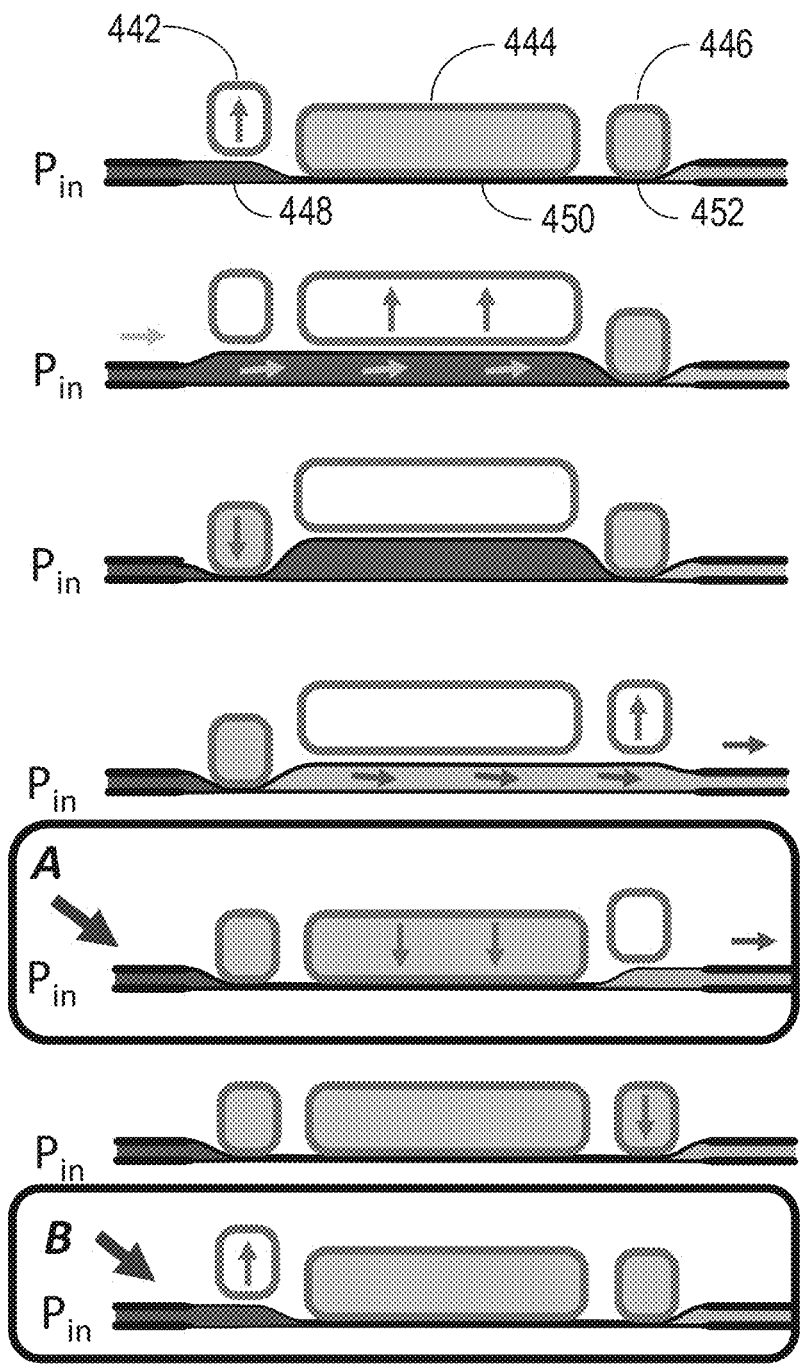
FIGS. 33A and 33B are, respectively, schematic depictions of the series of steps configured to deliver the predetermined dose of medication to the wearer, wherein the dosing pathway is not occluded and wherein the dosing pathway is occluded.
Figure 33B:
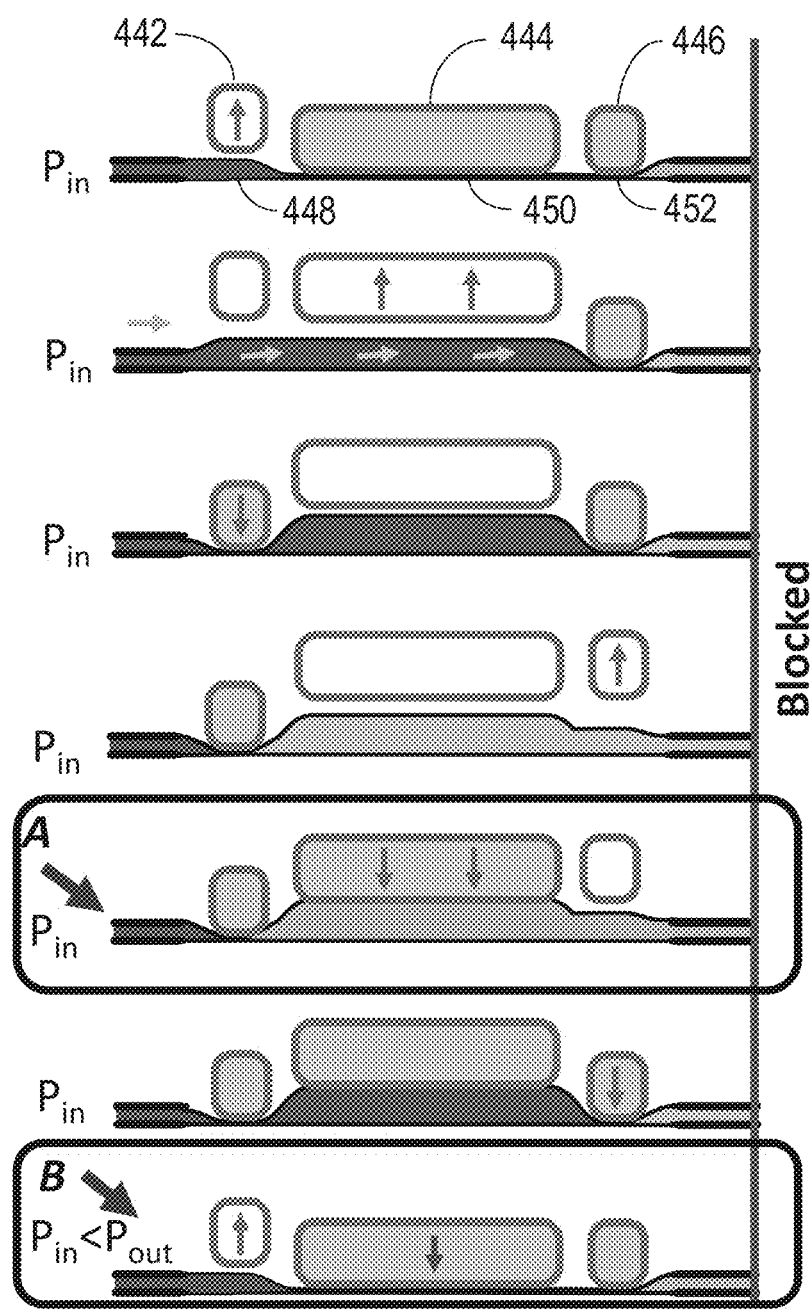

FIGS. 33A and 33B provide schematic depictions of the series of steps configured to deliver the predetermined dose of medication to the wearer, wherein the dosing pathway is not occluded and the dosing pathway is occluded, are illustrated. FIG. 33A is similar to FIG. 30, described above, and also includes arrows A and B pointing to two steps of the microdosing process. Arrow A is pointing to the sixth position of the microdosing system wherein middle lever 444 is configured to have moved from a raised position to a lowered position, thus forcing the predetermined dose of medication towards the wearer. Arrow B is pointing to the second position of the microdosing system wherein, first lever 442 is configured to have moved from a lowered position to a raised position, thus permitting medication to flow through dosing tube first portion 448 into dosing tube reservoir portion 450.

While FIG. 33A depicts proper operation of the microdosing system, FIG. 33B depicts a scenario in which there is an occlusion in the dosing pathway. For example, the block may be disposed near dosing tube second portion 452 and outflow needle 408 such that medication can flow through a portion of the dosing tube but cannot reach the wearer. In another example, the block may be disposed within the cannula. In FIG. 33B, arrow A is pointing to the sixth step, wherein middle lever 444 is configured to have moved to a lowered position such that predetermined dose of medication flows towards the wearer. However, dosing tube second portion 452 is blocked due to an occlusion in the dosing pathway, preventing the medication from flowing out of dosing tube reservoir portion 450 such that middle lever 444 is unable to move to a lowered position. In the next step, wherein the predetermined dose should be completely delivered to the wearer, second lever 446 is able to move to a lowered position, but the block prevents any delivery of medication. At arrow B, when the next dosing cycle starts, first lever 442 is configured to move to a raised position and middle lever 444 and second lever 446 are configured to remain in a lowered position. However, because the predetermined dose of medication was unable to move into outflow tube 408, middle lever 444 is finally able to move to the lowered position, pushing the predetermined dose of medication back into the inflow tube.

Figures 33C, 33D:
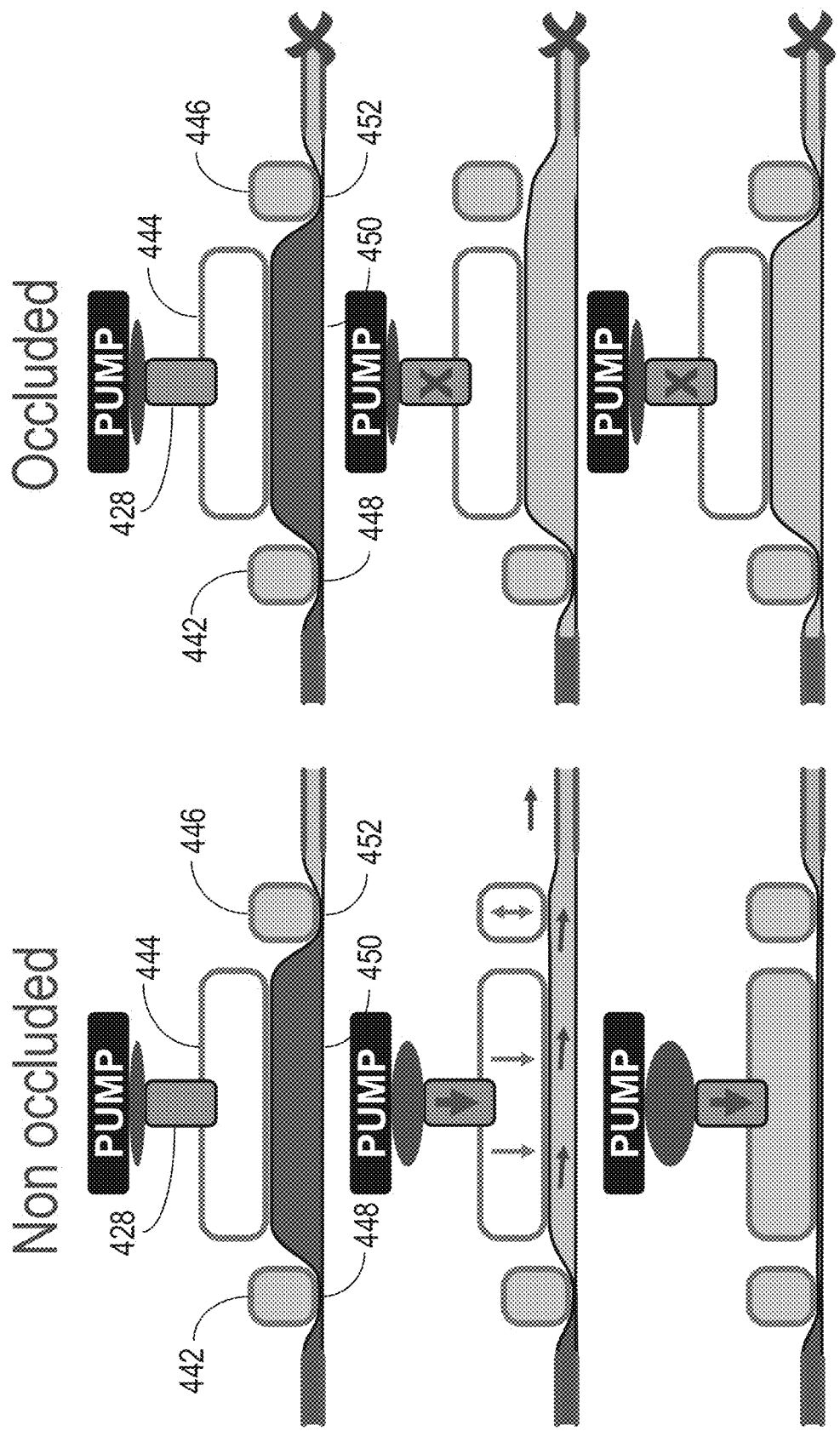
FIGS. 33C and 33D are, respectively, schematic depictions of the position of a lever of the microdosing system during a dosing cycle, wherein the dosing pathway is not occluded and wherein the dosing pathway is occluded.

FIGS. 33C and 33D illustrate the position of the magnet disposed on the middle lever of the microdosing system, wherein the dosing pathway is not occluded and wherein the dosing pathway is occluded. In FIG. 33C, magnet 428 changes positions when the medication is delivered to the outflow needle. In FIG. 33D, because there is an occlusion in the dosing pathway, for example, within the dosing tube, within the outflow needle, or within the cannula, middle lever 444 is not able to move to the lowered position and thus magnet 428 does not significantly change positions. By monitoring the value of a parameter(s) (e.g., the Hall-effect value), the sensor is able to determine the position of magnet 428 and middle lever 444, these values indicating whether there is an occlusion in the dosing pathway. For example, if the magnet does not move at least a predetermined distance relative to the pump (e.g., away from the pump) during each microdosing cycle, the controller is able to determine an occlusion in the fluid flow path. In FIG. 33D, the magnet does not move at least the predetermined distance away from the pump during a microdosing cycle, thereby indicating an occlusion. As such, the patch pump ensures real-time monitoring of each micro-dosing cycle resulting in ultrafast occlusion detection.

Figure 34:
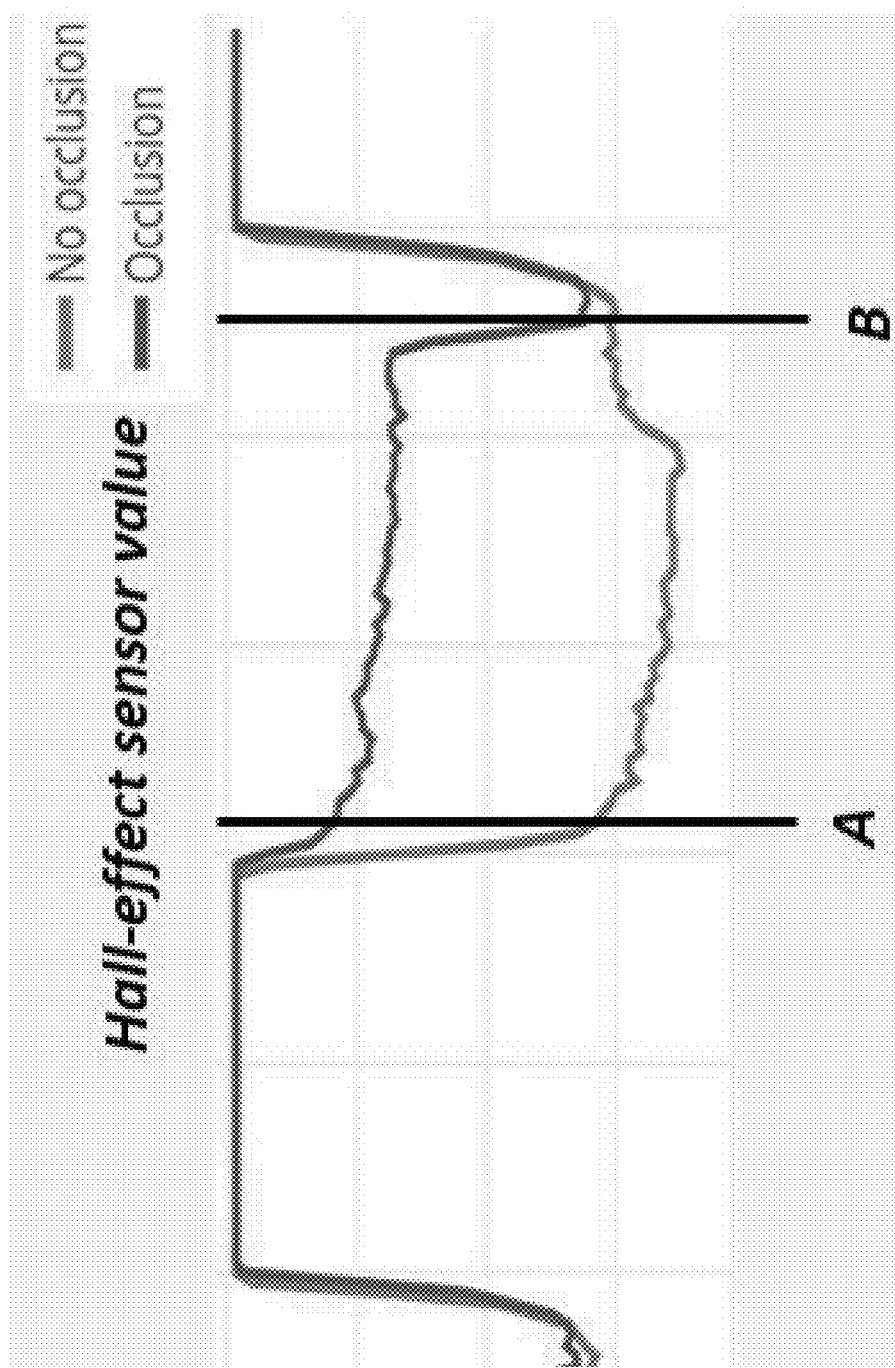
FIG. 34 is a graph showing hall-effect sensor values over time when the dosing pathway is not occluded and when the dosing pathway is occluded.

Referring now to FIG. 34, a graph showing Hall-effect sensor values over time when the dosing pathway is not occluded and when the dosing pathway is occluded is illustrated, and corresponds to the two situations presented in FIGS. 33A and 33B. At point A, in a non-occluded system, the middle lever would move to a lowered position such that the predetermined dose of medication was forced out of the dosing tube reservoir portion. When the middle lever moves to a lowered position, the magnet disposed at the end of the middle lever moves farther away from the hall-effect sensor and therefore the Hall-effect sensor value decreases. However, if there is a blockage within the dosing tube second portion, the outflow needle, or the cannula, middle lever would not be able to move to a lowered position and the position of the magnet would not either. The Hall-effect sensor value therefore would remain substantially the same.

At point B, in a non-occluded system, the middle lever would have remained in a lowered position while the dosing cycle was beginning again. However, if the predetermined dose of medication was unable to deliver the medication from the dosing tube reservoir portion, the middle lever would have started in a raised position. As the first lever is moved to a raised position, the middle lever is able to move to the lowered position, forcing medication within the dosing tube reservoir portion to flow back into the inflow tube. Therefore, in an occluded system, at point B, the magnet disposed at the end of the middle lever moves farther away from the Hall-effect sensor such that the Hall-effect sensor value decreases.

A controller may be operatively coupled to the sensor and may be configured to determine whether there is an occlusion in the dosing pathway. For example, the controller may be configured to monitor whether the measured Hall-effect sensor values are within predetermined Hall-effect sensor value ranges that are expected for each step of the dosing cycle or if the measured Hall-effect sensor values change at a time it should remain the same. If there is an occlusion, at point A, the measured Hall-effect sensor value may exceed the predetermined Hall-effect sensor value range for that step. At point B, the measured Hall-effect sensor value decreases while the predetermined Hall-effect sensor value remains the same. The controller may determine there is an occlusion based off of the measurements at point A, point B, or both point A and point B.

Referring now to FIGS. 35A-35D, an exemplary system configured to determine the position of the circular cam is described, wherein FIG. 35E is a graph showing signal strength over time as the circular cam rotates. Another way to validate that the predetermined doses of medication are properly delivered to the wearer and to ensure that the dosing cycle is fully completed is by determining the position of the cam plate. Monitoring of the position of the cam plate also helps the controller determine the absolute stopping position for each dosing cycle such that the controller can ensure that the patch pump remains locked, as described above. For example, a ferromagnetic blade having teeth may be coupled to the cam plate and, upon rotation, may generate an oscillation of a signal that can be used to count the teeth on the ferromagnetic blade. The generated oscillations may be used as an incremental sensor to determine the position of a cam plate and accordingly whether the dosing cycle is complete.

Preferably, pump 300 includes circuit board 314 having sensor 344 disposed on one side of circuit board 314 and magnet 396 disposed on the other side of circuit board 314 and adjacent to sensor 344. Pump 300 further may include gearbox 324 having ferromagnetic blade 323. Ferromagnetic blade 323 may have a plurality of teeth and the plurality of teeth may include one or more gaps 325. Gaps 325 may be spaced equally around ferromagnetic blade 323 and preferably align with the end of a dosing cycle. For example, one 360 degree rotation of cam plate 416 may complete two doses cycles. Ferromagnetic blade 323 may include two gaps 325 disposed opposite of each other and configured to align with the end of a dosing cycle.

Sensor 344 preferably is electrically coupled to a controller such that sensed signals are sent to the controller for determining the position of cam plate 416. Gaps 325 may create longer (dT1>dT2) and stronger (A1>A2) oscillations, as shown in FIG. 35E. By monitoring the oscillations, and determining the position of cam plate 416, the controller is able to determine the absolute stopping position for each dosing cycle. This determination also may help the controller ensure that the patch pump remains locked, as described above.

Figure 36A:
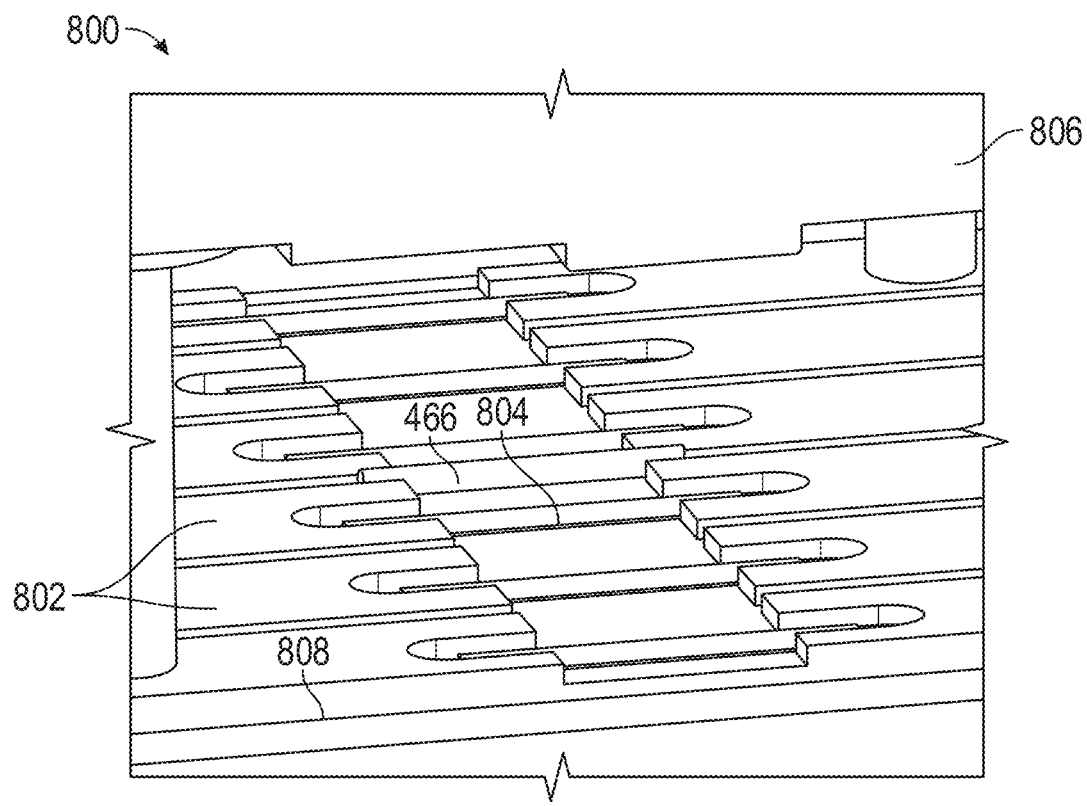
FIGS. 36A and 36B are, respectively perspective views of an exemplary tube flatting system before and after the dosing tube is flattened.
Figure 36B:
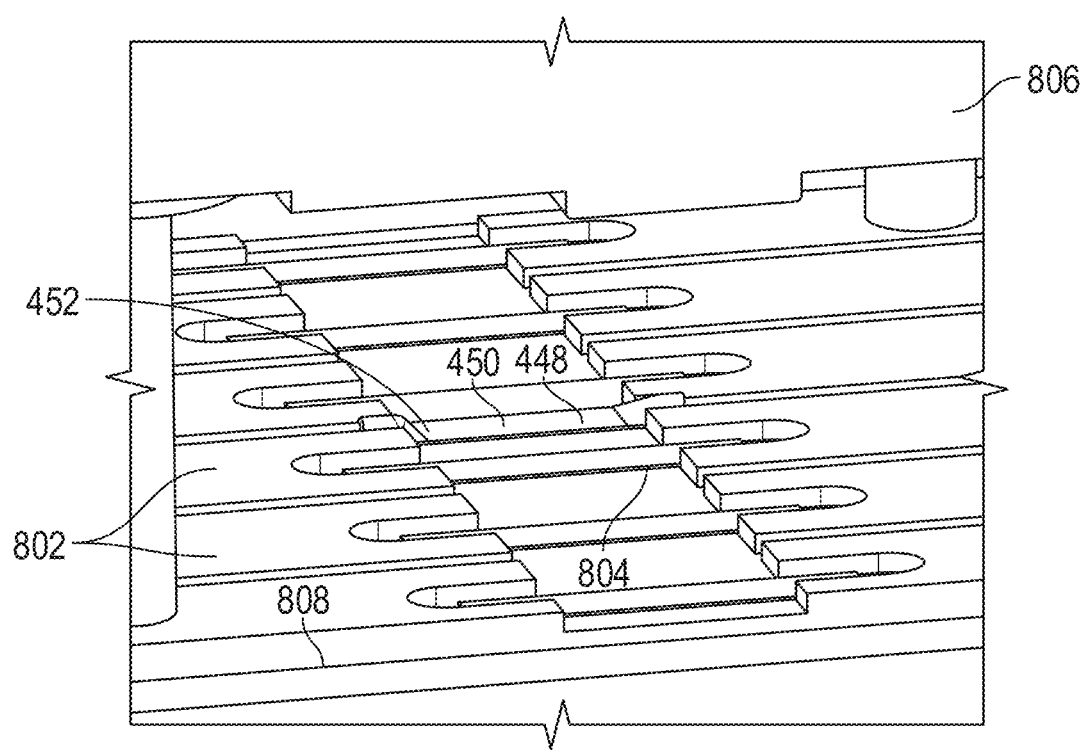

With respect to FIGS. 36A and 36B, an exemplary tube flattening system before and after the dosing tube is flattened is described. The dosing tube preferably is made from a flexible polymer such that the levers of the lever system may apply pressure to the dosing tube, causing the dosing tube to deflect and prevent the medication from flowing through the dosing tube. The dosing tube preferably includes dosing tube reservoir portion 450, which is designed to slightly expand such that the predetermined dose of medication is accurately measured. By monitoring the pressure within the cartridge and by measuring the predetermined dose of medication by volume, the accuracy of the dose is increased. Dosing tube reservoir portion 450 also may include welded portions that are configured to increase the accuracy of the volume within the reservoir.

Tube flattening system 800 is configured to flatten dosing tube reservoir portion 450. Tube flattening system 800 provides advantages over the methods of the prior art wherein the tube is blow molded and then flattened. One of the key benefits of this system is that it reduces the risk that the tubing walls within dosing tube reservoir portion 450 do not have a constant thickness and rigidity. Uniformity along the tubing walls helps ensure that each manufactured dosing tube reservoir portion 450 expands to the same size, thus ensuring that the predetermined doses of medication are similar among different devices.

Tube flattening system 800 may include two or more raised portions 802 that are spaced apart such that unflattened dosing tube 466 may fit between a first and second raised portion without significant excess space remaining. Tube flattening system 800 further may include press 806, which is configured to apply pressure onto unflattened dosing tube 466 to create a flattened dosing tube including dosing tube reservoir portion 450, which is designed to hold a predetermined dose of medication. Preferably, press 806 moves from a raised position such that press 806 does not contact unflattened dosing tube 466 to a lowered position such that press 806 presses on unflattened dosing tube 466 until it reaches thickness guide 804. Thickness guide 804 preferably is disposed on either side of unflattened dosing tube 466 and protrudes above lower portion 808 of tube flattening system 800 to a height that is substantially the same as the preferred thickness of dosing tube reservoir portion 450.

Figure 37:
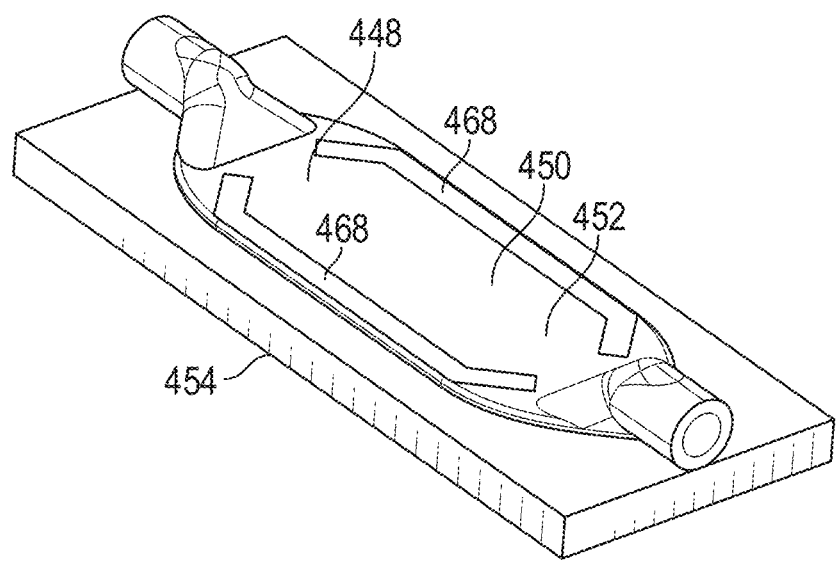
FIG. 37 is a perspective view of an exemplary welded dosing tube used in the microdosing system for precise medication dosing.

Turning to FIG. 37, an exemplary welded dosing tube is described. To further ensure that the predetermined dose of the medication is accurate, dosing tube reservoir portion 450 may include welded portions 468, which help define a specific volume to be filled with medication. Welded portions 468 also may increase the efficiency of the watertightness such that the levers can provide less pressure on the dosing tube while still preventing the medication from flowing towards the wearer. Welded portions 468 may be disposed on the outer portions of dosing tube reservoir portion 450 such that the medication may still flow through the dosing tube. Preferably, the dosing tube is welded onto dosing tube support 454 via laser welding. The dosing tube may be transparent to a laser and dosing tube support 454 may not be transparent to the laser. Dosing tube support 454 is configured to provide a support for the dosing tube during welding and also is configured to help position the dosing tube within the patch pump during assembly.

Figure 38A:
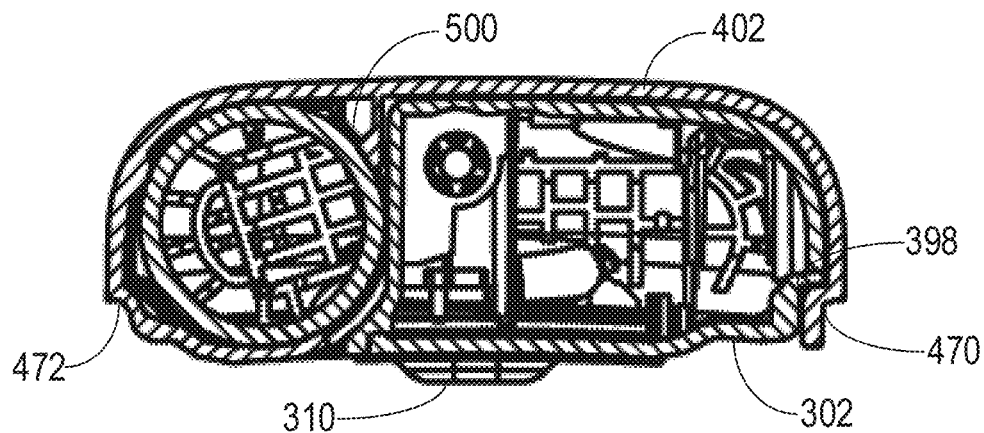
FIG. 38A is a cross-sectional side view of the pump-cap assembly when the pump and cap are locked together.
Figure 38B:
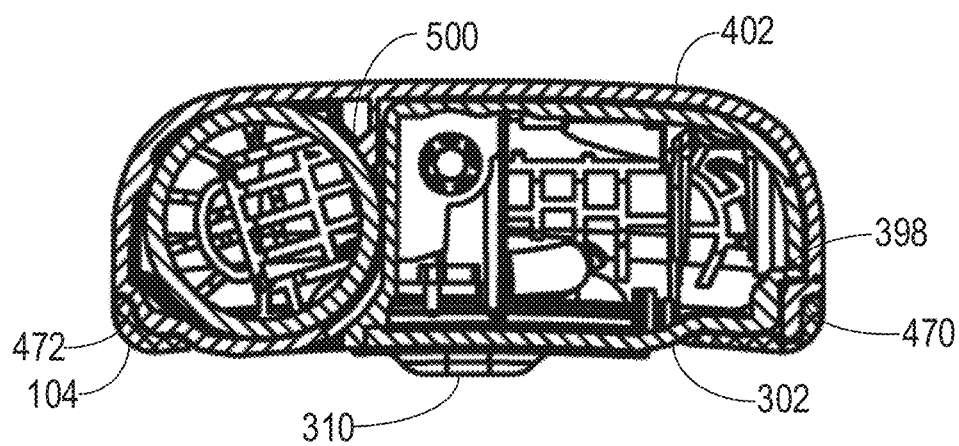
FIG. 38B is a cross-sectional side view of the pump-cap assembly when the pump-cap assembly and pad are locked together.
Figure 38C:
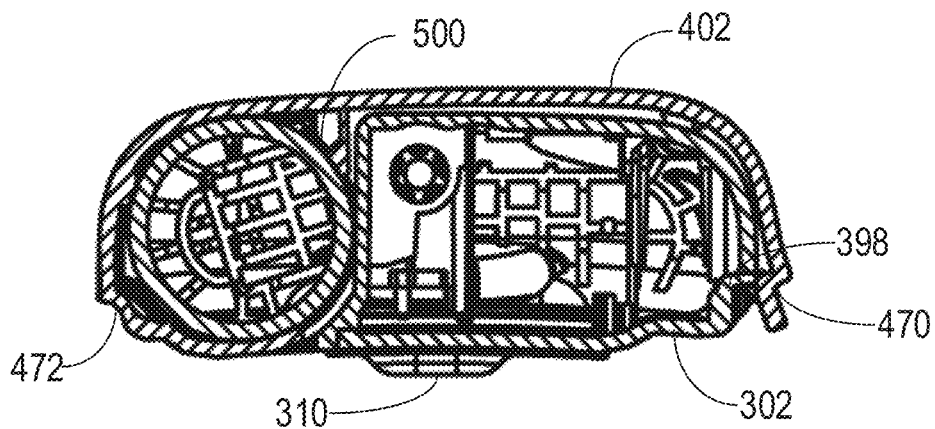
FIG. 38C is a cross-sectional side view of a distortion that may occur if the pump-cap assembly and pad are not locked together.

Referring now to FIGS. 38A-38C, exemplary mechanisms for locking the patch pump to the pad are described. The locking mechanisms preferably are configured such that the cap remains secured to the pump and the patch pump remains secured to the pad throughout the wearer's daily motions. In FIG. 38A, the pump-cap assembly when the pump are locked together. The patch pump may include a pump having pump housing 302 and a cap having cap housing 402 and may be configured to house cartridge 500. Cap housing 402 may include cap lock 470 and pump housing 302 may include pump housing lock 398, configured to interact with cap lock 470. The cap may be configured to couple to the pump via a twisting motion. For example, the cap may be placed onto the pump in a first position such that the inflow needle of the cap pierces the cartridge cap of cartridge 500. The cap may then be rotated until cap lock 470 couples to pump housing lock 398.

In FIG. 38B the pump-cap assembly and pad are locked together. In order to ensure that cartridge 500 remains within the patch pump and that the operation of the patch pump is not interrupted by the wearer, the patch pump is configured to couple to the pad such that the pump and cap cannot be uncoupled from each other until the patch pump is uncoupled from the pad. For example, cap housing 402 further may include pad interface 472 at a different edge of cap housing 402. Cap lock 470 and pad interface 472 may be configured to interact with corresponding features of pad skeleton 104. Once the patch pump is secured to the pad, the interaction between pad skeleton 104, cap lock 470 and pump housing lock 398 ensure that the patch pump cannot be opened when disposed on the skin of the wearer.

In FIG. 38C, distortion that may occur if the pump-cap assembly and pad are not locked together is described. In particular, if the patch pump is not properly coupled to the pad, cap housing 402 may deform, causing the cap to uncouple from the pump. This unlocking could cause serious consequences for the wearer, and thus must be prevented. One way to prevent the unlocking is to lock the patch pump to the pad, as in FIG. 38B.

Figure 39A:
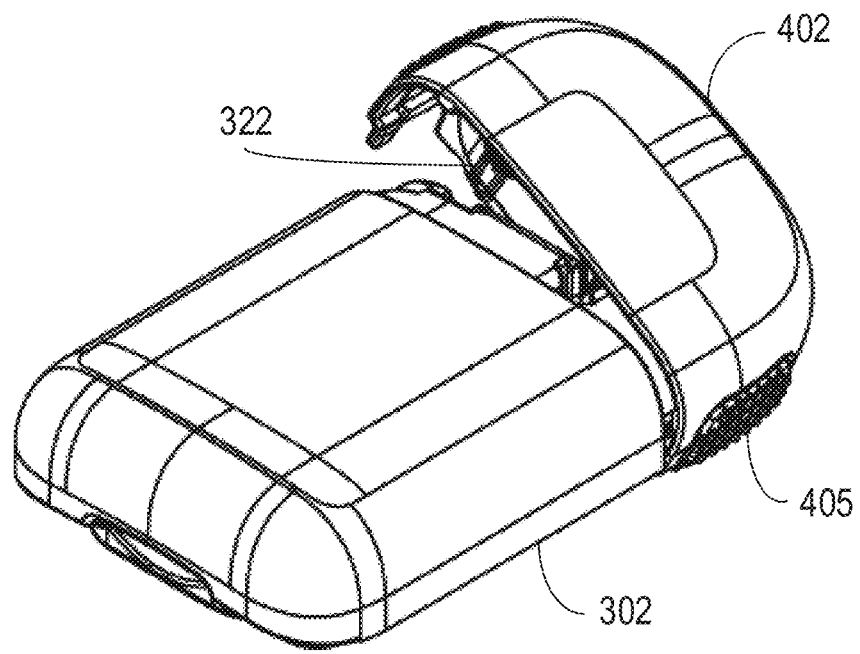
FIGS. 39A and 39B are, respectively, perspective and cross-sectional side views of the pump-cap assembly in an open, unlocked position.
Figure 39B:
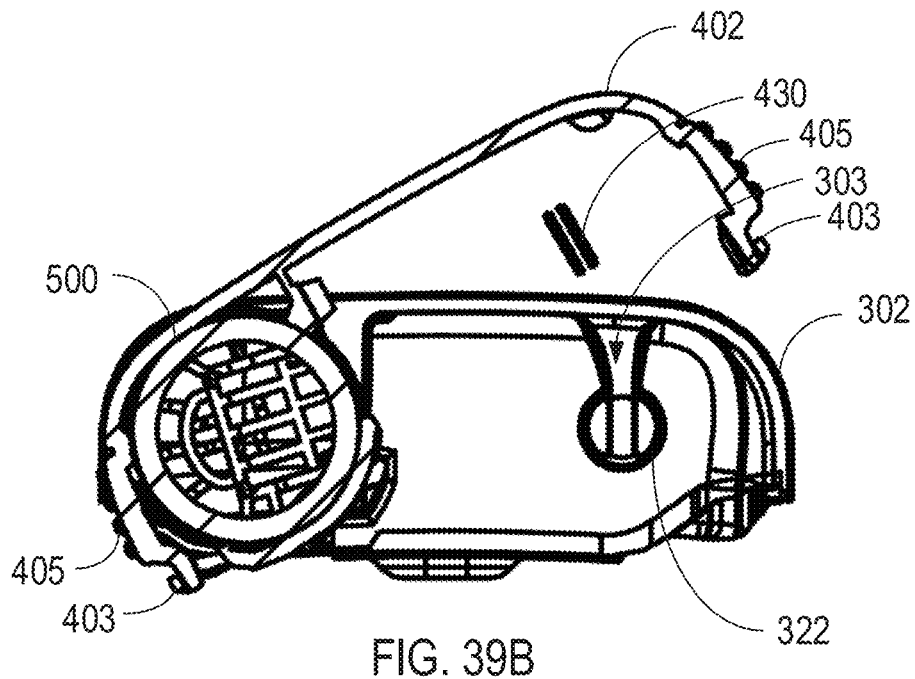

Referring now to FIGS. 39A-39F, exemplary mechanisms for locking the cap to the pump are described. In addition to the locking mechanisms noted above, the cap and pump further may include a rotational locking mechanism disposed between pump housing 302 and cap housing 402. This locking mechanism ensures that the wearer cannot uncouple the cap from the pump during delivery of medication. In FIGS. 39A and 39B, the cap may be placed onto the pump in an open, unlocked position such that the inflow needle of the cap pierces the cartridge cap of cartridge 500. The pump may include tabs 430, which are coupled to the microdosing system, and the cap may include mechanical coupling 322, which is coupled to the gearbox. Both tabs 430 and mechanical coupling 322 are configured to rotate upon actuation of the gearbox. Preferably, in the closed position, tabs 430 are configured to be disposed within mechanical coupling 322 such that rotation of mechanical coupling 322 causes rotation of tabs 430, which causes rotation of the circular cam described above. In the unlocked position, tabs 430 and mechanical coupling 322 may be disposed in a vertical position, perpendicular to the skin-facing side of the patch pump.

Figure 39C:
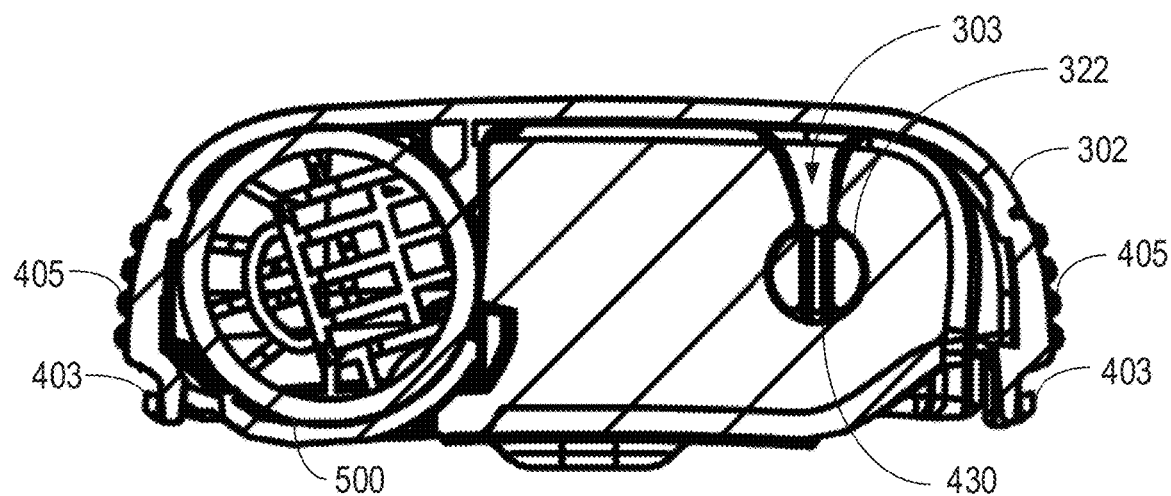
FIGS. 39C and 39D are, respectively, cross-sectional side views of the pump-cap assembly in closed, unlocked and locked positions.
Figure 39D:
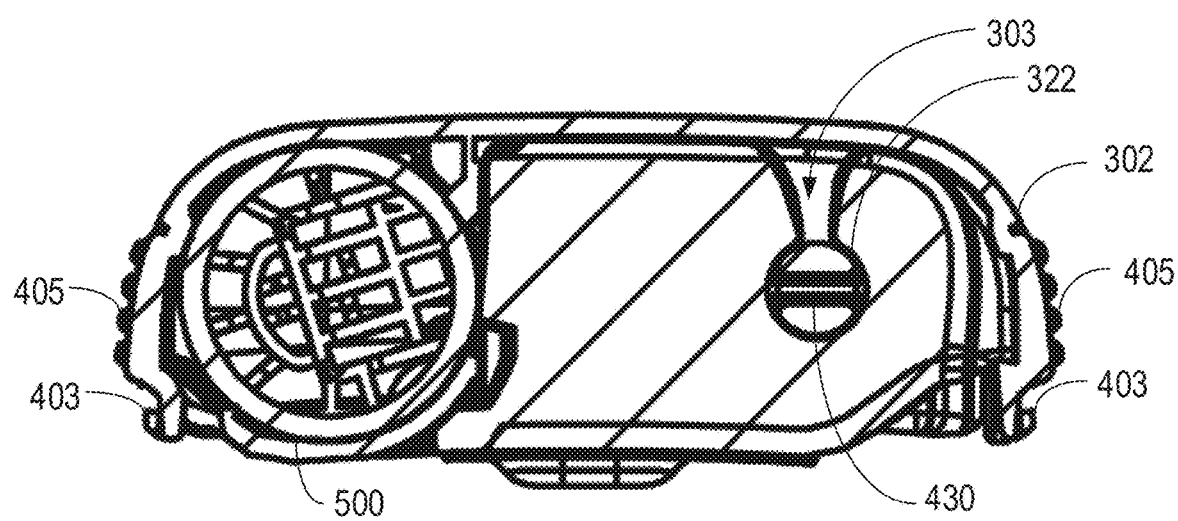
Figure 39E:
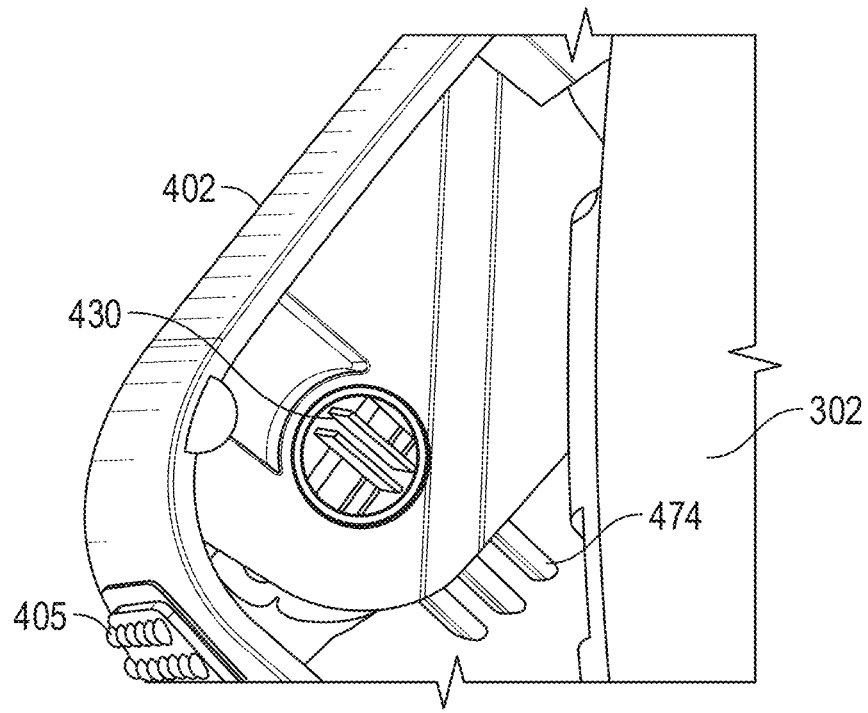
FIGS. 39E and 39F are, respectively, perspective views of the pump-cap assembly in open, unlocked, and locked positions.
Figure 39F:
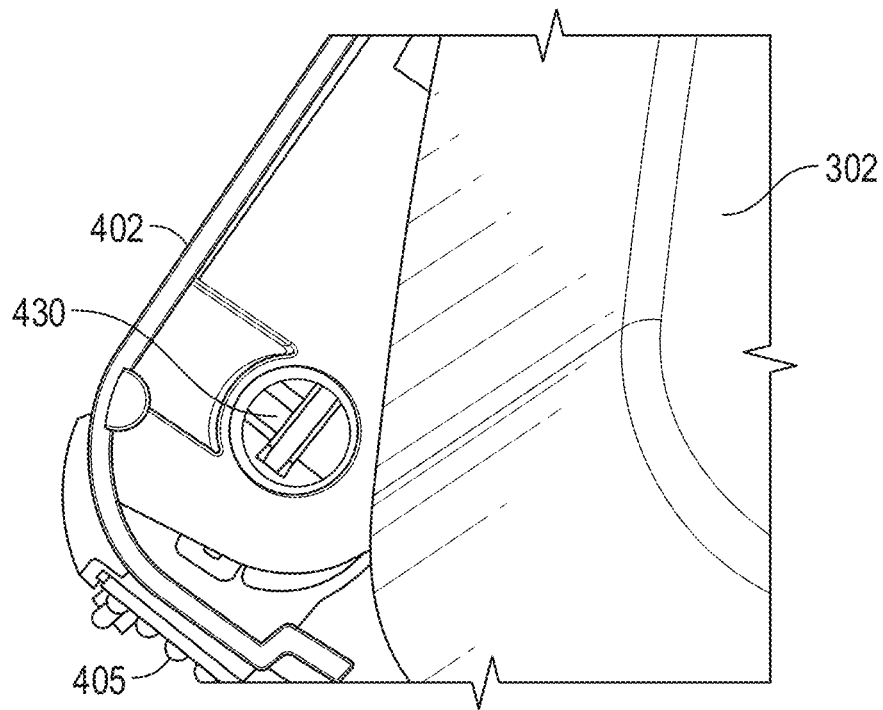

After the inflow needle of the cap is disposed within cartridge 500, the cap then may be rotated until the cap couples to the pump such that the pump and cap are in a closed, but unlocked position, as in FIG. 39C. Tabs 430 are configured to protrude from cap housing 402 such that tabs 430 must be in the vertical position in order to either couple or uncouple the cap from the pump. For example, tabs 430 may be configured to move through channel 303 of pump housing 302. Preferably, channel 303 is sufficiently narrow such that tabs 430 cannot travel through channel 303 when tabs 430 are in a horizontal position. After the cap is coupled to the pump, the controller may be configured to rotate mechanical coupling 322 such that mechanical coupling 322 and tabs 430 are in a locked position, as in FIG. 39D. In FIGS. 39E and 39F, tabs 430 are in an unlocked position and a locked position, respectively.

A microdosing system is disposed within the cap and is configured to measure and deliver a predetermined dose of medication. The microdosing system may include a dosing tube, circular cam, configured to rotate, and a lever system, configured to contact the dosing tube and release the predetermined dose of medication into an outflow needle. The circular cam may include a cam shaft and a cam plate coupled to the cam shaft. Preferably, the cam plate includes a top surface having one or more raised surfaces configured to interact with one or more levers of the lever system upon rotation of the cam shaft. Tabs 430 may be disposed at the end of the cam shaft such that tabs 430 may extend towards and interact with the pump. When the motor interacts with the gearbox, it causes both the pusher to move towards the plunger of the cartridge and mechanical coupling 322 to rotate, causing rotation of tabs 430, which causes the microdosing system to deliver medication to the wearer. Preferably, a 180 degree rotation of mechanical coupling 322 delivers one dose of medication.

Each dosing cycle may occur within a predetermined time period (e.g., 0.5 seconds) such that mechanical coupling 322 and tabs 430 are in the vertical position for a very limited amount of time such that the risk that the wearer may uncouple the cap and pump is reduced. In a preferred embodiment, tabs 430 are permitted to travel through channel 303 in a range of +− 10 degrees from the vertical position. Upon each rotation of mechanical coupling 322 and tabs 430, it may be possible to open the cap twice, each time for about 5 hundredths of a second. However, it may not be possible to open the cap when the pump-cap assembly is clipped to the pad because the cap lock secures the pump-cap assembly to the pad. Preferably, when the pump-cap assembly is not clipped to the pad, the skin detector does not detect the skin and the controller stops the pump such that mechanical coupling 322 and tabs 430 are disposed in a locked position and the wearer cannot unlock the pump-cap assembly.

The patch pump may be configured to remain locked even after cartridge 500 is empty. Preferably, mechanical coupling 322 and tabs 430 remain in a locked position until the pusher of the pump is reset to the home position and until the battery is sufficiently charged. The controller may be configured to monitor the battery level of the patch pump and unlock the pump and cap if both the battery level is at a sufficient level and a sensor senses that the contacting blade of the pusher is in contact with the contacting pins.

Figure 40A:
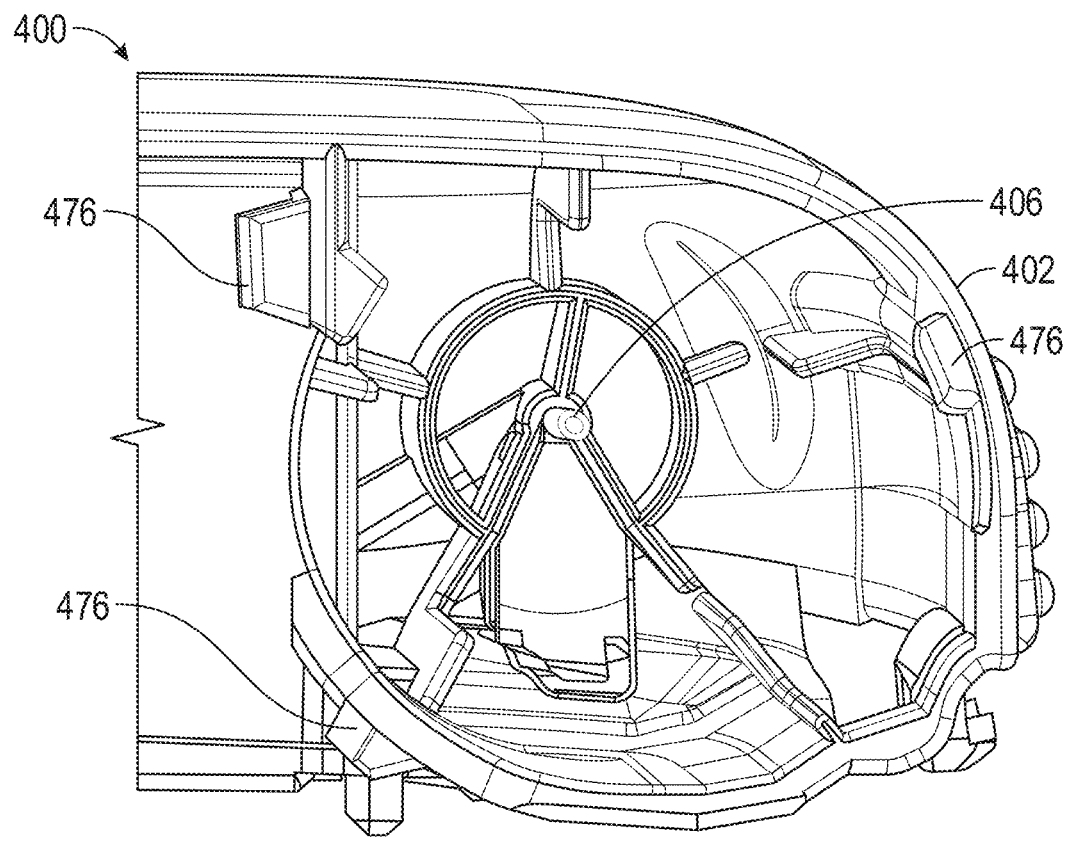
FIG. 40A is a perspective view of exemplary locking protrusions disposed on the cap.
Figure 40B:
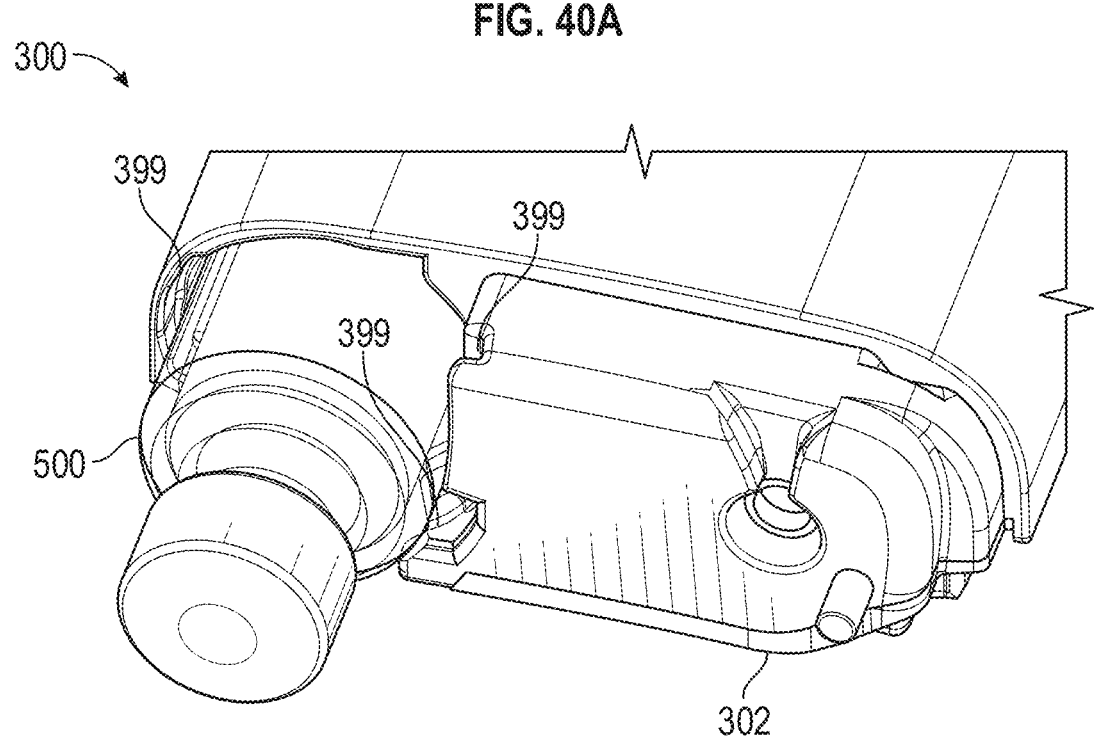
FIG. 40B is a perspective view of exemplary locking receptacles on the pump.

Referring now to FIGS. 40A and 40B, exemplary locking protrusions disposed on the cap and locking receptacles on the pump are described. Surrounding the cartridge, the cap may include one or more locking protrusions and the pump may include one or more corresponding locking receptacles configured to receive the locking protrusions. The locking protrusions and receptacles are configured to lock the cap to the pump such that the continuous force that the pusher places onto the cartridge does not uncouple the cap from the pump. Because the cartridge must remain pressurized in order to ensure accurate dosing, the cartridge may apply a considerable amount of force on the cap.

Cap 400 may include one or more locking protrusions 476 configured to surround the region of cap 400 where inflow needle 406 pierces the cartridge cap of cartridge 500. Pump 300 preferably includes one or more corresponding locking receptacles 399, each locking receptacle 399 configured to engage a locking protrusion 476. Locking protrusions 476 and locking receptacles 399 may be radially spaced surrounding the inflow needle, may be various sizes and shapes, and may be configured to lock to each other upon rotation of the cap from an open position to a closed position. Preferably, cap 400 includes at least three locking protrusions 476 and pump 300 includes at least three corresponding locking receptacles such that torque is minimized. Locking protrusions 476 may be configured to prevent the cap from rotating greater than 90 degrees. At least one locking protrusion 476 may include a first portion having a wide engagement slit and a second portion having a narrower engagement slit.

Because the cap preferably is configured to be disposable and the pump preferably is configured to be reusable, the cap and pump may be designed such that the material of the pump housing has a greater creep resistance than the material of the cap housing. Therefore, if the force from the cartridge becomes too great, the cap may be designed to fail, or deform, before the pump fails or deforms. For example, the material of pump housing 302 may be different than the material of cap housing 402. Additionally or alternatively, the material of pump housing 302 may have a greater thickness than the material of cap housing 402. The same principle may apply to the pad. Because the pad preferably is configured to be disposable and the pump preferably is configured to be reusable, the pad and pump may be designed such that the material of the pump housing has a greater creep resistance than the material of the pad skeleton.

Figure 41:
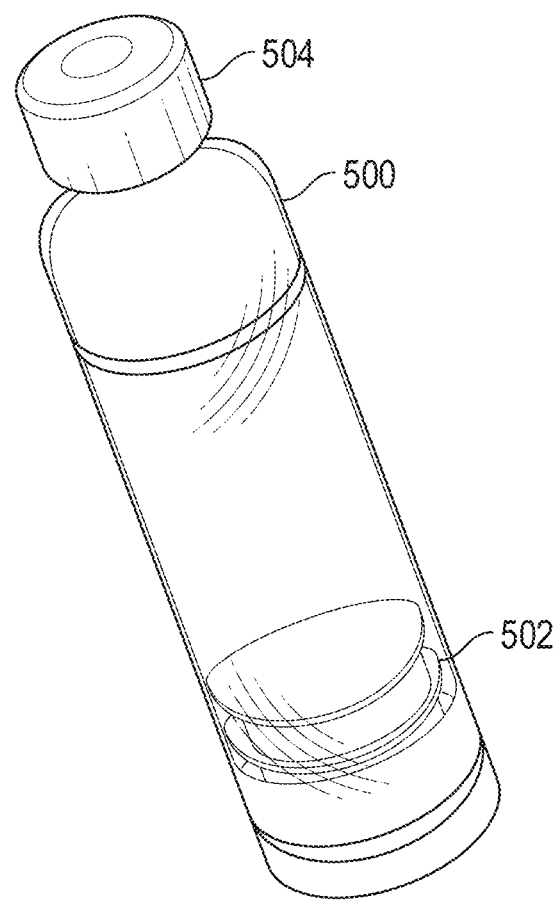
FIG. 41 is a perspective view of an exemplary cartridge that may be used and replaced in the system described herein.

With respect to FIG. 41, a preferred embodiment of a cartridge is described. The patch pump may include a pre-filled cartridge that is configured to be inserted into the patch pump. Cartridge 500 may be filled during manufacturing or may instead be filled by the wearer prior to inserting cartridge 500 into the pump. For example, the wearer may pre-fill several cartridges configured to last one month and store the pre-filled cartridges in the fridge until the cartridge are to be used. Preferably the wearer may insert the pre-filled cartridges into the patch pump directly after removal from the fridge and need not wait a certain period of time (e.g., 20 minutes) before inserting the cartridge. Preferably, the pre-filled cartridge includes a movable end that is configured to interact with the pusher of the pump and a cap that is configured to interact with the inflow needle of the cap. For example, the wearer may insert cartridge 500 into the pump. Cartridge 500 may be sized and shaped such that when the pump and cap are coupled together, forming the patch pump, cartridge 500 is completely enclosed by the patch pump. Preferably, cartridge 500 contains insulin and is pre-filled with an amount of insulin that is sufficient for the wearer for at least three days. Cartridge 500 may be a commercially available insulin container such as the NovoRapid PumpCart available from Novo Nordisk A/S of Bagsverd, Denmark.

Cartridge 500 further may include cartridge cap 504, which may be disposed at a first end of cartridge 500. Cartridge cap 504 may be configured to be inserted within the patch pump such that the inflow needle of the cap pierces cartridge cap 504 when the cap is coupled to the pump. Cartridge 500 further may include plunger 502, which may be disposed at a second end of cartridge 500, the second end opposite the first end, and may be configured to be inserted within the patch pump such that plunger 502 is disposed adjacent to the cartridge contactor of pusher. Upon movement of the cartridge contactor, plunger 502 preferably is configured to move towards cartridge cap 504 such that the medication with cartridge 500 is pushed into the inflow needle and towards the microdosing system of the cap. When cartridge 500 is emptied, the pusher may reset to an initial, home position and cartridge 500 may be removed and replaced with another pre-filled cartridge.

Figure 42:
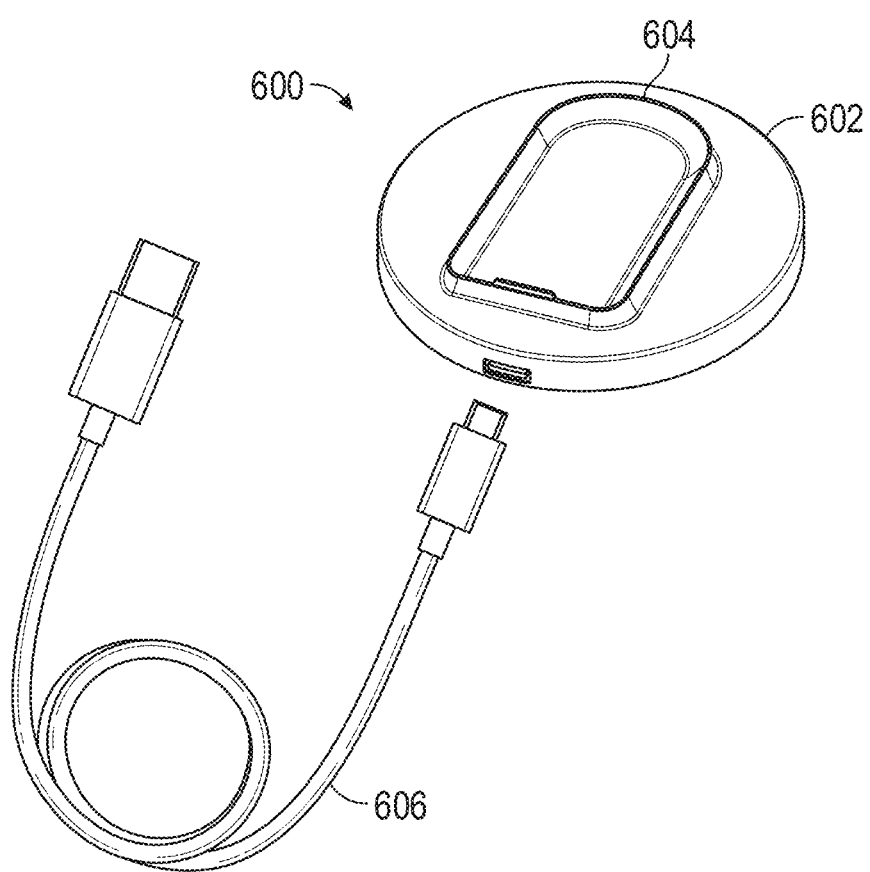
FIG. 42 is a perspective view of the charging system for charging the battery in the reusable pump.

Referring now to FIG. 42, charging system 600 suitable for use with the pumps of the present invention is described and may be used to charge one or more batteries within the pump. Preferably, charging system 600 charges the battery via an inductive coil disposed within the housing of charger 602 and the pump. Charger 602 may be plugged into a conventional socket. via cable 606 or a cord with an AC or DC power converter. Charging system 600 also may include charger support frame 604, which is configured to hold the pump while charging. Charger support frame 604 may be have a similar size and shape as the pad skeleton.

Referring now to FIG. 43A-G, illustrative screenshots of an exemplary mobile device and mobile application interfaces are described. The patch pump may be configured to communicate data to or from a mobile device running software application 700 such that the user may review the data and may activate the pump. Software application 700 may be a dedicated application or "app" and may be downloaded from an online store such as iTunes™ (Apple, Inc., Cupertino, Calif.), the App Store (Apple, Inc.), Google™ Play (Google, Inc., Mountain View, Calif.), the Android™ Marketplace (Google, Inc.), Windows™ Phone Store (Microsoft Corp., Redmond, Wash.), or BlackBerry™ World (BlackBerry, Waterloo, Ontario, Canada). Preferably, software application 700 need only be downloaded once, although updates also may be downloaded.

Figure 43B:
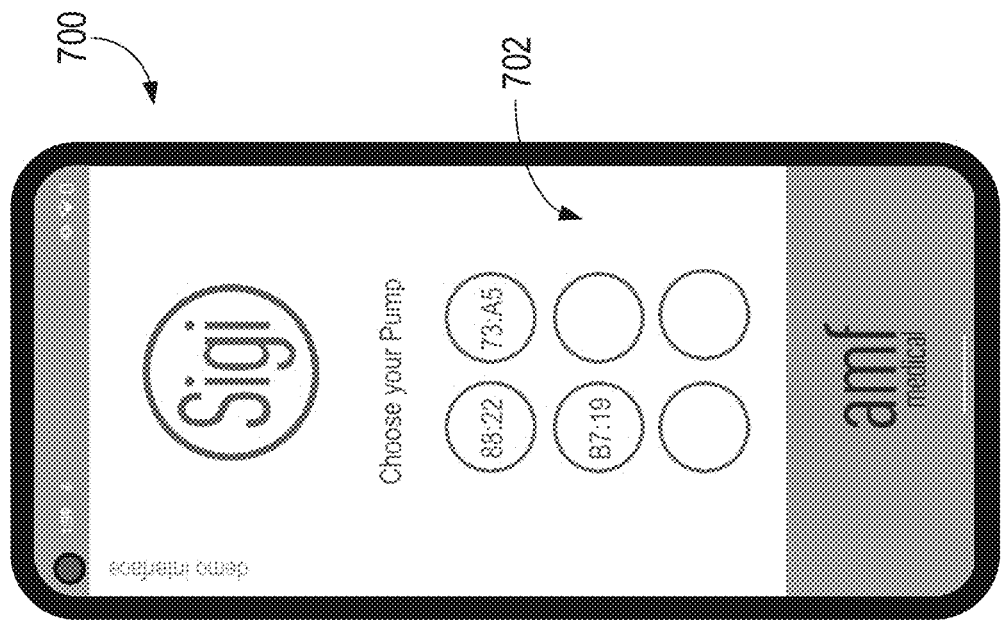
FIG. 43A-43G are screenshots of an exemplary software application that may be used in the systems described herein.
Figure 43A:
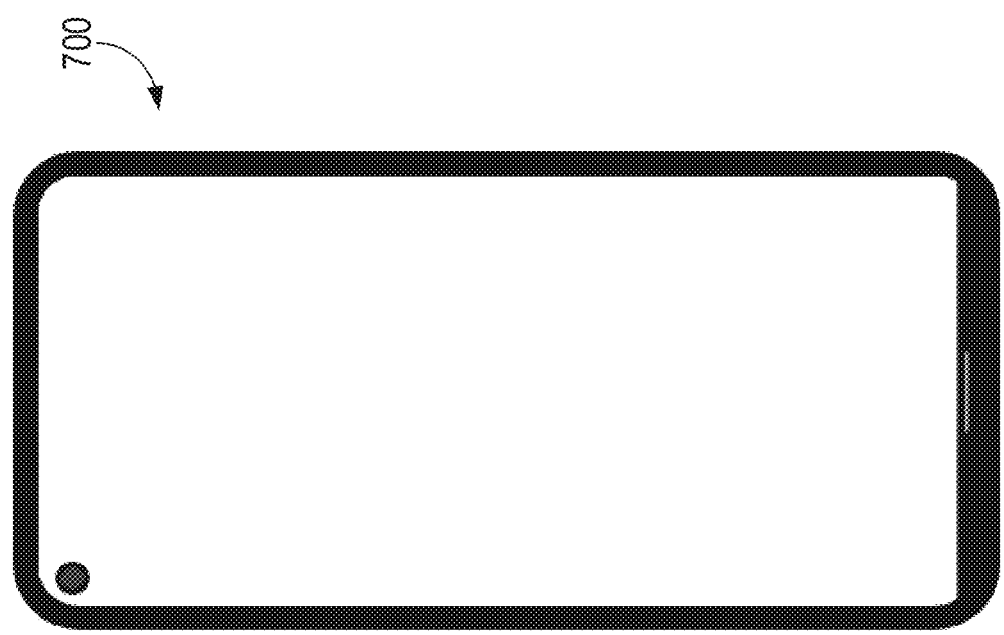
Figure 43D:
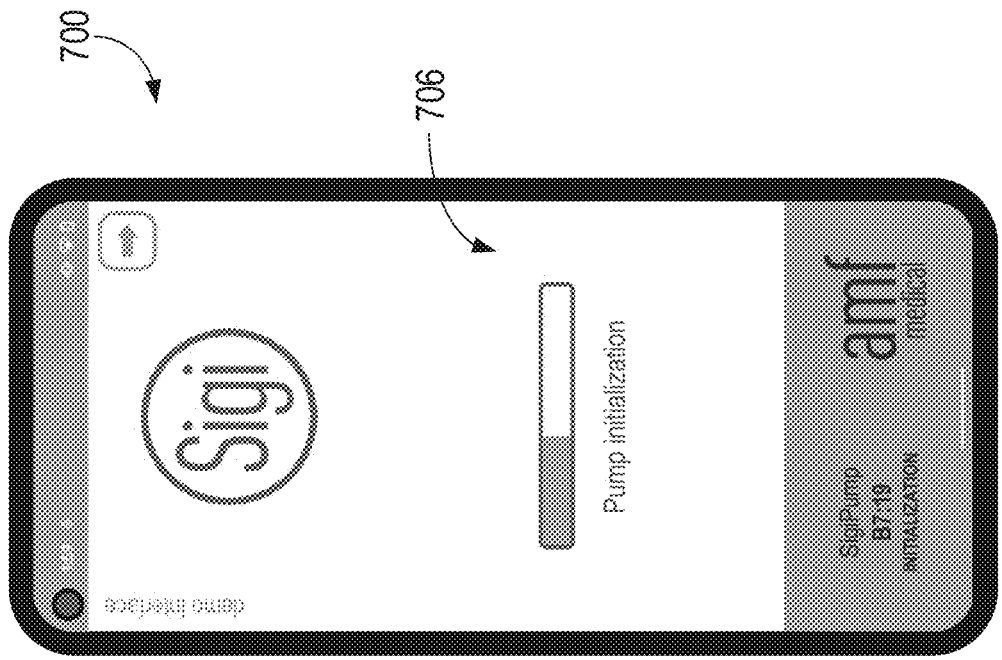
Figure 43C:
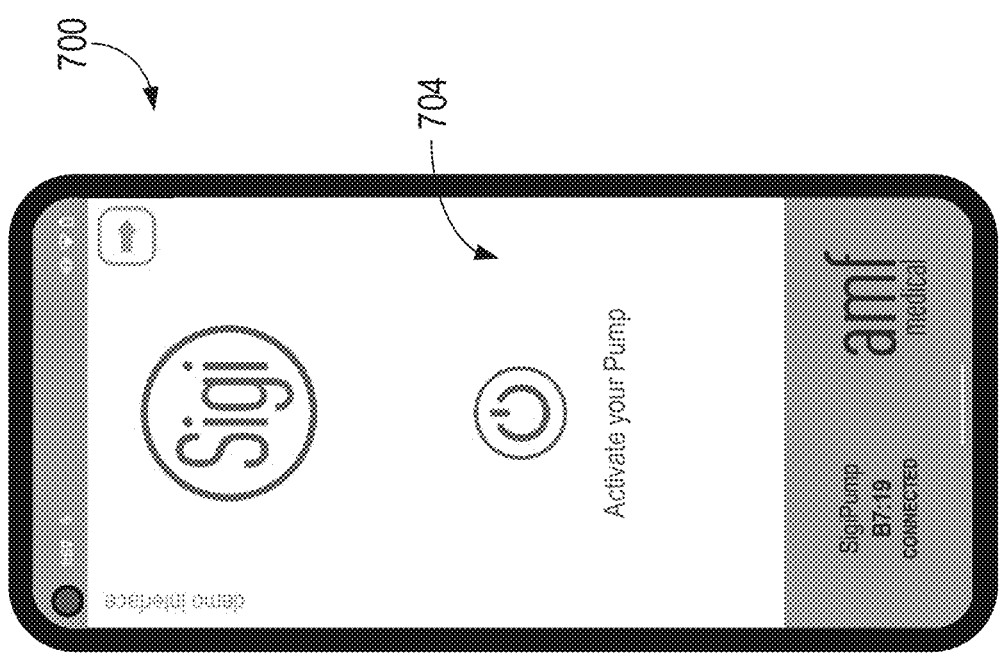

In FIG. 43B, interface 702 permits the user to select which of various pumps to control, with one or more icons depicting a type of pump. The wearer may choose the icon identifying the pump that the wearer is using. Upon identification of the type of pump, software application 700 may display activation interface 704, as in FIG. 43C. Activation interface 704 may include an "activate", "go", "run", "start", or other similar button or icon that the wearer may press to activate the pump. After activation of the pump, the pump may complete an initialization process to increase the pressure within the cartridge until it is within a predetermined range, as described above. The wearer may view the status of the initialization process on initialization interface 706, as in FIG. 43D.

Figure 43F:
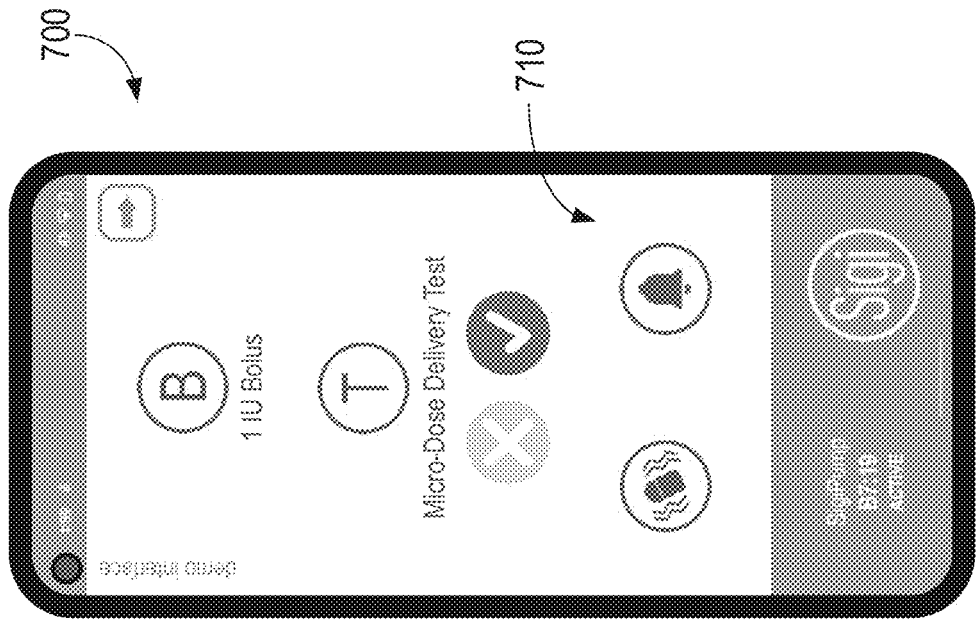
Figure 43E:
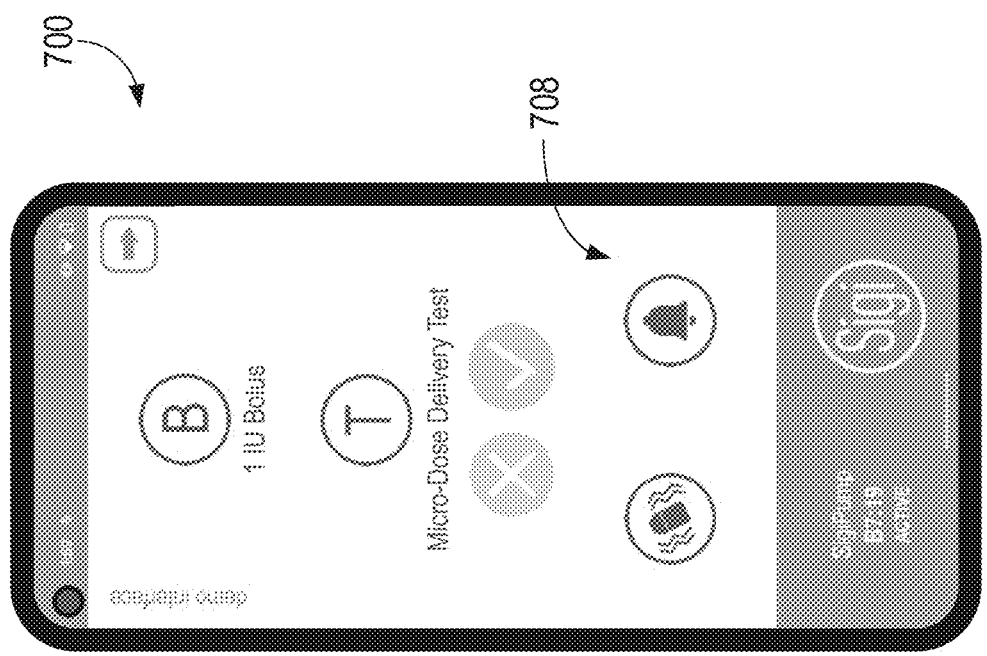
Figure 43G:
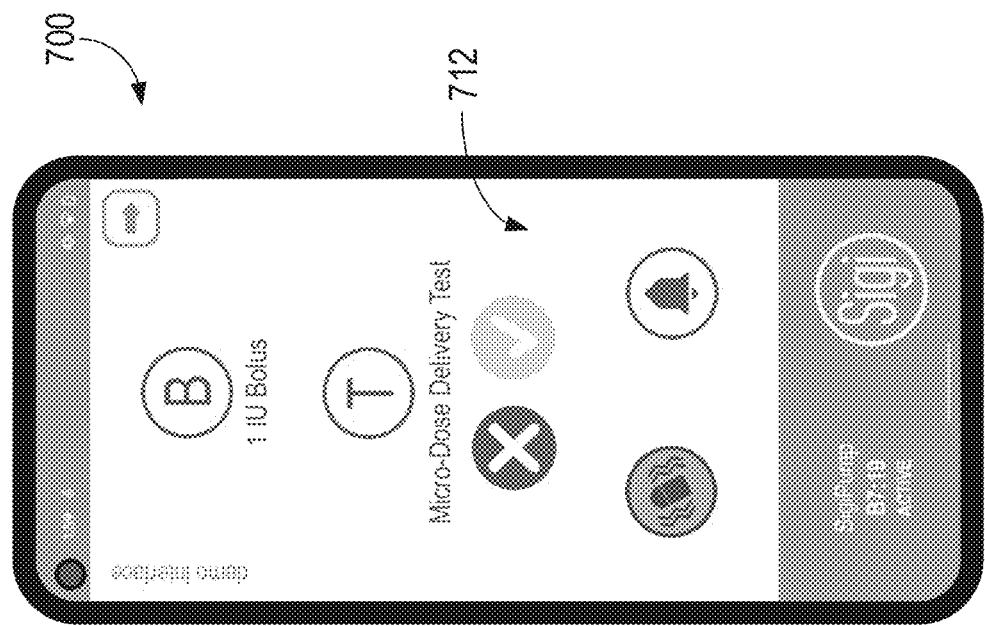

Once the pump is activated, the wearer may wish to run a test to determine whether the pump is working properly. Software application 700 may display testing interface 708, as in FIG. 43E, which may include an icon that may be pressed by the wearer. Software application 700 may communicate with the pump that a delivery test should be run. For example, the delivery test may include delivery of one microdose of medication. Upon completing the test, the pump may communicate with software application 700 that the test was either successful or unsuccessful. If the pump ran properly during the test, test successful interface 710 will be displayed, as shown in FIG. 43F, indicating that there were no issues. If the pump detected one or more issues during the test, test unsuccessful interface 712 will be displayed, as in FIG. 43G. Because more than one dosing cycle may be necessary to detect an occlusion due to the flexibility of the cannula, the user may run multiple delivery tests. Testing interface 708 and interfaces 710 and 712 also may include icons allowing the wearer to choose the type of alarm that the pump may emit. For example, the wearer may choose a vibrate mode such that the pump silently alerts the wearer or the wearer may choose an audible mode.

Software application 700 also may allow the user to input information regarding the type of cartridge that is inserted into the patch pump. For example, the cartridges that may be inserted into the patch pump may have different concentrations of medication. Each cartridge may have identification information such as concentration, volume, and/or manufacturer information that is readable by software application 700. For example, the user may scan the identification information on the cartridge (e.g., QR code, RFID, color recognition) using the device's camera. Software application 700 may process an image obtained from the device's camera using, for example, image recognition software to determine the identification information on the cartridge and then may transmit this information to the controller. Alternatively, in some embodiments, the patch pump may automatically identify information on the cartridge (e.g., cartridge type, concentration, etc.) without user intervention. For example, the patch pump may automatically scan the identification information on the cartridge upon insertion of the cartridge into the pump using an optical sensor. The controller may use the identification information of the cartridge to modify the delivery of the medication.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed is:

1. A medication infusion device comprising a patch pump configured to be removably adhered to a wearer's skin for delivering doses of medication from a container through a transcutaneous portion, the patch pump comprising:
 a first pumping system comprising a pusher configured to be coupled to a plunger of the container and a pump motor coupled to the pusher and configured to move the pusher towards the plunger of the container such that medication is moved out of the container; and
 a second pumping system configured to receive the medication pumped out of the container by the first pumping system, the second pumping system disposed between the container and the wearer's skin and comprising a plurality of levers configured to contact a dosing tube to move a predetermined dose of the medication towards the transcutaneous portion,
 wherein the plurality of levers are configured such that at least one lever is configured to be in a lowered position to close the flow between the container and the wearer's skin at all times.

2. The medication infusion device of claim 1, wherein the at least one lever is configured to be in the lowered position at all times to maintain pressure in the container at all times.

3. The medication infusion device of claim 1, wherein the second pumping system is configured to inject a volume of medication that varies around a predetermined volume according to its input pressure.

4. The medication infusion device of claim 3, wherein the predetermined volume is between 0.2 and 0.3 uL.

5. The medication infusion device of claim 1, wherein the plunger is flexible and configured to deform when a force is applied.

6. The medication infusion device of claim 1, wherein the plunger comprises a first end coupled to the pusher and a second end, opposite the first end and configured to contact the medication within the container.

7. The medication infusion device of claim 1, wherein the pusher applies force on the plunger of the container to maintain pressure within the container between 400 mbar and 1200 mbar.

8. The medication infusion device of claim 1, wherein the pusher comprises a screw, a nut configured to move along the screw, a bendable rod coupled to the nut, and a container contactor coupled to the nut and configured to deform the plunger.

9. The medication infusion device of claim 1, wherein the pusher comprises a screw, a nut configured to move along the screw, a bendable rod coupled to the nut, and a container contactor coupled to the nut and configured such that the pusher incorporates a certain strain.

10. The medication infusion device of claim 1, wherein the dosing tube comprises a flattened reservoir sized to hold the predetermined dose of medication for delivery to the wearer.

11. The medication infusion device of claim 1, wherein the second pumping system further comprises:
 a circular cam comprising a shaft oriented in a first plane and a circular plate oriented in a second plane, the circular plate coupled to the shaft and comprising surfaces configured to move the plurality of levers in a series of steps upon rotation of the shaft,
 wherein rotation of the shaft delivers the predetermined dose of medication towards the wearer.

12. The medication infusion device of claim 11, wherein the shaft is configured to rotate upon rotation of the screw.

13. The medication infusion system of claim 1, wherein the transcutaneous portion comprises a cannula configured to extend into the wearer's skin and having one or more apertures beneath the outer skin layer for delivery of the dose of medication.

14. The medication infusion system of claim 13, wherein the transcutaneous portion further comprises a needle configured to be fluidically coupled to the cannula.

15. The medication infusion system of claim 1, wherein the container is a pre-filled cartridge of insulin.

16. The medication infusion system of claim 1, further comprising a pump housing configured to house the first pumping system and a cap housing configured to house the second pumping system.

17. The medication infusion system of claim 16, wherein the pump housing and the cap housing are configured to be locked together to hold the container.

18. The medication infusion system of claim 16, wherein the pump housing and components therein are configured to be reusable and the cap housing and components therein are configured to be disposable.

19. A method of using a medication infusion device comprising a patch pump configured to be removably adhered to a wearer's skin for delivering doses of medication from a container through a transcutaneous portion, the method comprising:
    moving a pusher of a first pumping system to move a plunger of the container using a pump motor coupled to the pusher such that medication is moved out of the container; and
    receiving the medication pumped out of the container at a second pumping system comprising a dosing tube and a plurality of levers, the second pumping system disposed between the container and the wearer's skin; and
    moving a predetermined dose of the medication through the dosing tube using the plurality of levers and towards the transcutaneous portion for delivery to the wearer,
    wherein the plurality of levers is configured such that at least one lever is configured to be in a lowered position to close the flow between the container and the wearer's skin at all times.

20. The method of claim 19, wherein the at least one lever is configured to be in the lowered position at all times to maintain pressure in the container at all times.

21. The method of claim 19, wherein the second pumping system is configured to inject a volume of medication that varies around a predetermined volume according to its input pressure.

22. The method of claim 21, wherein the predetermined volume is between 0.2 and 0.3 uL.

23. The method of claim 19, further comprising deforming the plunger when a force is applied thereto.

24. The method of claim 19, further comprising adhering the patch pump to the wearer's skin.

25. The method of claim 19, wherein the dosing tube comprises a flattened reservoir sized to hold the predetermined dose of medication for delivery to the wearer.

26. The method of claim 19, wherein the second pumping system further comprises a circular cam comprising a shaft oriented in a first plane and a circular plate oriented in a second plane, the circular plate coupled to the shaft and comprising surfaces configured to move the plurality of levers in a series of steps upon rotation of the shaft,
    the method further comprising rotating the shaft to deliver the predetermined dose of medication towards the wearer.

27. The method of claim 19, wherein the patch pump comprises a pump housing configured to house the first pumping system and a cap housing configured to house the second pumping system.

28. The method of claim 27, further comprising locking the cap housing to the pump housing before moving the pusher to move the plunger.

29. The method of claim 27, further comprising sensing that the cap housing has been coupled to the pump housing.

30. The method of claim 19, wherein the pusher comprises a screw, a nut configured to move along the screw, a bendable rod coupled to the nut, and a container contactor coupled to the nut and configured to deform the plunger.

* * * * *